(12) United States Patent
Kudithipudi et al.

(10) Patent No.: US 11,034,969 B2
(45) Date of Patent: Jun. 15, 2021

(54) PLANT COMPRISING RECOMBINANT POLYNUCLEOTIDES ENCODING A PIGMENT REGULATORY TRANSCRIPTION FACTOR WITH A TISSUE-PREFERRED PROMOTER

(71) Applicant: Altria Client Services LLC, Richmond, VA (US)

(72) Inventors: Chengalrayan Kudithipudi, Midlothian, VA (US); Raja Payyavula, Henrico, VA (US); Dong Qi, Henrico, VA (US); Yanxin Shen, Glen Allen, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 16/228,035

(22) Filed: Dec. 20, 2018

(65) Prior Publication Data

US 2019/0241900 A1 Aug. 8, 2019

Related U.S. Application Data

(60) Provisional application No. 62/609,631, filed on Dec. 22, 2017.

(51) Int. Cl.
*C12N 15/82* (2006.01)
*C07K 14/415* (2006.01)

(52) U.S. Cl.
CPC .......... *C12N 15/825* (2013.01); *C07K 14/415* (2013.01); *C12N 15/8212* (2013.01); *C12N 15/8222* (2013.01); *C12N 15/8223* (2013.01); *C12N 15/8262* (2013.01)

(58) Field of Classification Search
None
See application file for complete search history.

(56) References Cited

U.S. PATENT DOCUMENTS

| | | |
|---|---|---|
| 4,762,785 A | 8/1988 | Comai |
| 4,945,050 A | 7/1990 | Sanford et al. |
| 5,004,863 A | 4/1991 | Umbeck |
| 5,104,310 A | 4/1992 | Saltin |
| 5,141,131 A | 4/1992 | Saltin |
| 5,149,645 A | 9/1992 | Hoekema et al. |
| 5,159,135 A | 10/1992 | Umbeck |
| 5,177,010 A | 1/1993 | Goldman et al. |
| 5,231,019 A | 7/1993 | Paszkowski |
| 5,316,931 A | 5/1994 | Donson et al. |
| 5,463,174 A | 10/1995 | Moloney et al. |
| 5,464,763 A | 11/1995 | Schilperoort et al. |
| 5,469,976 A | 11/1995 | Burchell |
| 5,491,081 A | 2/1996 | Webb |
| 5,563,055 A | 10/1996 | Townsend et al. |
| 5,565,350 A | 10/1996 | Kimiec |
| 5,589,367 A | 12/1996 | Donson et al. |
| 5,689,035 A | 11/1997 | Webb |
| 5,731,181 A | 3/1998 | Kmiec |
| 5,756,325 A | 5/1998 | Kmiec |
| 5,760,012 A | 6/1998 | Kmiec et al. |
| 5,795,972 A | 8/1998 | Kmiec |
| 5,866,785 A | 3/1999 | Tomes et al. |
| 5,879,918 A | 3/1999 | Tomes et al. |
| 5,889,190 A | 3/1999 | Donson et al. |
| 5,889,191 A | 3/1999 | Turpen |
| 5,932,782 A | 8/1999 | Bidney |
| 5,981,840 A | 11/1999 | Zhao et al. |
| 2019/0300893 A1* | 10/2019 | Kudithipudi ........... A24B 15/20 |

FOREIGN PATENT DOCUMENTS

| | | | | |
|---|---|---|---|---|
| WO | WO-9102059 A1 * | 2/1991 | ......... | C12N 15/8209 |
| WO | WO 1998/149350 | 11/1998 | | |
| WO | WO 1999/107865 | 2/1999 | | |
| WO | WO 1999/125921 | 5/1999 | | |
| WO | WO-2014150504 A2 * | 9/2014 | ............... | C12N 9/88 |

OTHER PUBLICATIONS

Telem et al. Cisgenics—a sustainable approach for crop improvement. (2013) Current Genomics; vol. 14; pp. 468-476 (Year: 2013).*
Lv et al. Constructions vascular-specific expression bi-directional promoters in plants. (2009) J. of Biotech.; vol. 141; pp. 104-108 (Year: 2009).*
Butelli et al. Enrichment of tomato fruit with health-promoting anthocyanins by expression of select transcription factors. (2008) Nature Biotechnology; vol. 26; pp. 1301-1308 (Year: 2008).*
Sato et al. Ethylene-induced gene expression of osmotin-like protein, a neutral isoform of tobacco PR-5, is mediated by the AGCCGCC cis-sequence. (1996) Plant Cell Physiology; vol. 37; pp. 249-255 (Year: 1996).*
Bailey et al. Evaluation of herbicide systems for dark fire-cured tobacco. (2013) Tobacco Science; vol. 50; 34-38 (Year: 2013).*
GenBank Accession XM_016600503; Predicted: Nicotiana tabacum 17.8 kDa class I heat shock portein-like (LOC107779995), mRNA. (2016) pp. 1-2 (Year: 2016).*
Velten et al. A spontaneous dominant-negative mutation within a 35S::AtMYB90 transgene inhibits flower pigment production in tobacco. (2010) PLoS ONE; vol. 5; pp. 1-12 (Year: 2010).*
Beetham et al., "A Tool for Functional Plant Genomics: Chimeric RNA/DNA Oligonucleotides Cause In Vivo Gene-Specific Mutations," *Proc. Natl. Acad. Sci. USA*, 96:8774-8778 (1999).

(Continued)

*Primary Examiner* — Cathy Kingdon Worley
(74) *Attorney, Agent, or Firm* — Arnold & Porter Kaye Scholer LLP

(57) ABSTRACT

The present specification provides for, and includes recombinant polynucleotides that encode plant-native, callus-preferred promoters operably linked to a coding region for a visual marker gene. The present specification also provides for, and includes plants comprising the recombinant nucleotides, methods to select callus comprising the disclosed recombinant nucleotides, and methods to create plants comprising the recombinant nucleotides.

21 Claims, 1 Drawing Sheet
Specification includes a Sequence Listing.

(56) References Cited

OTHER PUBLICATIONS

Canevascini et al., "Tissue-Specific Expression and Promoter Analysis of the Tobacco Itp1 Gene," *Plant Physiol.*, 112(2):513-524 (1996).
Crossway et al., "Micromanipulation Techniques in Plant Biotechnology," *Biotechniques*, 4:320-334 (1986).
D'Halluin et al., "Transgenic Maize Plants by Tissue Electroporation," *Plant Cell*, 4:1495-1505 (1992).
De Wet et al., "Exogenous Gene Transfer in Maize (*Zea mays*) Using DNA-Treated Pollen," *The Experimental Manipulation of Ovule Tissues*, pp. 197-209 (1985).
Dey et al., "The Plant Cell Biotechnology," *Plant Biochemistry*, 517-528 (1997).
Estruch et al., Transgenic plants: An Emerging Approach to Pest Control, *Nat. Biotechnol.*, 15:137 (1997).
Finer et al., "Transformation of Soybean Via Particle Bombardment of Embryogenic Suspension Culture Tissue," *In Vitro Cell Dev. Biol.*, 27P:175-182 (1991).
Guevara-Garcia et al., "Tissue-Specific and Wound-Inducible Pattern of Expression of the Mannopine Synthase Promoter is Determined by the Interaction Between Positive and Negative cis-regulatory Elements," *Plant J.*, 4(3):495-505 (1993).
Hansen et al., "Wound-Inducible and Organ-Specific Expression of ORF13 from Agrobacterium Rhizogenes 8196 T-DNA in Transgenic Tobacco Plants," *Mol. Gen. Genet.*, 254(3):337-343 (1997).
Kaeppler et al., "Silicon Carbide Fiber-mediated DNA Delivery into Plant Cells," *Plant Cell Reports*, 9:415-418 (1990).
Kaeppler et al., "Silicon Carbide Fiber-Mediated Stable Transformation of Plant Cells," *Theor. Appl. Genet.*, 84:560-566 (1992).
Kawamata et al., "Temporal and Spatial Pattern of Expression of the Pea Phenylalanine Ammonia-Lyase Gene1 Promoter in Transgenic Tobacco," *Plant Cell Physiol.*, 38(7):792-803 (1997).
Lam, "8 Analysis of Tissue-Specific Elements in the CaMV 35S Promoter," *Results Probl. Cell Differ.*, 20:181-196 (1994).
McCabe et al., "Stable Transformation of Soybean (*Glycine max*) by Particle Acceleration," *Biotechnology*, 6:923-926 (1988).
Matsuoka et al., "Tissue-Specific Light-Regulated Expression Directed by the Promoter of a $C_4$ Gene, Maize Pyruvate, Orthophosphate Dikinase, in a $C_3$ Plant, Rice," *Proc. Natl. Acad. Sci. USA*, 90(20):9586-9590.
Paszkowski et al., "Direct Gene Transfer to Plants," *EMBO J.*, 3(12):2717-2722 (1984).
Porta et al., "Use of Viral Replicons for the Expression of Genes in Plants," *Molecular Biotechnology*, 5:209-221 (1996).
Orozco et al., "Localization of Light-Inducible and Tissue-Specific Regions of the Spinach Ribulose Bisphosphate Carboxylase/Oxygenase (rubisco) Activase Promoter in Transgenic Tobacco Plants," *Plant Mol. Biol.*, 23(6):1129-1138 (1993).
Riggs et al., "Stable Transformation of Tobacco by Electroporation: Evidence for Plasmid Concatenation," *Proc. Natl. Acad. Sci. USA*, 83:5602-5606 (1986).
Rinehart et al., "Tissue-Specific and Developmental Regulation of Cotton Gene FbL2A," *Plant Physiol.*, 112(3):1331-1341 (1996).
Russell et al., "Tissue-Specific Expression in Transgenic Maize of Four Endosperm Promoters from Maize and Rice," *Transgenic Res.*, 6(2):157-168 (1997).
Shillito et al., "Direct Gene Transfer to Protoplasts of Dicotyledonous and Monocotyledonous Plants by a Number of Methods, Including Electroporation," *Meth. Enzymol.*, 153:313-336 (1987).
Singh et al., "Cytological Characterization of Transgenic Soybean," *Theor. Appl. Genet.*, 96:319-324 (1998).
Skoog and Tsui,, "Chemical Control of Growth and Bud Formation in Tobacco Stem Segments and Callus Cultured In Vitro," *Amer. J. of Bot.* 35(10):782-787 (1948).
Tomes et al., "16 Direct DNA Transfer into Intact Plant Cells Via Microprojectile Bombardment," *Plant Cell, Tissue, and Organ Culture Fundamental Methods*, pp. 197-198 (1995).
Van Camp et al., "Tissue-Specific Activity of Two Manganese Superoxide Dismutase Promoters in Transgenic Tobacco" *Plant Physiol.*, 112(2):525-535 (1996).
Weising et al., "Foreign Genes in Plants: Transfer, Structure, Expression, and Applications," *Annu. Rev. Genet.*, 22:421-477 (1988).
Yamamoto et al., "The Promoter of a Pine Photosynthetic Gene Allows Expression of a js-Glucuronidase Reporter Gene in Transgenic Rice Plants in a Light-Independent but Tissue-Specific Manner," *Plant Cell Physiol.*, 35(5):773-778 (1994).
Yamamoto et al., "Light-Responsive Elements of the Tobacco PSI-D Gene are Located both Upstream and within the Transcribed Region," *Plant J.*, 12(2):255-265 (1997).
Christou et al., "Stable Transformation of Soybean Callus by DNA-Coated Gold Particles," *Plant Physiol*, 87:671-674 (1988).
Horsch et al., "A Simple and General Method for Transferring Genes into Plants," *Science*, 227:1229-1231 (1985).
Mayo et al., "Genetic Transformation of Tobacco NT1 Cells with *Agrobacterium timefaciens*," *Nat. Protoc.*, 1:1105-11 (2006).
Sierro et al., "The tobacco genome sequences and its comparison with those of tomato and potato," *Nature Communications*, 5:3833 (2014).

* cited by examiner

PLANT COMPRISING RECOMBINANT POLYNUCLEOTIDES ENCODING A PIGMENT REGULATORY TRANSCRIPTION FACTOR WITH A TISSUE-PREFERRED PROMOTER

CROSS-REFERENCE TO RELATED APPLICATION

This application claims priority to U.S. Provisional Application No. 62/609,631, filed Dec. 22, 2017, and is incorporated by reference herein in its entirety.

INCORPORATION OF SEQUENCE LISTING

The file named "Sequence_Listing_P34519US01.txt containing a computer-readable form of the Sequence Listing was created on Jan. 8, 2019. This file is 130,987 bytes (measured in MS-Windows®), in compliance with 37 CFR 1.821(c), and serves as the paper copy, specification copy, and the computer readable form (CRF).

FIELD

The present disclosure provides for, and includes, recombinant nucleotides useful for visual selection of transformed plant-derived callus, plants comprising these recombinant nucleotides, and methods to select and breed plants comprising the disclosed recombinant nucleotides.

BACKGROUND OF THE INVENTION

Selectable marker genes usually encode proteins that are not of plant origin that render the transformed plant cells resistant to phytotoxic compounds such as antibiotics or herbicides. Negative selection is a general strategy by which transgenic cells harboring such resistance survive on selection medium following incorporation of a selectable marker gene while non-transgenic cells do not survive. The most commonly used negative selectable marker genes are the neomycin phosphotransferase II (npt II) gene and bar gene which confer resistance to kanamycin and phosphinothricin, respectively. However, presence of antibiotic resistance genes has been identified as a public concern against the use of genetically modified plants. There is a need to develop selectable marker genes that are of plant origin.

Visual marker genes provide a means of positive selection for a plant or plant cell harboring them. Visual marker genes have been used in co-transformation experiments to confirm transgenic events. Moreover, they have been used to improve transformation systems and the efficiency of recovering transgenic plants by allowing the visual detection of transformed tissues. Some of the important visual markers are β-glucuronidase (GUS), green fluorescence protein (GFP) and Luciferase. However, detection of these markers requires either destruction of cells or the use of a microscope. The use of these markers in selection of small callus cells is suboptimal because of the difficulties in separating non-transgenic cells from transgenic cells.

There remains a need in the art for a visual, pigment-based selection system comprising only plant-native selection marker sequences. The current specification provides for, and includes, plant-native recombinant nucleotides, plants comprising the plant-native recombinant nucleotides, and methods for selecting and growing plants comprising the plant-native recombinant nucleotides using a visual, pigment-based selection system.

SUMMARY OF THE INVENTION

In one aspect, the present specification provides for, and includes, a plant, or part thereof, comprising a recombinant polynucleotide comprising a heterologous tissue-preferred promoter; and a coding region from a pigment regulatory factor, where the polynucleotide sequence of the promoter and coding region are plant native polynucleotide sequences.

In one aspect, the present specification provides for, and includes, a recombinant polynucleotide comprising a heterologous tissue-preferred promoter; and a coding region from a pigment regulatory factor, where the polynucleotide sequence of said promoter and coding region are plant native polynucleotide sequences.

In one aspect, the present specification provides for, and includes, a method for selecting at least one modified plant cell comprising transforming at least one plant cell with a recombinant polynucleotide, and selecting at least one modified plant cell expressing a pigment as a visual marker.

In one aspect, the present specification provides for, and includes, a method for growing a modified plant comprising transforming at least one plant cell with a recombinant polynucleotide, selecting at least one modified plant cell comprising a recombinant polynucleotide and expressing a pigment as a visual marker, regenerating a plant from the modified plant cell, and growing a plant regenerated from the modified plant cell.

In one aspect, the present specification provides for, and includes, a plant cell comprising a recombinant polynucleotide comprising a heterologous tissue-preferred promoter and a coding region from a pigment regulatory factor, where the polynucleotide sequence of the promoter and coding region are plant polynucleotide sequences.

In one aspect, the present specification provides for, and includes, a method of transforming a plant comprising transforming at least one plant cell with a recombinant polynucleotide comprising a heterologous tissue-preferred promoter and a coding region from a pigment regulatory factor, where the polynucleotide sequence of the promoter and coding region are plant polynucleotide sequences; and selecting at least one modified plant cell expressing the recombinant polynucleotide.

BRIEF DESCRIPTION OF THE SEQUENCE LISTING

Table 1 provides a listing of nucleotide and protein sequences.

TABLE 1

| | | Nucleotide and protein sequences |
|---|---|---|
| SEQ ID NO: | Sequence Description | Nucleotide Sequence |
| 1 | pPR5 | TTTAGTGGACATTTTAGTAAGAAGATTGGTTGTTGGATGTATATATT GACATTTGAGTTAAGGGGGTTTATATAGTGGTATGGCGGCTTTTTGC ACTGTGGACATTAATATTTTGGCACTTGATATATTATTATTATTATTA TATTAATATAGGAATAATCATGAAAGATGCTTTGGTAAAGGTAGAGC TAGGCGGCTAAATGTGAAGGCCTGACAAGTGATAATTTATTATGCAC |

TABLE 1-continued

Nucleotide and protein sequences

| SEQ ID NO: | Sequence Description | Nucleotide Sequence |
|---|---|---|
| | | ACACATATATAGAAGCTAAATAATTTATTTGGTGATAATGATCACGA<br>GCAAACTTTGTCACGCTAATATGTCCACTTGAAATAATACGCCACCG<br>ATAATATCCACTATAAAACATGGACTGAACTAGAAATTCGGGTTGAG<br>CCCAATAGCTTTTGTTCAAATAATATATTTATGTTAAGTGTTTTATTA<br>AGTATGTACAAATATTAAATTTAGAATACAGTTATAATTATAAGCAC<br>TTGGAAACGTTGTTTTAAGATTCAAACCAATATAATTAAAATACTT<br>GCTCCGCTCCGTAAAACAAGATATACAGCCTTCAAGCAATACATTTT<br>GTTCAGTCGGGTCATATTCCACTATTTTTCACTACTTTTACTTCACGT<br>TTTTTACAAGCTATTTATCCAGTACATCCTTTGAACTGAAATCATAAT<br>TATTTACCTGCAATTATTACTATAGGTATCCCTAGCTACTTAATTTCA<br>TTTAAAATTAGCTATAACTAGCACTAGTTTATGGAATTTGGAGATGA<br>TTGTGCGCACAAGCTAGCTTTGTGGAATTTGGAGACGAGCTTTGCAG<br>CCGGTTTCAATCTTTCGACTACATTTGCTATTGGAGTCACTGAGTAAA<br>ATACTTATTTTCAGTCGGCTGTGTTTACACTAAATTTATGAATGCATG<br>CCATTAGTCTTCACACACACATATATAATATATAGCTTAATAACCCT<br>GGTTAAATGATACAATATATTATCAGTTTAATGAATAAATATTTGCC<br>TAATTATTACCCACTCTGCATTACCAAGTCTTCATAAATGAAAGATTT<br>ATAATCAAGAAATTAGATCAAGAATTCTAACATATATCAAGTGGATT<br>AACTAATAGAAACGTATATGCATCTACAGTTAAAAAAAGGTTAAG<br>CAAATGGGGTGGGTTGGATCTTCAACGTTGTGCAATTCGGAATTCCC<br>CAATTTATTGACCATTTACAGATCAAGTTCACATATTAGTTAGTCTGA<br>TTTTGACTTAACGTTTGTTACAATTCTCTTTTTCATTTTTAAGGAAAA<br>AAAAGTTCTGCATCCGATAATTGGAGATCAATATGTAATACAAGTTA<br>GCTTCTATGTTCATAATAATTGTCAGGCTCTTACGAATAGCCGCCAG<br>GCATCTTTCAAGATTATTCCTTTATTAATATAATATATCAAGTGCCAA<br>TATATATATGATTATTGTCTATAGTGCAAAAAGCCGCCACACCCCTA<br>TATAAACCCCCTTAACTCAAATGTCAATATATCAACACCAATTTTCTT<br>ACTAAAAAGTCCACTAAA |
| 2 | pPRP | ACCTCTTCCTTCTCTCTATCTCCATTTTTTATTTATGTTTTACTAAATT<br>ACTTTTATTTCATAACAACATGTCTTGTTCATGTTTTACTAAGTTGCT<br>TTTATTTCATAACAGCATCATAATAAAATACAGGAATTTTCAAGCGA<br>AGCAGAGTCACTTCCAAAAGTAGAAACACTTAGAACTTCTGCTAAG<br>GGTAATTAACAACTTTTGGTCCTTTAGGAGGCACAATATACTAGACG<br>AAGAATTGAACTTGATCTTACTTACGGCAAAGGCTAATAATAGCATC<br>ACGTTAGTGAACTACAACGCCAACTAAAAGAAAAAAGAAAATAAT<br>TAAGACCAGTAAATATGCATGTTCACTCTCAAATATTGAGGGGAAAA<br>AAACCGAGAATCTAATTATCTACAAATGTTCATTCATTAGGGTAGTA<br>GGAAAATTTTAATTTTATCTTAATTTGAACCAACTACAATATTTTATT<br>TTAAAACAAATAAAATTGGAATAGCACCGGTTTTTTATTTTATATTT<br>TTTGGGTATCCGAAAGTGTATGGGCGCTAGGAACTACCTCCGTCTTT<br>ACTTCTTTTGTTGCTAGTAATAGGAACTCCTTTAATGTTTTGACAGTG<br>AAAATACTAGTATATTAATTAACTAATTTGTCTCTATACCATGATTTA<br>TAATATTACGGTTGAAGTGATAGCTCATGGAAGAGGAAGCACTGAT<br>GGTGTGAAAATATTTACACAATCAGATCATTTATTATATTATTATGG<br>ATAAATTTCTCGATAAGTATTAATTGATAAGTATTCGGATAAAAGTA<br>GGTTATAATCTAATTTTTTTTATACTATTAGTATTAGTATATATAATT<br>CGTTACATTTACATATACATCTTCTATGTTTTATTCATAGATGTAGAC<br>ACTGGCGAGGAACATGGCAAATTGCAACACCTTATGTGGCTAATAA<br>TGCATTCAAGAGAATTTGAGTAAATATCTAATTTGCTTGTGCTGCCA<br>GCTAAAACCTTGGGGACACATGGTTTCTAGAACTTAATTTCTTTAAT<br>ATTTCTCTTTACTCTAATTCATACTTTTGCATCCTATATAAACCCACC<br>TTCTATAACCTTTGCAATATCAAACAAAGCAACAATCTACTTATAAC<br>TACTAAAGTTGATAGTTATATCAATCATTAAGAAATTTTAGACTCTT<br>AGAA |
| 3 | pAD | ACTAAAAGTGAATCCTTCCCCACAAAAAACTTAGTTTTGAATGCACG<br>AGATTCTACAAATAAAAAGAAAGAAAGAAATAAAAGGTATAATTAG<br>AGCGCACGTGAAATAAAAATACTATCAATTTGAATGAAAACTTGAA<br>AATAAAATAAAAATAGAAGTATCATGTTTTGAAGGATTCAATTTTA<br>GTATTATTTTAATTTATATATATGATTATTTTGTCAGGTGGGTCATTC<br>CTGTTTTAATTGAATTATTATTTATTAGACGAAAAAAAAATCTTGG<br>AATAAGAAATCTGGTGACTATTTATGAAATTTACCCTTCAATTGTA<br>TGTGTAAAACACTTATATCCAAGTTTATAAGATTTTTAGCAAAATAA<br>AATACTTCAAATTTTTAAGCTATTCGCTTGAAAATAAAATTAAGAC<br>ATGTTAACATAGATTACTTTCTCTATTACCAAATTCTTGTGTTACTTT<br>CTTAAAGTTGAGTCGAGTAGTATTGATAAATAAAATAGTCAATATGT<br>TTTCCACTGTTCTGAACAAAAATAGTTTTTTTTTTTTTTTTTTATG<br>TATTTTCATAATTTTGAATTATTTAAATTTGAGTTTTGGAAGATGAAT<br>TCACGTTTGACCAAAAAGGAGAGATGAATCGTGTCTATCCAAAAAT<br>AAAAACAAAATGGGCGTGTAAAAAATAACATTTTTTTGGTGGGTCA<br>AAACATCGTTAGGTTTAATAAATCAAATCGATTTTTCTCTTGAAATAT<br>TACCACCACCTTTTTCTTATTACTCGACAAAAACTCAAACAGTAACA<br>CAAAACAAACAGCCAAAAACCGGTTTCGAAAACCCAGCGACCAAAA<br>CATGGAAATGGTTTTACTTTGGCCTGTTGTATTCAACTTTTCGATTTC |

TABLE 1-continued

Nucleotide and protein sequences

| SEQ ID NO: | Sequence Description | Nucleotide Sequence |
|---|---|---|
| | | ACGATTCTATATTTTCAGGTATAAATACCCCAGCTAATGCAGTGCCA CATCACACCTCAAGATATTTAACTCAGTATTCAGAAACAACAAAAGT TCTTCTCTACATAAAATTTTCCTATTTTAGTGATCAGTGAAGGAAATC AAGAAAAATAA |
| 4 | pEX3-like | CATTGGAGTTTTATTAACCCGCCTCGATAGAGGCGGGGCTATACAAT CTGATAAGGTGATCGAGGATGAAAGGGAGCCCCTCGACTTTGCTCA CGAAGAATCGGAGCAGAATAACAATTTGCCAAAAGGAAGGATGGAT TTGGCCTAGGGTTATTTGGTATTGACGGCAAAAATTAACGATGACGG GGTCGAGGGGGCCCAACGTGAAAGGGTAAGTGTAAACACTTAGAAA CCCCTTCCACATGAGTGGTGATATCTTTTTCGGGGGTCGGGATCACCA CCTCTTTGCCTTCCCAGTTGCGGTCTTTCTTTACCTGCTTAAGGTATC CCTCAGTTATTGAGCATATATACCTCGACATTGGCTCGCATCGATCA GGAATCGACGAGGCTTTATCGGTCTTAAAATCGGAGTTTAGCACGCA CCCCCAAGAATGCATTCCTCAAGACGGGGATCCACCAGCGTTTTTCC GTCGGTCGGTTGAGAAGATGAAGCAACTTCTTTTTGTGGTACCATTT TCGATGTTTTTGCCATTCTTGTGTAAGTTTGAAGAAGAGGAAGATAA TAGGACTTGACATTTGAGACATGATTAACAGCAAAGCCTGAAGATTT GTAAAAGGGACGAACTTAAGAGATGTAAAAGCTTTAGATATTAGAA GGAAGTGAAAGTAAAGTTTGAATCAATGAGGAAGTGATCTATTTATT GGACTCACGGCGACAGTTCAAAGGCACTAGTGGCCGACAACCAACT AACACTCATTAATGACTTGGAAAACTGTACTGACGGGACGTTTTGGT CACTCCCGTCGCTTACGTCATGAGGATGTCGTCATTACAGGTCGAGA TAGAAAATTGAAGGCTCAATTCGTTTCTTGTCATTTCACTCCAAAAA ACGAGGAGACTATCTGTATACGGTTAAAATCGGGCCCACCCGATTTT ACTATTTGACCGAGACTAGGAGGTTGCATCGAAGAATGGCCTCGTA ACAGAACAGACTAAATCACGAGGATAAGGTACTGAGTTCATAATCG AGGTACCGGTCGAGATCGAGGCTAGTAGTGATCGAAACCAAATGAG ACAGACATCGAGCAAGATCGAAGATAGCACAATAACAGAAAGGCG AGATATCCACGACTGGTCGAGGATCATGGCATAAATCTCGAAACGA ATCAAATTAGAAACAGTTAATTAGCTAATCATGAATTTACTTCTGTA ATTAGAATTATACCATAAGTGAAATTCCTCTACTATTTATAGGGGGT TCTAATCATTTGGAAGACACATGGTTCACAGATATCAAAGAAATGTA ATTCTCTTTCTCGTTTATACTATTGTTCATCAGCTTGTTATATTTTAAT TGTTCTTACATCAACCAGTTCGAGGGTATCCAAACTTGAGGGCTGAG TTCCATTCTAACACAAGTTTGCTTTACTTTATAGTTTATTTCTATTATT AATCTTCATATTTATCAATTGGTATTAAGTGAAATTACGTGTACTTAG AACAATATTATAAATTTAATTGTTATCCAATTTTAAGGATAAATAAG AACATTCATTAAAGTAAAAGAGACATATAAAAAAAGCTATTGCTC AGATTTCTGCAACTGAAATCGTGCAAAGTTGAGGCATCCACACTTGT TTTTCAAAGCTTCGGTACTGTATACAAAGATAGAAAGTAAAGGAGA CTTTTCTCTTTAAATTATTGCATCAGAAATAGTATAGCTGCCATAATA GTTTATTAATTCCAGCTATGCTTAGCTTGCAGCCTCTATCGAACAAA AAAAGTATACCAACTCAAGTCAATTTGAGCCGACAACATGACAAAA CCAAATCAAAATGCATACTCTAGCTTTTTTACTTTGGTAGGTTTTAAG TAATCTAGTGAGACTTTTACCTTCATTCATGAAAATCTTGGAAAGGG TAATTGTATAATTGAAAGCTATATAAAGGGGTCGGAGTGAAGCTTAA GAGGACAACAACTTTTCTCATTTGTTTCAAAG |
| 5 | pEX1-like | CAGTAGGCATCAATTACTATATATTTTACAAGTAATTAAATGATAAA CAAATGCAATATTTGTTTAGTTTCCATATTTCTTTTTCAAGGCACTCC TTTAATTACTCATCCATTCAAATGGATCTTCTCATTTTTCAGACGGTT TTTAGGACTCCCTCTATCTCAAATTATCTATCGAGATTTTTAAAAAAA AAATTGTCTCAAATTATTTTCATTTTGGAAATTTAAGATAAAATTAAT TATATTTTTTCATTTACCCTTAATGGTAATTATTCTTGAATATGGAG ATAGCACATCGAGTAAATATTCAATAAAGAGAGATTATATCTTATAA CATAAATAAGAGTAAAATAGTCCAAAATTCCTCATAATTAATATTTT TTAAGGGTATGTAAAAGAAAAACACGACAAATAATTTGAGACGGAG AGAATACCTTCTTTTTGACCTTTTGTAAATAAATATTAAAATATCCTC AACATTTCCTAGGTTAATTTCTCTCTCTCCTAATAATTTCAAAAAGT TATCATTGTGATACTCAAATATATTGGTCTTAGCACAATTTGAGCATT GCATGTTGTATGCCTGGATCCTCCTGGGTGCCATTTTTCCTTTGCTTT TGGATACCTTTTTGCAACTTTAGTCCATTGCTGGAACATGATTTTTTG TACCTCTTGTCTGTTCCCATGATGATAAACTATGATAACTAACATTTT CAGAAATATTGGATTGAATTAGATATATTTTCAATATTGAGCTACAA AACTCGTTGAATATTTTGCCCTATTTGGTTGGTAATAAAAGTGGGTC ACATGCACAGTTTTTCTCTTGTCTTCTCTAGATTAAGCTCTTTGGAAA TGACCTACTGAAAATGCTACACATAAAACTCCCCCACTCCTCCCCAA GTTGAGGGGTGGGAGGTTTGATTTGGACCCTTACCCTATTGTTAATA TCGAAATAGATAATACAAAGGACGGGAACATAAAACCAAAACCTCC GATAAAACACCAAAGTTGATGATCTAAGTTAAGTTATTGATTCTTAT ACGTTGATTGGAAGTGCACAATGGTCTTTGCATACTATCAAAGTATG AATTGGTTCTTGAATTATATCTCTTAATATGATGTATTGTGTTTAATT AATTCTCTACTATTCTCTATTTTTATAGGCTAAAAGATCCTGACATGC TTCTTGAACACATGTGAAGGTTAGTTAACTATAGTCAGAAGTACACA |

TABLE 1-continued

Nucleotide and protein sequences

| SEQ ID NO: | Sequence Description | Nucleotide Sequence |
|---|---|---|
| | | AGAATTAACTTGTACACCTATCCGTGATCGAAAAACTTAACTTGTTC<br>TAAGCTGAACTGAGTCCTCCTATCCATGTCCGATTCTTCACTAGAAG<br>CATTAATCATACAAGGAGAATTCAACTTAATTTACTGTATTGGTTAT<br>CATTTACATAGTTTAGTTATAAAACTTTGGAGCGACACAATGATTGA<br>CACTACTAATCATGATTGAATATTAACTTCACTCGATTTATCAATTTC<br>TCATACAAGTGAATTAATTTCACTCTTTGTGATTTCAGTAGTAAATGT<br>CAAGTTTCATAGTTTTTTCTTTTTGAAATTAGTCATACATGTGAATAG<br>AACATTAATTTAAGTTAAAAGCTAGCTGCTCTGATTTCTGTAACTGA<br>AATCGTGCAAAGTTGAGGCATCCACATTTGTTTTTCAAAGTTCCAGT<br>ACTGTCTAAAAAGATAGAAAGTAAAAGGAGACTTTTCTCTTTGAATT<br>ATTGCATCAGAAATAGTATAGCTGCCATAATAGTTTATTCCTTTGCTT<br>AGCTTGCAGCCTCTATCGAACAAAAAAAGTGTACCAACTCAGGTCA<br>ATTTGAGCCGACAACATGACAAAACCAAATCAAAATGCATATATAC<br>TCTAGCTTTTTTACTTTACTTTGGTAGGTTTTAAGTGAGACTTTTACCT<br>TCATTTATGAAAATCTTGAAAAGGGTAATTGTCTAAATGAAAGCTAT<br>ATAAAGGGGTCGTAGTGAAGCTTAAGAAGACAACAACTTTTCTCATT<br>TGTTTCAAAG |
| 6 | pPR1a | CTATATAAGGCCATCCGTGAATTGAATAAACTATCCAATTATTTTCTT<br>CCACAAAAATTTCAATTCTACTTTTAGTTATTCTTTTTAATATTGAGC<br>TTGCAATTCTATTTTGATTCTTCACTCATGACATGCTACGTAGAGAAC<br>CTTCAATACATCATAAGAGATGGACCAAGCAATGCATAACTCAAAT<br>AAGTCCATACAAATTTGCTGAAAGATAAAGTTATTCTACTTTCTTTG<br>AACCCAAATCTGATAAATCTTGACAATCAGATTTGCTACTATGATTT<br>CTCACTGTATCATTTGTTTTATTCTATAAAGTTAATGAGGAATGTATT<br>AATTATTTAAGATACCTTACTTTTTCTGATTTTTGATCTTATAGTCAA<br>GTCGTGAGGCACAATTTGCGACCCTGATGGCGCAAACCTTTACCTAG<br>GGATCGTAGCACATAAACGTTTTTAAGGACTAAGATATACGAGGAT<br>GTCAATTATCATAATGTAGGGTCTAAGTTTTCATTTTTTTTTTGCAT<br>CTAATAGAGTATAATTTTTTTAATCATCACGATAACTTGATTTACAA<br>TAATATGTACTCTGTTTACTTTTACTTGACACGTTTTGATTTTTCACGC<br>CCTTTAAGAAAAAATGATTGAAATGCATAATTTACCATGATACTCAT<br>ATTAATTGATGCATATTTTATTGGATTTGAGAAAATGATTTGAAATG<br>AGTAATAAATATTGTGGGTATAACAGGAAAAAAAATTGTCTTCTCTT<br>AACATGCATAAAGTGAAGAGTAAAAAGAAAATCTATTTTTGTATAC<br>ATGTCAAACAAAAGTGAACGGAGGAGATGACAAATTGCTAAATGGC<br>AATAGTTACAAAATTCTTCAATTACTCTTTTTCATAACAAAACACTG<br>GTCTCTCTTGTAAGTATTGGTCTATACTTCACCACCTAAAGCATTGGC<br>CGAAGTCTTTTTAAGGAGTTTGGTTGTCATTTATCCATTTAAATTAAA<br>GGGAAAATAAGTGAACGCCATTACAGCGAGATGCTTTAGGGTGCTA<br>TTTCTTGGAAAAATAAAGTAGTTAAATCTTAAAACACCCTCGAGGAT<br>TTCAAACTCTAGCTTCACTAAAACTTGAGCTTTCTTTTCCACTAATGT<br>CGAAAAACGAAATAAACATAAGCTATTTACAAAAATAAAAAAATAC<br>TCCATTTGAATCTAAAGTCAAGTCGTGATTGGGATAAGAAAATAGAA<br>ATTTATTTATACTCCAGATCAAGCCGTGATTGGAATGAGATAATAGA<br>AAAGTATGATAGTACATGAGTAACATCAAGTTGGAAATTAAGGGAA<br>GGAAATTAGAGAAAGAACTGAAGAATATCCAAATATTCTTTACGTCC<br>AAATTTGATAGTTATTTAACGTCATCGAGATGACGGCCATGTTCAAG<br>TTTTCCACAAATATTGAGAAAAGAAAGAAAGCACAAACTGTGTTT<br>GGTATTATTATAGTTTTTTCTTTTAGAGAATTGATTGTACATATAAGA<br>AATTAATATAAGATTTAGAAATAAGATTATTAGAAAAATCAAACATC<br>AAAGTATTTATTTTAAATTCTTTTTCCAATGGACATTCCCATTCTGAA<br>AAAAAGAGATATAAAATGGAAGTAAAATTAATCAGATCGTTAAATG<br>TAGAAAATATTAATAACACTTAACCATAACCAGTCTACTTTATTTAA<br>CAAAAAGCACATCTGATAGATCAAAAAAGTGTTTAACTTCATGCATT<br>GACAATTTAAAATTATTTTGCAACATCGGGTAAAACTATTTTACAAC<br>AATTGGTAACTGCATATATAAGTTTAATATGGTAACCTAGAAAATAG<br>GATAAATTATCTATAACAGGATATATTACATTGATATTACCATGTCA<br>AAAAATTTAGTAAGTACATGAATAATCACCGTGAAATCTTCAAGATT<br>TCTCCTATAAATACCCTTGGTAGTAAATCTAGTTTTTCCATTCAAGAT<br>ACAACATTTCTCCTATAGTC |
| 7 | pSAHH | ATTAATTGTAAATAAATATACTTATCATTTTCGGAGAATATCCAATA<br>TTTATATATATAATTTTTATACTTATGAGTTTCGGGCTAGATATTTATT<br>CTAAGCTAAGTACTACAAATACTGTGATATAAGGCTCTAAACTTTCC<br>TACCCTAAAAGAGTCTACGTTTTACTACGCTAAAAAGGTCTACATTT<br>TACTACGCTAAAAAATAATCTAAACTAAACATCGCAAAAACAAACA<br>AGTAAACATGACAATTTAACAAATAAATTTTTTTGACTAATTTACAA<br>GTATATTTATACAACACTAAAATTAAATCCGGATAAAAATTAACATG<br>CTAGTTTTGGCAAAAATAAACACAAAACTATATACAAACCATACAA<br>ATCAAATAATATTCAATATTATACAAGTTTCAACTAAAATTAAATCG<br>AAATACCTGGATTCGGAAACTAAATAAATCGGATTTTTGACTTCAAA<br>AAAGAGATTCCAGCGTACCACGACCCTCAACTATAATGTGGGACCA<br>CCAATCTTCACCTTTTATGTGTCGGGGGACCCAAAAATTTTTTTTT<br>TTTTAAAAAACTGGGCAGATCGCTGAGGAGGGGACCAAATTTTTTTG |

TABLE 1-continued

Nucleotide and protein sequences

| SEQ ID NO: | Sequence Description | Nucleotide Sequence |
|---|---|---|
| | | AAAGTTTTCGGCTGAATGAAGAAGAAGAAGAAAGGTTTAGGGTTTT<br>GTTTTAGGGTATGGCGCCAACAGTATTGGCGCTATGCTGACACCGCC<br>TGAAAAGTAGGGGTATGGCGCCAACACTGTTGGCGCTATGCTGACA<br>TGTCAGTAAACTCTCTGATATGGCGCCAACTATGTTGGCGTTATATA<br>TATTTGTGTTACTTTTCCTTTTTTACACTTATTAATGTAGTTTGAGTCA<br>AAAAAAACAATAATAAAGTTCCGGACTCGAGATGTAAGGGGTTGTC<br>AATTTTCACTTTGTCAGTCGCTAAGAGTAATTATGAATATTCTTTTAT<br>CAATATTGGACCTCAAACTTTATCCATTGTAAGAAAAAAAAGTTGTA<br>AAATATTTGTGTCACTTAATTAAACGGTCGTAGTAGTTAGTAGTAGT<br>GACATAGTCCTTTCGTTTGATAGTATATCAAATTGGAACAATTTACA<br>TTTGCACCAAAGCATAAAGGGAAAGCATGAAAAAGAGAAAGTGCA<br>AAAGAGAAAAATACAACAACAACAAGAATATTTCAGTATAATTCTA<br>TAAGTAGGGTCTGGAGAGAGTAGAATACCCCTAACCTAGAAGGGCA<br>GGAAGAATATTAAAGTAAAAAGATAAAGATTACAAATAAAATAA<br>AGAAAAAACAAACAAACATACAAAATTAATTTGTGCATAATGCTT<br>ATAGTAATTGCCAATTTGCCATGAATATCTTCCACCGGGCTATCTTG<br>GTCATGTTAATCACTCTATCCTGTTTTCAAACAATTTTTACTCTAAAA<br>ATTTGCATGTTATATTAATTGGTGGGTGAGCCAGAAATTTTAAACAA<br>AAAATCAAATACGGTACACTAAAAGATTTTTTATAAAAAAGAATTC<br>ACCAAGTTATATATATACACAATCTTTCTTTTTTTAAATCTTACGAT<br>GACCAATTTTTTCGACAAAGAATATTCACTTAAACCCTTGTTCATAC<br>ATAGCTTGGCAATTGGATTAATAATGAAAATAATACTTTAAATTTTG<br>GAAAGAAAATATTATTTATTCTCCAAAAGAAACCAAGAAATTAGATT<br>CATCAAAAAATAATGACCACCATTAGCCCCACCTCCCAAATCTCTATT<br>CCTTTTAGACTTTTAACCAAATTTTCAGATCTACCAAACCCCAATTTA<br>TCCAATAAACTTTTCAGATCTAAAAATAAAAATATTCAGATCTGGAA<br>CAAATCTTGACCGTCCATTTTCATCATTCATATCTATTTAATACCACT<br>CACCTCCGCCCTTTACTCCTTGCAACACTCTTCTTCTCCTCTAAAAAC<br>CCTTATAGAAGAAGAGGAAAAAGCCTTTCAAATCTCATCTCAAACC<br>ACCTAATTTCTCTCATACTCGCTCGACCC |
| 8 | AtPAP1 | ATGGAGGGTTCGTCCAAAGGGCTGCGAAAAGGTGCTTGGACTACTG<br>AAGAAGATAGTCTCTTGAGACAGTGCATTAATAAGTATGGAGAAGG<br>CAAATGGCACCAAGTTCCTGTAAGAGCTGGGCTAAACCGGTGCAGG<br>AAAAGTTGTAGATTAAGATGGTTGAACTATTTGAAGCCAAGTATCAA<br>GAGAGGAAAACTTAGCTCTGATGAAGTCGATCTTCTTCTTCGCCTTC<br>ATAGGCTTCTAGGGAATAGGTGGTCTTTAATTGCTGGAAGATTACCT<br>GGTCGGACCGCAAATGACGTCAAGAATTACTGGAACACTCATCTGA<br>GTAAGAAACATGAACCGTGTTGTAAGATAAAGATGAAAAGAGAGA<br>CATTACGCCCATTCCTACAACACCGGCACTAAAAAACAATGTTTATA<br>AGCCTCGACCTCGATCCTTCACAGTTAACAACGACTGCAACCATCTC<br>AATGCCCCACCAAAAGTTGACGTTAATCCTCCATGCCTTGGACTTAA<br>CATCAATAATGTTTGTGACAATAGTATCATATACAACAAAGATAAGA<br>AGAAAGACCAACTAGTGAATAATTTGATTGATGGAGATAATATGTG<br>GTTAGAGAAATTCCTAGAGGAAAGCCAAGAGGTAGATATTTTGGTTC<br>CTGAAGCGACGACAACAGAAAAGGGGGACACCTTGGCTTTTGACGT<br>TGATCAACTTTGGAGTCTTTTCGATGGAGAGACTGTGAAATTTGATT<br>AG |
| 9 | NtAN1 | ATGACGGAGATACCGCCTAACAGCCAGATGAAAACCATGTTGCAGA<br>AGGCAGTGCAATCGGTTCAATGGACATATACTCTTTTCTGGCAATTA<br>TGTCCCCAACAAGGGGCGTTAGTGTGGAGAGATGGATATTACAATG<br>GGGCTATAAAGACTAGAAAGACAGTGCAGCCAATGGAAGTTAGCGC<br>TGAGGAAGCTTCTCTTCACAGAAGCCAACAGCTTAGAGAACTTTACG<br>AATCACTTTCCGCCGGCGAGTCAAATCAGCCAGCGAGAAGGCCGTC<br>GGCAGCTTTGTCACCGGAGGACTTGACGGAGTCCGAGTGGTTTTATC<br>TCATGTGTGTTTCTTTCTCTTTTCCTCCTGGCATCGGATTACCTGGCA<br>AGGCTTATTCGAAGAAACATCACATATGGATCATGGGCGCAAACGA<br>GGTTGATAGCAAAGTCTTCTGTAGAGCTATTCTTGCCAAGAGCGCCC<br>GCATACAGACGGTCGTTGGTATTCCTCTCTTGGATGGTGTACTGGAA<br>CTGGGAACTACAGAAAGGGTTCAAGAAGAGATTGGATTCATAAACC<br>ATGTAAAGAGCTTTTTCACTGAGCAACAACAACCTCAGCTACCAAAG<br>CCAGCCTTATCTGAGCACTCCACTTCCAATCCCACCACCTTTTCCGAG<br>CCACATTTTTACTCCGGCAATACTTCGCCATCTGCTAATGTTGATATT<br>GCGCATCAAGATGGCGGAGCTGCCGGCGAAGAAGATGAGGAGGAG<br>GAAGAAGAAGAAGATGATGATGAAGCCGAGTTGGACTCGGATAGTA<br>TAGCGATTCAAAGCGCGGCTAATCCTATTGCCGTTGAGGCTAGTGAA<br>CTCATGCAGCTTGATGTGTCCGAGGCTATACAGCTCGGCTCGCCCGA<br>TGATGACTCTGATAATATGGACTCTGATTTTCATTTGGTTGGCGCTGG<br>AAACACGGCTCATGACTACCAGCGCCAAGCTGACTCTTTCAAAGCCG<br>AGACCGCCATTAGCTGGCCGCACTTCCAAGACCTTCAACAATTACCA<br>GGTGGCTCTAGTTATGATGAATTATCACAAGAAGACACACACTATTC<br>TCAAACAGTGTCAACCATTCTCGAACACCGAAGCTCCAAATTTTCCT<br>CTACAACAATGGGCTGTATTTCTCATGACTCGGCCCAATCTGCCTTC<br>ACATTGTGCCCTAGCACCACCGTCTGCAGCCCGAATCCCGCCCACTG |

TABLE 1-continued

Nucleotide and protein sequences

| SEQ ID NO: | Sequence Description | Nucleotide Sequence |
|---|---|---|
| | | CCGCCACGACGACTCACTTGTCGACGGTGGCGGCGCCTCCCAGTGGC
TGCTCAAAAGCATACTCTTCACTGTCCCATTTCTTCACACTAAATACC
AATCTGAAGCTTCTCCAAAGTCACGTGACGTCGCCACTGTTGATTCC
TCCAGTACTGCTTCTCGCTTTCGCAAAGGCTGTAGTATAACGTCGCA
AGAAGAGCCAAGTGGAAACCATGTACTTGCAGAACGACGTCGTAGA
GAGAAGCTAAATGAGCGTTTTATCATATTAAGGTCTCTTGTACCTTTT
GTAACGAAAATGGACAAAGCCTCCATTTTGGGTGACACCATAGAGT
ATGTCAAGCAGTTACGTAAGAAAGTTCAGGATCTTGAAGCTCGTGCT
CGCGACACGGAGCACTCCAGAGATGCAGATAAAAAAGGTGGCACAG
CTACAGTGAAGGTGTTGCAAGGAAGGGGTAAGAGGAGAATGAATAC
GGTAGATGGAAGTGTTGGTGGAGGGCAGGCAACGATAACGGCGTCC
CCACCGTCAACGACGGAAAATGAGGAGGTTGTGCAAGTACAAGTAT
CAATTATCGAAAGCGATGCATTGGTGGAGCTCCGGTGTCCGTACAAA
GAGGGGTTGCTGTTAAATGTAATGCAGATGCTAAGGGAACTCAAAG
TGGAAGTTGTAGCCATTCAATCAGCTCTTAATAATGGCGTCTTCTTG
GCTGAGTTAAGAGCTAAGGTAAAAGAGAATATATGTGGAAGGAAAG
CAAGCATTTTGGAAGTAAAAAGGTCAATACATCAGATAATCCCTAG
AGATTAA |
| 10 | NtAN2 | ATGAATATTTGTACTAATAAGTCGTCGTCAGGAGTGAAGAAAGGTGC
ATGGACTGAAGAAGAAGATGTTCTATTGAAAAAATGCATCGAGAAA
TATGGAGAAGGAAAGTGGCATCAAGTTCCTCTTAGAGCTGGTTTGAA
TAGATGCAGAAAGAGCTGCAGATTAAGGTGGCTAAATTATCTAAGG
CCACATATAAAGAGAGGAGACTTCTCTTTTGATGAAGTAGATCTCAT
TTTGAGGCTTCATAAGCTGTTAGGCAACAGATGGTCACTTATTGCTG
GTAGACTTCCTGGAAGGACGGCAAACGATGTCAAAAACTACTGGAA
CAGCCATCTTCGCAAGAAGTTAATTGCTCCTCATGATCAAAAGGAGA
GCAAGCAAAAAGCAAAGAAGATCACCATATTCAGACCTCGGCCTCG
AACCTTCTCAAAGACAAATACTTGTGTTAAAAGTAACACAAATACTG
TAGATAAGGATATTGAAGGCAGCAGCGAAATAATTAGATTCAACGA
TAATTTGAAGCCAACAACTGAAGAATTGACGGATGATGGAATTCAA
TGGTGGGCCGATTTACTAGCTAACAATTACAACAATAATGGGATTGA
GGAAGCTGATAATTCATCACCAACTTTGTTGCATGAGGAAATGCCAC
TTCTCAGTTGA |
| 11 | HSP-T | AATAACAGAGGGCGCGCGAGCGGTGGCTACTGATCGCCTATGAGTT
CTGTGATTCTACTTGTAATTTCAGAAGTGTTTTCAGTGTCTTGTTTTCT
GGAAGTCCGTCTGGTTTTTAGTAACTTTTAGCTCAAAAATGTGTCTGT
ACGATGGTATTTGTATGTTTGTGGGTCTTTTACATATACGCTTGTAAT
CGATCAATGTAGAATGCTGTGTGCCTTTTCCGTCAACAGCTTATTTAG
TGTTTACTCTGTATACGTATATCTAATATATAGTACTGATTCTTTCAT
CTGGTGATTTGTTTTCCTAAAGAGATTATTATCATAGCTTTAATTGAA
TGATACAAAGAGGTGTTGCCTGGCTTCACCAGAGCAGAAATTTTCAT
TGATATAGGGTACAAATGTCATTCACATAATGTTAAGAGATAAGTTT
TTCAATGTCCTCAAGAGCCCACCAAGAGTTTCTTCCGGGAATTGCTT
AAATTATCTTAAATTTAAATTGTA |
| 12 | pPR5: AtPAP1: HSPT | CCCGGGTTTAGTGGACATTTTAGTAAGAAGATTGGTTGTTGGATGTA
TATATTGACATTTGAGTTAAGGGGGTTTATATAGTGGTATGGCGGCT
TTTTGCACTGTGGACATTAATATTTTGGCACTTGATATATTATTATTA
TTATTATATTAATATAGGAATAATCATGAAAGATGCTTTGGTAAAGG
TAGAGCTAGGCGGCTAAATGTGAAGGCCTGACAAGTGATAATTTATT
ATGCACACACATATATAGAAGCTAAATAATTTATTTGGTGATAATGA
TCACGAGCAAACTTTGTCACGCTAATATGTCCACTTGAAATAATACG
CCACCGATAATATCCACTATAAAACATGGACTGAACTAGAAATTCG
GGTTGAGCCCAATAGCTTTTGTTCAAATAATATATTTATGTTAAGTGT
TTTATTAAGTATGTACAAATATTAAATTTAGAATACAGTTATAATTAT
AAGCACTTGGAAACGTTGTTTTAAGATTCAAAACCAATATAATTAAA
ATACTTGCTCCGCTCCGTAAAACAAGATATACAGCCTTCAAGCAATA
CATTTTGTTCAGTCGGGTCATATTCCACTATTTTTCACTACTTTTACTT
CACGTTTTTTACAAGCTATTTATCCAGTACATCCTTTGAACTGAAATC
ATAATTATTTACCTGCAATTATTACTATAGGTATCCCTAGCTACTTAA
TTTCATTTAAAATTAGCTATAACTAGCACTAGTTTATGGAATTTGGA
GATGATTGTGCGCACAAGCTAGCTTTGTGGAATTTGGAGACGAGCTT
TGCAGCCGGTTTCAATCTTTCGACTACATTTGCTATTGGAGTCACTGA
GTAAAATACTTATTTTCAGTCGGCTGTGTTTACACTAAATTTATGAAT
GCATGCCATTAGTCTTCACACACACATATATAATATATAGCTTAATA
ACCCTGGTTAAATGATCAATATATTATCAGTTTAATGAATAAATAT
TTGCCTAATTATTACCCACTCTGCATTACCAAGTCTTCATAAATGAA
AGATTTATAATCAAGAAATTAGATCAAGAATTCTAACATATATCAAG
TGGATTAACTAATAGAAAACGTATATGCATCTACAGTTAAAAAAAG
GTTAAGCAAATGGGGTGGGTTGGATCTTCAACGTTGTGCAATTCGGA
ATTCCCCAATTTATTGACCATTTACAGATCAAGTTCACATATTAGTTA
GTCTGATTTTGACTTAACGTTTGTTACAATTCTCTTTTTCATTTTTAAG
GAAAAAAAAGTTCTGCATCCGATAATTGGAGATCAATATGTAATAC |

TABLE 1-continued

Nucleotide and protein sequences

| SEQ ID NO: | Sequence Description | Nucleotide Sequence |
|---|---|---|
| | | AAGTTAGCTTCTATGTTCATAATAATTGTCAGGCTCTTACGAATAGC<br>CGCCAGGCATCTTTCAAGATTATTCCTTTATTAATATAATATATCAAG<br>TGCCAATATATATATGATTATTGTCTATAGTGCAAAAAGCCGCCACA<br>CCCCTATATAAACCCCCTTAACTCAAATGTCAATATATCAACACCAA<br>TTTTCTTACTAAAAAGTCCACTAAA<u>CTCGAG</u>ATGGAGGGTTCGTCCA<br>AAGGGCTGCGAAAAGGTGCTTGGACTACTGAAGAAGATAGTCTCTT<br>GAGACAGTGCATTAATAAGTATGGAGAAGGCAAATGGCACCAAGTT<br>CCTGTAAGAGCTGGGCTAAACCGGTGCAGGAAAAGTTGTAGATTAA<br>GATGGTTGAACTATTTGAAGCCAAGTATCAAGAGAGGAAAACTTAG<br>CTCTGATGAAGTCGATCTTCTTCTTCGCCTTCATAGGCTTCTAGGGAA<br>TAGGTGGTCTTTAATTGCTGGAAGATTACCTGGTCGGACCGCAAATG<br>ACGTCAAGAATTACTGGAACACTCATCTGAGTAAGAAACATGAACC<br>GTGTTGTAAGATAAAGATGAAAAAGAGAGACATTACGCCCATTCCT<br>ACAACACCGGCACTAAAAACAATGTTTATAAGCCTCGACCTCGATC<br>CTTCACAGTTAACAACGACTGCAACCATCTCAATGCCCCACCAAAAG<br>TTGACGTTAATCCTCCATGCCTTGGACTTAACATCAATAATGTTTGTG<br>ACAATAGTATCATATACAACAAAGATAAGAAGAAAGACCAACTAGT<br>GAATAATTTGATTGATGGAGATAATATGTGGTTAGAGAAATTCCTAG<br>AGGAAAGCCAAGAGGTAGATATTTTGGTTCCTGAAGCGACGACAAC<br>AGAAAAGGGGACACCTTGGCTTTTGACGTTGATCAACTTTGGAGTC<br>TTTTCGATGGAGAGACTGTGAAATTTGATTAG<u>TCTAGA</u>AATAACAGA<br>GGGCGCGCGAGCGGTGGCTACTGATCGCCTATGAGTTCTGTGATTCT<br>ACTTGTAATTTCAGAAGTGTTTTCAGTGTCTTGTTTTCTGGAAGTCCG<br>TCTGGTTTTAGTAACTTTTAGCTCAAAAATGTGTCTGTACGATGGTA<br>TTTGTATGTTTGTGGGTCTTTTACATATACGCTTGTAATCGATCAATG<br>TAGAATGCTGTGTGCCTTTTCCGTCAACAGCTTATTTAGTGTTTACTC<br>TGTATACGTATATCTAATATATAGTACTGATTCTTTCATCTGGTGATT<br>TGTTTTCCTAAAGAGATTATTATCATAGCTTTAATTGAATGATACAA<br>AGAGGTGTTGCCTGGCTTCACCAGAGCAGAAATTTTCATTGATATAG<br>GGTACAAATGTCATTCACATAATGTTAAGAGATAAGTTTTTCAATGT<br>CCTCAAGAGCCCACCAAGAGTTTCTTCCGGGAATTGCTTAAATTATC<br>TTAAATTTAAATTGTA<u>GTTTAAAC</u> |
| 13 | pPRP:<br>AtPAP1:<br>HSPT | <u>CCCGGG</u>ACCTCTTCCTTCTCTCTATCTCCATTTTTTATTTATGTTTTAC<br>TAAATTACTTTTATTTCATAACAACATGTCTTGTTCATGTTTTACTAA<br>GTTGCTTTTATTTCATAACAGCATCATAATAAAATACAGGAATTTTC<br>AAGCGAAGCAGAGTCACTTCCAAAAGTAGAAACACTTAGAACTTCT<br>GCTAAGGGTAATTAACAACTTTTGGTCCTTTAGGAGGCACAATATAC<br>TAGACGAAGAATTGAACTTGATCTTACTTACGGCAAAGGCTAATAAT<br>AGCATCACGTTAGTGAACTACAACGCCAACTAAAAAGAAAAAAGAA<br>AATAATTAAGACCAGTAAATATGCATGTTCACTCTCAAATATTGAGG<br>GGAAAAAAACCGAGAATCTAATTATCTACAAATGTTCATTCATTAGG<br>GTAGTAGGAAATTTTAATTTTATCTTAATTTGAACCAACTACAATA<br>TTTTATTTTAAAACAAATAAAATTGGAATAGCACCGGTTTTTTATTT<br>TATATTTTTGGGTATCCGAAAGTGTATGGGCGCTAGGAACTACCTC<br>CGTCTTTACTTCTTTTGTTGCTAGTAATAGGAACTCCTTTAATGTTTT<br>GACAGTGAAAATACTAGTATATTAATTAACTAATTTGTCTCTATACC<br>ATGATTTATAATATTACGGTTGAAGTGATAGCTCATGGAAGAGGAAG<br>CACTGATGGTGTGAAAATATTTACACAATCAGATCATTTATTATATT<br>ATTATGGATAAATTTCTCGATAAGTATTAATTGATAAGTATTCGGAT<br>AAAAGTAGGTTATAATCTAATTTTTTTTATACTATTAGTATTAGTATA<br>TATAATTCGTTACATTTACATATACATCTTCTATGTTTTATTCATAGA<br>TGTAGACACTGGCGAGGAACATGGCAAATTGCAACACCTTATGTGG<br>CTAATAATGCATTCAAGAGAATTTGAGTAAATATCTAATTTGCTTGT<br>GCTGCCAGCTAAAACCTTGGGGACACATGGTTTCTAGAACTTAATTT<br>CTTTAATATTTCTCTTTACTCTAATTCATACTTTTGCATCCTATATAAA<br>CCCACCTTCTATAACCTTTGCAATATCAAACAAAGCAACAATCTACT<br>TATAACTACTAAAGTTGATAGTTATATCAATCATTAAGAAATTTTAG<br>ACTCTTAGAA<u>CTCGAG</u>ATGGAGGGTTCGTCCAAAGGGCTGCGAAAA<br>GGTGCTTGGACTACTGAAGAAGATAGTCTCTTGAGACAGTGCATTAA<br>TAAGTATGGAGAAGGCAAATGGCACCAAGTTCCTGTAAGAGCTGGG<br>CTAAACCGGTGCAGGAAAAGTTGTAGATTAAGATGGTTGAACTATTT<br>GAAGCCAAGTATCAAGAGAGGAAAACTTAGCTCTGATGAAGTCGAT<br>CTTCTTCTTCGCCTTCATAGGCTTCTAGGGAATAGGTGGTCTTTAATT<br>GCTGGAAGATTACCTGGTCGGACCGCAAATGACGTCAAGAATTACT<br>GGAACACTCATCTGAGTAAGAAACATGAACCGTGTTGTAAGATAAA<br>GATGAAAAGAGAGACATTACGCCCATTCCTACAACACCGGCACTA<br>AAAACAATGTTTATAAGCCTCGACCTCGATCCTTCACAGTTAACAA<br>CGACTGCAACCATCTCAATGCCCCACCAAAAGTTGACGTTAATCCTC<br>CATGCCTTGGACTTAACATCAATAATGTTTGTGACAATAGTATCATA<br>TACAACAAAGATAAGAAGAAAGACCAACTAGTGAATAATTTGATTG<br>ATGGAGATAATATGTGGTTAGAGAAATTCCTAGAGGAAAGCCAAGA<br>GGTAGATATTTTGGTTCCTGAAGCGACGACAACAGAAAAGGGGGAC<br>ACCTTGGCTTTTGACGTTGATCAACTTTGGAGTCTTTTCGATGGAGAG<br>ACTGTGAAATTTGATTAG<u>TCTAGA</u>AATAACAGAGGGCGCGCGAGCG |

TABLE 1-continued

Nucleotide and protein sequences

| SEQ ID NO: | Sequence Description | Nucleotide Sequence |
|---|---|---|
| | | GTGGCTACTGATCGCCTATGAGTTCTGTGATTCTACTTGTAATTTCAG<br>AAGTGTTTTCAGTGTCTTGTTTTCTGGAAGTCCGTCTGGTTTTAGTA<br>ACTTTTAGCTCAAAAATGTGTCTGTACGATGGTATTTGTATGTTTGTG<br>GGTCTTTTACATATACGCTTGTAATCGATCAATGTAGAATGCTGTGT<br>GCCTTTTCCGTCAACAGCTTATTTAGTGTTTACTCTGTATACGTATAT<br>CTAATATATAGTACTGATTCTTTCATCTGGTGATTTGTTTTCCTAAAG<br>AGATTATTATCATAGCTTTAATTGAATGATACAAAGAGGTGTTGCCT<br>GGCTTCACCAGAGCAGAAATTTTCATTGATATAGGGTACAAATGTCA<br>TTCACATAATGTTAAGAGATAAGTTTTTCAATGTCCTCAAGAGCCCA<br>CCAAGAGTTTCTTCCGGGAATTGCTTAAATTATCTTAAATTTAAATTG<br>TAG<u>GTTTAAAC</u> |
| 14 | pAD:<br>AtPAP1:<br>HSPT | <u>CCCGGG</u>ACTAAAAGTGAATCCTTCCCCACAAAAAACTTAGTTTTGAA<br>TGCACGAGATTCTACAAATAAAAAGAAAGAAAGAAATAAAAGGTAT<br>AATTAGAGCGCACGTGAAATAAAAATACTATCAATTTGAATGAAAA<br>CTTGAAAATAAAATAAAAAATAGAAGTATCATGTTTTGAAGGATTCA<br>ATTTTAGTATTATTTTAATTTATATATATGATTATTTTGTCAGGTGGG<br>TCATTCCTGTTTTAATTGAATTATTATTTATTAGACGAAAAAAAAAT<br>CTTGGAATAAGAAAATCTGGTGACTATTTATGAAATTTACCCTTCAA<br>TTGTATGTGTAAAACACTTATATCCAAGTTTATAAGATTTTTAGCAA<br>AATAAAATACTTCAAATTTTTTAAGCTATTCGCTTGAAAATAAAATT<br>AAGACATGTTAACATAGATTACTTTCTCTATTACCAAATTCTTGTGTT<br>ACTTTCTTAAAGTTGAGTCGAGTAGTATTGATAAATAAAATAGTCAA<br>TATGTTTTCCACTGTTCTGAACAAAAATAGTTTTTTTTTTTTTTTTTT<br>TTATGTATTTTCATAATTTTGAATTATTTAAATTTGAGTTTTGGAAGA<br>TGAATTCACGTTTGACCAAAAAGGAGAGATGAATCGTGTCTATCCAA<br>AAATAAAAACAAAATGGGCGTGTAAAAAATAACATTTTTTGGTGG<br>GTCAAAACATCGTTAGGTTTAATAAATCAAATCGATTTTTCTCTTGA<br>AATATTACCACCACCTTTTTCTTATTACTCGACAAAAACTCAAACAG<br>TAACACAAAACAAACAGCCAAAAACCGGTTTCGAAAACCCAGCGAC<br>CAAAACATGGAAATGGTTTTACTTTGGCTGTTGTATTCAACTTTTCG<br>ATTTCACGATTCTATATTTTCAGGTATAAATACCCCAGCTAATGCAGT<br>GCCACATCACACCTCAAGATATTTAACTCAGTATTCAGAAACAACAA<br>AAGTTCTTCTCTACATAAAATTTTCCTATTTTAGTGATCAGTGAAGGA<br>AATCAAGAAAAATAA<u>CTCGAG</u>ATGGAGGGTTCGTCCAAAGGGCTGC<br>GAAAAGGTGCTTGGACTACTGAAGAAGATAGTCTCTTGAGACAGTG<br>CATTAATAAGTATGGAGAAGGCAAATGGCACCAAGTTCCTGTAAGA<br>GCTGGGCTAAACCGGTGCAGGAAAAGTTGTAGATTAAGATGGTTGA<br>ACTATTTGAAGCAAGTATCAAGAGAGGAAACTTAGCTCTGATGA<br>AGTCGATCTTCTTCTTCGCCTTCATAGGCTTCTAGGGAATAGGTGGTC<br>TTTAATTGCTGGAAGATTACCTGGTCGGACCGCAAATGACGTCAAGA<br>ATTACTGGAACACTCATCTGAGTAAGAAACATGAACCGTGTTGTAAG<br>ATAAAGATGAAAAGAGAGACATTACGCCCATTCCTACAACACCGG<br>CACTAAAAAACAATGTTTATAAGCCTCGACCTCGATCCTTCACAGTT<br>AACAACGACTGCAACCATCTCAATGCCCCACCAAAAGTTGACGTTA<br>ATCCTCCATGCCTTGGACTTAACATCAATAATGTTTGTGACAATAGT<br>ATCATATACAACAAAGATAAGAAGAAAGACCAACTAGTGAATAATT<br>TGATTGATGGAGATAATATGTGGTTAGAGAAATTCCTAGAGGAAAG<br>CCAAGAGGTAGATATTTTGGTTCCTGAAGCGACGACAACAGAAAAG<br>GGGGACACCTTGGCTTTTGACGTTGATCAACTTTGGAGTCTTTTCGAT<br>GGAGAGACTGTGAAATTTGATTAG<u>TCTAGA</u>AATAACAGAGGGCGCG<br>CGAGCGGTGGCTACTGATCGCCTATGAGTTCTGTGATTCTACTTGTA<br>ATTTCAGAAGTGTTTTCAGTGTCTTGTTTTCTGGAAGTCCGTCTGGTT<br>TTTAGTAACTTTTAGCTCAAAAATGTGTCTGTACGATGGTATTTGTAT<br>GTTTGTGGGTCTTTTACATATACGCTTGTAATCGATCAATGTAGAATG<br>CTGTGTGCCTTTTCCGTCAACAGCTTATTTAGTGTTTACTCTGTATAC<br>GTATATCTAATATATAGTACTGATTCTTTCATCTGGTGATTTGTTTTC<br>CTAAAGAGATTATTATCATAGCTTTAATTGAATGATACAAAGAGGTG<br>TTGCCTGGCTTCACCAGAGCAGAAATTTTCATTGATATAGGGTACAA<br>ATGTCATTCACATAATGTTAAGAGATAAGTTTTTCAATGTCCTCAAG<br>AGCCCACCAAGAGTTTCTTCCGGGAATTGCTTAAATTATCTTAAATTT<br>AAATTGTA<u>GTTTAAAC</u> |
| 15 | pEX3-like:<br>AtPAP1:<br>HSPT | <u>CCCGGG</u>CATTGGAGTTTTATTAACCCGCCTCGATAGAGGCGGGGCTA<br>TACAATCTGATAAGGTGATCGAGGATGAAAGGGAGCCCCTCGACTT<br>TGCTCACGAAGAATCGGAGCAGAATAACAATTTGCCAAAAGGAAGG<br>ATGGATTTGGCCTAGGGTTATTTGGTATTGACGGCAAAAATTAACGA<br>TGACGGGGTCGAGGGGGCCCAACGTGAAAGGGTAAGTGTAAACACT<br>TAGAAACCCTTCCACATGAGTGGTGATATCTTTTTCGGGGTCGGGA<br>TCACCACCTCTTTGCCTTCCCAGTTGCGGTCTTTCTTTACCTGCTTAA<br>GGTATCCCTCAGTTATTGAGCATATATACCTCGACATTGGCTCGCAT<br>CGATCAGGAATCGACGAGGCTTTATCGGTCTTAAAATCGGAGTTTAG<br>CACGCACCCCCAAGAATGCATTCCTCAAGACGGGGATCCACCAGCG<br>TTTTTTCCGTCGGTCGGTTGAGAAGATGAAGCAACTTCTTTTTGTGTA<br>CCATTTTCGATGTTTTTGCCATTCTTGTGTAAGTTTGAAGAAGAGGAA |

TABLE 1-continued

Nucleotide and protein sequences

| SEQ ID NO: | Sequence Description | Nucleotide Sequence |
|---|---|---|
| | | GATAATAGGACTTGACATTTGAGACATGATTAACAGCAAAGCCTGA<br>AGATTTGTAAAAGGGACGAACTTAAGAGATGTAAAAGCTTTAGATA<br>TTAGAAGGAAGTGAAAGTAAAGTTTGAATCAATGAGGAAGTGATCT<br>ATTTATTGGACTCACGGCGACAGTTCAAAGGCACTAGTGGCCGACA<br>ACCAACTAACACTCATTAATGACTTGGAAAACTGTACTGACGGGAC<br>GTTTTGGTCACTCCCGTCGCTTACGTCATGAGGATGTCGTCATTACA<br>GGTCGAGATAGAAAATTGAAGGCTCAATTCGTTTCTTGTCATTTCAC<br>TCCAAAAAACGAGGAGACTATCTGTATACGGTTAAAATCGGGCCCA<br>CCCGATTTTACTATTTGACCGAGACTAGGAGGTTGCATCGAAGAATG<br>GCCTCGTAACAGAACAGACTAAATCACGAGGATAAGGTACTGAGTT<br>CATAATCGAGGTACCGGTCGAGATCGAGGCTAGTAGTGATCGAAAC<br>CAAATGAGACAGACATCGAGCAAGATCGAAGATAGCACAATAACAG<br>AAAGGCGAGATATCCACGACTGGTCGAGGATCATGGCATAAATCTC<br>GAAACGAATCAAATTAGAAACAGTTAATTAGCTAATCATGAATTTAC<br>TTCTGTAATTAGAATTATACCATAAGTGAAATTCCTCTACTATTTATA<br>GGGGGTTCTAATCATTTGGAAGACACATGGTTCACAGATATCAAAGA<br>AATGTAATTCTCTTTCTCGTTTATACTATTGTTCATCAGCTTGTTATAT<br>TTTAATTGTTCTTACATCAACCAGTTCGAGGGTATCCAAACTTGAGG<br>GCTGAGTTCCATTCTAACACAAGTTTGCTTTACTTTATAGTTTATTTC<br>TATTATTAATCTTCATATTTATCAATTGGTATTAAGTGAAATTACGTG<br>TACTTAGAACAATATTATAAATTTAATTGTTATCCAATTTTAAGGATA<br>AATAAGAACATTCATTAAAGTTAAAAGAGACATATAAAAAAAGCTA<br>TTGCTCAGATTTCTGCAACTGAAATCGTGCAAAGTTGAGGCATCCAC<br>ACTTGTTTTTCAAAGCTTCGGTACTGTATACAAAGATAGAAAGTAAA<br>GGAGACTTTTCTCTTTAAATTATTGCATCAGAAATAGTATAGCTGCC<br>ATAATAGTTTATTAATTCCAGCTATGCTTAGCTTGCAGCCTCTATCGA<br>ACAAAAAAGTATACCAACTCAAGTCAATTTGAGCCGACAACATGA<br>CAAAACCAAATCAAAATGCATACTCTAGCTTTTTTACTTTGGTAGGT<br>TTTAAGTAATCTAGTGAGACTTTTACCTTCATTCATGAAAATCTTGGA<br>AAGGGTAATTGTATAATTGAAAGCTATATAAGGGGTCGGAGTGAA<br>GCTTAAGAGGACAACAACTTTTCTCATTTGTTTCAAAG<u>CTCGAG</u>ATG<br>GAGGGTTCGTCCAAAGGGCTGCGAAAAGGTGCTTGGACTACTGAAG<br>AAGATAGTCTCTTGAGACAGTGCATTAATAAGTATGGAGAAGGCAA<br>ATGGCACCAAGTTCCTGTAAGAGCTGGGCTAAACCGGTGCAGGAAA<br>AGTTGTAGATTAAGATGGTTGAACTATTTGAAGCCAAGTATCAAGAG<br>AGGAAAACTTAGCTCTGATGAAGTCGATCTTCTTCTTCGCCTTCATA<br>GGCTTCTAGGGAATAGGTGGTCTTTAATTGCTGGAAGATTACCTGGT<br>CGGACCGCAAATGACGTCAAGAATTACTGGAACACTCATCTGAGTA<br>AGAAACATGAACCGTGTTGTAAGATAAAGATGAAAAGAGAGACAT<br>TACGCCCATTCCTACAACACCGGCACTAAAAAACAATGTTTATAAGC<br>CTCGACCTCGATCCTTCACAGTTAACAACGACTGCAACCATCTCAAT<br>GCCCCACCAAAAGTTGACGTTAATCCTCCATGCCTTGGACTTAACAT<br>CAATAATGTTTGTGACAATAGTATCATATACAACAAAGATAAGAAG<br>AAAGACCAACTAGTGAATAATTTGATTGATGGAGATAATATGTGGTT<br>AGAGAAATTCCTAGAGGAAAGCCAAGAGGTAGATATTTTGGTTCCT<br>GAAGCGACGACAACAGAAAAGGGGGACACCTTGGCTTTTGACGTTG<br>ATCAACTTTGGAGTCTTTTCGATGGAGAGACTGTGAAATTTGATTAG<br><u>TCTAGA</u>AATAACAGAGGGCGCGCGAGCGGTGGCTACTGATCGCCTA<br>TGAGTTCTGTGATTCTACTTGTAATTTCAGAAGTGTTTTCAGTGTCTT<br>GTTTTCTGGAAGTCCGTCTGGTTTTTAGTAACTTTTAGCTCAAAAATG<br>TGTCTGTACGATGGTATTTGTATGTTTGTGGGTCTTTTACATATACGC<br>TTGTAATCGATCAATGTAGAATGCTGTGTGCCTTTTCCGTCAACAGCT<br>TATTTAGTGTTTACTCTGTATACGTATATCTAATATATAGTACTGATT<br>CTTTCATCTGGTGATTTGTTTTCCTAAAGAGATTATTATCATAGCTTT<br>AATTGAATGATACAAAGAGGTGTTGCCTGGCTTCACCAGAGCAGAA<br>ATTTTCATTGATATAGGGTACAAATGTCATTCACATAATGTTAAGAG<br>ATAAGTTTTTCAATGTCCTCAAGAGCCCACCAAGAGTTTCTTCCGGG<br>AATTGCTTAAATTATCTTAAATTTAAATTGTA<u>GTTTAAAC</u> |
| 16 | pEX1-like:<br>AtPAP1:<br>HSPT | <u>CCCGGG</u>CAGTAGGCATCAATTACTATATATTTTACAAGTAATTAAAT<br>GATAAACAAATGCAATATTTGTTTAGTTTCCATATTTCTTTTTCAAGG<br>CACTCCTTTAATTACTCATCCATTCAAATGGATCTTCTCATTTTTCAG<br>ACGGTTTTTAGGACTCCCTCTATCTCAAATTATCTATCGAGATTTTTA<br>AAAAAAAAATTGTCTCAAATTATTTTCATTTTGGAAATTTAAGATAA<br>AATTAATTATATTTTTTTCATTTACCCTTAATGGTAATTATTCTTGAAT<br>ATGGAGATAGCACATCGAGTAAATATTCAATAAAGAGAGATTATAT<br>CTTATAACATAAATAAGAGTAAAATAGTCCAAAATTCCTCATAATTA<br>ATATTTTTTAAGGGTATGTAAAAGAAAAACACGACAAATAATTTGAG<br>ACGGAGAGAATACCTTCTTTTTGACCTTTTGTAAATAAATATTAAAA<br>TATCCTCAACATTTCCTAGGTTAATTTCTCTCTCCCTAATAATTTC<br>AAAAAGTTATCATTGTGATACTCAAATATATTGGTCTTAGCACAATT<br>TGAGCATTGCATGTTGTATGCCTGGATCCTCCTGGGTGCCATTTTTCC<br>TTTGCTTTTGGATACCTTTTTGCAACTTTAGTCCATTGCTGGAACATG<br>ATTTTTTGTACCTCTTGTCTGTTCCCATGATGATAAACTATGATAACT<br>AACATTTTCAGAAATATTGGATTGAATTAGATATATTTTCAATATTG |

TABLE 1-continued

Nucleotide and protein sequences

| SEQ ID NO: | Sequence Description | Nucleotide Sequence |
|---|---|---|
| | | AGCTACAAAACTCGTTGAATATTTTGCCCTATTTGGTTGGTAATAAA
AGTGGGTCACATGCACAGTTTTTCTCTTGTCTTCTCTAGATTAAGCTC
TTTGGAAATGACCTACTGAAAATGCTACACATAAAACTCCCCCACTC
CTCCCCAAGTTGAGGGGTGGGAGGTTTGATTTGGACCCTTACCCTAT
TGTTAATATCGAAATAGATAATACAAAGGACGGGAACATAAAACCA
AAACCTCCGATAAAACACCAAAGTTGATGATCTAAGTTAAGTTATTG
ATTCTTATACGTTGATTGGAAGTGCACAATGGTCTTTGCATACTATCA
AAGTATGAATTGGTTCTTGAATTATATCTCTTAATATGATGTATTGTG
TTTAATTAATTCTCTACTATTCTCTATTTTTATAGGCTAAAAGATCCT
GACATGCTTCTTGAACACATGTGAAGGTTAGTTAACTATAGTCAGAA
GTACACAAGAATTAACTTGTACACCTATCCGTGATCGAAAAACTTAA
CTTGTTCTAAGCTGAACTGAGTCCTCCTATCCATGTCCGATTCTTCAC
TAGAAGCATTAATCATACAAGGAGAATTCAACTTAATTTACTGTATT
GGTTATCATTTACATAGTTTAGTTATAAAACTTTGGAGCGACACAAT
GATTGACACTACTAATCATGATTGAATATTAACTTCACTCGATTTATC
AATTTCTCATACAAGTGAATTAATTTCACTCTTTGTGATTTCAGTAGT
AAATGTCAAGTTCATAGTTTTTCTTTTTGAAATTAGTCATACATGT
GAATAGAACATTAATTTAAGTTAAAAGCTAGCTGCTCTGATTTCTGT
AACTGAAATCGTGCAAAGTTGAGGCATCCACATTTGTTTTCAAAGT
TCCAGTACTGTCTAAAAAGATAGAAAGTAAAAGGGAGACTTTTCTCTT
TGAATTATTGCATCAGAAATAGTATAGCTGCCATAATAGTTTATTCC
TTTGCTTAGCTTGCAGCCTCTATCGAACAAAAAAAGTGTACCAACTC
AGGTCAATTTGAGCCGACAACATGACAAAACCAAATCAAAATGCAT
ATATACTCTAGCTTTTTTACTTTACTTTGGTAGGTTTTAAGTGAGACT
TTTACCTTCATTTATGAAAATCTTGAAAAGGGTAATTGTCTAAATGA
AAGCTATATAAAGGGGTCGTAGTGAAGCTTAAGAAGACAACAACTT
TTCTCATTTGTTTCAAAG<u>CTCGAG</u>ATGGAGGGTTCGTCCAAAGGGCT
GCGAAAAGGTGCTTGGACTACTGAAGAAGATAGTCTCTTGAGACAG
TGCATTAATAAGTATGGAGAAGGCAAATGGCACCAAGTTCCTGTAA
GAGCTGGGCTAAACCGGTGCAGGAAAAGTTGTAGATTAAGATGGTT
GAACTATTTGAAGCCAAGTATCAAGAGAGGAAAACTTAGCTCTGAT
GAAGTCGATCTTCTTCTTCGCCTTCATAGGCTTCTAGGGAATAGGTG
GTCTTTAATTGCTGGAAGATTACCTGGTCGGACCGCAAATGACGTCA
AGAATTACTGGAACACTCATCTGAGTAAGAAACATGAACCGTGTTGT
AAGATAAAGATGAAAAGAGAGACATTACGCCCATTCCTACAACAC
CGGCACTAAAAACAATGTTTATAAGCCTCGACCTCGATCCTTCACA
GTTAACAACGACTGCAACCATCTCAATGCCCCACCAAAAGTTGACGT
TAATCCTCCATGCCTTGGACTTAACATCAATAATGTTTGTGACAATA
GTATCATATACAACAAAGATAAGAAGAAAGACCAACTAGTGAATAA
TTTGATTGATGGAGATAAATATGTGGTTAGAGAAATTCCTAGAGGAAA
GCCAAGAGGTAGATATTTTGGTTCCTGAAGCGACGACAACAGAAAA
GGGGGACACCTTGGCTTTTGACGTTGATCAACTTTGGAGTCTTTTCG
ATGGGAGAGACTGTGAAATTTGATTAGTCTAGAAATAACAGAGGGCG
CGCGAGCGGTGGCTACTGATCGCCTATGAGTTCTGTGATTCTACTTG
TAATTTCAGAAGTGTTTTCAGTGTCTTGTTTTCTGGAAGTCCGTCTGG
TTTTTAGTAACTTTTAGCTCAAAAATGTGTCTGTACGATGGTATTTGT
ATGTTTGTGGGTCTTTTACATATACGCTTGTAATCGATCAATGTAGAA
TGCTGTGTGCCTTTTCCGTCAACAGCTTATTTAGTGTTTACTCTGTAT
ACGTATATCTAATATATAGTACTGATTCTTTCATCTGGTGATTTGTTT
TCCTAAAGAGATTATTATCATAGCTTTAATTGAATGATACAAAGAGG
TGTTGCCTGGCTTCACCAGAGCAGAAATTTTCATTGATATAGGGTAC
AAATGTCATTCACATAATGTTAAGAGATAAGTTTTTCAATGTCCTCA
AGAGCCCACCAAGAGTTTCTTCCGGGAATTGCTTAAATTATCTTAAA
TTTAAATTGTA<u>GTTTAAAC</u> |
| 17 | pPR1a:
AtPAP1:
HSPT | <u>CCCGGG</u>CTATATAAGGCCATCCGTGAATTGAATAAACTATCCAATTA
TTTTCTTCCACAAAAATTTCAATTCTACTTTTAGTTATTCTTTTTAATA
TTGAGCTTGCAATTCTATTTTGATTCTTCACTCATGACATGCTACGTA
GAGAACCTTCAATACATCATAAGAGATGGACCAAGCAATGCATAAC
TCAAATAAGTCCATACAAATTTGCTGAAAGATAAAGTTATTCTACTT
TCTTTGAACCCAAATCTGATAAATCTTGACAATCAGATTTGCTACTAT
GATTTCTCACTGTATCATTTGTTTTATTCTATAAAGTTAATGAGGAAT
GTATTAATTATTTAAGATACCTTACTTTTTCTGATTTTTGATCTTATAG
TCAAGTCGTGAGGCACAATTTGCGACCCTGATGGCGCAAACCTTTAC
CTAGGGATCGTAGCACATAAACGTTTTAAGGACTAAGATATACGAG
GATGTCAATTATCATAATGTAGGGTCTAAGTTTTCATTTTTTTTTTG
CATCTAATAGAGTATAATTTTTTTAATCATCACGATAACTTGATTTA
CAATAATATGTACTCTGTTTACTTTTACTTGACACGTTTTGATTTTTC
ACGCCCTTTAAGAAAAATGATTGAAATGCATAATTTACCATGATAC
TCATATTAATTGATGCATATTTTATTGGATTTGAGAAAATGATTTGAA
ATGAGTAATAAATATTGTGGGTATAACAGGAAAAAAAATTGTCTTCT
CTTAACATGCATAAAGTGAAGAGTAAAAAGAAAATCTATTTTTGTAT
ACATGTCAAACAAAAGTGAACGGAGGAGATGACAAATTGCTAAATG
GCAATAGTTACAAAATTCTTCAATTACTCTTTTTCATAACAAAACACT
GGTCTCTCTTGTAAGTATTGGTCTATACTTCACCACCTAAAGCATTGG |

TABLE 1-continued

Nucleotide and protein sequences

| SEQ ID NO: | Sequence Description | Nucleotide Sequence |
|---|---|---|
| | | CCGAAGTCTTTTTAAGGAGTTTGGTTGTCATTTATCCATTTAAATTAA<br>AGGGAAAATAAGTGAACGCCATTACAGCGAGATGCTTTAGGGTGCT<br>ATTTCTTGGAAAAATAAAGTAGTTAAATCTTAAAACACCCTCGAGGA<br>TTTCAAACTCTAGCTTCACTAAAACTTGAGCTTTCTTTTCCACTAATG<br>TCGAAAAACGAAATAAACATAAGCTATTTACAAAAATAAAAAAATA<br>CTCCATTTGAATCTAAAGTCAAGTCGTGATTGGGATAAGAAAATAGA<br>AATTTATTTATACTCCAGATCAAGCCGTGATTGGAATGAGATAATAG<br>AAAAGTATGATAGTACATGAGTAACATCAAGTTGGAAATTAAGGGA<br>AGGAAATTAGAGAAAGAACTGAAGAATATCCAAATATTCTTTACGT<br>CCAAATTTGATAGTTATTTAACGTCATCGAGATGACGGCCATGTTCA<br>AGTTTTCCACAAATATTGAGAAAAGAAAGAAAGACACAAACTGTGT<br>TTGGTATTATTATAGTTTTTTCTTTTAGAGAATTGATTGTACATATAA<br>GAAATTAATATAAGATTTAGAAATAAGATTATTAGAAAAATCAAAC<br>ATCAAAGTATTTATTTTAAATTCTTTTTCCAATGGACATTCCCATTCT<br>GAAAAAAAGAGATATAAAATGGAAGTAAAATTAATCAGATCGTTAA<br>ATGTAGAAAATATTAATAACACTTAACCATAACCAGTCTACTTTATT<br>TAACAAAAAGCACATCTGATAGATCAAAAAAGTGTTTAACTTCATGC<br>ATTGACAATTTAAAATTATTTTGCAACATCGGGTAAAACTATTTTAC<br>AACAATTGGTAACTGCATATATAAGTTTAATATGGTAACCTAGAAAA<br>TAGGATAAATTATCTATAACAGGATATATTACATTGATATTACCATG<br>TCAAAAAATTTAGTAAGTACATGAATAATCACCGTGAAATCTTCAAG<br>ATTTCTCCTATAAATACCCTTGGTAGTAAATCTAGTTTTTCCATTCAA<br>GATACAACATTTCTCCTATAGTC<u>CTCGAG</u>ATGGAGGGTTCGTCCAAA<br>GGGCTGCGAAAAGGTGCTTGGACTACTGAAGAAGATAGTCTCTTGA<br>GACAGTGCATTAATAAGTATGGAGAAGGCAAATGGCACCAAGTTCC<br>TGTAAGAGCTGGGCTAAACCGGTGCAGGAAAAGTTGTAGATTAAGA<br>TGGTTGAACTATTTGAAGCCAAGTATCAAGAGAGGAAAACTTAGCTC<br>TGATGAAGTCGATCTTCTTCTTCGCCTTCATAGGCTTCTAGGGAATAG<br>GTGGTCTTTAATTGCTGGAAGATTACCTGGTCGGACCGCAAATGACG<br>TCAAGAATTACTGGAACACTCATCTGAGTAAGAAACATGAACCGTG<br>TTGTAAGATAAAGATGAAAAGAGAGACATTACGCCCATTCCTACA<br>ACACCGGCACTAAAAAACAATGTTTATAAGCCTCGACCTCGATCCTT<br>CACAGTTAACAACGACTGCAACCATCTCAATGCCCCACCAAAAGTTG<br>ACGTTAATCCTCCATGCCTTGGACTTAACATCAATAATGTTTGTGAC<br>AATAGTATCATATACAACAAAGATAAGAAGAAAGACCAACTAGTGA<br>ATAATTTGATTGATGGAGATAATATGTGGTTAGAGAAATTCCTAGAG<br>GAAAGCCAAGAGGTAGATATTTTGGTTCCTGAAGCGACGACAACAG<br>AAAAGGGGGACACCTTGGCTTTTGACGTTGATCAACTTTGGAGTCTT<br>TTCGATGGAGAGACTGTGAAATTTGATTAG<u>TCTAGA</u>AATAACAGAG<br>GGCGCGCGAGCGGTGGCTACTGATCGCCTATGAGTTCTGTGATTCTA<br>CTTGTAATTTCAGAAGTGTTTTCAGTGTCTTGTTTTCTGGAAGTCCGT<br>CTGGTTTTTAGTAACTTTTAGCTCAAAAATGTGTCTGTACGATGGTAT<br>TTGTATGTTTGTGGGTCTTTTACATATACGCTTGTAATCGATCAATGT<br>AGAATGCTGTGTGCCTTTTCCGTCAACAGCTTATTTAGTGTTTACTCT<br>GTATACGTATATCTAATATATAGTACTGATTCTTTCATCTGGTGATTT<br>GTTTTCCTAAAGAGATTATTATCATAGCTTTAATTGAATGATACAAA<br>GAGGTGTTGCCTGGCTTCACCAGAGCAGAAATTTTCATTGATATAGG<br>GTACAAATGTCATTCACATAATGTTAAGAGATAAGTTTTTCAATGTC<br>CTCAAGAGCCCACCAAGAGTTTCTTCCGGGAATTGCTTAAATTATCT<br>TAAATTTAAATTGTA<u>GTTTAAAC</u> |
| 18 | pSAHH:<br>AtPAP1:<br>HSPT | <u>CCCGGG</u>ATTAATTGTAAATAAATATACTTATCATTTTCGGAGAATAT<br>CCAATATTATATATATAATTTTTATACTTATGAGTTTCGGGCTAGATA<br>TTTATTCTAAGCTAAGTACTACAAATACTGTGATATAAGGCTCTAAA<br>CTTTCCTACCCTAAAAGAGTCTACGTTTTACTACGCTAAAAAGGTCT<br>ACATTTTACTACGCTAAAAAATAATCTAAACTAAACATCGCAAAAAC<br>AAACAAGTAAACATGACAATTTAACAAATAAATTTTTTTGACTAATT<br>TACAAGTATATTTATACAACACTAAAATTAAATCCGGATAAAAATTA<br>ACATGCTAGTTTTGGCAAAAATAAACACAAAACTATATACAAACCA<br>TACAAATCAAATAATATTCAATATTATACAAGTTTCAACTAAAATTA<br>AATCGAAATACCTGGATTCGGAAACTAAATAAATCGGATTTTTGACT<br>TCAAAAAAGAGATTCCAGCGTACCACGACCCTCAACTATAATGTGG<br>GACCACCAATCTTCACCTTTTATGTGTCGGGGGACCCAAAAATTTT<br>TTTTTTTTTAAAAAACTGGGCAGATCGCTGAGGAGGGGACCAAATT<br>TTTTTGAAAGTTTTCGGCTGAATGAAGAAGAAGAAGAAAGGTTTAG<br>GGTTTTGTTTTAGGGTATGGCGCCAACAGTATTGGCGCTATGCTGAC<br>ACCGCCTGAAAAGTAGGGGTATGGCGCCAACACTGTTGGCGCTATG<br>CTGACATGTCAGTAAACTCTCTGATATGGCGCCAACTATGTTGGCGT<br>TATATATATTTGTGTTACTTTTCCTTTTTTACACTTATTAATGTAGTTT<br>GAGTCAAAAAAAACAATAATAAAGTTCCGGACTCGAGATGTAGGGG<br>GTTGTCAATTTTCACTTTGTCAGTCGCTAAGAGTAATTATGAATATTC<br>TTTTATCAATATTGGACCTCAAACTTTATCCATTGTAAGAAAAAAAA<br>GTTGTAAAATATTTGTGTCACTTAATTAAACGGTCGTAGTAGTTAGT<br>AGTAGTGACATAGTCCTTTCGTTTGATAGTATATCAAATTGGAACAA<br>TTTACATTTGCACCAAAGCATAAAGGGAAAGCATGAAAAAGAGAAA |

TABLE 1-continued

Nucleotide and protein sequences

| SEQ ID NO: | Sequence Description | Nucleotide Sequence |
|---|---|---|
|  |  | GTGCAAAAGAGAAAAATACAACAACAACAAGAATATTTCAGTATAA<br>TTCTATAAGTAGGGTCTGGAGAGAGTAGAATACCCCTAACCTAGAA<br>GGGCAGGAAGAATATTAAAGTAAAAAAGATAAAAGATTACAAATAA<br>AATAAAAGAAAAAACAAACAAACATACAAAATTAATTTGTGCATAA<br>TGCTTATAGTAATTGCCAATTTGCCATGAATATCTTCCACCGGGCTAT<br>CTTGGTCATGTTAATCACTCTATCCTGTTTTCAAACAATTTTTACTCT<br>AAAAATTTGCATGTTATATTAATTGGTGGGTGAGCCAGAAATTTTAA<br>ACAAAAAATCAAAATACGGTACACTAAAAGATTTTTTATAAAAAAG<br>AATTCACCAAGTTATATATATACACAATCTTTCTTTTTTTAAATCTT<br>ACGATGACCAATTTTTTCGACAAAGAATATTCACTTAAACCCTTGTT<br>CATACATAGCTTGGCAATTGGATTAATAATGAAAATAATACTTTAAA<br>TTTTGGAAAGAAAATATTATTTATTCTCCAAAAGAAACCAAGAAATT<br>AGATTCATCAAAAAATAATGACCACCATTAGCCCACCTCCCAAATCT<br>CTATTCCTTTTAGACTTTTAACCAAATTTTCAGATCTACCAAACCCCA<br>ATTTATCCAATAAACTTTTCAGATCTAAAAATAAAAATATTCAGATC<br>TGGAACAAATCTTGACCGTCCATTTTCATCATTCATATCTATTTAATA<br>CCACTCACCTCCGCCCTTTACTCCTTGCAACACTCTTCTTCTCCTCTA<br>AAAACCCTTATAGAAGAAGAGGAAAAAGCCTTTCAAATCTCATCTC<br>AAACCACCTAATTTCTCTCATACTCGCTCGACCC<u>CTCGAG</u>ATGGAGG<br>GTTCGTCCAAAGGGCTGCGAAAAGGTGCTTGGACTACTGAAGAAGA<br>TAGTCTCTTGAGACAGTGCATTAATAAGTATGGAGAAGGCAAATGG<br>CACCAAGTTCCTGTAAGAGCTGGGCTAAACCGGTGCAGGAAAAGTT<br>GTAGATTAAGATGGTTGAACTATTTGAAGCCAAGTATCAAGAGAGG<br>AAAACTTAGCTCTGATGAAGTCGATCTTCTTCTTCGCCTTCATAGGCT<br>TCTAGGGAATAGGTGGTCTTTAATTGCTGGAAGATTACCTGGTCGGA<br>CCGCAAATGACGTCAAGAATTACTGGAACACTCATCTGAGTAAGAA<br>ACATGAACCGTGTTGTAAGATAAAGATGAAAAAGAGAGACATTACG<br>CCCCATTCCTACAACACCGGCACTAAAAAACAATGTTTATAAGCCTCG<br>ACCTCGATCCTTCACAGTTAACAACGACTGCAACCATCTCAATGCCC<br>CACCAAAAGTTGACGTTAATCCTCCATGCCTTGGACTTAACATCAAT<br>AATGTTTGTGACAATAGTATCATATACAACAAAGATAAGAAGAAAG<br>ACCAACTAGTGAATAATTTGATTGATGGAGATAATATGTGGTTAGAG<br>AAATTCCTAGAGGAAAGCCAAGAGGTAGATATTTTGGTTCCTGAAGC<br>GACGACAACAGAAAAGGGGGACACCTTGGCTTTTGACGTTGATCAA<br>CTTTGGAGTCTTTTCGATGGAGAGACTGTGAAATTTGATTAGT<u>CTAG<br>A</u>AATAACAGAGGGCGCGCGAGCGGTGGCTACTGATCGCCTATGAGT<br>TCTGTGATTCTACTTGTAATTTCAGAAGTGTTTTCAGTGTCTTGTTTTC<br>TGGAAGTCCGTCTGGTTTTTAGTAACTTTTAGCTCAAAAATGTGTCTG<br>TACGATGGTATTTGTATGTTTGTGGGTCTTTTACATATACGCTTGTAA<br>TCGATCAATGTAGAATGCTGTGTGCCTTTTCCGTCAACAGCTTATTTA<br>GTGTTTACTCTGTATACGTATATCTAATATATAGTACTGATTCTTTCA<br>TCTGGTGATTTGTTTTCCTAAAGAGATTATTATCATAGCTTTAATTGA<br>ATGATACAAAGAGGTGTTGCCTGGCTTCACCAGAGCAGAAATTTTCA<br>TTGATATAGGGTACAAATGTCATTCACATAATGTTAAGAGATAAGTT<br>TTTCAATGTCCTCAAGAGCCCACCAAGAGTTTCTTCCGGGAATTGCT<br>TAAATTATCTTAAATTTAAATTGTA<u>GTTTAAAC</u> |
| 19 | pPR5:<br>NtAN1:<br>HSPT | <u>CCCGGG</u>TTTAGTGGACATTTTAGTAAGAAGATTGGTTGTTGGATGTA<br>TATATTGACATTTGAGTTAAGGGGGTTTATATAGTGGTATGGCGGCT<br>TTTTGCACTGTGGACATTAATATTTTGGCACTTGATATATTATTATTA<br>TTATTATATTAATATAGGAATAATCATGAAAGATGCTTTGGTAAAGG<br>TAGAGCTAGGCGGCTAAATGTGAAGGCCTGACAAGTGATAATTTATT<br>ATGCACACACATATATAGAAGCTAAATAATTTATTTGGTGATAATGA<br>TCACGAGCAAACTTTGTCACGCTAATATGTCCACTTGAAATAATACG<br>CCACCGATAATATCCACTATAAAACATGGACTGAACTAGAAATTCG<br>GGTTGAGCCCAATAGCTTTTGTTCAAATAATATATTTATGTTAAGTGT<br>TTTATTAAGTATGTACAAATATTAAATTTAGAATACAGTTATAATTAT<br>AAGCACTTGGAAACGTTGTTTTAAGATTCAAAACCAATATAATTAAA<br>ATACTTGCTCCGCTCCGTAAAACAAGATATACAGCCTTCAAGCAATA<br>CATTTTGTTCAGTCGGGTCATATTCCACTATTTTTCACTACTTTTACTT<br>CACGTTTTTTACAAGCTATTTATCCAGTACATCCTTTGAACTGAAATC<br>ATAATTATTTACCTGCAATTATTACTATAGGTATCCCTAGCTACTTAA<br>TTTCATTTAAAATTAGCTATAACTAGCACTAGTTTATGGAATTTGGA<br>GATGATTGTGCGCACAAGCTAGCTTTGTGGAATTTGGAGACGAGCTT<br>TGCAGCCGGTTTCAATCTTTCGACTACATTTGCTATTGGAGTCACTGA<br>GTAAAAATACTTATTTTCAGTCGGCTGTGTTTACACTAAATTTATGAAT<br>GCATGCCATTAGTCTTCACACACACATATATAATATATAGCTTAATA<br>ACCCTGGTTAAATGATACAATATATTATCAGTTTAATGAATAAATAT<br>TTGCCTAATTATTACCCACTCTGCATTACCAAGTCTTCATAAATGAA<br>AGATTTATAATCAAGAAATTAGATCAAGAATTCTAACATATATCAAG<br>TGGATTAACTAATAGAAAACGTATATGCATCTACAGTTAAAAAAAG<br>GTTAAGCAAATGGGGTGGGTTGGATCTTCAACGTTGTGCAATTCGGA<br>ATTCCCCAATTTATTGACCATTTACAGATCAAGTTCACATATTAGTTA<br>GTCTGATTTTGACTTAACGTTTGTTACAATTCTCTTTTTCATTTTTAAG<br>GAAAAAAAAGTTCTGCATCCGATAATTGGAGATCAAATATGTAATAC |

TABLE 1-continued

Nucleotide and protein sequences

| SEQ ID NO: | Sequence Description | Nucleotide Sequence |
|---|---|---|
| | | AAGTTAGCTTCTATGTTCATAATAATTGTCAGGCTCTTACGAATAGC<br>CGCCAGGCATCTTTCAAGATTATTCCTTTATTAATATAATATATCAAG<br>TGCCAATATATATATGATTATTGTCTATAGTGCAAAAAGCCGCCACA<br>CCCCTATATAAACCCCCTTAACTCAAATGTCAATATATCAACACCAA<br>TTTTCTTACTAAAAAGTCCACTAAA<u>CTCGAG</u>ATGACGGAGATACCGC<br>CTAACAGCCAGATGAAAACCATGTTGCAGAAGGCAGTGCAATCGGT<br>TCAATGGACATATACTCTTTTCTGGCAATTATGTCCCCAACAAGGGG<br>CGTTAGTGTGGAGAGATGGATATTACAATGGGCTATAAAGACTAG<br>AAAGACAGTGCAGCCAATGGAAGTTAGCGCTGAGGAAGCTTCTCTT<br>CACAGAAGCCAACAGCTTAGAGAACTTTACGAATCACTTTCCGCCGG<br>CGAGTCAAATCAGCCAGCGAGAAGGCCGTCGGCAGCTTTGTCACCG<br>GAGGCACTTGACGGAGTCCGAGTGGTTTTATCTCATGTGTGTTTCTTTC<br>TCTTTTCCTCCTGGCATCGGATTACCTGGCAAGGCTTATTCGAAGAA<br>ACATCACATATGGATCATGGGCGCAAACGAGGTTGATAGCAAAGTC<br>TTCTGTAGAGCTATTCTTGCCAAGAGCGCCCGCATACAGACGGTCGT<br>TGGTATTCCTCTCTTGGATGGTGTACTGGAACTGGGAACTACAGAAA<br>GGGTTCAAGAAGAGATTGGATTCATAAACCATGTAAAGAGCTTTTTC<br>ACTGAGCAACAACAACCTCAGCTACCAAAGCCAGCCTTATCTGAGC<br>ACTCCACTTCCAATCCCACCACCTTTTCCGAGCCACATTTTTACTCCG<br>GCAATACTTCGCCATCTGCTAATGTTGATATTGCGCATCAAGATGGC<br>GGAGCTGCCGGCGAAGAAGATGAGGAGGAGGAAGAAGAAGAAGAT<br>GATGATGAAGCCGAGTTGGACTCGGATAGTATAGCGATTCAAAGCG<br>CGGCTAATCCTATTGCCGTTGAGGCTAGTGAACTCATGCAGCTTGAT<br>GTGTCCGAGGCTATACAGCTCGGCTCGCCCGATGATGACTCTGATAA<br>TATGGACTCTGATTTTCATTTGGTTGGCGCTGGAAACACGGCTCATG<br>ACTACCAGCGCCAAGCTGACTCTTTCAAAGCCGAGACCGCCATTAGC<br>TGGCCGCACTTCCAAGACCTTCAACAATTACCAGGTGGCTCTAGTTA<br>TGATGAATTATCACAAGAAGACACACACTATTCTCAAACAGTGTCAA<br>CCATTCTCGAACACCGAAGCTCCAAATTTTCCTCTACAACAATGGGC<br>TGTATTTCTCATGACTCGGCCCAATCTGCCTTCACATTGTGCCCTAGC<br>ACCACCGTCTGCAGCCCGAATCCCGCCCACTGCCGCCACGACGACTC<br>ACTTGTCGACGGTGGCGGCGCCTCCCAGTGGCTGCTCAAAAGCATAC<br>TCTTCACTGTCCCATTTCTTCACACTAAATACCAATCTGAAGCTTCTC<br>CAAAGTCACGTGACGTCGCCACTGTTGATTCCTCCAGTACTGCTTCT<br>CGCTTTCGCAAAGGCTGTAGTATAACGTCGCAAGAAGAGCCAAGTG<br>GAAACCATGTACTTGCAGAACGACGTCGTAGAGAGAAGCTAAATGA<br>GCGTTTTATCATATTAAGGTCTCTTGTACCTTTTGTAACGAAAATGGA<br>CAAAGCCTCCATTTTGGGTGACACCATAGAGTATGTCAAGCAGTTAC<br>GTAAGAAAGTTCAGGATCTTGAAGCTCGTGCTCGCGACACGGAGCA<br>CTCCAGAGATGCAGATAAAAAAGGTGGCACAGCTACAGTGAAGGTG<br>TTGCAAGGAAGGGGTAAGAGGAGAATGAATACGGTAGATGGAAGTG<br>TTGGTGGAGGGCAGGCAACGATAACGGCGTCCCCACCGTCAACGAC<br>GGAAAATGAGGAGGTTGTGCAAGTACAAGTATCAATTATCGAAAGC<br>GATGCATTGGTGGAGCTCCGGTGTCCGTACAAAGAGGGGTTGCTGTT<br>AAATGTAATGCAGATGCTAAGGGAACTCAAAGTGGAAGTTGTAGCC<br>ATTCAATCAGCTCTTAATAATGGCGTCTTCTTGGCTGAGTTAAGAGC<br>TAAGGTAAAAGAGAATATATGTGGAAGGAAAGCAAGCATTTTGGAA<br>GTAAAAAGGTCAATACATCAGATAATCCCTAGAGATTAA<u>TCTAGA</u>A<br>ATAACAGAGGGCGCGCGAGCGGTGGCTACTGATCGCCTATGAGTTC<br>TGTGATTCTACTTGTAATTTCAGAAGTGTTTTCAGTGTCTTGTTTTCT<br>GGAAGTCCGTCTGGTTTTTAGTAACTTTTAGCTCAAAAATGTGTCTGT<br>ACGATGGTATTTGTATGTTTGTGGGTCTTTTACATATACGCTTGTAAT<br>CGATCAATGTAGAATGCTGTGTGCCTTTTCCGTCAACAGCTTATTTAG<br>TGTTTACTCTGTATACGTATATCTAATATATAGTACTGATTCTTTCAT<br>CTGGTGATTTGTTTCCTAAAGAGATTATTATCATAGCTTTAATTGAA<br>TGATACAAAGAGGTGTTGCCTGGCTTCACCAGAGCAGAAATTTTCAT<br>TGATATAGGGTACAAATGTCATTCACATAATGTTAAGAGATAAGTTT<br>TTCAATGTCCTCAAGAGCCCACCAAGAGTTTCTTCCGGGAATTGCTT<br>AAATTATCTTAAATTTAAATTGTA<u>GTTTAAAC</u> |
| 20 | pPRP:<br>NtAN1:<br>HSPT | <u>CCCGGG</u>ACCTCTTCCTTCTCTCTATCTCCATTTTTTATTTATGTTTTAC<br>TAAATTACTTTTATTTCATAACAACATGTCTTGTTCATGTTTTACTAA<br>GTTGCTTTTATTTCATAACAGCATCATAATAAAATACAGGAATTTTC<br>AAGCGAAGCAGAGTCACTTCCAAAAGTAGAAACACTTAGAACTTCT<br>GCTAAGGGTAATTAACAACTTTTGGTCCTTTAGGAGGCACAATATAC<br>TAGACGAAGAATTGAACTTGATCTTACTTACGGCAAAGGCTAATAAT<br>AGCATACGTTAGTGAACTACAACGCCAACTAAAAAGAAAAAAGAA<br>AATAATTAAGACCAGTAAATATGCATGTTCACTCTCAAATATTGAGG<br>GGAAAAAAACCGAGAATCTAATTATCTACAAATGTTCATTCATTAGG<br>GTAGTAGGAAAATTTTAATTTTATCTTAATTTGAACCAACTACAATA<br>TTTTATTTTAAAACAAATAAAATTGGAATAGCACCGGTTTTTTATTT<br>TATATTTTTTGGGTATCCGAAAGTGTATGGGCGCTAGGAACTACCTC<br>CGTCTTTACTTCTTTTGTTGCTAGTAATAGGAACTCCTTTAATGTTTT<br>GACAGTGAAAATACTAGTATATTAATTAACTAATTTGTCTCTATACC<br>ATGATTTATAATATTACGGTTGAAGTGATAGCTCATGGAAGAGGAAG |

TABLE 1-continued

Nucleotide and protein sequences

| SEQ ID NO: | Sequence Description | Nucleotide Sequence |
|---|---|---|
|  |  | CACTGATGGTGTGAAAATATTTACACAATCAGATCATTTATTATATT<br>ATTATGGATAAATTTCTCGATAAGTATTAATTGATAAGTATTCGGAT<br>AAAAGTAGGTTATAATCTAATTTTTTTTATACTATTAGTATTAGTATA<br>TATAATTCGTTACATTTACATATACATCTTCTATGTTTTATTCATAGA<br>TGTAGACACTGGCGAGGAACATGGCAAATTGCAACACCTTATGTGG<br>CTAATAATGCATTCAAGAGAATTTGAGTAAATATCTAATTTGCTTGT<br>GCTGCCAGCTAAAACCTTGGGGACACATGGTTTCTAGAACTTAATTT<br>CTTTTAATATTTCTCTTTACTCTAATTCATACTTTTGCATCCTATATAAA<br>CCCACCTTCTATAACCTTTGCAATATCAAACAAAGCAACAATCTACT<br>TATAACTACTAAAGTTGATAGTTATATCAATCATTAAGAAATTTTAG<br>ACTCTTAGAA<u>CTCGAG</u>ATGACGGAGATACCGCCTAACAGCCAGATG<br>AAAACCATGTTGCAGAAGGCAGTGCAATCGGTTCAATGGACATATA<br>CTCTTTTCTGGCAATTATGTCCCCAACAAGGGGCGTTAGTGTGGAGA<br>GATGGATATTACAATGGGCTATAAAGACTAGAAAGACAGTGCAGC<br>CAATGGAAGTTAGCGCTGAGGAAGCTTCTCTTCACAGAAGCCAACA<br>GCTTAGAGAACTTTACGAATCACTTTCCGCCGGCGAGTCAAATCAGC<br>CAGCGAGAAGGCCGTCGGCAGCTTTGTCACCGGAGGACTTGACGGA<br>GTCCGAGTGGTTTTATCTCATGTGTGTTTCTTTCTCTTTTCCTCCTGGC<br>ATCGGATTACCTGGCAAGGCTTATTCGAAGAAACATCACATATGGAT<br>CATGGGCGCAAACGAGGTTGATAGCAAAGTCTTCTGTAGAGCTATTC<br>TTGCCAAGAGCGCCCGCATACAGACGGTCGTTGGTATTCCTCTCTTG<br>GATGGTGTACTGGAACTGGGAACTACAGAAAGGGTTCAAGAAGAGA<br>TTGGATTCATAAACCATGTAAAGAGCTTTTTCACTGAGCAACAACAA<br>CCTCAGCTACCAAAGCCAGCCTTATCTGAGCACTCCACTTCCAATCC<br>CACCACCTTTTCCGAGCCACATTTTTACTCCGGCAATACTTCGCCATC<br>TGCTAATGTTGATATTGCGCATCAAGATGGCGGAGCTGCCGGCGAA<br>GAAGATGAGGAGGAGGAAGAAGAAGAAGATGATGATGAAGCCGAG<br>TTGGACTCGGATAGTATAGCGATTCAAAGCGCGGCTAATCCTATTGC<br>CGTTGAGGCTAGTGAACTCATGCAGCTTGATGTGTCCGAGGCTATAC<br>AGCTCGGCTCGCCCGATGATGACTCTGATAATATGGACTCTGATTTT<br>CATTTGGTTGGCGCTGGAAACACGGCTCATGACTACCAGCGCCAAGC<br>TGACTCTTTCAAAGCCGAGACCGCCATTAGCTGGCCGCACTTCCAAG<br>ACCTTCAACAATTACCAGGTGGCTCTAGTTATGATGAATTATCACAA<br>GAAGACACACACTATTCTCAAACAGTGTCAACCATTCTCGAACACCG<br>AAGCTCCAAATTTTCCTCTACAACAATGGGCTGTATTTCTCATGACTC<br>GGCCCAATCTGCCTTCACATTGTGCCCTAGCACCACCGTCTGCAGCC<br>CGAATCCCGCCCACTGCCGCCACGACGACTCACTTGTCGACGGTGGC<br>GGCGCCTCCCAGTGGCTGCTCAAAAGCATACTCTTCACTGTCCCATT<br>TCTTCACACTAAATACCAATCTGAAGCTTCTCCAAAGTCACGTGACG<br>TCGCCACTGTTGATTCCTCCAGTACTGCTTCTCGCTTTCGCAAAGGCT<br>GTAGTATAACGTCGCAAGAAGAGCCAAGTGGAAACCATGTACTTGC<br>AGAACGACGTCGTAGAGAGAAGCTAAATGAGCGTTTTATCATATTA<br>AGGTCTCTTGTACCTTTTGTAACGAAAATGGACAAAGCCTCCATTTT<br>GGGTGACACCATAGAGTATGTCAAGCAGTTACGTAAGAAAGTTCAG<br>GATCTTGAAGCTCGTGCTCGCGACACGGAGCACTCCAGAGATGCAG<br>ATAAAAAAGGTGGCACAGCTACAGTGAAGGTGTTGCAAGGAAGGGG<br>TAAGAGGAGAATGAATACGGTAGATGGAAGTGTTGGTGGAGGGCAG<br>GCAACGATAACGGCGTCCCCACCGTCAACGACGGAAAATGAGGAGG<br>TTGTGCAAGTACAAGTATCAATTATCGAAAGCGATGCATTGGTGGAG<br>CTCCGGTGTCCGTACAAAGAGGGGTTGCTGTTAAATGTAATGCAGAT<br>GCTAAGGGAACTCAAAGTGGAAGTTGTAGCCATTCAATCAGCTCTTA<br>ATAATGGCGTCTTCTTGGCTGAGTTAAGAGCTAAGGTAAAAGAGAAT<br>ATATGTGGAAGGAAAGCAAGCATTTTGGAAGTAAAAAGGTCAATAC<br>ATCAGATAATCCCTAGAGATTAA<u>TCTAGA</u>AATAACAGAGGGCGCGC<br>GAGCGGTGGCTACTGATCGCCTATGAGTTCTGTGATTCTACTTGTAA<br>TTTCAGAAGTGTTTTCAGTGTCTTGTTTTCTGGAAGTCCGTCTGGTTT<br>TTAGTAACTTTTAGCTCAAAAATGTGTCTGTACGATGGTATTTGTATG<br>TTTGTGGGTCTTTTACATATACGCTTGTAATCGATCAATGTAGAATGC<br>TGTGTGCCTTTTCCGTCAACAGCTTATTTAGTGTTTACTCTGTATACG<br>TATATCTAATATATAGTACTGATTCTTTCATCGGTGATTTGTTTTCCT<br>AAAGAGATTATTATCATAGCTTTAATTGAATGATACAAAGAGGTGTT<br>GCCTGGCTTCACCAGAGCAGAAATTTTCATTGATATAGGGTACAAAT<br>GTCATTCACATAATGTTAAGAGATAAGTTTTTCAATGTCCTCAAGAG<br>CCCACCAAGAGTTTCTTCCGGGAATTGCTTAAATTATCTTAAATTTAA<br>ATTGTA<u>GTTTAAAC</u> |
| 21 | pAD:<br>NtAN1:<br>HSPT | <u>CCCGGG</u>ACTAAAAGTGAATCCTTCCCCACAAAAAACTTAGTTTTGAA<br>TGCACGAGATTCTACAAATAAAAAGAAAGAAAGAAATAAAAGGTAT<br>AATTAGAGCGCACGTGAAATAAAAATACTATCAATTTGAATGAAAA<br>CTTGAAAATAAAATAAAAAAATAGAAGTATCATGTTTTGAAGGATTCA<br>ATTTTAGTATTATTTTAATTTATATATATGATTATTTTGTCAGGTGGG<br>TCATTCCTGTTTTAATTGAATTATTATTTATTAGACGAAAAAAAAAT<br>CTTGGAATAAGAAATCTGGTGACTATTTATGAAATTTACCCTTCAA<br>TTGTATGTGTAAAACACTTATATCCAAGTTTATAAGATTTTTAGCAA<br>AATAAAATACTTCAAATTTTTTAAGCTATTCGCTTGAAAATAAAATT |

TABLE 1-continued

Nucleotide and protein sequences

| SEQ ID NO: | Sequence Description | Nucleotide Sequence |
|---|---|---|
| | | AAGACATGTTAACATAGATTACTTTCTCTATTACCAAATTCTTGTGTT ACTTTCTTAAAGTTGAGTCGAGTAGTATTGATAAATAAAATAGTCAA TATGTTTTCCACTGTTCTGAACAAAAATAGTTTTTTTTTTTTTTTTT TTATGTATTTTCATAATTTTGAATTATTTAAATTTGAGTTTTGGAAGA TGAATTCACGTTTGACCAAAAAGGAGAGATGAATCGTGTCTATCCAA AAATAAAAACAAAATGGGCGTGTAAAAAATAACATTTTTTTGGTGG GTCAAAACATCGTTAGGTTTAATAAATCAAATCGATTTTTCTCTTGA AATATTACCACCACCTTTTTCTTATTACTCGACAAAAACTCAAACAG TAACACAAAACAAACAGCCAAAAACCGGTTTCGAAAACCCAGCGAC CAAAACATGGAAATGGTTTTACTTTGGCCTGTTGTATTCAACTTTTCG ATTTCACGATTCTATATTTTCAGGTATAAATACCCCAGCTAATGCAGT GCCACATCACACCTCAAGATATTTAACTCAGTATTCAGAAACAACAA AAGTTCTTCTCTACATAAAATTTTCCTATTTTAGTGATCAGTGAAGGA AATCAAGAAAAATAA<u>CTCGAG</u>ATGACGGAGATACCGCCTAACAGCC AGATGAAAACCATGTTGCAGAAGGCAGTGCAATCGGTTCAATGGAC ATATACTCTTTTCTGGCAATTATGTCCCCAACAAGGGGCGTTAGTGT GGAGAGATGGATATTACAATGGGGCTATAAAGACTAGAAAGACAGT GCAGCCAATGGAAGTTAGCGCTGAGGAAGCTTCTCTTCACAGAAGC CAACAGCTTAGAGAACTTTACGAATCACTTTCCGCCGGCGAGTCAAA TCAGCCAGCGAGAAGGCCGTCGGCAGCTTTGTCACCGGAGGACTTG ACGGAGTCCGAGTGGTTTTATCTCATGTGTGTTTCTTTCTCTTTTCCTC CTGGCATCGGATTACCTGGCAAGGCTTATTCGAAGAAACATCACATA TGGATCATGGGCGCAAACGAGGTTGATAGCAAAGTCTTCTGTAGAG CTATTCTTGCCAAGAGCGCCCGCATACAGACGGTCGTTGGTATTCCT CTCTTGGATGGTGTACTGGAACTGGGAACTACAGAAAGGGTTCAAG AAGAGATTGGATTCATAAACCATGTAAAGAGCTTTTTCACTGAGCAA CAACAACCTCAGCTACCAAAGCCAGCCTTATCTGAGCACTCCACTTC CAATCCCACCACCTTTTCCGAGCCACATTTTTACTCCGGCAATACTTC GCCATCTGCTAATGTTGATATTGCGCATCAAGATGGCGGAGCTGCCG GCGAAGAAGATGAGGAGGAGGAAGAAGAAGAAGATGATGATGAAG CCGAGTTGGACTCGGATAGTATAGCGATTCAAAGCGCGGCTAATCCT ATTGCCGTTGAGGCTAGTGAACTCATGCAGCTTGATGTGTCCGAGGC TATACAGCTCGGCTCGCCCGATGATGACTCTGATAATATGGACTCTG ATTTTCATTTGGTTGGCGCTGGAAACACGGCTCATGACTACCAGCGC CAAGCTGACTCTTTCAAAGCCGAGACCGCCATTAGCTGGCCGCACTT CCAAGACCTTCAACAATTACCAGGTGGCTCTAGTTATGATGAATTAT CACAAGAAGACACACACTATTCTCAAACAGTGTCAACCATTCTCGAA CACCGAAGCTCCAAATTTTCCTCTACAACAATGGGCTGTATTTCTCA TGACTCGGCCCAATCTGCCTTCACATTGTGCCCTAGCACCACCGTCT GCAGCCCGAATCCCGCCCACTGCCGCCACGACGACTCACTTGTCGAC GGTGGCGGCGCCTCCCAGTGGCTGCTCAAAAGCATACTCTTCACTGT CCCATTTCTTCACACTAAATACCAATCTGAAGCTTCTCCAAAGTCAC GTGACGTCGCCACTGTTGATTCCTCCAGTACTGCTTCTCGCTTTCGCA AAGGCTGTAGTATAACGTCGCAAGAAGAGCCAAGTGGAAACCATGT ACTTGCAGAACGACGTCGTAGAGAGAAGCTAAATGAGCGTTTTATC ATATTAAGGTCTCTTGTACCTTTTGTAACGAAAATGGACAAAGCCTC CATTTTGGGTGACACCATAGAGTATGTCAAGCAGTTACGTAAGAAAG TTCAGGATCTTGAAGCTCGTGCTCGCGACACGGAGCACTCCAGAGAT GCAGATAAAAAAGGTGGCACAGCTACAGTGAAGGTGTTGCAAGGAA GGGGTAAGAGGAGAATGAATACGGTAGATGGAAGTGTTGGTGGAGG GCAGGCAACGATAACGGCGTCCCCACCGTCAACGACGGAAAATGAG GAGGTTGTGCAAGTACAAGTATCAATTATCGAAAGCGATGCATTGGT GGAGCTCCGGTGTCCGTACAAAGAGGGGTTGCTGTTAAATGTAATGC AGATGCTAAGGGAACTCAAAGTGGAAGTTGTAGCCATTCAATCAGC TCTTAATAATGGCGTCTTCTTGGCTGAGTTAAGAGCTAAGGTAAAAG AGAATATATGTGGAAGGAAAGCAAGCATTTTGGAAGTAAAAAGGTC AATACATCAGATAATCCCTAGAGATTAA<u>TCTAGA</u>AATAACAGAGGG CGCGCGAGCGGTGGCTACTGATCGCCTATGAGTTCTGTGATTCTACT TGTAATTTCAGAAGTGTTTTCAGTGTCTTGTTTTCTGGAAGTCCGTCT GGTTTTTAGTAACTTTTAGCTCAAAAATGTGTCTGTACGATGGTATTT GTATGTTTGTGGGTCTTTTACATATACGCTTGTAATCGATCAATGTAG AATGCTGTGTGCCTTTTCCGTCAACAGCTTATTTAGTGTTTACTCTGT ATACGTATATCTAATATATAGTACTGATTCTTTCATCTGGTGATTTGT TTTCCTAAAGAGATTATTATCATAGCTTTAATTGAATGATACAAAGA GGTGTTGCCTGGCTTCACCAGAGCAGAAATTTTCATTGATATAGGGT ACAAATGTCATTCACATAATGTTAAGAGATAAGTTTTTCAATGTCCT CAAGAGCCCACCAAGAGTTTCTTCCGGGAATTGCTTAAATTATCTTA AATTTAAATTGTA<u>GTTTAAAC</u> |
| 22 | pEX3-like: NtAN1: HSPT | <u>CCCGGG</u>CATTGGAGTTTTATTAACCCGCCTCGATAGAGGCGGGGCTA TACAATCTGATAAGGTGATCGAGGATGAAAGGGAGCCCCTCGACTT TGCTCACGAAGAATCGGAGCAGAATAACAATTTGCCAAAAGGAAGG ATGGATTTGGCCTAGGGTTATTTGGTATTGACGGCAAAAATTAACGA TGACGGGGTCGAGGGGGCCCAACGTGAAAGGGTAAGTGTAAACACT TAGAAACCCTTCCACATGAGTGGTGTATATCTTTTTCGGGGGTCGGGA |

TABLE 1-continued

Nucleotide and protein sequences

| SEQ ID NO: | Sequence Description | Nucleotide Sequence |
|---|---|---|
| | | TCACCACCTCTTTGCCTTCCCAGTTGCGGTCTTTCTTTACCTGCTTAA
GGTATCCCTCAGTTATTGAGCATATATACCTCGACATTGGCTCGCAT
CGATCAGGAATCGACGAGGCTTTATCGGTCTTAAAATCGGAGTTTAG
CACGCACCCCCAAGAATGCATTCCTCAAGACGGGGATCCACCAGCG
TTTTTCCGTCGGTCGGTTGAGAAGATGAAGCAACTTCTTTTTGTGGTA
CCATTTTCGATGTTTTTGCCATTCTTGTGTAAGTTTGAAGAAGAGGAA
GATAATAGGACTTGACATTTGAGACATGATTAACAGCAAAGCCTGA
AGATTTGTAAAAGGGACGAACTTAAGAGATGTAAAAGCTTTAGATA
TTAGAAGGAAGTGAAAGTAAAGTTTGAATCAATGAGGAAGTGATCT
ATTTATTGGACTCACGGCGACAGTTCAAAGGCACTAGTGGCCGACA
ACCAACTAACACTCATTAATGACTTGGAAAACTGTACTGACGGGAC
GTTTTGGTCACTCCCGTCGCTTACGTCATGAGGATGTCGTCATTACA
GGTCGAGATAGAAAATTGAAGGCTCAATTCGTTTCTTGTCATTTCAC
TCCAAAAAACGAGGAGACTATCTGTATACGGTTAAAATCGGGCCCA
CCCGATTTTACTATTTGACCGAGACTAGGAGGTTGCATCGAAGAATG
GCCTCGTAACAGAACAGACTAAATCACGAGGATAAGGTACTGAGTT
CATAATCGAGGTACCGGTCGAGATCGAGGCTAGTAGTGATCGAAAC
CAAATGAGACAGACATCGAGCAAGATCGAAGATAGCACAATAACAG
AAAGGCGAGATATCCACGACTGGTCGAGGATCATGGCATAAATCTC
GAAACGAATCAAATTAGAAACAGTTAATTAGCTAATCATGAATTTAC
TTCTGTAATTAGAATTATACCATAAGTGAAATTCCTCTACTATTTATA
GGGGGTTCTAATCATTTGGAAGACACATGGTTCACAGATATCAAGA
AATGTAATTCTCTTTCTCGTTTATACTATTGTTCATCAGCTTGTTATAT
TTTAATTGTTCTTACATCAACCAGTTCGAGGGTATCCAAACTTGAGG
GCTGAGTTCCATTCTAACACAAGTTTGCTTTACTTTATAGTTTATTTC
TATTATTAATCTTCATATTTATCAATTGGTATTAAGTGAAATTACGTG
TACTTAGAACAATATTATAAATTTAATTGTTATCCAATTTTAAGGATA
AATAAGAACATTCATTAAAGTTAAAAGAGACATATAAAAAAAGCTA
TTGCTCAGATTTCTGCAACTGAAATCGTGCAAAGTTGAGGCATCCAC
ACTTGTTTTTCAAAGCTTCGGTACTGTATACAAAGATAGAAAGTAAA
GGAGACTTTTCTCTTTAAATTATTGCATCAGAAATAGTATAGCTGCC
ATAATAGTTTATTAATTCCAGCTATGCTTAGCTTGCAGCCTCTATCGA
ACAAAAAAAGTATACCAACTCAAGTCAATTTGAGCCGACAACATGA
CAAAACCAAATCAAAATGCATACTCTAGCTTTTTTACTTTGGTAGGT
TTTAAGTAATCTAGTGAGACTTTTACCTTCATTCATGAAAATCTTGGA
AAGGGTAATTGTATAATTGAAAGCTATATAAAGGGGTCGGAGTGAA
GCTTAAGAGGACAACAACTTTTCTCATTTGTTTCAAAG<u>CTCGAG</u>ATG
ACGGAGATACCGCCTAACAGCCAGATGAAAACCATGTTGCAGAAGG
CAGTGCAATCGGTTCAATGGACATATACTCTTTTCTGGCAATTATGTC
CCCAACAAGGGGCGTTAGTGTGGAGAGATGGATATTACAATGGGGC
TATAAAGACTAGAAAGACAGTGCAGCCAATGGAAGTTAGCGCTGAG
GAAGCTTCTCTTCACAGAAGCCAACAGCTTAGAGAACTTTACGAATC
ACTTTCCGCCGGCGAGTCAAATCAGCCAGCGAGAAGGCCGTCGGCA
GCTTTGTCACCGGAGGACTTGACGGAGTCCGAGTGGTTTTATCTCAT
GTGTGTTTCTTTCTCTTTTCCTCCTGGCATCGATTACCTGGCAAGGC
TTATTCGAAGAAACATCACATATGGATCATGGGCGCAAACGAGGTT
GATAGCAAAGTCTTCTGTAGAGCTATTCTTGCCAAGAGCGCCCGCAT
ACAGACGGTCGTTGGTATTCCTCTCTTGGATGGTGTACTGGAACTGG
GAACTACAGAAAGGGTTCAAGAAGAGATTGGATTCATAAACCATGT
AAAGAGCTTTTTCACTGAGCAACAACAACCTCAGCTACCAAAGCCA
GCCTTATCTGAGCACTCCACTTCCAATCCCACCACCTTTTCCGAGCCA
CATTTTTACTCCGGCAATACTTCGCCATCTGCTAATGTTGATATTGCG
CATCAAGATGGCGGAGCTGCCGGCGAAGAAGATGAGGAGGAGGAA
GAAGAAGAAGATGATGATGAAGCCGAGTTGGACTCGGATAGTATAG
CGATTCAAAGCGCGGCTAATCCTATTGCCGTTGAGGCTAGTGAACTC
ATGCAGCTTGATGTGTCCGAGGCTATACAGCTCGGCTCGCCCGATGA
TGACTCTGATAATATGGACTCTGATTTTCATTTGGTTGGCGCTGGAA
ACACGGCTCATGACTACCAGCGCCAAGCTGACTCTTTCAAAGCCGAG
ACCGCCATTAGCTGGCCGCACTTCCAAGACCTTCAACAATTACCAGG
TGGCTCTAGTTATGATGAATTATCACAAGAAGACACACACTATTCTC
AAACAGTGTCAACCATTCTCGAACACCGAAGCTCCAAATTTTCCTCT
ACAACAATGGGCTGTATTTCTCATGACTCGGCCCAATCTGCCTTCAC
ATTGTGCCCTAGCACCACCGTCTGCAGCCCGAATCCCGCCCACTGCC
GCCACGACGACTCACTTGTCGACGGTGGCGGCGCCTCCCAGTGGCTG
CTCAAAAGCATACTCTTCACTGTCCCATTTCTTCACACTAAATACCA
ATCTGAAGCTTCTCCAAAGTCACGTGACGTCGCCACTGTTGATTCCT
CCAGTACTGCTTCTCGCTTTCGCAAAGGCTGTAGTATAACGTCGCAA
GAAGAGCCAAGTGGAAACCATGTACTTGCAGAACGACGTCGTAGAG
AGAAGCTAAATGAGCGTTTTATCATATTAAGGTCTCTTGTACCTTTTG
TAACGAAAATGGACAAAGCCTCCATTTTGGGTGACACCATAGAGTA
TGTCAAGCAGTTACGTAAGAAAGTTCAGGATCTTGAAGCTCGTGCTC
GCGACACGGAGCACTCCAGAGATGCAGATAAAAAAGGTGGCACAGC
TACAGTGAAGGTGTTGCAAGGAAGGGGTAAGAGGAGAATGAATACG
GTAGATGAAGTGTTGGTGGAGGGCAGGCAACGATAACGGCGTCCC
CACCGTCAACGACGGAAAATGAGGAGGTTGTGCAAGTACAAGTATC |

TABLE 1-continued

Nucleotide and protein sequences

| SEQ ID NO: | Sequence Description | Nucleotide Sequence |
|---|---|---|
|  |  | AATTATCGAAAGCGATGCATTGGTGGAGCTCCGGTGTCCGTACAAA<br>GAGGGGTTGCTGTTAAATGTAATGCAGATGCTAAGGGAACTCAAAG<br>TGGAAGTTGTAGCCATTCAATCAGCTCTTAATAATGGCGTCTTCTTG<br>GCTGAGTTAAGAGCTAAGGTAAAAGAGAATATATGTGGAAGGAAAG<br>CAAGCATTTTGGAAGTAAAAAGGTCAATACATCAGATAATCCCTAG<br>AGATTAA<u>TCTAGA</u>AATAACAGAGGGCGCGCGAGCGGTGGCTACTGA<br>TCGCCTATGAGTTCTGTGATTCTACTTGTAATTTCAGAAGTGTTTTCA<br>GTGTCTTGTTTTCTGGAAGTCCGTCTGGTTTTTAGTAACTTTTAGCTC<br>AAAAATGTGTCTGTACGATGGTATTTGTATGTTTGTGGGTCTTTTACA<br>TATACGCTTGTAATCGATCAATGTAGAATGCTGTGTGCCTTTTCCGTC<br>AACAGCTTATTTAGTGTTTACTCTGTATACGTATATCTAATATATAGT<br>ACTGATTCTTTCATCTGGTGATTTGTTTTCCTAAAGAGATTATTATCA<br>TAGCTTTAATTGAATGATACAAAGAGGTGTTGCCTGGCTTCACCAGA<br>GCAGAAATTTTCATTGATATAGGGTACAAATGTCATTCACATAATGT<br>TAAGAGATAAGTTTTTCAATGTCCTCAAGAGCCCACCAAGAGTTTCT<br>TCCGGGAATTGCTTAAATTATCTTAAATTTAAATTGTA<u>GTTTAAAC</u> |
| 23 | pEX1-like:<br>NtAN1:<br>HSPT | <u>CCCGGG</u>CAGTAGGCATCAATTACTATATATTTTACAAGTAATTAAAT<br>GATAAACAAATGCAATATTTGTTTAGTTTCCATATTTCTTTTTCAAGG<br>CACTCCTTTAATTACTCATCCATTCAAATGGATCTTCTCATTTTTCAG<br>ACGGTTTTTAGGACTCCCTCTATCTCAAATTATCTATCGAGATTTTTA<br>AAAAAAAAATTGTCTCAAATTATTTTCATTTTGGAAATTTAAGATAA<br>AATTAATTATATTTTTTTCATTTACCCTTAATGGTAATTATTCTTGAAT<br>ATGGAGATAGCACATCGAGTAAATATTCAATAAAGAGAGATTATAT<br>CTTATAACATAAATAAGAGTAAAATAGTCCAAAATTCCTCATAATTA<br>ATATTTTTTAAGGGTATGTAAAAGAAAAACACGACAAATAATTTGAG<br>ACGGAGAGAATACCTTCTTTTTGACCTTTTGTAAATAAATATTAAAA<br>TATCCTCAACATTTCCTAGGTTAATTTCTCTCTCTCCCTAATAATTTC<br>AAAAAGTTATCATTGTGATACTCAAATATATTGGTCTTAGCACAATT<br>TGAGCATTGCATGTTGTATGCCTGGATCCTCCTGGGTGCCATTTTTCC<br>TTTGCTTTTGGATACCTTTTTGCAACTTTAGTCCATTGCTGGAACATG<br>ATTTTTTTGTACCTCTTGTCTGTTCCCATGATGATAAACTATGATAACT<br>AACATTTTCAGAAATATTGGATTGAATTAGATATATTTTCAATATTG<br>AGCTACAAAACTCGTTGAATATTTTGCCCTATTTGGTTGGTAATAAA<br>AGTGGGTCACATGCACAGTTTTTCTCTTGTCTTCTCTAGATTAAGCTC<br>TTTGGAAATGACCTACTGAAAATGCTACACATAAAACTCCCCCACTC<br>CTCCCCAAGTTGAGGGGTGGGAGGTTTGATTTGGACCCTTACCCTAT<br>TGTTAATATCGAAATAGATAATACAAAGGACGGGAACATAAAACCA<br>AAACCTCCGATAAAACACCAAAGTTGATGATCTAAGTTAAGTTATTG<br>ATTCTTATACGTTGATTGGAAGTGCACAATGGTCTTTGCATACTATCA<br>AAGTATGAATTGGTTCTTGAATTATATCTCTTAATATGATGTATTGTG<br>TTTAATTAATTCTCTACTATTCTCTATTTTTATAGGCTAAAAGATCCT<br>GACATGCTTCTTGAACACATGTGAAGGTTAGTTAACTATAGTCAGAA<br>GTACACAAGAATTAACTTGTACACCTATCCGTGATCGAAAAACTTAA<br>CTTGTTCTAAGCTGAACTGAGTCCTCCTATCCATGTCCGATTCTTCAC<br>TAGAAGCATTAATCATACAAGGAGAATTCAACTTAATTTACTGTATT<br>GGTTATCATTTACATAGTTTAGTTATAAAACTTTGGAGCGACACAAT<br>GATTGACACTACTAATCATGATTGAATATTAACTTCACTCGATTTATC<br>AATTTCTCATACAAGTGAATTAATTTCACTCTTTGTGATTTCAGTAGT<br>AAATGTCAAGTTTCATAGTTTTTTCTTTTTGAAATTAGTCATACATGT<br>GAATAGAACATTAATTTAAGTTAAAAGCTAGCTGCTCTGATTCTGT<br>AACTGAAATCGTGCAAAGTTGAGGCATCCACATTTGTTTTCAAAGT<br>TCCAGTACTGTCTAAAAAGATAGAAAGTAAAAGGAGACTTTTCTCTT<br>TGAATTATTGCATCAGAAATAGTATAGCTGCCATAATAGTTTATTCC<br>TTTGCTTAGCTTGCAGCCTCTATCGAACAAAAAAAGTGTACCAACTC<br>AGGTCAATTTGAGCCGACAACATGACAAAACCAAATCAAAATGCAT<br>ATATACTCTAGCTTTTTACTTTACTTTGGTAGGTTTTAAGTGAGACT<br>TTTACCTTCATTTATGAAAATCTTGAAAAGGGTAATTGTCTAAATGA<br>AAGCTATATAAAGGGGTCGTAGTGAAGCTTAAGAAGACAACAACTT<br>TTCTCATTTGTTTCAAAG<u>CTCGAG</u>ATGACGGAGATACCGCCTAACAG<br>CCAGATGAAAACCATGTTGCAGAAGGCAGTGCAATCGGTTCAATGG<br>ACATATACTCTTTTCTGGCAATTATGTCCCCAACAAGGGGCGTTAGT<br>GTGGAGAGATGGATATTACAATGGGGCTATAAAGACTAGAAAGACA<br>GTGCAGCCAATGGAAGTTAGCGCTGAGGAAGCTTCTCTTCACAGAA<br>GCCAACAGCTTAGAGAACTTTACGAATCACTTTCCGCCGGCGAGTCA<br>AATCAGCCAGCGAGAAGGCCGTCGGCAGCTTTGTCACCGGAGGACT<br>TGACGGAGTCCGAGTGGTTTTATCTCATGTGTGTTTCTTTCTCTTTTC<br>CTCCTGGCATCGGATTACCTGGCAAGGCTTATTCGAAGAAACATCAC<br>ATATGGATCATGGGCGCAAACGAGGTTGATAGCAAAGTCTTCTGTAG<br>AGCTATTCTTGCCAAGAGCGCCCGCATACAGACGGTCGTTGGTATTC<br>CTCTCTTGGATGGTGTACTGGAACTGGGAACTACAGAAAGGGTTCAA<br>GAAGAGATTGGATTCATAAACCATGTAAAGAGCTTTTTCACTGAGCA<br>ACAACAACCTCAGCTACCAAAGCCAGCCTTATCTGAGCACTCCACTT<br>CCAATCCCACCACCTTTTCCGAGCCACATTTTTACTCCGGCAATACTT<br>CGCCATCTGCTAATGTTGATATTGCGCATCAAGATGGCGGAGCTGCC |

TABLE 1-continued

Nucleotide and protein sequences

| SEQ ID NO: | Sequence Description | Nucleotide Sequence |
|---|---|---|
| | | GGCGAAGAAGATGAGGAGGAGGAAGAAGAAGAAGATGATGATGAA GCCGAGTTGGACTCGGATAGTATAGCGATTCAAAGCGCGGCTAATC CTATTGCCGTTGAGGCTAGTGAACTCATGCAGCTTGATGTGTCCGAG GCTATACAGCTCGGCTCGCCCGATGATGACTCTGATAATATGGACTC TGATTTTCATTTGGTTGGCGCTGGAAACACGGCTCATGACTACCAGC GCCAAGCTGACTCTTTCAAAGCCGAGACCGCCATTAGCTGGCCGCAC TTCCAAGACCTTCAACAATTACCAGGTGGCTCTAGTTATGATGAATT ATCACAAGAAGACACACACTATTCTCAAACAGTGTCAACCATTCTCG AACACCGAAGCTCCAAATTTTCCTCTACAACAATGGGCTGTATTTCT CATGACTCGGCCCAATCTGCCTTCACATTGTGCCCTAGCACCACCGT CTGCAGCCCGAATCCCGCCCACTGCCGCCACGACGACTCACTTGTCG ACGGTGGCGGCGCCTCCCAGTGGCTGCTCAAAAGCATACTCTTCACT GTCCCATTTCTTCACACTAAATACCAATCTGAAGCTTCTCCAAAGTC ACGTGACGTCGCCACTGTTGATTCCTCCAGTACTGCTTCTCGCTTTCG CAAAGGCTGTAGTATAACGTCGCAAGAAGAGCCAAGTGGAAACCAT GTACTTGCAGAACGACGTCGTAGAGAGAAGCTAAATGAGCGTTTTAT CATATTAAGGTCTCTTGTACCTTTTGTAACGAAAATGGACAAAGCCT CCATTTTGGGTGACACCATAGAGTATGTCAAGCAGTTACGTAAGAAA GTTCAGGATCTTGAAGCTCGTGCTCGCGACACGGAGCACTCCAGAG ATGCAGATAAAAAAGGTGGCACAGCTACAGTGAAGGTGTTGCAAGG AAGGGGTAAGAGGAGAATGAATACGGTAGATGGAAGTGTTGGTGGA GGGCAGGCAACGATAACGGCGTCCCCACCGTCAACGACGGAAAATG AGGAGGTTGTGCAAGTACAAGTATCAATTATCGAAAGCGATGCATT GGTGGAGCTCCGGTGTCCGTACAAAGAGGGGTTGCTGTTAAATGTAA TGCAGATGCTAAGGGAACTCAAAGTGGAAGTTGTAGCCATTCAATC AGCTCTTAATAATGGCGTCTTCTTGGCTGAGTTAAGAGCTAAGGTAA AAGAGAATATATGTGGAAGGAAAGCAAGCATTTTGGAAGTAAAAAG GTCAATACATCAGATAATCCCTAGAGATTAA<u>TCTAGA</u>AATAACAGA GGGCGCGCGAGCGGTGGCTACTGATCGCCTATGAGTTCTGTGATTCT ACTTGTAATTTCAGAAGTGTTTTCAGTGTCTTGTTTTCTGGAAGTCCG TCTGGTTTTTAGTAACTTTTAGCTCAAAAATGTGTCTGTACGATGGTA TTTGTATGTTTGTGGGTCTTTTACATATACGCTTGTAATCGATCAATG TAGAATGCTGTGTGCCTTTTCCGTCAACAGCTTATTTAGTGTTTACTC TGTATACGTATATCTAATATATAGTACTGATTCTTTCATCTGGTGATT TGTTTTCCTAAAGAGATTATTATCATAGCTTTAATTGAATGATACAA AGAGGTGTTGCCTGGCTTCACCAGAGCAGAAATTTTCATTGATATAG GGTACAAATGTCATTCACATAATGTTAAGAGATAAGTTTTTCAATGT CCTCAAGAGCCCACCAAGAGTTTCTTCCGGGAATTGCTTAAATTATC TTAAATTTAAATTGTA<u>GTTTAAAC</u> |
| 24 | pPR1a: NtAN1: HSPT | <u>CCCGGG</u>CTATATAAGGCCATCCGTGAATTGAATAAACTATCCAATTA TTTTCTTCCACAAAAATTTCAATTCTACTTTTAGTTATTCTTTTTAATA TTGAGCTTGCAATTCTATTTTGATTCTTCACTCATGACATGCTACGTA GAGAACCTTCAATACATCATAAGAGATGGACCAAGCAATGCATAAC TCAAATAAGTCCATACAAATTTGCTGAAAGATAAAGTTATTCTACTT TCTTTGAACCCAAATCTGATAAATCTTGACAATCAGATTTGCTACTAT GATTTCTCACTGTATCATTTGTTTTATTCTATAAAGTTAATGAGGAAT GTATTAATTATTTAAGATACCTTACTTTTTCTGATTTTTGATCTTATAG TCAAGTCGTGAGGCACAATTTGCGACCCTGATGGCGCAAACCTTTAC CTAGGGATCGTAGCACATAAACGTTTTTAAGGACTAAGATATACGAG GATGTCAATTATCATAATGTAGGGTCTAAGTTTTCATTTTTTTTTTG CATCTAATAGAGTATAATTTTTTTAATCATCACGATAACTTGATTTA CAATAATATGTACTCTGTTTACTTTTACTTGACACGTTTTGATTTTTC ACGCCCTTTAAGAAAAATGATTGAAATGCATAATTTACCATGATAC TCATATTAATTGATGCATATTTTATTGGATTTGAGAAAATGATTTGAA ATGAGTAATAAATATTGTGGGTATAACAGGAAAAAAAATTGTCTTCT CTTAACATGCATAAAGTGAAGAGTAAAAGAAAATCTATTTTTGTAT ACATGTCAAACAAAAGTGAACGGAGGAGATGACAAATTGCTAAATG GCAATAGTTACAAAATTCTTCAATTACTCTTTTTCATAACAAAACACT GGTCTCTCTTGTAAGTATTGGTCTATACTTCACCACCTAAAGCATTGG CCGAAGTCTTTTTAAGGAGTTTGGTTGTCATTTATCCATTTAAATTAA AGGGAAAATAAGTGAACGCCATTACAGCGAGATGCTTTAGGGTGCT ATTTCTTGGAAAAATAAAGTAGTTAAATCTTAAAACACCCTCGAGGA TTTCAAACTCTAGCTTCACTAAAACTTGAGCTTTCTTTTCCACTAATG TCGAAAAACGAAATAAACATAAGCTATTTACAAAAATAAAAAAATA CTCCATTTGAATCTAAAGTCAAGTCGTGATTGGGATAAGAAAATAGA AATTTATTTATACTCCAGATCAAGCCGTGATTGGAATGAGATAATAG AAAAGTATGATAGTACATGAGTAACATCAAGTTGGAAATTAAGGGA AGGAAATTAGAGAAAGAACTGAAGAATATCCAAATATTCTTTACGT CCAAATTTGATAGTTATTTAACGTCATCGAGATGACGGCCATGTTCA AGTTTTCCACAAATATTGAGAAAAGAAAGAAAGACACAAACTGTGT TTGGTATTATTATAGTTTTTCTTTTAGAGAATTGATTGTACATATAA GAAATTAATATAAGATTTAGAAATAAGATTATTAGAAAAATCAAAC ATCAAAGTATTTATTTTAAATTCTTTTTCCAATGGACATTCCCATTCT GAAAAAAAGAGATATAAAATGGAAGTAAAATTAATCAGATCGTTAA |

TABLE 1-continued

Nucleotide and protein sequences

| SEQ ID NO: | Sequence Description | Nucleotide Sequence |
|---|---|---|
| | | ATGTAGAAAATATTAATAACACTTAACCATAACCAGTCTACTTTATT<br>TAACAAAAAGCACATCTGATAGATCAAAAAAGTGTTTAACTTCATGC<br>ATTGACAATTTAAAATTATTTTGCAACATCGGGTAAAACTATTTTAC<br>AACAATTGGTAACTGCATATATAAGTTTAATATGGTAACCTAGAAAA<br>TAGGATAAATTATCTATAACAGGATATATTACATTGATATTACCATG<br>TCAAAAAATTTAGTAAGTACATGAATAATCACCGTGAAATCTTCAAG<br>ATTTCTCCTATAAATACCCTTGGTAGTAAATCTAGTTTTTCCATTCAA<br>GATACAACATTTCTCCTATAGTC<u>CTCGAG</u>ATGACGGAGATACCGCCT<br>AACAGCCAGATGAAAACCATGTTGCAGAAGGCAGTGCAATCGGTTC<br>AATGGACATATACTCTTTTCTGGCAATTATGTCCCCAACAAGGGGCG<br>TTAGTGTGGAGAGATGGATATTACAATGGGGCTATAAAGACTAGAA<br>AGACAGTGCAGCCAATGGAAGTTAGCGCTGAGGAAGCTTCTCTTCA<br>CAGAAGCCAACAGCTTAGAGAACTTTACGAATCACTTTCCGCCGGCG<br>AGTCAAATCAGCCAGCGAGAAGGCCGTCGGCAGCTTTGTCACCGGA<br>GGACTTGACGGAGTCCGAGTGGTTTTATCTCATGTGTGTTTCTTTCTC<br>TTTTCCTCCTGGCATCGGATTACCTGGCAAGGCTTATTCGAAGAAAC<br>ATCACATATGGATCATGGGCGCAAACGAGGTTGATAGCAAAGTCTT<br>CTGTAGAGCTATTCTTGCCAAGAGCGCCCGCATACAGACGGTCGTTG<br>GTATTCCTCTCTTGGATGGTGTACTGGAACTGGGAACTACAGAAAGG<br>GTTCAAGAAGAGATTGGATTCATAAACCATGTAAAGAGCTTTTTCAC<br>TGAGCAACAACAACCTCAGCTACCAAAGCCAGCCTTATCTGAGCACT<br>CCACTTCCAATCCCACCACCTTTTCCGAGCCACATTTTTACTCCGGCA<br>ATACTTCGCCATCTGCTAATGTTGATATTGCGCATCAAGATGGCGGA<br>GCTGCCGGCGAAGAAGATGAGGAGGAGGAAGAAGAAGAAGATGAT<br>GATGAAGCCGAGTTGGACTCGGATAGTATAGCGATTCAAAGCGCGG<br>CTAATCCTATTGCCGTTGAGGCTAGTGAACTCATGCAGCTTGATGTG<br>TCCGAGGCTATACAGCTCGGCTCGCCCGATGATGACTCTGATAATAT<br>GGACTCTGATTTTCATTTGGTTGGCGCTGGAAACACGGCTCATGACT<br>ACCAGCGCCAAGCTGACTCTTTCAAAGCCGAGACCGCCATTAGCTGG<br>CCGCACTTCCAAGACCTTCAACAATTACCAGGTGGCTCTAGTTATGA<br>TGAATTATCACAAGAAGACACACACTATTCTCAAACAGTGTCAACCA<br>TTCTCGAACACCGAAGCTCCAAATTTTCCTCTACAACAATGGGCTGT<br>ATTTCTCATGACTCGGCCCAATCTGCCTTCACATTGTGCCCTAGCACC<br>ACCGTCTGCAGCCCGAATCCCGCCCACTGCCGCCACGACGACTCACT<br>TGTCGACGGTGGCGGCGCCTCCCAGTGGCTGCTCAAAAGCATACTCT<br>TCACTGTCCCATTTCTTCACACTAAATACCAATCTGAAGCTTCTCCAA<br>AGTCACGTGACGTCGCCACTGTTGATTCCTCCAGTACTGCTTCTCGCT<br>TTCGCAAAGGCTGTAGTATAACGTCGCAAGAAGAGCCAAGTGGAAA<br>CCATGTACTTGCAGAACGACGTCGTAGAGAGAAGCTAAATGAGCGT<br>TTTATCATATTAAGGTCTCTTGTACCTTTTGTAACGAAAATGGACAA<br>AGCCTCCATTTTGGGTGACACCATAGAGTATGTCAAGCAGTTACGTA<br>AGAAAGTTCAGGATCTTGAAGCTCGTGCTCGCGACACGGAGCACTC<br>CAGAGATGCAGATAAAAAAGGTGGCACAGCTACAGTGAAGGTGTTG<br>CAAGGAAGGGGTAAGAGGAGAATGAATACGGTAGATGGAAGTGTTG<br>GTGGAGGGCAGGCAACGATAACGGCGTCCCCACCGTCAACGACGGA<br>AAATGAGGAGGTTGTGCAAGTACAAGTATCAATTATCGAAAGCGAT<br>GCATTGGTGGAGCTCCGGTGTCCGTACAAAGAGGGGTTGCTGTTAAA<br>TGTAATGCAGATGCTAAGGGAACTCAAAGTGGAAGTTGTAGCCATTC<br>AATCAGCTCTTAATAATGGCGTCTTCTTGGCTGAGTTAAGAGCTAAG<br>GTAAAAGAGAATATATGTGGAAGGAAAGCAAGCATTTTGGAAGTAA<br>AAAGGTCAATACATCAGATAATCCCTAGAGATTAA<u>TCTAGA</u>AATAA<br>CAGAGGGCGCGCGAGCGGTGGCTACTGATCGCCTATGAGTTCTGTG<br>ATTCTACTTGTAATTTCAGAAGTGTTTTCAGTGTCTTGTTTTCTGGAA<br>GTCCGTCTGGTTTTTAGTAACTTTTAGCTCAAAAATGTGTCTGTACGA<br>TGGTATTTGTATGTTTGTGGGTCTTTTACATATACGCTTGTAATCGAT<br>CAATGTAGAATGCTGTGTGCCTTTTCCGTCAACAGCTTATTTAGTGTT<br>TACTCTGTATACGTATATCTAATATATAGTACTGATTCTTTCATCTGG<br>TGATTTGTTTTCCTAAAGAGAATTATTATCATAGCTTTAATTGAATGAT<br>ACAAAGAGGTGTTGCCTGGCTTCACCAGAGCAGAAATTTTCATTGAT<br>ATAGGGTACAAATGTCATTCACATAATGTTAAGAGATAAGTTTTTCA<br>ATGTCCTCAAGAGCCCACCAAGAGTTTCTTCCGGGAATTGCTTAAAT<br>TATCTTAAATTTAAATTGTA<u>GTTTAAAC</u> |
| 25 | pSAHH:<br>NtAN1:<br>HSPT | <u>CCCGGG</u>ATTAATTGTAAATAAATATACTTATCATTTTCGGAGAATAT<br>CCAATATTATATATAATTTTTATACTTATGAGTTTCGGGCTAGATA<br>TTTATTCTAAGCTAAGTACTACAAATACTGTGATATAAGGCTCTAAA<br>CTTTCCTACCCTAAAAGAGTCTACGTTTTACTACGCTAAAAAGGTCT<br>ACATTTTACTACGCTAAAAAATAATCTAAACTAAACATCGCAAAAAC<br>AAACAAGTAAACATGACAATTTAACAAATAAATTTTTTGACTAATT<br>TACAAGTATATTTATACAACACTAAAATTAAATCCGGATAAAAATTA<br>ACATGCTAGTTTTGGCAAAAATAAACACAAAACTATATACAAACCA<br>TACAAATCAAATAATATTCAATATTATACAAGTTTCAACTAAAATTA<br>AATCGAAATACCTGGATTCGGAAACTAAATAAATCGGATTTTTGACT<br>TCAAAAAAGAGATTCCAGCGTACCACGACCCTCAACTATAATGTGG<br>GACCACCAATCTTCACCTTTTATGTGTCGGGGGGACCCAAAAATTTT |

TABLE 1-continued

Nucleotide and protein sequences

| SEQ ID NO: | Sequence Description | Nucleotide Sequence |
|---|---|---|

TTTTTTTTTTAAAAAACTGGGCAGATCGCTGAGGAGGGGACCAAATT
TTTTTGAAAGTTTTCGGCTGAATGAAGAAGAAGAAGAAAGGTTTAG
GGTTTTGTTTTAGGGTATGGCGCCAACAGTATTGGCGCTATGCTGAC
ACCGCCTGAAAAGTAGGGGTATGGCGCCAACACTGTTGGCGCTATG
CTGACATGTCAGTAAACTCTCTGATATGGCGCCAACTATGTTGGCGT
TATATATATTTGTGTTACTTTTCCTTTTTTACACTTATTAATGTAGTTT
GAGTCAAAAAAAACAATAATAAAGTTCCGGACTCGAGATGTAAGGG
GTTGTCAATTTTCACTTTGTCAGTCGCTAAGAGTAATTATGAATATTC
TTTTATCAATATTGGACCTCAAACTTTATCCATTGTAAGAAAAAAAA
GTTGTAAAATATTTGTGTCACTTAATTAAACGGTCGTAGTAGTTAGT
AGTAGTGACATAGTCCTTTCGTTTGATAGTATATCAAATTGGAACAA
TTTACATTTGCACCAAAGCATAAAGGGAAAGCATGAAAAAGAGAAA
GTGCAAAAGAGAAAAATACAACAACAACAAGAATATTTCAGTATAA
TTCTATAAGTAGGGTCTGGAGAGAGTAGAATACCCCTAACCTAGAA
GGGCAGGAAGAATATTAAAGTAAAAAAGATAAAAGATTACAAATAA
AATAAAAGAAAAAACAAACAAACATACAAAATTAATTTGTGCATAA
TGCTTATAGTAATTGCCAATTTGCCATGAATATCTTCCACCGGGCTAT
CTTGGTCATGTTAATCACTCTATCCTGTTTTCAAACAATTTTTACTCT
AAAAATTTGCATGTTATATTAATTGGTGGGTGAGCCAGAAATTTTAA
ACAAAAAATCAAATACGGTACACTAAAAGATTTTTTATAAAAAAG
ACGATGACCAATTTTTTCGACAAAGAATATTCACTTAAACCCTTGTT
CATACATAGCTTGGCAATTGGATTAATAATGAAAATAATACTTTAAA
TTTTGGAAAGAAAATATTATTTATTCTCCAAAAGAAACCAAGAAATT
AGATTCATCAAAAAATAATGACCACCATTAGCCCCACCTCCCAAATCT
CTATTCCTTTTAGACTTTTAACCAAATTTTCAGATCTACCAAACCCCA
ATTTATCCAATAAACTTTTCAGATCTAAAAATAAAAATATTCAGATC
TGGAACAAATCTTGACCGTCCATTTTCATCATTCATATCTATTTAATA
CCACTCACCTCCGCCCTTTACTCCTTGCAACACTCTTCTTCTCCTCTA
AAAACCCTTATAGAAGAAGAGGAAAAAGCCTTTCAAATCTCATCTC
AAACCACCTAATTTCTCTCATACTCGCTCGACCCCTCGAGATGACGG
AGATACCGCCTAACAGCCAGATGAAAACCATGTTGCAGAAGGCAGT
GCAATCGGTTCAATGGACATATACTCTTTTCTGGCAATTATGTCCCC
AACAAGGGGCGTTAGTGTGGAGAGATGGATATTACAATGGGCTAT
AAAGACTAGAAAGACAGTGCAGCCAATGGAAGTTAGCGCTGAGGAA
GCTTCTCTTCACAGAAGCCAACAGCTTAGAGAACTTTACGAATCACT
TTCCGCCGGCGAGTCAAATCAGCCAGCGAGAAGGCCGTCGGCAGCT
TTGTCACCGGAGGACTTGACGGAGTCCGAGTGGTTTTATCTCATGTG
TGTTTCTTTCTCTTTTCCTCCTGGCATCGGATTACCTGGCAAGGCTTA
TTCGAAGAAACATCACATATGGATCATGGGCGCAAACGAGGTTGAT
AGCAAAGTCTTCTGTAGAGCTATTCTTGCCAAGAGCGCCCGCATACA
GACGGTCGTTGGTATTCCTCTCTTGGATGGTGTACTGGAACTGGGAA
CTACAGAAAGGGTTCAAGAAGAGATTGGATTCATAAACCATGTAAA
GAGCTTTTTTCACTGAGCAACAACAACCTCAGCTACCAAAGCCAGCCT
TATCTGAGCACTCCACTTCCAATCCCACCACCTTTTCCGAGCCACATT
TTTACTCCGGCAATACTTCGCCATCTGCTAATGTTGATATTGCGCATC
AAGATGGCGGAGCTGCCGGCGAAGAAGATGAGGAGGAGGAAGAAG
AAGAAGATGATGATGAAGCCGAGTTGGACTCGGATAGTATAGCGAT
TCAAAGCGCGGCTAATCCTATTGCCGTTGAGGCTAGTGAACTCATGC
AGCTTGATGTGTCCGAGGCTATACAGCTCGGCTCGCCCGATGATGAC
TCTGATAATATGGACTCTGATTTTCATTTGGTTGGCGCTGGAAACAC
GGCTCATGACTACCAGCGCCAAGCTGACTCTTTCAAAGCCGAGACCG
CCATTAGCTGGCCGCACTTCCAAGACCTTCAACAATTACCAGGTGGC
TCTAGTTATGATGAATTATCACAAGAAGACACACACTATTCTCAAAC
AGTGTCAACCATTCTCGAACACCGAAGCTCCAAATTTTCCTCTACAA
CAATGGGCTGTATTTCTCATGACTCGGCCCAATCTGCCTTCACATTGT
GCCCTAGCACCACCGTCTGCAGCCCGAATCCCGCCCACTGCCGCCAC
GACGACTCACTTGTCGACGGTGGCGGCGCCTCCCAGTGGCTGCTCAA
AAGCATACTCTTCACTGTCCCATTTCTTCACACTAAATACCAATCTGA
AGCTTCTCCAAAGTCACGTGACGTCGCCACTGTTGATTCCTCCAGTA
CTGCTTCTCGCTTTCGCAAAGGCTGTAGTATAACGTCGCAAGAAGAG
CCAAGTGGAAACCATGTACTTGCAGAACGACGTCGTAGAGAGAAGC
TAAATGAGCGTTTTATCATATTAAGGTCTCTTGTACCTTTTGTAACGA
AAATGGACAAAGCCTCCATTTTGGGTGACACCATAGAGTATGTCAA
GCAGTTACGTAAGAAAGTTCAGGATCTTGAAGCTCGTGCTCGCGACA
CGGAGCACTCCAGAGATGCAGATAAAAAAGGTGGCACAGCTACAGT
GAAGGTGTTGCAAGGAAGGGGTAAGAGGAGAATGAATACGGTAGAT
GGAAGTGTTGGTGGAGGGCAGGCAACGATAACGGCGTCCCCACCGT
CAACGACGGAAAATGAGGAGGTTGTGCAAGTACAAGTATCAATTAT
CGAAAGCGATGCATTGGTGGAGCTCCGGTGTCCGTACAAAGAGGGG
TTGCTGTTAAATGTAATGCAGATGCTAAGGGAACTCAAAGTGGAAGT
TGTAGCCATTCAATCAGCTCTTAATAATGGCGTCTTCTTGGCTGAGTT
AAGAGCTAAGGTAAAAGAGAATATATGTGGAAGGAAAGCAAGCATT
TTGGAAGTAAAAAGGTCAATACATCAGATAATCCCTAGAGATTAATC
TAGAAATAACAGAGGGCGCGCGAGCGGTGGCTACTGATCGCCTATG
AGTTCTGTGATTCTACTTGTAATTTCAGAAGTGTTTTCAGTGTCTTGT

US 11,034,969 B2

TABLE 1-continued

Nucleotide and protein sequences

| SEQ ID NO: | Sequence Description | Nucleotide Sequence |
|---|---|---|
| | | TTTCTGGAAGTCCGTCTGGTTTTTAGTAACTTTTAGCTCAAAAATGTG<br>TCTGTACGATGGTATTTGTATGTTTGTGGGTCTTTTACATATACGCTT<br>GTAATCGATCAATGTAGAATGCTGTGTGCCTTTTCCGTCAACAGCTT<br>ATTTAGTGTTTACTCTGTATACGTATATCTAATATATAGTACTGATTC<br>TTTCATCTGGTGATTTGTTTTCCTAAAGAGATTATTATCATAGCTTTA<br>ATTGAATGATACAAAGAGGTGTTGCCTGGCTTCACCAGAGCAGAAA<br>TTTTCATTGATATAGGGTACAAATGTCATTCACATAATGTTAAGAGA<br>TAAGTTTTTCAATGTCCTCAAGAGCCCACCAAGAGTTTCTTCCGGGA<br>ATTGCTTAAATTATCTTAAATTTAAATTGTA<u>GTTTAAAC</u> |
| 26 | pPR5:<br>NtAN2:<br>HSP-T | <u>CCCGGG</u>TTTAGTGGACATTTTAGTAAGAAGATTGGTTGTTGGATGTA<br>TATATTGACATTTGAGTTAAGGGGGTTTATATAGTGGTATGGCGGCT<br>TTTTGCACTGTGGACATTAATATTTTGGCACTTGATATATTATTATTA<br>TTATTATATTAATATAGGAATAATCATGAAAGATGCTTTGGTAAAGG<br>TAGAGCTAGGCGGCTAAATGTGAAGGCCTGACAAGTGATAATTTATT<br>ATGCACACACATATATAGAAGCTAAATAATTTATTTGGTGATAATGA<br>TCACGAGCAAACTTTGTCACGCTAATATGTCCACTTGAAATAATACG<br>CCACCGATAATATCCACTATAAAACATGGACTGAACTAGAAATTCG<br>GGTTGAGCCCAATAGCTTTTGTTCAAATAATATATTTATGTTAAGTGT<br>TTTATTAAGTATGTACAAATATTAAATTTAGAATACAGTTATAATTAT<br>AAGCACTTGGAAACGTTGTTTTAAGATTCAAAACCAATATAATTAAA<br>ATACTTGCTCCGCTCCGTAAAACAAGATATACAGCCTTCAAGCAATA<br>CATTTTGTTCAGTCGGGTCATATTCCACTATTTTTCACTACTTTTACTT<br>CACGTTTTTTACAAGCTATTTATCCAGTACATCCTTTGAACTGAAATC<br>ATAATTATTTACCTGCAATTATTACTATAGGTATCCCTAGCTACTTAA<br>TTTCATTTAAAATTAGCTATAACTAGCACTAGTTTATGGAATTTGGA<br>GATGATTGTGCGCACAAGCTAGCTTTGTGGAATTTGGAGACGAGCTT<br>TGCAGCCGGTTTCAATCTTTCGACTACATTTGCTATTGGAGTCACTGA<br>GTAAAATACTTATTTTCAGTCGGCTGTGTTTACACTAAATTTATGAAT<br>GCATGCCATTAGTCTTCACACACACATATATAATATATAGCTTAATA<br>ACCCTGGTTAAATGATCAATATATTATCAGTTTAATGAATAAATAT<br>TTGCCTAATTATTACCCACTCTGCATTACCAAGTCTTCATAAATGAA<br>AGATTTATAATCAAGAAATTAGATCAAGAATTCTAACATATATCAAG<br>TGGATTAACTAATAGAAAACGTATATGCATCTACAGTTAAAAAAAG<br>GTTAAGCAAATGGGGTGGGTTGGATCTTCAACGTTGTGCAATTCGGA<br>ATTCCCCAATTTATTGACCATTTACAGATCAAGTTCACATATTAGTTA<br>GTCTGATTTTGACTTAACGTTTGTTACAATTCTCTTTTTCATTTTTAAG<br>GAAAAAAAAGTTCTGCATCCGATAATTGGAGATCAATATGTAATAC<br>AAGTTAGCTTCTATGTTCATAATAATTGTCAGGCTCTTACGAATAGC<br>CGCCAGGCATCTTTCAAGATTATTCCTTTATTAATATAATATATCAAG<br>TGCCAATATATATGATTATTGTCTATAGTGCAAAAAGCCGCCACA<br>CCCCTATATAAACCCCCTTAACTCAAATGTCAATATATCAACACCAA<br>TTTTCTTACTAAAAAGTCCACTAAA<u>CTCGAG</u>ATGAATATTTGTACTA<br>ATAAGTCGTCGTCAGGAGTGAAGAAAGGTGCATGGACTGAAGAAGA<br>AGATGTTCTATTGAAAAAATGCATCGAGAAATATGGAGAAGGAAAG<br>TGGCATCAAGTTCCTCTTAGAGCTGGTTTGAATAGATGCAGAAAGAG<br>CTGCAGATTAAGGTGGCTAAATTATCTAAGGCCACATATAAAGAGA<br>GGGAGACTTCTCTTTTGATGAAGTAGATCTCATTTTGAGGCTTCATAA<br>GCTGTTAGGCAACAGATGGTCACTTATTGCTGGTAGACTTCCTGGAA<br>GGACGGCAAACGATGTCAAAAACTACTGGAACAGCCATCTTCGCAA<br>GAAGTTAATTGCTCCTCATGATCAAAAGGAGAGCAAGCAAAAAGCA<br>AAGAAGATCACCATATTCAGACCTCGGCCTCGAACCTTCTCAAAGAC<br>AAATACTTGTGTTAAAAGTAACACAAATACTGTAGATAAGGATATTG<br>AAGGCAGCAGCGAAATAATTAGATTCAACGATAATTTGAAGCCAAC<br>AACTGAAGAATTGACGGATGATGGAATTCAATGGTGGGCCGATTTA<br>CTAGCTAACAATTACAACAATAATGGGATTGAGGAAGCTGATAATTC<br>ATCACCAACTTTGTTGCATGAGGAAATGCCACTTCTCAGTTGA<u>TCTA</u><br><u>GA</u>AATAACAGAGGGCGCGCGAGCGGTGGCTACTGATCGCCTATGAG<br>TTCTGTGATTCTACTTGTAATTTCAGAAGTGTTTTCAGTGTCTTGTTTT<br>CTGGAAGTCCGTCTGGTTTTTAGTAACTTTTAGCTCAAAAATGTGTCT<br>GTACGATGGTATTTGTATGTTTGTGGGTCTTTTACATATACGCTTGTA<br>ATCGATCAATGTAGAATGCTGTGTGCCTTTTCCGTCAACAGCTTATTT<br>AGTGTTTACTCTGTATACGTATATCTAATATATAGTACTGATTCTTTC<br>ATCTGGTGATTTGTTTTCCTAAAGAGATTATTATCATAGCTTTAATTG<br>AATGATACAAAGAGGTGTTGCCTGGCTTCACCAGAGCAGAAATTTTC<br>ATTGATATAGGGTACAAATGTCATTCACATAATGTTAAGAGATAAGT<br>TTTTCAATGTCCTCAAGAGCCCACCAAGAGTTTCTTCCGGGAATTGC<br>TTAAATTATCTTAAATTTAAATTGTA<u>GTTTAAAC</u> |
| 27 | pPRP:<br>NtAN2:<br>HSP-T | <u>CCCGGG</u>ACCTCTTCCTTCTCTCTATCTCCATTTTTTATTTATGTTTTAC<br>TAAATTACTTTTATTTCATAACAACATGTCTTGTTCATGTTTTACTAA<br>GTTGCTTTTATTTCATAACAGCATCATAATAAAATACAGGAATTTTC<br>AAGCGAAGCAGAGTCACTTCCAAAAGTAGAAACACTTAGAACTTCT<br>GCTAAGGGTAATTAACAACTTTTGGTCCTTTAGGAGGCACAATATAC<br>TAGACGAAGAATTGAACTTGATCTTACTTACGGCAAAGGCTAATAAT |

TABLE 1-continued

Nucleotide and protein sequences

| SEQ ID NO: | Sequence Description | Nucleotide Sequence |
|---|---|---|
| | | AGCATCACGTTAGTGAACTACAACGCCAACTAAAAAGAAAAAAGAA
AATAATTAAGACCAGTAAATATGCATGTTCACTCTCAAATATTGAGG
GGAAAAAAACCGAGAATCTAATTATCTACAAATGTTCATTCATTAGG
GTAGTAGGAAAATTTTAATTTTATCTTAATTTGAACCAACTACAATA
TTTTATTTTAAAACAAATAAAATTGGAATAGCACCGGTTTTTTTATTT
TATATTTTTGGGTATCCGAAAGTGTATGGGCGCTAGGAACTACCTC
CGTCTTTACTTCTTTTGTTGCTAGTAATAGGAACTCCTTTAATGTTTT
GACAGTGAAAATACTAGTATATTAATTAACTAATTTGTCTCTATACC
ATGATTTATAATATTACGGTTGAAGTGATAGCTCATGGAAGAGGAAG
CACTGATGGTGTGAAATATTTCACAATCAGATCATTTATTATATT
ATTATGGATAAATTTCTCGATAAGTATTAATTGATAAGTATTCGGAT
AAAAGTAGGTTATAATCTAATTTTTTTTATACTATTAGTATTAGTATA
TATAATTCGTTACATTTACATATACATCTTCTATGTTTTATTCATAGA
TGTAGACACTGGCGAGGAACATGGCAAATTGCAACACCTTATGTGG
CTAATAATGCATTCAAGAGAATTTGAGTAAATATCTAATTTGCTTGT
GCTGCCAGCTAAAACCTTGGGGACACATGGTTTCTAGAACTTAATTT
CTTTAATATTTCTCTTTACTCTAATTCATACTTTTGCATCCTATATAAA
CCCACCTTCTATAACCTTTGCAATATCAAACAAAGCAACAATCTACT
TATAACTACTAAAGTTGATAGTTATATCAATCATTAAGAAATTTTAG
ACTCTTAGAACTCGAGATGAATATTTGTACTAATAAGTCGTCGTCAG
GAGTGAAGAAAGGTGCATGGACTGAAGAAGAAGATGTTCTATTGAA
AAAATGCATCGAGAAATATGGAGAAGGAAAGTGGCATCAAGTTCCT
CTTAGAGCTGGTTTGAATAGATGCAGAAAGAGCTGCAGATTAAGGT
GGCTAAATTATCTAAGGCCACATATAAAGAGAGGGAGACTTCTCTTTT
GATGAAGTAGATCTCATTTTGAGGCTTCATAAGCTGTTAGGCAACAG
ATGGTCACTTATTGCTGGTAGACTTCCTGGAAGGACGGCAAACGATG
TCAAAACTACTGGAACAGCCATCTTCGCAAGAAGTTAATTGCTCCT
CATGATCAAAAGGAGAGCAAGCAAAAAGCAAAGAAGATCACCATA
TTCAGACCTCGGCCTCGAACCTTCTCAAAGACAAATACTTGTGTTAA
AAGTAACACAAATACTGTAGATAAGGATATTGAAGGCAGCAGCGAA
ATAATTAGATTCAACGATAATTTGAAGCCAACAACTGAAGAATTGAC
GGATGATGGAATTCAATGGTGGCCGATTTACTAGCTAACAATTACA
ACAATAATGGGATTGAGGAAGCTGATAATTCATCACCAACTTTGTTG
CATGAGGAAATGCCACTTCTCAGTTGATCTAGAATAACAGAGGGC
GCGCGAGCGGTGGCTACTGATCGCCTATGAGTTCTGTGATTCTACTT
GTAATTTCAGAAGTGTTTTCAGTGTCTTGTTTTCTGGAAGTCCGTCTG
GTTTTTAGTAACTTTTAGCTCAAAAATGTGTCTGTACGATGGTATTG
TATGTTTGTGGGTCTTTTACATATACGCTTGTAATCGATCAATGTAGA
ATGCTGTGTGCCTTTTCCGTCAACAGCTTATTAGTGTTTACTCTGTA
TACGTATATCTAATATATAGTACTGATTCTTTCATCTGGTGATTTGTT
TTCCTAAAGAGATTATTATCATAGCTTTAATTGAATGATACAAAGAG
GTGTTGCCTGGCTTCACCAGAGCAGAAATTTTCATTGATATAGGGTA
CAAATGTCATTCACATAATGTTAAGAGATAAGTTTTTCAATGTCCTC
AAGAGCCCACCAAGAGTTTCTTCCGGGAATTGCTTAAATTATCTTAA
ATTTAAATTGTAGTTTAAAC |
| 28 | pAD:
NtAN2:
HSP-T | CCCGGGACTAAAAGTGAATCCTTCCCCACAAAAAACTTAGTTTTGAA
TGCACGAGATTCTACAAATAAAAAGAAAGAAAGAAATAAAAGGTAT
AATTAGAGCGCACGTGAAATAAAAATACTATCAATTTGAATGAAAA
CTTGAAAATAAAATAAAAAATAGAAGTATCATGTTTTGAAGGATTCA
ATTTTAGTATTATTTTAATTTATATATATGATTATTTTGTCAGGTGGG
TCATTCCTGTTTTAATTGAATTATTATTATTAGACGAAAAAAAAAAT
CTTGGAATAAGAAAATCTGGTGACTATTTATGAAATTTACCCTTCAA
TTGTATGTGTAAAACACTTATATCCAAGTTTATAAGATTTTTAGCAA
AATAAAATACTTCAAATTTTTTAAGCTATTCGCTTGAAAATAAAATT
AAGACATGTTAACATAGATTACTTTCTCTATTACCAAATTCTTGTGTT
ACTTTCTTAAAGTTGAGTCGAGTAGTATTGATAAATAAAATAGTCAA
TATGTTTTCCACTGTTCTGAACAAAAATAGTTTTTTTTTTTTTTTTTTT
TTATGTATTTTCATAATTTTGAATTATTTAAATTTGAGTTTTGGAAGA
TGAATTCACGTTTGACCAAAAGGAGAGATGAATCGTGTCTATCCAA
AAATAAAAACAAATGGGCGTGTAAAAAATAACATTTTTTTGGTGG
GTCAAAACATCGTTAGGTTTAATAAATCAAATCGATTTTTCTCTTGA
AATATTACCACCACCTTTTTCTTATTACTCGACAAAAAACTCAAACAG
TAACACAAAACAAACAGCCAAAAACCGGTTTCGAAAACCCAGCGAC
CAAAACATGGAAATGGTTTTACTTTGGCCTGTTGTATTCAACTTTTCG
ATTTCACGATTCTATATTTTCAGGTATAAATACCCCAGCTAATGCAGT
GCCACATCACACCTCAAGATATTTAACTCAGTATTCAGAAACAACAA
AAGTTCTTCTCTACATAAAATTTTCCTATTTTAGTGATCAGTGAAGGA
AATCAAGAAAATAACTCGAGATGAATATTTGTACTAATAAGTCGTC
GTCAGGAGTGAAGAAAGGTGCATGGACTGAAGAAGAAGATGTTCTA
TTGAAAAAATGCATCGAGAAATATGGAGAAGGAAAGTGGCATCAAG
TTCCTCTTAGAGCTGGTTTGAATAGATGCAGAAAGAGCTGCAGATTA
AGGTGGCTAAATTATCTAAGGCCACATATAAAGAGAGGAGACTTCT
CTTTTGATGAAGTAGATCTCATTTTGAGGCTTCATAAGCTGTTAGGC
AACAGATGGTCACTTATTGCTGGTAGACTTCCTGGAAGGACGGCAA |

TABLE 1-continued

Nucleotide and protein sequences

| SEQ ID NO: | Sequence Description | Nucleotide Sequence |
|---|---|---|
| | | ACGATGTCAAAAACTACTGGAACAGCCATCTTCGCAAGAAGTTAATT GCTCCTCATGATCAAAGGAGAGCAAGCAAAAAGCAAAGAAGATCA CCATATTCAGACCTCGGCCTCGAACCTTCTCAAAGACAAATACTTGT GTTAAAAGTAACACAAATACTGTAGATAAGGATATTGAAGGCAGCA GCGAAATAATTAGATTCAACGATAATTTGAAGCCAACAACTGAAGA ATTGACGGATGATGGAATTCAATGGTGGGCCGATTTACTAGCTAACA ATTACAACAATAATGGGATTGAGGAAGCTGATAATTCATCACCAACT TTGTTGCATGAGGAAATGCCACTTCTCAGTTGA<u>TCTAGA</u>AATAACAG AGGGCGCGCGAGCGGTGGCTACTGATCGCCTATGAGTTCTGTGATTC TACTTGTAATTTCAGAAGTGTTTTCAGTGTCTTGTTTTCTGGAAGTCC GTCTGGTTTTTAGTAACTTTTAGCTCAAAAATGTGTCTGTACGATGGT ATTTGTATGTTTGTGGGTCTTTTACATATACGCTTGTAATCGATCAAT GTAGAATGCTGTGTGCCTTTTCCGTCAACAGCTTATTTAGTGTTTACT CTGTATACGTATATCTAATATATAGTACTGATTCTTTCATCTGGTGAT TTGTTTTCCTAAAGAGATTATTATCATAGCTTTAATTGAATGATACAA AGAGGTGTTGCCTGGCTTCACCAGAGCAGAAATTTTCATTGATATAG GGTACAAATGTCATTCACATAATGTTAAGAGATAAGTTTTTCAATGT CCTCAAGAGCCCACCAAGAGTTTCTTCCGGGAATTGCTTAAATTATC TTAAATTTAAATTGTA<u>GTTTAAAC</u> |
| 29 | pEX3-like: NtAN2: HSP-T | <u>CCCGGG</u>CATTGGAGTTTTATTAACCCGCCTCGATAGAGGCGGGGCTA TACAATCTGATAAGGTGATCGAGGATGAAAGGGAGCCCCTCGACTT TGCTCACGAAGAATCGGAGCAGAATAACAATTTGCCAAAAGGAAGG ATGGATTTGGCCTAGGGTTATTTGGTATTGACGGCAAAAATTAACGA TGACGGGGTCGAGGGGGCCCAACGTGAAAGGGTAAGTGTAAACACT TAGAAACCCTTCCACATGAGTGGTGATATCTTTTTCGGGGGTCGGGA TCACCACCTCTTTGCCTTCCCAGTTGCGGTCTTTCTTTACCTGCTTAA GGTATCCCTCAGTTATTGAGCATATATACCTCGACATTGGCTCGCAT CGATCAGGAATCGACGAGGCTTTATCGGTCTTAAAATCGGAGTTTAG CACGCACCCCCAAGAATGCATTCCTCAAGACGGGGATCCACCAGCG TTTTTCCGTCGGTCGGTTGAGAAGATGAAGCAACTTCTTTTTGTGGTA CCATTTTCGATGTTTTGCCATTCTTGTGTAAGTTTGAAGAAGAGGAA GATAATAGGACTTGACATTTGAGACATGATTAACAGCAAAGCCTGA AGATTTGTAAAAGGGACGAACTTAAGAGATGTAAAAGCTTTAGATA TTAGAAGGAAGTGAAAGTAAAGTTTGAATCAATGAGGAAGTGATCT ATTTATTGGACTCACGGCGACAGTTCAAAGGCACTAGTGGCCGACA ACCAACTAACACTCATTAATGACTTGGAAAACTGTACTGACGGGAC GTTTTGGTCACTCCCGTCGCTTACGTCATGAGGATGTCGTCATTACA GGTCGAGATAGAAAATTGAAGGCTCAATTCGTTTCTTGTCATTTCAC TCCAAAAAACGAGGAGACTATCTGTATACGGTTAAAATCGGGCCCA CCCGATTTTACTATTTGACCGAGACTAGGAGGTTGCATCGAAGAATG GCCTCGTAACAGAACAGACTAAATCACGAGGATAAGGTACTGAGTT CATAATCGAGGTACCGGTCGAGATCGAGGCTAGTAGTGATCGAAAC CAAATGAGACAGACATCGAGCAAGATCGAAGATAGCACAATAACAG AAAGGCGAGATATCCACGACTGGTCGAGGATCATGGCATAAATCTC GAAACGAATCAAATTAGAAACAGTTAATTAGCTAATCATGAATTTAC TTCTGTAATTAGAATTATACCATAAGTGAAATTCCTCTACTATTTATA GGGGGGTTCTAATCATTTGGAAGACACATGGTTCACAGATATCAAAGA AATGTAATTCTCTTTCTCGTTTATACTATTGTTCATCAGCTTGTTATAT TTTAATTGTTCTTACATCAACCAGTTCGAGGGTATCCAAACTTGAGG GCTGAGTTCCATTCTAACACAAGTTTGCTTTACTTTATAGTTTATTTC TATTATTAATCTTCATATTTATCAATTGGTATTAAGTGAAATTACGTG TACTTAGAACAATATTATAAATTTAATTGTTATCCAATTTTAAGGATA AATAAGAACATTCATTAAAGTTAAAAGAGACATATAAAAAAAGCTA TTGCTCAGATTTCTGCAACTGAAATCGTGCAAAGTTGAGGCATCCAC ACTTGTTTTTCAAAGCTTCGGTACTGTATACAAAGATAGAAAGTAAA GGAGACTTTTCTCTTTAAATTATTGCATCAGAAATAGTATAGCTGCC ATAATAGTTTATTAATTCCAGCTATGCTTAGCTTGCAGCCTCTATCGA ACAAAAAAAGTATACCAACTCAAGTCAATTTGAGCCGACAACATGA CAAAACCAAATCAAAATGCATACTCTAGCTTTTTTACTTTGGTAGGT TTTAAGTAATCTAGTGAGACTTTTACCTTCATTCATGAAAATCTTGGA AAGGGTAATTGTATAATTGAAAGCTATATAAAGGGGTCGGAGTGAA GCTTAAGAGGACAACAACTTTTCTCATTTGTTTCAAAG<u>CTCGAG</u>ATG AATATTTGTACTAATAAGTCGTCGTCAGGAGTGAAGAAAGGTGCATG GACTGAAGAAGAAGATGTTCTATTGAAAAAATGCATCGAGAAATAT GGAGAAGGAAAGTGGCATCAAGTTCCTCTTAGAGCTGGTTTGAATA GATGCAGAAAGAGCTGCAGATTAAGGTGGCTAAATTATCTAAGGCC ACATATAAAGAGGAGACTTCTCTTTTGATGAAGTAGATCTCATTT TGAGGCTTCATAAGCTGTTAGGCAACAGATGGTCACTTATTGCTGGT AGACTTCCTGGAAGGACGGCAAACGATGTCAAAAACTACTGGAACA GCCATCTTCGCAAGAAGTTAATTGCTCCTCATGATCAAAGGAGAGC AAGCAAAAAGCAAAGAAGATCACCATATTCAGACCTCGGCCTCGAA CCTTCTCAAAGACAAATACTTGTGTTAAAAGTAACACAAATACTGTA GATAAGGATATTGAAGGCAGCAGCGAAATAATTAGATTCAACGATA ATTTGAAGCCAACAACTGAAGAATTGACGGATGATGGAATTCAATG |

TABLE 1-continued

Nucleotide and protein sequences

| SEQ ID NO: | Sequence Description | Nucleotide Sequence |
|---|---|---|
| | | GTGGGCCGATTTACTAGCTAACAATTACAACAATAATGGGATTGAGG<br>AAGCTGATAATTCATCACCAACTTTGTTGCATGAGGAAATGCCACTT<br>CTCAGTTGA<u>TCTAGA</u>AATAACAGAGGGCGCGCGAGCGGTGGCTACT<br>GATCGCCTATGAGTTCTGTGATTCTACTTGTAATTTCAGAAGTGTTTT<br>CAGTGTCTTGTTTTCTGGAAGTCCGTCTGGTTTTTAGTAACTTTTAGC<br>TCAAAAATGTGTCTGTACGATGGTATTTGTATGTTTGTGGGTCTTTTA<br>CATATACGCTTGTAATCGATCAATGTAGAATGCTGTGTGCCTTTTCCG<br>TCAACAGCTTATTTAGTGTTTACTCTGTATACGTATATCTAATATATA<br>GTACTGATTCTTTCATCTGGTGATTTGTTTTCCTAAAGAGATTATTAT<br>CATAGCTTTAATTGAATGATACAAAGAGGTGTTGCCTGGCTTCACCA<br>GAGCAGAAATTTTCATTGATATAGGGTACAAATGTCATTCACATAAT<br>GTTAAGAGATAAGTTTTTCAATGTCCTCAAGAGCCCACCAAGAGTTT<br>CTTCCGGGAATTGCTTAAATTATCTTAAATTTAAATTGTA<u>GTTTAAAC</u> |
| 30 | pEX1-like:<br>NtAN2:<br>HSP-T | <u>CCCGGG</u>CAGTAGGCATCAATTACTATATATTTTACAAGTAATTAAAT<br>GATAAACAAATGCAATATTTGTTTAGTTTCCATATTTCTTTTTCAAGG<br>CACTCCTTTAATTACTCATCCATTCAAATGGATCTTCTCATTTTTCAG<br>ACGGTTTTTAGGACTCCCTCTATCTCAAATTATCTATCGAGATTTTTA<br>AAAAAAAAATTGTCTCAAATTATTTTCATTTTGGAAATTTAAGATAA<br>AATTAATTATATTTTTTTCATTTACCCTTAATGGTAATTATTCTTGAAT<br>ATGGAGATAGCACATCGAGTAAATATTCAATAAAGAGAGATTATAT<br>CTTATAACATAAATAAGAGTAAAATAGTCCAAAATTCCTCATAATTA<br>ATATTTTTTAAGGGTATGTAAAAGAAAAACACGACAAATAATTTGAG<br>ACGGAGAGAATACCTTCTTTTTGACCTTTTGTAAATAAATATTAAAA<br>TATCCTCAACATTTCCTAGGTTAATTTCTCTCTCTCCCTAATAATTTC<br>AAAAGTTATCATTGTGATACTCAAATATATTGGTCTTAGCACAATT<br>TGAGCATTGCATGTTGTATGCCTGGATCCTCCTGGGTGCCATTTTTCC<br>TTTGCTTTTGGATACCTTTTTGCAACTTTAGTCCATTGCTGGAACATG<br>ATTTTTTGTACCTCTTGTCTGTTCCCATGATGATAAACTATGATAACT<br>AACATTTTCAGAAATATTGGATTGAATTAGATATATTTTCAATATTG<br>AGCTACAAAACTCGTTGAATATTTTGCCCTATTTGGTTGGTAATAAA<br>AGTGGGTCACATGCACAGTTTTTCTCTTGTCTTCTCTAGATTAAGCTC<br>TTTGGAAATGACCTACTGAAAATGCTACACATAAAACTCCCCCACTC<br>CTCCCCAAGTTGAGGGGTGGGAGGTTTGATTTGGACCCTTACCCTAT<br>TGTTAATATCGAAATAGATAATACAAAGGACGGGAACATAAAACCA<br>AAACCTCCGATAAAACACCAAAGTTGATGATCTAAGTTAAGTTATTG<br>ATTCTTATACGTTGATTGGAAGTGCACAATGGTCTTTGCATACTATCA<br>AAGTATGAATTGGTTCTTGAATTATATCTCTTAATATGATGTATTGTG<br>TTTAATTAATTCTCTACTATTCTCTATTTTTATAGGCTAAAAGATCCT<br>GACATGCTTCTTGAACACATGTGAAGGTTAGTTAACTATAGTCAGAA<br>GTACACAAGAATTAACTTGTACACCTATCCGTGATCGAAAAACTTAA<br>CTTGTTCTAAGCTGAACTGAGTCCTCCTATCCATGTCCGATTCTTCAC<br>TAGAAGCATTAATCATACAAGGAGAATTCAACTTAATTTACTGTATT<br>GGTTATCATTTACATAGTTTAGTTATAAAACTTTGGAGCGACACAAT<br>GATTGACACTACTAATCATGATTGAATATTAACTTCACTCGATTTATC<br>AATTTCTCATACAAGTGAATTAATTTCACTCTTTGTGATTTCAGTAGT<br>AAATGTCAAGTTTCATAGTTTTTTCTTTTTGAAATTAGTCATACATGT<br>GAATAGAACATTAATTTAAGTTAAAAGCTAGCTGCTCTGATTTCTGT<br>AACTGAAATCGTGCAAAGTTGAGGCATCCACATTTGTTTTTCAAAGT<br>TCCAGTACTGTCTAAAAAGATAGAAAGTAAAAGGAGACTTTTCTCTT<br>TGAATTATTGCATCAGAAATAGTATAGCTGCCATAATAGTTTATTCC<br>TTTGCTTAGCTTGCAGCCTCTATCGAACAAAAAAGTGTACCAACTC<br>AGGTCAATTTGAGCCGACAACATGACAAAACCAAATCAAAATGCAT<br>ATATACTCTAGCTTTTTTACTTTACTTTGGTAGGTTTTAAGTGAGACT<br>TTTACCTTCATTTATGAAAATCTTGAAAAGGGTAATTGTCTAAATGA<br>AAGCTATATAAAGGGGTCGTAGTGAAGCTTAAGAAGACAACAACTT<br>TTCTCATTTGTTTCAAAG<u>CTCGAG</u>ATGAATATTTGTACTAATAAGTCG<br>TCGTCAGGAGTGAAGAAAGGTGCATGGACTGAAGAAGAAGATGTTC<br>TATTGAAAAAATGCATCGAGAAATATGGAGAAGGAAAGTGGCATCA<br>AGTTCCTCTTAGAGCTGGTTTGAATAGATGCAGAAAGAGCTGCAGAT<br>TAAGGTGGCTAAATTATCTAAGGCCACATATAAAGAGAGGAGACTT<br>CTCTTTTGATGAAGTAGATCTCATTTTGAGGCTTCATAAGCTGTTAGG<br>CAACAGATGGTCACTTATTGCTGGTAGACTTCCTGGAAGGACGGCAA<br>ACGATGTCAAAAACTACTGGAACAGCCATCTTCGCAAGAAGTTAATT<br>GCTCCTCATGATCAAAAGGGAGAGCAAGCAAAAGCAAAGAAGATCA<br>CCATATTCAGACCTCGGCCTCGAACCTTCTCAAAGACAAATACTTGT<br>GTTAAAAGTAACACAAATACTGTAGATAAGGATATTGAAGGCAGCA<br>GCGAAATAATTAGATTCAACGATAATTTGAAGCCAACAACTGAAGA<br>ATTGACGGATGATGGAATTCAATGGTGGGCCGATTTACTAGCTAACA<br>ATTACAACAATAATGGGATTGAGGAAGCTGATAATTCATCACCAACT<br>TTGTTGCATGAGGAAATGCCACTTCTCAGTTGA<u>TCTAGA</u>AATAACAG<br>AGGGCGCGCGAGCGGTGGCTACTGATCGCCTATGAGTTCTGTGATTC<br>TACTTGTAATTTCAGAAGTGTTTTCAGTGTCTTGTTTTCTGGAAGTCC<br>GTCTGGTTTTTAGTAACTTTTAGCTCAAAAATGTGTCTGTACGATGGT<br>ATTTGTATGTTTGTGGGTCTTTTACATATACGCTTGTAATCGATCAAT |

TABLE 1-continued

Nucleotide and protein sequences

| SEQ ID NO: | Sequence Description | Nucleotide Sequence |
|---|---|---|
| | | GTAGAATGCTGTGTGCCTTTTCCGTCAACAGCTTATTTAGTGTTTACT<br>CTGTATACGTATATCTAATATATAGTACTGATTCTTTCATCTGGTGAT<br>TTGTTTTCCTAAAGAGATTATTATCATAGCTTTAATTGAATGATACAA<br>AGAGGTGTTGCCTGGCTTCACCAGAGCAGAAATTTTCATTGATATAG<br>GGTACAAATGTCATTCACATAATGTTAAGAGATAAGTTTTTCAATGT<br>CCTCAAGAGCCCACCAAGAGTTTCTTCCGGGAATTGCTTAAATTATC<br>TTAAATTTAAATTGTA<u>GTTTAAAC</u> |
| 31 | pPR1a:<br>NtAN2:<br>HSP-T | <u>CCCGGG</u>CTATATAAGGCCATCCGTGAATTGAATAAACTATCCAATTA<br>TTTTCTTCCACAAAAATTTCAATTCTACTTTTAGTTATTCTTTTTAATA<br>TTGAGCTTGCAATTCTATTTTGATTCTTCACTCATGACATGCTACGTA<br>GAGAACCTTCAATACATCATAAGGATGGACCAAGCAATGCATAAC<br>TCAAATAAGTCCATACAAATTTGCTGAAAGATAAAGTTATTCTACTT<br>TCTTTGAACCCAAATCTGATAAATCTTGACAATCAGATTTGCTACTAT<br>GATTTCTCACTGTATCATTTGTTTTATTCTATAAAGTTAATGAGGAAT<br>GTATTAATTATTTAAGATACCTTACTTTTTCTGATTTTTGATCTTATAG<br>TCAAGTCGTGAGGCACAATTTGCGACCCTGATGGCGCAAACCTTTAC<br>CTAGGGATCGTAGCACATAAACGTTTTTAAGGACTAAGATATACGAG<br>GATGTCAATTATCATAATGTAGGGTCTAAGTTTTCATTTTTTTTTTG<br>CATCTAATAGAGTATAATTTTTTTTAATCATCACGATAACTTGATTTA<br>CAATAATATGTACTCTGTTTACTTTTACTTGACACGTTTTGATTTTTC<br>ACGCCCTTTAAGAAAAAATGATTGAAATGCATAATTTACCATGATAC<br>TCATATTAATTGATGCATATTTTATTGGATTTGAGAAAATGATTTGAA<br>ATGAGTAATAAATATTGTGGGTATAACAGGAAAAAAAATTGTCTTCT<br>CTTAACATGCATAAAGTGAAGAGTAAAAAGAAAATCTATTTTTGTAT<br>ACATGTCAAACAAAGTGAACGGAGGAGATGACAAATTGCTAAATG<br>GCAATAGTTACAAAATTCTTCAATTACTCTTTTTCATAACAAAACACT<br>GGTCTCTCTTGTAAGTATTGGTCTATACTTCACCACCTAAAGCATTGG<br>CCGAAGTCTTTTTAAGGAGTTTGGTTGTCATTTATCCATTTAAATTAA<br>AGGGAAAATAAGTGAACGCCATTACAGCGAGATGCTTTAGGGTGCT<br>ATTTCTTGGAAAAATAAAGTAGTTAAATCTTAAAACACCCTCGAGGA<br>TTTCAAACTCTAGCTTCACTAAAACTTGAGCTTTCTTTTCCACTAATG<br>TCGAAAAACGAAATAAACATAAGCTATTTACAAAAATAAAAAAATA<br>CTCCATTTGAATCTAAAGTCAAGTCGTGATTGGGATAAGAAAATAGA<br>AATTTATTTATACTCCAGATCAAGCCGTGATTGGAATGAGATAATAG<br>AAAAGTATGATAGTACATGAGTAACATCAAGTTGGAAATTAAGGGA<br>AGGAAATTAGAGAAAGAACTGAAGAATATCCAAATATTCTTTACGT<br>CCAAATTTGATAGTTATTTAACGTCATCGAGATGACGGCCATGTTCA<br>AGTTTTCCACAAATATTGAGAAAAGAAAGAAAGACACAAACTGTGT<br>TTGGTATTATTATAGTTTTTTCTTTTAGAGAATTGATTGTACATATAA<br>GAAATTAATATAAGATTTAGAAATAAGATTATTAGAAAAATCAAAC<br>ATCAAAGTATTTATTTTAAATTCTTTTTCCAATGGACATTCCCATTCT<br>GAAAAAAAGAGATATAAAATGGAAGTAAAATTAATCAGATCGTTAA<br>ATGTAGAAAATATTAATAACACTTAACCATAACCAGTCTACTTTATT<br>TAACAAAAAGCACATCTGATAGATCAAAAAAGTGTTTAACTTCATGC<br>ATTGACAATTTAAAATTATTTTGCAACATCGGGTAAAACTATTTTAC<br>AACAATTGGTAACTGCATATATAAGTTTAATATGGTAACCTAGAAAA<br>TAGGATAAATTATCTATAACAGGATATATTACATTGATATTACCATG<br>TCAAAAAATTTAGTAAGTACATGAATAATCACCGTGAAATCTTCAAG<br>ATTTCTCCTATAAATACCCTTGGTAGTAAATCTAGTTTTTCCATTCAA<br>GATACAACATTTCTCCTATAGTC<u>CTCGAG</u>ATGAATATTTGTACTAAT<br>AAGTCGTCGTCAGGAGTGAAGAAAGGTGCATGGACTGAAGAAGAAG<br>ATGTTCTATTGAAAAAATGCATCGAGAAATATGGAGAAGGAAAGTG<br>GCATCAAGTTCCTCTTAGAGCTGGTTTGAATAGATGCAGAAAGAGCT<br>GCAGATTAAGGTGGCTAAATTATCTAAGGCCACATATAAAGAGAGG<br>AGACTTCTCTTTTGATGAAGTAGATCTCATTTTGAGGCTTCATAAGCT<br>GTTAGGCAACAGATGGTCACTTATTGCTGGTAGACTTCCTGGAAGGA<br>CGGCAAACGATGTCAAAAACTACTGGAACAGCCATCTTCGCAAGAA<br>GTTAATTGCTCCTCATGATCAAAAGGAGAGCAAGCAAAAGCAAAG<br>AAGATCACCATATTCAGACCTCGGCCTCGAACCTTCTCAAAGACAAA<br>TACTTGTGTTAAAAGTAACACAAATACTGTAGATAAGGATATTGAAG<br>GCAGCAGCGAAATAATTAGATTCAACGATAATTTGAAGCCAACAAC<br>TGAAGAATTGACGGATGATGGAATTCAATGGTGGGCCGATTTACTAG<br>CTAACAATTACAACAATAATGGGATTGAGGAAGCTGATAATTCATCA<br>CCAACTTTGTTGCATGAGGAAATGCCACTTCTCAGTTGA<u>TCTAGA</u>AA<br>TAACAGAGGGCGCGAGCGGTGGCTACTGATCGCCTATGAGTTCT<br>GTGATTCTACTTGTAATTTCAGAAGTGTTTTCAGTGTCTTGTTTTCTG<br>GAAGTCCGTCTGGTTTTTAGTAACTTTTAGCTCAAAAATGTGTCTGTA<br>CGATGGTATTTGTATGTTTGTGGGTCTTTTACATATACGCTTGTAATC<br>GATCAATGTAGAATGCTGTGTGCCTTTTCCGTCAACAGCTTATTTAGT<br>GTTTACTCTGTATACGTATATCTAATATATAGTACTGATTCTTTCATC<br>TGGTGATTTGTTTTCCTAAAGAGATTATTATCATAGCTTTAATTGAAT<br>GATACAAAGAGGTGTTGCCTGGCTTCACCAGAGCAGAAATTTTCATT |

TABLE 1-continued

Nucleotide and protein sequences

| SEQ ID NO: | Sequence Description | Nucleotide Sequence |
|---|---|---|
|  |  | GATATAGGGTACAAATGTCATTCACATAATGTTAAGAGATAAGTTTT TCAATGTCCTCAAGAGCCCACCAAGAGTTTCTTCCGGGAATTGCTTA AATTATCTTAAATTTAAATTGTA<u>GTTTAAAC</u> |
| 32 | pSAHH: NtAN2: HSP-T | <u>CCCGGG</u>ATTAATTGTAAATAAATATACTTATCATTTTCGGAGAATAT CCAATATTATATATATAATTTTTATACTTATGAGTTTCGGGCTAGATA TTTATTCTAAGCTAAGTACTACAAATACTGTGATATAAGGCTCTAAA CTTTCCTACCCTAAAAGAGTCTACGTTTTACTACGCTAAAAAGGTCT ACATTTTACTACGCTAAAAAATAATCTAAACTAAACATCGCAAAAAC AAACAAGTAAACATGACAATTTAACAAATAAATTTTTTTGACTAATT TACAAGTATATTTATACAACACTAAAATTAAATCCGGATAAAAATTA ACATGCTAGTTTTGGCAAAAATAAACACAAAACTATATACAAACCA TACAAATCAAATAATATTCAATATTATACAAGTTTCAACTAAAATTA AATCGAAATACCTGGATTCGGAAACTAAATAAATCGGATTTTTGACT TCAAAAAAGAGATTCCAGCGTACCACGACCCTCAACTATAATGTGG GACCACCAATCTTCACCTTTTATGTGTCGGGGGGACCCAAAAATTTT TTTTTTTTTTAAAAAACTGGGCAGATCGCTGAGGAGGGGACCAAATT TTTTTGAAAGTTTTCGGCTGAATGAAGAAGAAGAAGAAAGGTTTAG GGTTTTGTTTTAGGGTATGGCGCCAACAGTATTGGCGCTATGCTGAC ACCGCCTGAAAAGTAGGGGTATGGCGCCAACACTGTTGGCGCTATG CTGACATGTCAGTAAACTCTCTGATATGGCGCCAACTATGTTGGCGT TATATATATTTGTGTTACTTTTCCTTTTTTACACTTATTAATGTAGTTT GAGTCAAAAAAAACAATAATAAAGTTCCGGACTCGAGATGTAAGGG GTTGTCAATTTTCACTTTGTCAGTCGCTAAGAGTAATTATGAATATTC TTTTATCAATATTGGACCTCAAACTTTATCCATTGTAAGAAAAAAAA GTTGTAAAATATTTGTGTCACTTAATTAAACGGTCGTAGTAGTTAGT AGTAGTGACATAGTCCTTTCGTTTGATAGTATATCAAATTGGAACAA TTTACATTTGCACCAAAGCATAAAGGGAAAGCATGAAAAAGAGAAA GTGCAAAAGAGAAAAATACAACAACAACAAGAATATTTCAGTATAA TTCTATAAGTAGGGTCTGGAGAGTAGAATACCCCTAACCTAGAA GGGCAGGAAGAATATTAAAGTAAAAAAGATAAAAGATTACAAATAA AATAAAAGAAAAACAAACAAACATACAAAATTAATTTGTGCATAA TGCTTATAGTAATTGCCAATTTGCCATGAATATCTTCCACCGGGCTAT CTTGGTCATGTTAATCACTCTATCCTGTTTTCAAACAATTTTTACTCT AAAAATTTGCATGTTATATTAATTGGTGGGTGAGCCAGAAATTTTAA ACAAAAAATCAAAATACGGTACACTAAAAGATTTTTTATAAAAAAG AATTCACCAAGTTATATATATACACAATCTTTCTTTTTTTTAAATCTT ACGATGACCAATTTTTTCGACAAAGAATATTCACTTAAACCCTTGTT CATACATAGCTTGGCAATTGGATTAATAATGAAAATAATACTTTAAA TTTTGGAAAGAAAATATTATTTATTCTCCAAAAGAAACCAAGAAATT AGATTCATCAAAAAATAATGACCACCATTAGCCCACCTCCCAAATCT CTATTCCTTTTAGACTTTTAACCAAATTTTCAGATCTACCAAACCCCA ATTTATCCAATAAACTTTTCAGATCTAAAAATAAAAATATTCAGATC TGGAACAAATCTTGACCGTCCATTTTCATCATTCATATCTATTTAATA CCACTCACCTCCGCCCTTTACTCCTTGCAACACTCTTCTTCTCCTCTA AAAACCCTTATAGAAGAAGAGGAAAAAGCCTTTCAAATCTCATCTC AAACCACCTAATTTCTCTCATACTCGCTCGACCC<u>CTCGAG</u>ATGAATA TTTGTACTAATAAGTCGTCGTCAGGAGTGAAGAAAGGTGCATGGACT GAAGAAGAAGATGTTCTATTGAAAAAATGCATCGAGAAATATGGAG AAGGAAAGTGGCATCAAGTTCCTCTTAGAGCTGGTTTGAATAGATGC AGAAAGAGCTGCAGATTAAGGTGGCTAAATTATCTAAGGCCACATA TAAAGAGAGGAGACTTCTCTTTTGATGAAGTAGATCTCATTTTGAGG CTTCATAAGCTGTTAGGCAACAGATGGTCACTTATTGCTGGTAGACT TCCTGGAAGGACGGCAAACGATGTCAAAAACTACTGGAACAGCCAT CTTCGCAAGAAGTTAATTGCTCCTCATGATCAAAAGGAGAGCAAGC AAAAAGCAAAGAAGATCACCATATTCAGACCTCGGCCTCGAACCTT CTCAAAGACAAATACTTGTGTTAAAAGTAACACAAATACTGTAGATA AGGATATTGAAGGCAGCAGCGAAATAATTAGATTCAACGATAATTT GAAGCCAACAACTGAAGAATTGACGGATGATGGAATTCAATGGTGG GCCGATTTACTAGCTAACAATTACAACAATAATGGGATTGAGGAAG CTGATAATTCATCACCAACTTTGTTGCATGAGGAAATGCCACTTCTC AGTTGAT<u>CTAGA</u>AATAACAGAGGGCGCGCGAGCGGTGGCTACTGAT CGCCTATGAGTTCTGTGATTCTACTTGTAATTTCAGAAGTGTTTTCAG TGTCTTGTTTTCTGGAAGTCCGTCTGGTTTTTAGTAACTTTTAGCTCA AAAATGTGTCTGTACGATGGTATTTGTATGTTTGTGGGTCTTTTACAT ATACGCTTGTAATCGATCAATGTAGAATGCTGTGTGCCTTTTCCGTCA ACAGCTTATTTAGTGTTTACTCTGTATACGTATATCTAATATATAGTA CTGATTCTTTCATCTGGTGATTGTTTTCCTAAAGAGATTATTATCAT AGCTTTAATTGAATGATACAAAGAGGTGTTGCCTGGCTTCACCAGAG CAGAAATTTTCATTGATATAGGGTACAAATGTCATTCACATAATGTT AAGAGATAAGTTTTTCAATGTCCTCAAGAGCCCACCAAGAGTTTCTT CCGGGAATTGCTTAAATTATCTTAAATTTAAATTGTA<u>GTTTAAAC</u> |

TABLE 1-continued

Nucleotide and protein sequences

| SEQ ID NO: | Sequence Description | Nucleotide Sequence |
|---|---|---|
| 33 | AtPAP1 protein | MEGSSKGLRKGAWTTEEDSLLRQCINKYGEGKWHQVPVRAGLNRCRK SCRLRWLNYLKPSIKRGKLSSDEVDLLLRLHRLLGNRWSLIAGRLPGRT ANDVKNYWNTHLSKKHEPCCKIKMKKRDITPIPTTPALKNNVYKPRPR SFTVNNDCNHLNAPPKVDVNPPCLGLNINNVCDNSIIYNKDKKKDQLV NNLIDGDNMWLEKFLEESQEVDILVPEATTTEKGDTLAFDVDQLWSLF DGETVKFD |
| 34 | NtAN1 protein | MTEIPPNSQMKTMLQKAVQSVQWTYTLFWQLCPQQGALVWRDGYYN GAIKTRKTVQPMEVSAEEASLHRSQQLRELYESLSAGESNQPARRPSAA LSPEDLTESEWFYLMCVSFSFPPGIGLPGKAYSKKHHIWIMGANEVDSK VFCRAILAKSARIQTVVGIPLLDGVLELGTTERVQEEIGFINHVKSFFTEQ QQPQLPKPALSEHSTSNPTTFSEPHFYSGNTSPSANVDIAHQDGGAAGEE DEEEEEEDDDEAELDSDSIAIQSAANPIAVEASELMQLDVSEAIQLGSP DDDSDNMDSDFHLVGAGNTAHDYQRQADSFKAETAISWPHFQDLQQL PGGSSYDELSQEDTHYSQTVSTILEHRSSKFSSTTMGCISHDSAQSAFTL CPSTTVCSPNPAHCRHDDSLVDGGGASQWLLKSILFTVPFLHTKYQSEA SPKSRDVATVDSSSTASRFRKGCSITSQEEPSGNHVLAERRRREKLNERF IILRSLVPFVTKMDKASILGDTIEYVKQLRKKVQDLEARARDTEHSRDA DKKGGTATVKVLQGRGKRRMNTVDGSVGGGQATITASPPSTTENEEV VQVQVSIIESDALVELRCPYKEGLLLNVMQMLRELKVEVVAIQSALNN GVFLAELRAKVKENICGRKASILEVKRSIHQIIPRD |
| 35 | NtAN2 protein | MNICTNKSSSGVKKGAWTEEEDVLLKKCIEKYGEGKWHQVPLRAGLN RCRKSCRLRWLNYLRPHIKRGDFSFDEVDLILRLHKLLGNRWSLIAGRL PGRTANDVKNYWNSHLRKKLIAPHDQKESKQKAKKITIFRPRPRTFSKT NTCVKSNTNTVDKDIEGSSEIIRFNDNLKPTTEELTDDGIQWWADLLAN NYNNNGIEEADNSSPTLLHEEMPLLS |
| 36 | pUBI: AtPAP1: HSPT | CCCGGGTTAGTATTCAAACCGAATAAATCAAAGTTACCAAACCGAA TAAATCGAAACCGAAAGGAGAAACCGCACCATACCGAATTTAATTA GGTACGATATTGATATTGTATTTTAAAAAATCGAATACCAAAATAC CGAATTAAAATATCTAAATATCGTACAGTACCGACCGATAAATACTC TATAAGCATCATCATGTCACCATTCCTGCTTGGAAATAGATGTAATA ATGTAATTCAAGGTGAAGATCATTGAAAATGAGATATTTGGACTCTT AGATAATTGTGCAACTGATATTTTTATTTACTTTTTTCTTTCATCCAA TAATTGCGTTACATTAAAAATGAGATATTTGGATTAATATTCTTCTCC TTGACCACAAAGCAAGGAAAGCCTAAGGACCGATAGTAAAGTTGTA TTCGTGTGGTTGCGTGTTAGTTTTGAGCGGCAAAATAAATTATGTTA AGGTAAATTATTTTTGGAACAATAATAAAATTATTTCTGTATAATAT ATAAATCATATATTTGAACCGTAGAATTATCAGTTAATACTTGTATA TGAGGAGGCTAACTACGTTAGAGCGCTAACGAGAATACTTCATATA CCGTATTTTTTACGATAATAATAATGTAATGTGAAATTGCTATCCAA AAGGCACCTAATTTTGTCCACCGTTCAAAGGAAAGGACAAGGAAGT AGTAGCGTGTAGGTTTGGTGCTGTACAAAATAAGCAAGACACGTGTT GCCTTATTATAGGATAATCCATAAGGCAATTTCGTCTTAAGTCGGCC ATTGCACCTTTAAAAGGAGCCTCTTTGTTCCCAAAATCTTCATCCTTT GATTTCTCTATTCTCAATATCTCCTCAATTTTTCTCTAGTCTTCAAACA CTTCTCAAGGTACATTAACTTCTTCTTTCTTTTTGTTCCTCTTATTTTA TGCTACTTTTATTTAATTTCGATCTATATTTTTAGGATCTAAATACTC ATTTTTGATTTGTTTAATCGCTCTGTATATATGCACCAAGTTGAAATT TTTGTAAGTTTATTTTGTTCGGTCTATATTTTAAGATCTGAAATACCC TTTACTGAGAAAAAAAAAACTCAACCTTGATTTTGTTGTACCTGGTT GAATTTGTTATTGTTGTGTATACAGTTAAAAAACTCAAGTCTTGATTT TATTGTTTCCCTTTTGTAGTTTGTATATACATAGAGCTGAATTGGTGT TCTAATTTTGGTTGATTTTTATGTATACAGTATAAAATCGATCTTAGT TTTGTTCATTGATTTGTATTTGCACAAAGTTGGAATTTTGCGTTTGTT ATTTTGATGATTGAAACCTTTTCTGTATATACAGCTCGAGATGGAGG GTTCGTCCAAGGGCTGCGAAAAGGTGCTTGGACTACTGAAGAAGA TAGTCTCTTGAGACAGTGCATTAATAAGTATGGAGAAGGCAAATGG CACCAAGTTCCTGTAAGAGCTGGGCTAAACCGGTGCAGGAAAAGTT GTAGATTAAGATGGTTGAACTATTTGAAGCCAAGTATCAAGAGAGG AAAACTTAGCTCTGATGAAGTCGATCTTCTTCTTCGCCTTCATAGGCT TCTAGGGAATAGGTGGTCTTTAATTGCTGGAAGATTACCTGGTCGGA CCGCAAATGACGTCAAGAATTACTGGAACACTCATCTGAGTAAGAA ACATGAACCGTGTTGTAAGATAAAGATGAAAAAGAGAGACATTACG CCCATTCCTACAACACCGGCACTAAAAAACAATGTTTATAAGCCTCG ACCTCGATCCTTCACAGTTAACAACGACTGCAACCATCTCAATGCCC CACCAAAAGTTGACGTTAATCCTCCATGCCTTGGACTTAACATCAAT AATGTTTGTGACAATAGTATCATATACAACAAAGATAAGAAGAAG ACCAACTAGTGAATAATTTGATTGATGGAGATAATATGTGGTTAGAG AAATTCCTAGAGGAAAGCCAAGAGGTAGATATTTTGGTTCCTGAAGC GACGACAACAGAAAAGGGGGACACCTTGGCTTTTGACGTTGATCAA CTTTGGAGTCTTTTCGATGGAGAGACTGTGAAATTTGATTAGTCTAG AAATAACAGAGGGCGCGCGAGCGGTGGCTACTGATCGCCTATGAGT |

TABLE 1-continued

Nucleotide and protein sequences

| SEQ ID NO: | Sequence Description | Nucleotide Sequence |
|---|---|---|
| | | TCTGTGATTCTACTTGTAATTTCAGAAGTGTTTTCAGTGTCTTGTTTTC<br>TGGAAGTCCGTCTGGTTTTTAGTAACTTTTAGCTCAAAAATGTGTCTG<br>TACGATGGTATTTGTATGTTTGTGGGTCTTTTACATATACGCTTGTAA<br>TCGATCAATGTAGAATGCTGTGTGCCTTTTCCGTCAACAGCTTATTTA<br>GTGTTTACTCTGTATACGTATATCTAATATATAGTACTGATTCTTTCA<br>TCTGGTGATTTGTTTTCCTAAAGAGATTATTATCATAGCTTTAATTGA<br>ATGATACAAAGAGGTGTTGCCTGGCTTCACCAGAGCAGAAATTTTCA<br>TTGATATAGGGTACAAATGTCATTCACATAATGTTAAGAGATAAGTT<br>TTTCAATGTCCTCAAGAGCCCACCAAGAGTTTCTTCCGGGAATTGCT<br>TAAATTATCTTAAATTTAAATTGTAGTTTAAAC |

DETAILED DESCRIPTION OF THE INVENTION

Figure 1A:
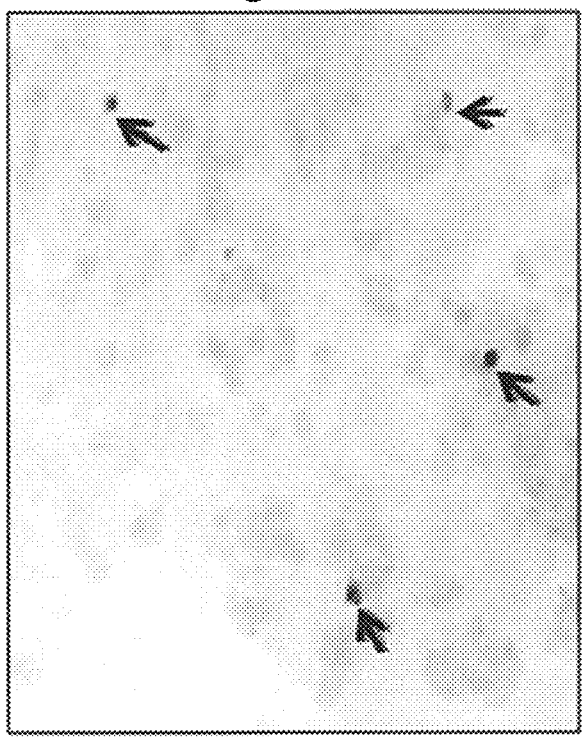
FIG. 1A is an image of a selection for protoplast-derived calli comprising pUBI:AtPAP1. The construct serves as a visual selection marker.

Unless defined otherwise, technical and scientific terms used herein have the same meaning as commonly understood by one of ordinary skill in the art. One skilled in the art will recognize many methods can be used in the practice of the present disclosure. Indeed, the present disclosure is in no way limited to the methods and materials described. For purposes of the present disclosure, the following terms are defined below.

Any references cited herein, including, e.g., all patents, published patent applications, and non-patent publications, are incorporated by reference in their entirety.

As used herein, the singular form "a," "an," and "the" include plural references unless the context clearly dictates otherwise. For example, the term "a compound" or "at least one compound" may include a plurality of compounds, including mixtures thereof.

As used herein, a tobacco plant can be from any plant from the *Nicotiana tabacum* genus including, but not limited to *Nicotiana tabacum tabacum; Nicotiana tabacum amplexicaulis* PI 271989; *Nicotiana tabacum benthamiana* PI 555478; *Nicotiana tabacum bigelovii* PI 555485; *Nicotiana tabacum debneyi; Nicotiana tabacum excelsior* PI 224063; *Nicotiana tabacum glutinosa* PI 555507; *Nicotiana tabacum goodspeedii* PI 241012; *Nicotiana tabacum gossei* PI 230953; *Nicotiana tabacum hesperis* PI 271991; *Nicotiana tabacum knightiana* PI 555527; *Nicotiana tabacum maritima* PI 555535; *Nicotiana tabacum megalosiphon* PI 555536; *Nicotiana tabacum nudicaulis* PI 555540; *Nicotiana tabacum paniculata* PI 555545; *Nicotiana tabacum plumbaginifolia* PI 555548; *Nicotiana tabacum repanda* PI 555552; *Nicotiana tabacum rustica; Nicotiana tabacum suaveolens* PI 230960; *Nicotiana tabacum sylvestris* PI 555569; *Nicotiana tabacum tomentosa* PI 266379; *Nicotiana tabacum tomentosiformis*; and *Nicotiana tabacum trigonophylla* PI 555572.

In one aspect, a plant component provided herein includes, but not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In a further aspect, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic tobacco plant cells. Somatic cells, contrary to germline cells, do not mediate plant reproduction.

Provided cells, tissues and organs can be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, and vascular tissue. In another aspect, this disclosure provides a tobacco plant chloroplast. In a further aspect, this disclosure provides an epidermal cell, a stomata cell, a leaf hair (trichome), a root hair, or a storage root. In another aspect, this disclosure provides a tobacco protoplast.

Skilled artisans understand that tobacco plants naturally reproduce via seeds, not via asexual reproduction or vegetative propagation. In one aspect, this disclosure provides tobacco endosperm. In another aspect, this disclosure provides a tobacco endosperm cell. In a further aspect, this disclosure provides a male or female sterile tobacco plant, which cannot reproduce without human intervention.

In one aspect, this disclosure provides methods and compositions related to modified tobacco plants, seeds, plant components, plant cells, and products made from modified tobacco plants, seeds, plant parts, and plant cells. In one aspect, a modified seed provided herein gives rise to a modified plant provided herein. In one aspect, a modified plant, seed, plant component, plant cell, or plant genome provided herein comprises a recombinant DNA construct provided herein.

As used herein, "modified" refers to plants, seeds, plant components, plant cells, and plant genomes that have been subjected to mutagenesis, genome editing, genetic transformation, or a combination thereof.

In one aspect, the present specification provides a modified plant comprising a recombinant polynucleotide comprising a heterologous tissue-preferred promoter and a coding region from a pigment regulatory factor where the polynucleotide sequence of the promoter and coding region are plant native polynucleotide sequences. In another aspect, a modified plant is a eudicot. In another aspect, a modified plant is a Solanaceae. In a another aspect, a modified plant is a *Nicotiana* plant. In a preferred aspect, a modified plant is a *Nicotiana tabacum* plant. In a preferred aspect, a modified plant comprises a recombinant polynucleotide where the polynucleotide sequences are native to a *Nicotiana* genome.

In another aspect, a plant of the present specification comprises a heterologous tissue-preferred promoter that is expressed in a plant cell. In a further aspect, a plant cell comprising a recombinant nucleotide of the present specification is a callus cell. In a further aspect, a plant comprises a recombinant polynucleotide that further comprises a tissue-preferred promoter that is a callus-preferred promoter. In a preferred aspect, a plant comprises a recombinant polynucleotide that further comprises a callus-preferred promotor that is expressed in a callus cell.

In another aspect, a modified plant of the present specification comprises a recombinant polynucleotide comprising the coding region from a pigment regulatory factor. In an aspect, a pigment regulatory factor can be selected from the group consisting of a pigment biosynthetic enzyme, a pigment regulatory transcription factor, a pigment transporter, a pigment metabolic enzyme, and a pigment catabolic enzyme. In a further aspect, a pigment regulatory factor can be selected from the group consisting of a phenylpropanoid biosynthetic enzyme, a phenylpropanoid regulatory transcription factor, a phenylpropanoid transporter, a phenylpropanoid metabolic enzyme, and a phenylpropanoid catabolic enzyme. In a further aspect, a pigment regulatory factor can be selected from the group consisting of an anthocyanin biosynthetic enzyme, an anthocyanin regulatory transcription factor, an anthocyanin transporter, an anthocyanin metabolic enzyme, and an anthocyanin catabolic enzyme.

In a further aspect, the present specification provides for a plant comprising any combination of recombinant polynucleotides disclosed herein.

In another aspect, the present specification provides for a plant comprising a recombinant polynucleotide that comprises a tissue-preferred promoter comprising a sequence selected form the group consisting of SEQ ID NO:1 to 7 a complement thereof, or a functional fragment thereof. In a further aspect, a tissue-preferred promoter comprises a sequence that is at least 70% identical to or complementary to a sequence selected from the group consisting of SEQ ID NO:1 to 7. In a further aspect, a tissue-preferred promoter comprises a sequence that is at least 75% identical to or complementary to a sequence selected from the group consisting of SEQ ID NO:1 to 7. In a further aspect, a tissue-preferred promoter comprises a sequence that is at least 80% identical to or complementary to a sequence selected from the group consisting of SEQ ID NO:1 to 7. In a further aspect, a tissue-preferred promoter comprises a sequence that is at least 85% identical to or complimentary to a sequence selected from the group consisting of SEQ ID NO:1 to 7. In a further aspect, a tissue-preferred promoter comprises a sequence that is at least 90% identical to or complimentary to a sequence selected from the group consisting of SEQ ID NO:1 to 7. In a further aspect, a tissue-preferred promoter comprises a sequence that is at least 95% identical to or complimentary to a sequence selected from the group consisting of SEQ ID NO:1 to 7. In a further aspect, a tissue-preferred promoter comprises a sequence that is at least 96% identical to or complimentary to a sequence selected from the group consisting of SEQ ID NO:1 to 7. In a further aspect, a tissue-preferred promoter comprises a sequence that is at least 97% identical to or complimentary to a sequence selected from the group consisting of SEQ ID NO:1 to 7. In a further aspect, a tissue-preferred promoter comprises a sequence that is at least 98% identical to or complimentary to a sequence selected from the group consisting of SEQ ID NO:1 to 7. In a further aspect, a tissue-preferred promoter comprises a sequence that is at least 99% identical to or complimentary to a sequence selected from the group consisting of SEQ ID NO:1 to 7. In a further aspect, a tissue-preferred promoter comprises a sequence that is between 70 and 99% identical to or complimentary to a sequence selected from the group consisting of SEQ ID NO:1 to 7. In a further aspect, a tissue-preferred promoter comprises a sequence that is between 75 and 95% identical to or complimentary to a sequence selected from the group consisting of SEQ ID NO:1 to 7. In a further aspect, a tissue-preferred promoter comprises a sequence that is between 80 and 90% identical to or complimentary to a sequence selected from the group consisting of SEQ ID NO:1 to 7. In a further aspect, a tissue-preferred promoter comprises a sequence that is between 80 and 85% identical to or complimentary to a sequence selected from the group consisting of SEQ ID NO:1 to 7. In a further aspect, a tissue-preferred promoter comprises a sequence that is between 85 and 90% identical to or complimentary to a sequence selected from the group consisting of SEQ ID NO:1 to 7. In a further aspect, a tissue-preferred promoter comprises a sequence that is between 95 and 99% identical to or complimentary to a sequence selected from the group consisting of SEQ ID NO:1 to 7. In a further aspect, a tissue-preferred promoter comprises a sequence that is between 96 and 99% identical to or complimentary to a sequence selected from the group consisting of SEQ ID NO:1 to 7. In a further aspect, a tissue-preferred promoter comprises a sequence that is between 97 and 99% identical to or complimentary to a sequence selected from the group consisting of SEQ ID NO:1 to 7. In a further aspect, a tissue-preferred promoter comprises a sequence that is between 98 and 99% identical to or complimentary to a sequence selected from the group consisting of SEQ ID NO:1 to 7.

In another aspect, the present specification provides a plant comprising a recombinant polynucleotide that comprises a coding region having a sequence selected from the group consisting of SEQ ID NO:8 to 10 a complement thereof, or a functional fragment thereof. In a further aspect, a coding region comprises a sequence that is at least 70% identical to or complimentary to a sequence selected from the group consisting of SEQ ID NO:8 to 10. In a further aspect, a coding region comprises a sequence that is at least 75% identical to or complimentary to a sequence selected from the group consisting of SEQ ID NO:8 to 10. In a further aspect, a coding region comprises a sequence that is at least 80% identical to or complimentary to a sequence selected from the group consisting of SEQ ID NO:8 to 10. In a further aspect, a coding region comprises a sequence that is at least 85% identical to or complimentary to a sequence selected from the group consisting of SEQ ID NO:8 to 10. In a further aspect, a coding region comprises a sequence that is at least 90% identical to or complimentary to a sequence selected from the group consisting of SEQ ID NO:8 to 10. In a further aspect, a coding region comprises a sequence that is at least 95% identical to or complimentary to a sequence selected from the group consisting of SEQ ID NO:8 to 10. In a further aspect, a coding region comprises a sequence that is at least 96% identical to or complimentary to a sequence selected from the group consisting of SEQ ID NO:8 to 10. In a further aspect, a coding region comprises a sequence that is at least 97% identical to or complimentary to a sequence selected from the group consisting of SEQ ID NO:8 to 10. In a further aspect, a coding region comprises a sequence that is at least 98% identical to or complimentary to a sequence selected from the group consisting of SEQ ID NO:8 to 10. In a further aspect, a coding region comprises a sequence that is at least 99% identical to or complimentary to a sequence selected from the group consisting of SEQ ID NO:8 to 10. In a further aspect, a coding region comprises a sequence that is between 70 and 99% identical to or complimentary to a sequence selected from the group consisting of SEQ ID NO:8 to 10. In a further aspect, a coding region comprises a sequence that is between 75 and 95% identical to or complimentary to a sequence selected from the group consisting of SEQ ID NO:8 to 10. In a further aspect, a coding region comprises a sequence that is between 80 and 90% identical to or complimentary to a sequence selected from the group consisting of SEQ ID NO:8 to 10. In a further aspect, a coding region comprises a sequence that is between 80 and 85% identical to or complimentary to a sequence selected from the group consisting of SEQ ID NO:8 to 10. In a further aspect, a coding region comprises a sequence that is between 85 and 90% identical to or complimentary to a sequence selected from the group consisting of SEQ ID NO:8 to 10. In a further aspect, a coding region comprises a sequence that is between 95 and 99% identical to or complimentary to a sequence selected from the group consisting of SEQ ID NO:8 to 10. In a further aspect, a coding region comprises a sequence that is between 96 and 99% identical to or complimentary to a sequence selected from the group consisting of SEQ ID NO:8 to 10. In a further aspect, a coding region comprises a sequence that is between 97 and 99% identical to or complimentary to a sequence selected from the group consisting of SEQ ID NO:8 to 10. In a further aspect, a coding region comprises a sequence that is between 98 and 99% identical to or complimentary to a sequence selected from the group consisting of SEQ ID NO:8 to 10.

In another aspect, the present specification provides a plant comprising a recombinant polynucleotide that further comprises a sequence encoding a transcription terminator. In a further aspect, the present specification provides for a terminator comprising the sequence of SEQ ID NO:11, a complement thereof, or a functional fragment thereof. In a further aspect, a terminator comprises a sequence that is at least 70% identical to or complimentary to SEQ ID NO:11. In a further aspect, a terminator comprises a sequence that is at least 75% identical to or complementary to SEQ ID NO:11. In a further aspect, a terminator comprises a sequence that is at least 80% identical to or complimentary to SEQ ID NO:11. In a further aspect, a terminator comprises a sequence that is at least 85% identical to or complimentary to SEQ ID NO:11. In a further aspect, a terminator comprises a sequence that is at least 90% identical to or complimentary to SEQ ID NO:11. In a further aspect, a terminator comprises a sequence that is at least 95% identical to or complimentary to SEQ ID NO:11. In a further aspect, a terminator comprises a sequence that is at least 96% identical to or complimentary to SEQ ID NO:11. In a further aspect, a terminator comprises a sequence that is at least 97% identical to or complimentary to SEQ ID NO:11. In a further aspect, a terminator comprises a sequence that is at least 98% identical to or complimentary to SEQ ID NO:11. In a further aspect, a terminator comprises a sequence that is at least 99% identical to or complimentary to SEQ ID NO:11. In a further aspect, a terminator comprises a sequence that is between 70 and 99% identical to or complimentary to SEQ ID NO:11. In a further aspect, a terminator comprises a sequence that is between 75 and 95% identical to or complimentary to SEQ ID NO:11. In a further aspect, a terminator comprises a sequence that is between 80 and 90% identical to or complimentary to SEQ ID NO:11. In a further aspect, a terminator comprises a sequence that is between 80 and 85% identical to or complimentary to SEQ ID NO:11. In a further aspect, a terminator comprises a sequence that is between 85 and 90% identical to or complimentary to SEQ ID NO:11.

In another aspect, the present specification provides a plant comprising a recombinant polynucleotide comprising a sequence selected from the group consisting of SEQ ID NO:12 to 32 (See Table 2). In a further aspect, the present specification provides a plant comprising a recombinant polynucleotide comprising a sequence that is at least 70% identical to or complementary to the sequence selected from the group consisting of SEQ ID NO:12 to 32. In a further aspect, a recombinant polynucleotide comprises a sequence that is at least 75% identical to or complimentary to the sequence selected from the group consisting of SEQ ID NO:12 to 32. In a further aspect, a recombinant polynucleotide comprises a sequence that is at least 80% identical to or complimentary to the sequence selected from the group consisting of SEQ ID NO:12 to 32. In a further aspect, a recombinant polynucleotide comprises a sequence that is at least 85% identical to or complimentary to the sequence selected from the group consisting of SEQ ID NO:12 to 32. In a further aspect, a recombinant polynucleotide comprises a sequence that is at least 90% identical to or complimentary to the sequence selected from the group consisting of SEQ ID NO:12 to 32. In a further aspect, a recombinant polynucleotide comprises a sequence that is at least 95% identical to or complimentary to the sequence selected from the group consisting of SEQ ID NO:12 to 32. In a further aspect, a recombinant polynucleotide comprises a sequence that is at least 96% identical to or complimentary to the sequence selected from the group consisting of SEQ ID NO:12 to 32. In a further aspect, a recombinant polynucleotide comprises a sequence that is at least 97% identical to or complimentary to the sequence selected from the group consisting of SEQ ID NO:12 to 32. In a further aspect, a recombinant polynucleotide comprises a sequence that is at least 98% identical to or complimentary to the sequence selected from the group consisting of SEQ ID NO:12 to 32. In a further aspect, a recombinant polynucleotide comprises a sequence that is at least 99% identical to or complimentary to the sequence selected from the group consisting of SEQ ID NO:12 to 32. In a further aspect, a recombinant polynucleotide comprises a sequence that is between 70 and 99% identical to or complimentary to the sequence selected from the group consisting of SEQ ID NO:12 to 32. In a further aspect, a recombinant polynucleotide comprises a sequence that is between 75 and 95% identical to or complimentary to the sequence selected from the group consisting of SEQ ID NO:12 to 32. In a further aspect, a recombinant polynucleotide comprises a sequence that is between 80 and 90% identical to or complimentary to the sequence selected from the group consisting of SEQ ID NO:12 to 32. In a further aspect, a recombinant polynucleotide comprises a sequence that is between 80 and 85% identical to or complimentary to the sequence selected from the group consisting of SEQ ID NO:12 to 32. In a further aspect, a recombinant polynucleotide comprises a sequence that is between 85 and 90% identical to or complimentary to the sequence selected from the group consisting of SEQ ID NO:12 to 32. In a further aspect, a recombinant polynucleotide comprises a sequence that is between 95 and 99% identical to or complimentary to the sequence selected from the group consisting of SEQ ID NO:12 to 32. In a further aspect, a recombinant polynucleotide comprises a sequence that is between 96 and 99% identical to or complimentary to the sequence selected from the group consisting of SEQ ID NO:12 to 32. In a further aspect, a recombinant polynucleotide comprises a sequence that is between 97 and 99% identical to or complimentary to the sequence selected from the group consisting of SEQ ID NO:12 to 32. In a further aspect, a recombinant polynucleotide comprises a sequence that is between 98 and 99% identical to or complimentary to the sequence selected from the group consisting of SEQ ID NO:12 to 32.

TABLE 2

Visual marker constructs are created combining a callus preferred promoter from column A, a visual marker coding region from column B, and, optionally, a Terminator from Column C. Every possible combination is contemplated.

| A<br>Callus-preferred promoter | B<br>Visual marker coding region | C<br>terminator |
| --- | --- | --- |
| pNtPR5 | AtPAP1 | Nt-HSP-T |
| pNtPRP | NtAN1 | |
| pNtAD | NtAn2 | |
| pNtEX3-like | | |
| pNtEX1-like | | |
| pNtPR1a | | |
| pNtSAHH | | |

In one aspect, the present specification provides a plant comprising a recombinant polynucleotide comprising a heterologous tissue-preferred promoter and a coding region from a pigment regulatory factor where the polynucleotide sequence of the promoter and coding region are plant native polynucleotide sequences. In a further aspect, the present specification provides a recombinant polynucleotide comprising a nucleotide sequence selected from the group consisting of SEQ ID NO:1 to 40. In a further aspect, a recombinant polynucleotide comprises nucleotide sequences that are native to a plant genome. In a further aspect, a recombinant polynucleotide comprises nucleotide sequences that are native to a *Nicotiana* genome. In a further aspect, a recombinant polynucleotide comprises nucleotide sequences that are native to a *Nicotiana tabacum* genome. In a further aspect, a recombinant polynucleotide comprises nucleotide sequences that are native to only a plant genome. In a further aspect, a recombinant polynucleotide comprises nucleotide sequences that are native to only a *Nicotiana* genome.

In another aspect, the present specification provides a recombinant polynucleotide comprising the coding region from a pigment regulatory factor. In an aspect, a pigment regulatory factor can be selected from the group consisting of a pigment biosynthetic enzyme, a pigment regulatory transcription factor, a pigment transporter, a pigment metabolic enzyme, and a pigment catabolic enzyme. In a further aspect, a pigment regulatory factor can be selected from the group consisting of a phenylpropanoid biosynthetic enzyme, a phenylpropanoid regulatory transcription factor, a phenylpropanoid transporter, a phenylpropanoid metabolic enzyme, and a phenylpropanoid catabolic enzyme. In a further aspect, a pigment regulatory factor can be selected from the group consisting of an anthocyanin biosynthetic enzyme, an anthocyanin regulatory transcription factor, an anthocyanin transporter, an anthocyanin metabolic enzyme, and an anthocyanin catabolic enzyme.

In another aspect, the present specification provides a recombinant polynucleotide that comprises a tissue-preferred promoter comprising a sequence selected form the group consisting of SEQ ID NO:1 to 7 a complement thereof, or a functional fragment thereof. In a further aspect, a tissue-preferred promoter comprises a sequence that is at least 70% identical to or complimentary to a sequence selected from the group consisting of SEQ ID NO:1 to 7. In a further aspect, a tissue-preferred promoter comprises a sequence that is at least 75% identical to or complimentary to a sequence selected from the group consisting of SEQ ID NO:1 to 7. In a further aspect, a tissue-preferred promoter comprises a sequence that is at least 80% identical to or complimentary to a sequence selected from the group consisting of SEQ ID NO:1 to 7. In a further aspect, a tissue-preferred promoter comprises a sequence that is at least 85% identical to or complimentary to a sequence selected from the group consisting of SEQ ID NO:1 to 7. In a further aspect, a tissue-preferred promoter comprises a sequence that is at least 90% identical to or complimentary to a sequence selected from the group consisting of SEQ ID NO:1 to 7. In a further aspect, a tissue-preferred promoter comprises a sequence that is at least 95% identical to or complimentary to a sequence selected from the group consisting of SEQ ID NO:1 to 7. In a further aspect, a tissue-preferred promoter comprises a sequence that is at least 96% identical to or complimentary to a sequence selected from the group consisting of SEQ ID NO:1 to 7. In a further aspect, a tissue-preferred promoter comprises a sequence that is at least 97% identical to or complimentary to a sequence selected from the group consisting of SEQ ID NO:1 to 7. In a further aspect, a tissue-preferred promoter comprises a sequence that is at least 98% identical to or complimentary to a sequence selected from the group consisting of SEQ ID NO:1 to 7. In a further aspect, a tissue-preferred promoter comprises a sequence that is at least 99% identical to or complimentary to a sequence selected from the group consisting of SEQ ID NO:1 to 7. In a further aspect, a tissue-preferred promoter comprises a sequence that is between 70 and 99% identical to or complimentary to a sequence selected from the group consisting of SEQ ID NO:1 to 7. In a further aspect, a tissue-preferred promoter comprises a sequence that is between 75 and 95% identical to or complimentary to a sequence selected from the group consisting of SEQ ID NO:1 to 7. In a further aspect, a tissue-preferred promoter comprises a sequence that is between 80 and 90% identical to or complimentary to a sequence selected from the group consisting of SEQ ID NO:1 to 7. In a further aspect, a tissue-preferred promoter comprises a sequence that is between 80 and 85% identical to or complimentary to a sequence selected from the group consisting of SEQ ID NO:1 to 7. In a further aspect, a tissue-preferred promoter comprises a sequence that is between 85 and 90% identical to or complimentary to a sequence selected from the group consisting of SEQ ID NO:1 to 7. In a further aspect, the present specification provides for a recombinant polynucleotide comprising any combination of recombinant polynucleotides disclosed herein. In a further aspect, a tissue-preferred promoter comprises a sequence that is between 95 and 99% identical to or complimentary to a sequence selected from the group consisting of SEQ ID NO:1 to 7. In a further aspect, a tissue-preferred promoter comprises a sequence that is between 96 and 99% identical to or complimentary to a sequence selected from the group consisting of SEQ ID NO:1 to 7. In a further aspect, a tissue-preferred promoter comprises a sequence that is between 97 and 99% identical to or complimentary to a sequence selected from the group consisting of SEQ ID NO:1 to 7. In a further aspect, a tissue-preferred promoter comprises a sequence that is between 98 and 99% identical to or complimentary to a sequence selected from the group consisting of SEQ ID NO:1 to 7.

In a further aspect, the present specification provides for a recombinant polynucleotide comprising any combination of recombinant polynucleotides disclosed herein.

In another aspect, the present specification provides a recombinant polynucleotide that comprises a coding region having a sequence selected from the group consisting of SEQ ID NO: 8 to 11 a complement thereof, or a functional fragment thereof. In a further aspect, a coding region comprises a sequence that is at least 70% identical to or complimentary to a sequence selected from the group consisting of SEQ ID NO:8 to 10. In a further aspect, a coding region comprises a sequence that is at least 75% identical to or complimentary to a sequence selected from the group consisting of SEQ ID NO:8 to 10. In a further aspect, a coding region comprises a sequence that is at least 80% identical to or complimentary to a sequence selected from the group consisting of SEQ ID NO:8 to 10. In a further aspect, a coding region comprises a sequence that is at least 85% identical to or complimentary to a sequence selected from the group consisting of SEQ ID NO:8 to 10. In a further aspect, a coding region comprises a sequence that is at least 90% identical to or complimentary to a sequence selected from the group consisting of SEQ ID NO:8 to 10. In a further aspect, a coding region comprises a sequence that is at least 95% identical to or complimentary to a sequence selected from the group consisting of SEQ ID NO:8 to 10. In a further aspect, a coding region comprises a sequence that is at least 96% identical to or complimentary to a sequence selected from the group consisting of SEQ ID NO:8 to 10. In a further aspect, a coding region comprises a sequence that is at least 97% identical to or complimentary to a sequence selected from the group consisting of SEQ ID NO:8 to 10. In a further aspect, a coding region comprises a sequence that is at least 98% identical to or complimentary to a sequence selected from the group consisting of SEQ ID NO:8 to 10. In a further aspect, a coding region comprises a sequence that is at least 99% identical to or complimentary to a sequence selected from the group consisting of SEQ ID NO:8 to 10. In a further aspect, a coding region comprises a sequence that is between 70 and 99% identical to or complimentary to a sequence selected from the group consisting of SEQ ID NO:8 to 10. In a further aspect, a coding region comprises a sequence that is between 75 and 95% identical to or complimentary to a sequence selected from the group consisting of SEQ ID NO:8 to 10. In a further aspect, a coding region comprises a sequence that is between 80 and 90% identical to or complimentary to a sequence selected from the group consisting of SEQ ID NO:8 to 10. In a further aspect, a coding region comprises a sequence that is between 80 and 85% identical to or complimentary to a sequence selected from the group consisting of SEQ ID NO:8 to 10. In a further aspect, a coding region comprises a sequence that is between 85 and 90% identical to or complimentary to a sequence selected from the group consisting of SEQ ID NO:8 to 10. In a further aspect, a coding region comprises a sequence that is between 95 and 99% identical to or complimentary to a sequence selected from the group consisting of SEQ ID NO:8 to 10. In a further aspect, a coding region comprises a sequence that is between 96 and 99% identical to or complimentary to a sequence selected from the group consisting of SEQ ID NO:8 to 10. In a further aspect, a coding region comprises a sequence that is between 97 and 99% identical to or complimentary to a sequence selected from the group consisting of SEQ ID NO:8 to 10. In a further aspect, a coding region comprises a sequence that is between 98 and 99% identical to or complimentary to a sequence selected from the group consisting of SEQ ID NO:8 to 10.

In another aspect, the present specification provides a recombinant polynucleotide that further comprises a sequence encoding a transcription terminator. In a further aspect, the present specification provides for a terminator comprising the sequence of SEQ ID NO:11, a complement thereof, or a functional fragment thereof. In a further aspect, a terminator comprises a sequence that is at least 70% identical to or complimentary to SEQ ID NO:11. In a further aspect, a terminator comprises a sequence that is at least 75% identical to or complimentary to SEQ ID NO:11. In a further aspect, a terminator comprises a sequence that is at least 80% identical to or complimentary to SEQ ID NO:11. In a further aspect, a terminator comprises a sequence that is at least 85% identical to or complimentary to SEQ ID NO:11. In a further aspect, a terminator comprises a sequence that is at least 90% identical to or complimentary to SEQ ID NO:11. In a further aspect, a terminator comprises a sequence that is at least 95% identical to or complimentary to SEQ ID NO:11. In a further aspect, a terminator comprises a sequence that is at least 96% identical to or complimentary to SEQ ID NO:11. In a further aspect, a terminator comprises a sequence that is at least 97% identical to or complimentary to SEQ ID NO:11. In a further aspect, a terminator comprises a sequence that is at least 98% identical to or complimentary to SEQ ID NO:11. In a further aspect, a terminator comprises a sequence that is at least 99% identical to or complimentary to SEQ ID NO:11. In a further aspect, a terminator comprises a sequence that is between 70 and 99% identical to or complimentary to SEQ ID NO:11. In a further aspect, a terminator comprises a sequence that is between 75 and 95% identical to or complimentary to SEQ ID NO:11. In a further aspect, a terminator comprises a sequence that is between 80 and 90% identical to or complimentary to SEQ ID NO:11. In a further aspect, a terminator comprises a sequence that is between 80 and 85% identical to or complimentary to SEQ ID NO:11. In a further aspect, a terminator comprises a sequence that is between 85 and 90% identical to or complimentary to SEQ ID NO:11. In a further aspect, a terminator comprises a sequence that is between 95 and 99% identical to or complimentary to SEQ ID NO:11. In a further aspect, a terminator comprises a sequence that is between 96 and 99% identical to or complimentary to SEQ ID NO:11. In a further aspect, a terminator comprises a sequence that is between 97 and 99% identical to or complimentary to SEQ ID NO:11. In a further aspect, a terminator comprises a sequence that is between 98 and 99% identical to or complimentary to SEQ ID NO:11.

In another aspect, the present specification provides a recombinant polynucleotide comprising a sequence selected from the group consisting of SEQ ID NO:12 to 32 (See Table 2). In a further aspect, the present specification provides a recombinant polynucleotide comprising a sequence that is at least 70% identical to or complimentary to the sequence selected from the group consisting of SEQ ID NO:12 to 32. In a further aspect, a recombinant polynucleotide comprises a sequence that is at least 75% identical to or complimentary to the sequence selected from the group consisting of SEQ ID NO:12 to 32. In a further aspect, a recombinant polynucleotide comprises a sequence that is at least 80% identical to or complimentary to the sequence selected from the group consisting of SEQ ID NO:12 to 32. In a further aspect, a recombinant polynucleotide comprises a sequence that is at least 85% identical to or complimentary to the sequence selected from the group consisting of SEQ ID NO:12 to 32. In a further aspect, a recombinant polynucleotide comprises a sequence that is at least 90% identical to or complimentary to the sequence selected from the group consisting of SEQ ID NO:12 to 32. In a further aspect, a recombinant polynucleotide comprises a sequence that is at least 95% identical to or complimentary to the sequence selected from the group consisting of SEQ ID NO:12 to 32. In a further aspect, a recombinant polynucleotide comprises a sequence that is at least 95% identical to or complimentary to the sequence selected from the group consisting of SEQ ID NO:12 to 32. In a further aspect, a recombinant polynucleotide comprises a sequence that is at least 96% identical to or complimentary to the sequence selected from the group consisting of SEQ ID NO:12 to 32. In a further aspect, a recombinant polynucleotide comprises a sequence that is at least 97% identical to or complimentary to the sequence selected from the group consisting of SEQ ID NO:12 to 32. In a further aspect, a recombinant polynucleotide comprises a sequence that is at least 98% identical to or complimentary to the sequence selected from the group consisting of SEQ ID NO:12 to 32. In a further aspect, a recombinant polynucleotide comprises a sequence that is at least 99% identical to or complimentary to the sequence selected from the group consisting of SEQ ID NO:12 to 32. In a further aspect, a recombinant polynucleotide comprises a sequence that is between 70 and 99% identical to or complimentary to the sequence selected from the group consisting of SEQ ID NO:12 to 32. In a further aspect, a recombinant polynucleotide comprises a sequence that is between 75 and 95% identical to or complimentary to the sequence selected from the group consisting of SEQ ID NO:12 to 32. In a further aspect, a recombinant polynucleotide comprises a sequence that is between 80 and 90% identical to or complimentary to the sequence selected from the group consisting of SEQ ID NO:12 to 32. In a further aspect, a recombinant polynucleotide comprises a sequence that is between 80 and 85% identical to or complimentary to the sequence selected from the group consisting of SEQ ID NO:12 to 32. In a further aspect, a recombinant polynucleotide comprises a sequence that is between 85 and 90% identical to or complimentary to the sequence selected from the group consisting of SEQ ID NO:12 to 32. In a further aspect, a recombinant polynucleotide comprises a sequence that is between 95 and 99% identical to or complimentary to the sequence selected from the group consisting of SEQ ID NO:12 to 32. In a further aspect, a recombinant polynucleotide comprises a sequence that is between 96 and 99% identical to or complimentary to the sequence selected from the group consisting of SEQ ID NO:12 to 32. In a further aspect, a recombinant polynucleotide comprises a sequence that is between 97 and 99% identical to or complimentary to the sequence selected from the group consisting of SEQ ID NO:12 to 32. In a further aspect, a recombinant polynucleotide comprises a sequence that is between 98 and 99% identical to or complimentary to the sequence selected from the group consisting of SEQ ID NO:12 to 32.

The present disclosure also provides a container of seeds capable of producing a plant comprising a recombinant polynucleotide selected from the group consisting of SEQ ID NOs:1 to 40. A container of seeds can be a container of Eudicot seeds, Solanaceae seeds, *Nicotiana* seeds, or any combination thereof. A container of seeds of the present disclosure may contain any number, weight, or volume of seeds. For example, a container can contain at least, or greater than, 100, 200, 300, 400, 500, 600, 700, 800, 900, 1000, 1500, 2000, 2500, 3000, 3500, 4000 or more seeds. Alternatively, the container can contain at least, or greater than, 1 ounce, 5 ounces, 10 ounces, 1 pound, 2 pounds, 3 pounds, 4 pounds, 5 pounds or more seeds. A container may contain at least 100 seeds. A container may contain at least 200 seeds. A container may contain at least 300 seeds. A container may contain at least 400 seeds. A container may contain at least 500 seeds. A container may contain at least 600 seeds. A container may contain at least 700 seeds. A container may contain at least 800 seeds. A container may contain at least 900 seeds. A container may contain at least 1000 seeds. A container may contain at least 1500 seeds. A container may contain at least 2000 seeds. A container may contain at least 2500 seeds. A container may contain at least 3000 seeds. A container may contain at least 3500 seeds. A container may contain at least 4000 seeds. A container may contain greater than 4000 seeds. Alternatively, the container may contain at least 1 ounce, at least 5 ounces, at least 10 ounces, at least 1 pound, at least 2 pounds, at least 3 pounds, at least 4 pounds, at least 5 pounds, or more *Nicotinia* seeds. The container may contain at least 1 ounce of seeds. The container may contain at least 5 ounces of seeds. The container may contain at least 10 ounces of seeds. The container may contain at least 1 pound of seeds. The container may contain at least 2 pounds of seeds. The container may contain at least 3 pounds of seeds. The container may contain at least 4 pounds of seeds. The container may contain at least 5 pounds of seeds. By way of a non-limiting example, a container may be a box, a bag, a packet, a pouch, a tape roll, a pail, a foil, or a tube.

In an aspect, the present specification provides a method for selecting at least one modified plant cell comprising transforming at least one plant cell comprising a recombinant polynucleotide and selecting at least one modified plant cell expressing a pigment as a visual marker.

In a further aspect of a method provided herein, at least one plant cell is transformed via *Agrobacterium* mediated transformation. In another aspect of a method provided herein, at least one plant cell is transformed via biolistic mediated transformation. In a further aspect of a method provided herein, a plant cell is transformed with at least one recombinant polynucleotide. In a further aspect of a method provided herein, a plant cell is transformed concurrently with at least two recombinant polynucleotides. In a further aspect of a method provided herein, a plant cell is transformed concurrently with at least three recombinant polynucleotides. In a further aspect of a method provided herein, a plant cell is transformed concurrently with at least four recombinant polynucleotides. In a further aspect of a method provided herein, a plant cell is transformed concurrently with at least five recombinant polynucleotides. In a further aspect of a method provide herein, a selected plant cell is regenerated into a plant.

In a another aspect, a method provided for, and disclosed, in the present specification comprises transforming at least one plant cell comprising a recombinant polynucleotide where a recombinant polynucleotide comprises a tissue-preferred promoter and a coding region from a pigment regulatory factor. In a further aspect of this method, a tissue-preferred promoter and a coding region are native to a plant genome. In a further aspect of this method, a tissue-preferred promoter and a coding region are native to a *Nicotiana* genome. In another aspect of this method, a recombinant polynucleotide comprises a terminator. In a further aspect of this method, a tissue-preferred promoter, coding region, and terminator are native to a plant genome. In a further aspect of this method, a tissue-preferred promoter, coding region, and terminator are native to a *Nicotiana* genome. In another aspect of this method, a recombinant polynucleotide further comprises a second promoter and a second coding region. In a further aspect of this method, a recombinant polynucleotide further comprises a second terminator. In a further aspect of this method, a second coding region encodes a small RNA. In a further aspect, a small RNA is selected from the group consisting of a small RNA precursor, microRNA (miRNA), transfer RNA (tRNA), small interfering RNA (siRNA), trans-acting siRNA (tasiRNA), and ribosomal RNA (rRNA). In a further aspect, a second coding region encodes a protein.

In another aspect, a method provided for, and disclosed, in the present specification comprises selecting at least one modified plant cell. In a further aspect of this method, a modified plant cell is a transgenic plant cell. In another aspect of this method, a plant cell to be transformed is a callus cell derived from a plant cell.

In another aspect, a method provided for, and disclosed, in the present specification comprises selecting at least one modified plant cell expressing a pigment as a visual marker. In a further aspect of this method, a plant cell expresses a carotenoid as a visual marker. In a further aspect of this method, a plant cell expresses a phenylpropanoid as a visual marker. In a further aspect of this method, a plant cell expresses an anthocyanin as a visual marker.

In another aspect, a method provided for, and disclosed, in the present specification comprises selecting at least one modified plant cell comprising transforming at least one plant cell comprising a recombinant polynucleotide. In a further aspect of this method, a recombinant polynucleotide that comprises a tissue-preferred promoter comprises a sequence selected form the group consisting of SEQ ID NO:1 to 7 a complement thereof, or a functional fragment thereof. In a further aspect of this method, a tissue-preferred promoter comprises a sequence that is at least 70% identical to or complimentary to a sequence selected from the group consisting of SEQ ID NO:1 to 7. In a further aspect of this method, a tissue-preferred promoter comprises a sequence that is at least 75% identical to or complimentary to a sequence selected from the group consisting of SEQ ID NO:1 to 7. In a further aspect of this method, a tissue-preferred promoter comprises a sequence that is at least 80% identical to or complimentary to a sequence selected from the group consisting of SEQ ID NO:1 to 7. In a further aspect of this method, a tissue-preferred promoter comprises a sequence that is at least 85% identical to or complimentary to a sequence selected from the group consisting of SEQ ID NO:1 to 7. In a further aspect of this method, a tissue-preferred promoter comprises a sequence that is at least 90% identical to or complimentary to a sequence selected from the group consisting of SEQ ID NO:1 to 7. In a further aspect of this method, a tissue-preferred promoter comprises a sequence that is at least 95% identical to or complimentary to a sequence selected from the group consisting of SEQ ID NO:1 to 7. In a further aspect of this method, a tissue-preferred promoter comprises a sequence that is at least 96% identical to or complimentary to a sequence selected from the group consisting of SEQ ID NO:1 to 7. In a further aspect of this method, a tissue-preferred promoter comprises a sequence that is at least 97% identical to or complimentary to a sequence selected from the group consisting of SEQ ID NO:1 to 7. In a further aspect of this method, a tissue-preferred promoter comprises a sequence that is at least 98% identical to or complimentary to a sequence selected from the group consisting of SEQ ID NO:1 to 7. In a further aspect of this method, a tissue-preferred promoter comprises a sequence that is at least 99% identical to or complimentary to a sequence selected from the group consisting of SEQ ID NO:1 to 7. In a further aspect of this method, a tissue-preferred promoter comprises a sequence that is between 70 and 99% identical to or complimentary to a sequence selected from the group consisting of SEQ ID NO:1 to 7. In a further aspect of this method, a tissue-preferred promoter comprises a sequence that is between 75 and 95% identical to or complimentary to a sequence selected from the group consisting of SEQ ID NO:1 to 7. In a further aspect of this method, a tissue-preferred promoter comprises a sequence that is between 80 and 90% identical to or complimentary to a sequence selected from the group consisting of SEQ ID NO:1 to 7. In a further aspect of this method, a tissue-preferred promoter comprises a sequence that is between 80 and 85% identical to or complimentary to a sequence selected from the group consisting of SEQ ID NO:1 to 7. In a further aspect of this method, a tissue-preferred promoter comprises a sequence that is between 85 and 90% identical to or complimentary to a sequence selected from the group consisting of SEQ ID NO:1 to 7. In a further aspect of this method, a tissue-preferred promoter comprises a sequence that is between 95 and 99% identical to or complimentary to a sequence selected from the group consisting of SEQ ID NO:1 to 7. In a further aspect of this method, a tissue-preferred promoter comprises a sequence that is between 96 and 99% identical to or complimentary to a sequence selected from the group consisting of SEQ ID NO:1 to 7. In a further aspect of this method, a tissue-preferred promoter comprises a sequence that is between 97 and 99% identical to or complimentary to a sequence selected from the group consisting of SEQ ID NO:1 to 7. In a further aspect of this method, a tissue-preferred promoter comprises a sequence that is between 98 and 99% identical to or complimentary to a sequence selected from the group consisting of SEQ ID NO:1 to 7.

In another aspect, a method provided for, and disclosed, in the present specification comprises selecting at least one modified plant cell comprising transforming at least one plant cell comprising a recombinant polynucleotide. In a further aspect of this method, a recombinant polynucleotide comprises a coding region having a sequence selected from the group consisting of SEQ ID NO:8 to 10, a complement thereof, or a functional fragment thereof. In a further aspect of this method, a coding region comprises a sequence that is at least 70% identical to or complimentary to a sequence selected from the group consisting of SEQ ID NO:8 to 10. In a further aspect of this method, a coding region comprises a sequence that is at least 75% identical to or complimentary to a sequence selected from the group consisting of SEQ ID NO:8 to 10. In a further aspect of this method, a coding region comprises a sequence that is at least 80% identical to or complimentary to a sequence selected from the group consisting of SEQ ID NO:8 to 10. In a further aspect of this method, a coding region comprises a sequence that is at least 85% identical to or complimentary to a sequence selected from the group consisting of SEQ ID NO:8 to 10. In a further aspect of this method, a coding region comprises a sequence that is at least 90% identical to or complimentary to a sequence selected from the group consisting of SEQ ID NO:8 to 10. In a further aspect of this method, a coding region comprises a sequence that is at least 95% identical to or complimentary to a sequence selected from the group consisting of SEQ ID NO:8 to 10. In a further aspect of this method, a coding region comprises a sequence that is at least 96% identical to or complimentary to a sequence selected from the group consisting of SEQ ID NO:8 to 10. In a further aspect of this method, a coding region comprises a sequence that is at least 97% identical to or complimentary to a sequence selected from the group consisting of SEQ ID NO:8 to 10. In a further aspect of this method, a coding region comprises a sequence that is at least 98% identical to or complimentary to a sequence selected from the group consisting of SEQ ID NO:8 to 10. In a further aspect of this method, a coding region comprises a sequence that is at least 99% identical to or complimentary to a sequence selected from the group consisting of SEQ ID NO:8 to 10. In a further aspect of this method, a coding region comprises a sequence that is between 70 and 99% identical to or complimentary to a sequence selected from the group consisting of SEQ ID NO:8 to 10. In a further aspect of this method, a coding region comprises a sequence that is between 75 and 95% identical to or complimentary to a sequence selected from the group consisting of SEQ ID NO:8 to 10. In a further aspect of this method, a coding region comprises a sequence that is between 80 and 90% identical to or complimentary to a sequence selected from the group consisting of SEQ ID NO:8 to 10. In a further aspect of this method, a coding region comprises a sequence that is between 80 and 85% identical to or complimentary to a sequence selected from the group consisting of SEQ ID NO:8 to 10. In a further aspect of this method, a coding region comprises a sequence that is between 85 and 90% identical to or complimentary to a sequence selected from the group consisting of SEQ ID NO:8 to 10. In a further aspect of this method, a coding region comprises a sequence that is between 95 and 99% identical to or complimentary to a sequence selected from the group consisting of SEQ ID NO:8 to 10. In a further aspect of this method, a coding region comprises a sequence that is between 96 and 99% identical to or complimentary to a sequence selected from the group consisting of SEQ ID NO:8 to 10. In a further aspect of this method, a coding region comprises a sequence that is between 97 and 99% identical to or complimentary to a sequence selected from the group consisting of SEQ ID NO:8 to 10. In a further aspect of this method, a coding region comprises a sequence that is between 98 and 99% identical to or complimentary to a sequence selected from the group consisting of SEQ ID NO:8 to 10.

In another aspect, a method provided for, and disclosed, in the present specification comprises selecting at least one modified plant cell comprising transforming at least one plant cell comprising a recombinant polynucleotide. In a further aspect of this method, a recombinant polynucleotide further comprises a sequence encoding a transcription terminator. In a further aspect of this method, the present specification provides for a terminator comprising the sequence of SEQ ID NO:11, a complement thereof, or a functional fragment thereof. In a further aspect of this method, a terminator comprises a sequence that is at least 70% identical to or complimentary to SEQ ID NO:11. In a further aspect of this method, a terminator comprises a sequence that is at least 75% identical to or complimentary to SEQ ID NO:11. In a further aspect of this method, a terminator comprises a sequence that is at least 80% identical to or complimentary to SEQ ID NO:11. In a further aspect of this method, a terminator comprises a sequence that is at least 85% identical to or complimentary to SEQ ID NO:11. In a further aspect of this method, a terminator comprises a sequence that is at least 90% identical to or complimentary to SEQ ID NO:11. In a further aspect of this method, a terminator comprises a sequence that is at least 95% identical to or complimentary to SEQ ID NO:11. In a further aspect of this method, a terminator comprises a sequence that is at least 96% identical or complimentary to SEQ ID NO:11. In a further aspect of this method, a terminator comprises a sequence that is at least 97% identical to or complimentary to SEQ ID NO:11. In a further aspect of this method, a terminator comprises a sequence that is at least 98% identical to or complimentary to SEQ ID NO:11. In a further aspect of this method, a terminator comprises a sequence that is at least 99% identical to or complimentary to SEQ ID NO:11. In a further aspect of this method, a terminator comprises a sequence that is between 70 and 99% identical to or complimentary to SEQ ID NO:11. In a further aspect of this method, a terminator comprises a sequence that is between 75 and 95% identical to or complimentary to SEQ ID NO:11. In a further aspect of this method, a terminator comprises a sequence that is between 80 and 90% identical to or complimentary to SEQ ID NO:11. In a further aspect of this method, a terminator comprises a sequence that is between 80 and 85% identical to or complimentary to SEQ ID NO:11. In a further aspect of this method, a terminator comprises a sequence that is between 85 and 90% identical to or complimentary to SEQ ID NO:11. In a further aspect of this method, a terminator comprises a sequence that is between 95 and 99% identical to or complimentary to SEQ ID NO:11. In a further aspect of this method, a terminator comprises a sequence that is between 96 and 99% identical to or complimentary to SEQ ID NO:11. In a further aspect of this method, a terminator comprises a sequence that is between 97 and 99% identical to or complimentary to SEQ ID NO:11. In a further aspect of this method, a terminator comprises a sequence that is between 98 and 99% identical to or complimentary to SEQ ID NO:11.

In a further aspect, the present specification provides, and includes, a method for selecting a plant comprising any combination of recombinant polynucleotides disclosed herein.

In another aspect, a method provided for, and disclosed, in the present specification comprises selecting at least one modified plant cell comprising transforming at least one plant cell comprising a recombinant polynucleotide. In a further aspect of this method, a recombinant polynucleotide comprises a sequence selected from the group consisting of SEQ ID NO:12 to 32 (See Table 2). In a further aspect of this method, the present specification provides a recombinant polynucleotide comprising a sequence that is at least 70% identical to or complimentary to the sequence selected from the group consisting of SEQ ID NO:12 to 32. In a further aspect of this method, a recombinant polynucleotide comprises a sequence that is at least 75% identical to or complimentary to the sequence selected from the group consisting of SEQ ID NO:12 to 32. In a further aspect of this method, a recombinant polynucleotide comprises a sequence that is at least 80% identical to or complimentary to the sequence selected from the group consisting of SEQ ID NO:12 to 32. In a further aspect of this method, a recombinant polynucleotide comprises a sequence that is at least 85% identical to or complimentary to the sequence selected from the group consisting of SEQ ID NO:12 to 32. In a further aspect of this method, a recombinant polynucleotide comprises a sequence that is at least 90% identical to or complimentary to the sequence selected from the group consisting of SEQ ID NO:12 to 32. In a further aspect of this method, a recombinant polynucleotide comprises a sequence that is at least 95% identical to or complimentary to the sequence selected from the group consisting of SEQ ID NO:12 to 32. In a further aspect of this method, a recombinant polynucleotide comprises a sequence that is at least 96% identical to or complimentary to the sequence selected from the group consisting of SEQ ID NO:12 to 32. In a further aspect of this method, a recombinant polynucleotide comprises a sequence that is at least 97% identical to or complimentary to the sequence selected from the group consisting of SEQ ID NO:12 to 32. In a further aspect of this method, a recombinant polynucleotide comprises a sequence that is at least 98% identical to or complimentary to the sequence selected from the group consisting of SEQ ID NO:12 to 32. In a further aspect of this method, a recombinant polynucleotide comprises a sequence that is at least 99% identical to or complimentary to the sequence selected from the group consisting of SEQ ID NO:12 to 32. In a further aspect of this method, a recombinant polynucleotide comprises a sequence that is between 70 and 99% identical to or complimentary to the sequence selected from the group consisting of SEQ ID NO:12 to 32. In a further aspect of this method, a recombinant polynucleotide comprises a sequence that is between 75 and 95% identical to or complimentary to the sequence selected from the group consisting of SEQ ID NO:12 to 32. In a further aspect of this method, a recombinant polynucleotide comprises a sequence that is between 80 and 90% identical to or complimentary to the sequence selected from the group consisting of SEQ ID NO:12 to 32. In a further aspect of this method, a recombinant polynucleotide comprises a sequence that is between 80 and 85% identical to or complimentary to the sequence selected from the group consisting of SEQ ID NO:12 to 32. In a further aspect of this method, a recombinant polynucleotide comprises a sequence that is between 85 and 90% identical to or complimentary to the sequence selected from the group consisting of SEQ ID NO:12 to 32. In a further aspect of this method, a recombinant polynucleotide comprises a sequence that is between 95 and 99% identical to or complimentary to the sequence selected from the group consisting of SEQ ID NO:12 to 32. In a further aspect of this method, a recombinant polynucleotide comprises a sequence that is between 96 and 99% identical to or complimentary to the sequence selected from the group consisting of SEQ ID NO:12 to 32. In a further aspect of this method, a recombinant polynucleotide comprises a sequence that is between 97 and 99% identical to or complimentary to the sequence selected from the group consisting of SEQ ID NO:12 to 32. In a further aspect of this method, a recombinant polynucleotide comprises a sequence that is between 98 and 99% identical to or complimentary to the sequence selected from the group consisting of SEQ ID NO:12 to 32.

In an aspect, the present specification provides for, and includes, a method for growing a modified plant comprising transforming at least one plant cell with a recombinant polynucleotide, selecting at least one modified plant cell comprising a recombinant polynucleotide and expressing a pigment as a visual marker, regenerating a plant from at least one modified plant cell, and growing a plant regenerated from a modified plant cell.

In a further aspect of a method provided herein, a modified plant is grown comprising at least one transformed cell is transformed via *Agrobacterium* mediated transformation. In another aspect of a method provided herein, a modified plant is grown comprising at least one transformed cell is transformed via biolistic mediated transformation. In s further aspect of a method provided herein, a modified plant is grown comprising a plant cell that has been transformed concurrently with at least one recombinant polynucleotide. In a further aspect of a method provided herein, a modified plant is grown comprising a plant cell that has been transformed concurrently with at least two recombinant polynucleotides. In a further aspect of a method provided herein, a modified plant is grown comprising a plant cell that has been transformed concurrently with at least three recombinant polynucleotides. In a further aspect of a method provided herein, a modified plant is grown comprising a plant cell that has been transformed concurrently with at least four recombinant polynucleotides. In a further aspect of a method provided herein, a modified plant is grown comprising a plant cell that has been transformed concurrently with at least five recombinant polynucleotides.

In another aspect, a method provided for, and disclosed, in the present specification comprises growing a modified plant that comprises a recombinant polynucleotide. In a further aspect of this method, a recombinant polynucleotide comprises a tissue-preferred promoter and a coding region from a pigment regulatory factor. In a further aspect of this method, a tissue-preferred promoter and a coding region are native to a plant genome. In a further aspect of this method, a tissue-preferred promoter and a coding region are native to a *Nicotiana* genome. In another aspect of this method, a recombinant polynucleotide comprises a terminator. In a further aspect of this method, a tissue-preferred promoter, coding region, and terminator are native to a plant genome. In a further aspect of this method, a tissue-preferred promoter, coding region, and terminator are native to a *Nicotiana* genome. In another aspect of this method, a recombinant polynucleotide further comprises a second promoter and a second coding region. In a further aspect of this method, a recombinant polynucleotide further comprises a second terminator. In a further aspect of this method, a second coding region encodes a small RNA. In a further aspect, a small RNA is selected from the group consisting of a small RNA precursor, microRNA (miRNA), transfer RNA (tRNA), small interfering RNA (siRNA), trans-acting siRNA (tasiRNA), and ribosomal RNA (rRNA). In a further aspect, a second coding region encodes a protein.

In another aspect, a method provided for, and disclosed, in the present specification comprises regenerating a plant from at least one modified plant cell. In a further aspect of this method, a modified plant cell is a transgenic plant cell. In another aspect of this method, a plant cell to be transformed is a callus cell derived from a plant cell.

In another aspect, a method provided for, and disclosed, in the present specification comprises selecting at least one modified plant cell comprising a recombinant polynucleotide and expressing a pigment as a visual marker. In a further aspect of this method, a plant cell expresses a carotenoid as a visual marker. In a further aspect of this method, a plant cell expresses a phenylpropanoid as a visual marker. In a further aspect of this method, a plant cell expresses an anthocyanin as a visual marker.

In another aspect, a method provided for, and disclosed, in the present specification comprises growing a modified plant comprising a recombinant polynucleotide. In a further aspect of this method, a recombinant polynucleotide that comprises a tissue-preferred promoter comprises a sequence selected form the group consisting of SEQ ID NO:1 to 7 a complement thereof, or a functional fragment thereof. In a further aspect of this method, a tissue-preferred promoter comprises a sequence that is at least 70% identical to or complimentary to a sequence selected from the group consisting of SEQ ID NO:1 to 7. In a further aspect of this method, a tissue-preferred promoter comprises a sequence that is at least 75% identical to or complimentary to a sequence selected from the group consisting of SEQ ID NO:1 to 7. In a further aspect of this method, a tissue-preferred promoter comprises a sequence that is at least 80% identical to or complimentary to a sequence selected from the group consisting of SEQ ID NO:1 to 7. In a further aspect of this method, a tissue-preferred promoter comprises a sequence that is at least 85% identical to or complimentary to a sequence selected from the group consisting of SEQ ID NO:1 to 7. In a further aspect of this method, a tissue-preferred promoter comprises a sequence that is at least 90% identical to or complimentary to a sequence selected from the group consisting of SEQ ID NO:1 to 7. In a further aspect of this method, a tissue-preferred promoter comprises a sequence that is at least 95% identical to or complimentary to a sequence selected from the group consisting of SEQ ID NO:1 to 7. In a further aspect of this method, a tissue-preferred promoter comprises a sequence that is at least 96% identical to or complimentary to a sequence selected from the group consisting of SEQ ID NO:1 to 7. In a further aspect of this method, a tissue-preferred promoter comprises a sequence that is at least 97% identical to or complimentary to a sequence selected from the group consisting of SEQ ID NO:1 to 7. In a further aspect of this method, a tissue-preferred promoter comprises a sequence that is at least 98% identical to or complimentary to a sequence selected from the group consisting of SEQ ID NO:1 to 7. In a further aspect of this method, a tissue-preferred promoter comprises a sequence that is at least 99% identical to or complimentary to a sequence selected from the group consisting of SEQ ID NO:1 to 7. In a further aspect of this method, a tissue-preferred promoter comprises a sequence that is between 70 and 99% identical to or complimentary to a sequence selected from the group consisting of SEQ ID NO:1 to 7. In a further aspect of this method, a tissue-preferred promoter comprises a sequence that is between 75 and 95% identical to or complimentary to a sequence selected from the group consisting of SEQ ID NO:1 to 7. In a further aspect of this method, a tissue-preferred promoter comprises a sequence that is between 80 and 90% identical to or complimentary to a sequence selected from the group consisting of SEQ ID NO:1 to 7. In a further aspect of this method, a tissue-preferred promoter comprises a sequence that is between 80 and 85% identical to or complimentary to a sequence selected from the group consisting of SEQ ID NO:1 to 7. In a further aspect of this method, a tissue-preferred promoter comprises a sequence that is between 85 and 90% identical to or complimentary to a sequence selected from the group consisting of SEQ ID NO:1 to 7. In a further aspect of this method, a tissue-preferred promoter comprises a sequence that is between 95 and 99% identical to or complimentary to a sequence selected from the group consisting of SEQ ID NO:1 to 7. In a further aspect of this method, a tissue-preferred promoter comprises a sequence that is between 96 and 99% identical to or complimentary to a sequence selected from the group consisting of SEQ ID NO:1 to 7. In a further aspect of this method, a tissue-preferred promoter comprises a sequence that is between 97 and 99% identical to or complimentary to a sequence selected from the group consisting of SEQ ID NO:1 to 7. In a further aspect of this method, a tissue-preferred promoter comprises a sequence that is between 98 and 99% identical to or complimentary to a sequence selected from the group consisting of SEQ ID NO:1 to 7.

In another aspect, a method provided for, and disclosed, in the present specification comprises growing a modified plant comprising a recombinant polynucleotide. In a further aspect of this method, a recombinant polynucleotide comprises a coding region having a sequence selected from the group consisting of SEQ ID NO:8 to 10, a complement thereof, or a functional fragment thereof. In a further aspect of this method, a coding region comprises a sequence that is at least 70% identical to or complimentary to a sequence selected from the group consisting of SEQ ID NO:8 to 10. In a further aspect of this method, a coding region comprises a sequence that is at least 75% identical to or complimentary to a sequence selected from the group consisting of SEQ ID NO:8 to 10. In a further aspect of this method, a coding region comprises a sequence that is at least 80% identical to or complimentary to a sequence selected from the group consisting of SEQ ID NO:8 to 10. In a further aspect of this method, a coding region comprises a sequence that is at least 85% identical to or complimentary to a sequence selected from the group consisting of SEQ ID NO:8 to 10. In a further aspect of this method, a coding region comprises a sequence that is at least 90% identical to or complimentary to a sequence selected from the group consisting of SEQ ID NO:8 to 10. In a further aspect of this method, a coding region comprises a sequence that is at least 95% identical to or complimentary to a sequence selected from the group consisting of SEQ ID NO:8 to 10. In a further aspect of this method, a coding region comprises a sequence that is at least 96% identical to or complimentary to a sequence selected from the group consisting of SEQ ID NO:8 to 10. In a further aspect of this method, a coding region comprises a sequence that is at least 97% identical to or complimentary to a sequence selected from the group consisting of SEQ ID NO: 8 to 10. In a further aspect of this method, a coding region comprises a sequence that is at least 98% identical to or complimentary to a sequence selected from the group consisting of SEQ ID NO:8 to 10. In a further aspect of this method, a coding region comprises a sequence that is at least 99% identical to or complimentary to a sequence selected from the group consisting of SEQ ID NO:8 to 10. In a further aspect of this method, a coding region comprises a sequence that is between 70 and 99% identical to or complimentary to a sequence selected from the group consisting of SEQ ID NO:8 to 10. In a further aspect of this method, a coding region comprises a sequence that is between 75 and 95% identical to or complimentary to a sequence selected from the group consisting of SEQ ID NO:8 to 10. In a further aspect of this method, a coding region comprises a sequence that is between 80 and 90% identical to or complimentary to a sequence selected from the group consisting of SEQ ID NO:8 to 10. In a further aspect of this method, a coding region comprises a sequence that is between 80 and 85% identical to or complimentary to a sequence selected from the group consisting of SEQ ID NO:8 to 10. In a further aspect of this method, a coding region comprises a sequence that is between 85 and 90% identical to or complimentary to a sequence selected from the group consisting of SEQ ID NO:8 to 10. In a further aspect of this method, a coding region comprises a sequence that is between 95 and 99% identical to or complimentary to a sequence selected from the group consisting of SEQ ID NO:8 to 10. In a further aspect of this method, a coding region comprises a sequence that is between 96 and 99% identical to or complimentary to a sequence selected from the group consisting of SEQ ID NO:8 to 10. In a further aspect of this method, a coding region comprises a sequence that is between 97 and 99% identical to or complimentary to a sequence selected from the group consisting of SEQ ID NO:8 to 10. In a further aspect of this method, a coding region comprises a sequence that is between 98 and 99% identical to or complimentary to a sequence selected from the group consisting of SEQ ID NO:8 to 10.

In another aspect, a method provided for, and disclosed, in the present specification comprises growing a modified plant comprising a recombinant polynucleotide. In a further aspect of this method, a recombinant polynucleotide further comprises a sequence encoding a transcription terminator. In a further aspect of this method, the present specification provides for a terminator comprising the sequence of SEQ ID NO:11, a complement thereof, or a functional fragment thereof. In a further aspect of this method, a terminator comprises a sequence that is at least 70% identical to or complimentary to SEQ ID NO:11. In a further aspect of this method, a terminator comprises a sequence that is at least 75% identical to or complimentary to SEQ ID NO:11. In a further aspect of this method, a terminator comprises a sequence that is at least 80% identical to or complimentary to SEQ ID NO:11. In a further aspect of this method, a terminator comprises a sequence that is at least 85% identical to or complimentary to SEQ ID NO:11. In a further aspect of this method, a terminator comprises a sequence that is at least 90% identical to or complimentary to SEQ ID NO:11. In a further aspect of this method, a terminator comprises a sequence that is at least 95% identical to or complimentary to SEQ ID NO:11. In a further aspect of this method, a terminator comprises a sequence that is at least 96% identical to or complimentary to SEQ ID NO:11. In a further aspect of this method, a terminator comprises a sequence that is at least 97% identical to or complimentary to SEQ ID NO:11. In a further aspect of this method, a terminator comprises a sequence that is at least 98% identical to or complimentary to SEQ ID NO:11. In a further aspect of this method, a terminator comprises a sequence that is at least 99% identical to or complimentary to SEQ ID NO:11. In a further aspect of this method, a terminator comprises a sequence that is between 70 and 99% identical to or complimentary to SEQ ID NO:11. In a further aspect of this method, a terminator comprises a sequence that is between 75 and 95% identical to or complimentary to SEQ ID NO:11. In a further aspect of this method, a terminator comprises a sequence that is between 80 and 90% identical to or complimentary to SEQ ID NO:11. In a further aspect of this method, a terminator comprises a sequence that is between 80 and 85% identical to or complimentary to SEQ ID NO:11. In a further aspect of this method, a terminator comprises a sequence that is between 85 and 90% identical to or complimentary to SEQ ID NO:11. In a further aspect of this method, a terminator comprises a sequence that is between 95 and 99% identical to or complimentary to SEQ ID NO:11. In a further aspect of this method, a terminator comprises a sequence that is between 96 and 99% identical to or complimentary to SEQ ID NO:11. In a further aspect of this method, a terminator comprises a sequence that is between 97 and 99% identical to or complimentary to SEQ ID NO:11. In a further aspect of this method, a terminator comprises a sequence that is between 98 and 99% identical to or complimentary to SEQ ID NO:11.

In another aspect, a method provided for, and disclosed, in the present specification comprises growing a modified plant comprising a recombinant polynucleotide In a further aspect of this method, a recombinant polynucleotide comprises a sequence selected from the group consisting of SEQ ID NO:12 to 32 (See Table 2). In a further aspect of this method, the present specification provides a recombinant polynucleotide comprising a sequence that is at least 70% identical to or complimentary to the sequence selected from the group consisting of SEQ ID NO:12 to 32. In a further aspect of this method, a recombinant polynucleotide comprises a sequence that is at least 75% identical to or complimentary to the sequence selected from the group consisting of SEQ ID NO:12 to 32. In a further aspect of this method, a recombinant polynucleotide comprises a sequence that is at least 80% identical to or complimentary to the sequence selected from the group consisting of SEQ ID NO:12 to 32. In a further aspect of this method, a recombinant polynucleotide comprises a sequence that is at least 85% identical to or complimentary to the sequence selected from the group consisting of SEQ ID NO:12 to 32. In a further aspect of this method, a recombinant polynucleotide comprises a sequence that is at least 90% identical to or complimentary to the sequence selected from the group consisting of SEQ ID NO:12 to 32. In a further aspect of this method, a recombinant polynucleotide comprises a sequence that is at least 95% identical to or complimentary to the sequence selected from the group consisting of SEQ ID NO:12 to 32. In a further aspect of this method, a recombinant polynucleotide comprises a sequence that is at least 96% identical to or complimentary to the sequence selected from the group consisting of SEQ ID NO:12 to 32. In a further aspect of this method, a recombinant polynucleotide comprises a sequence that is at least 97% identical to or complimentary to the sequence selected from the group consisting of SEQ ID NO:12 to 32. In a further aspect of this method, a recombinant polynucleotide comprises a sequence that is at least 98% identical to or complimentary to the sequence selected from the group consisting of SEQ ID NO:12 to 32. In a further aspect of this method, a recombinant polynucleotide comprises a sequence that is at least 99% identical to or complimentary to the sequence selected from the group consisting of SEQ ID NO:12 to 32. In a further aspect of this method, a recombinant polynucleotide comprises a sequence that is between 70 and 99% identical to or complimentary to the sequence selected from the group consisting of SEQ ID NO:12 to 32. In a further aspect of this method, a recombinant polynucleotide comprises a sequence that is between 75 and 95% identical to or complimentary to the sequence selected from the group consisting of SEQ ID NO:12 to 32. In a further aspect of this method, a recombinant polynucleotide comprises a sequence that is between 80 and 90% identical to or complimentary to the sequence selected from the group consisting of SEQ ID NO:12 to 32. In a further aspect of this method, a recombinant polynucleotide comprises a sequence that is between 80 and 85% identical to or complimentary to the sequence selected from the group consisting of SEQ ID NO:12 to 32. In a further aspect of this method, a recombinant polynucleotide comprises a sequence that is between 85 and 90% identical to or complimentary to the sequence selected from the group consisting of SEQ ID NO:12 to 32. In a further aspect of this method, a recombinant polynucleotide comprises a sequence that is between 95 and 99% identical to or complimentary to the sequence selected from the group consisting of SEQ ID NO:12 to 32. In a further aspect of this method, a recombinant polynucleotide comprises a sequence that is between 96 and 99% identical to or complimentary to the sequence selected from the group consisting of SEQ ID NO:12 to 32. In a further aspect of this method, a recombinant polynucleotide comprises a sequence that is between 97 and 99% identical to or complimentary to the sequence selected from the group consisting of SEQ ID NO:12 to 32. In a further aspect of this method, a recombinant polynucleotide comprises a sequence that is between 98 and 99% identical to or complimentary to the sequence selected from the group consisting of SEQ ID NO:12 to 32.

In an aspect, the present specification provides for, and includes, a host cell comprising a recombinant polynucleotide. In another aspect, a host cell comprises a recombinant polynucleotide having a sequence selected from the group consisting of SEQ ID NO: 1 to 40. In a another aspect, a host cell of the present specification is a bacterial cell. In a further aspect, a bacterial host cell is a bacterial cell of the genus *Escherichia, Agrobacterium,* or *Rhizobium.* In another aspect, a host cell of the present specification is a plant cell. In a further aspect, a plant host cell is a plant cell of the genus *Nicotiana.*

In an aspect, the present specification provides for, and includes, a plant cell comprising a recombinant polynucleotide comprising a heterologous tissue-preferred promoter and a coding region from a pigment regulatory factor, where the polynucleotide sequence of the promoter and coding region are plant polynucleotide sequences. In a further aspect, the present specification provides for, and includes, a *Nicotiana* cell comprising a recombinant polynucleotide comprising a heterologous tissue-preferred promoter and a coding region from a pigment regulatory factor, where the polynucleotide sequence of the promoter and coding region are plant polynucleotide sequences.

In an aspect, the present specification provides for, and includes, a method of transforming a plant comprising transforming at least one plant cell with a recombinant polynucleotide comprising a heterologous tissue-preferred promoter and a coding region from a pigment regulatory factor where the polynucleotide sequence of the promoter and coding region are plant polynucleotide sequences and selecting at least one modified plant cell expressing the recombinant polynucleotide. In another aspect of this method, a modified plant cell that is selected is a cell of a eudicot plant. In another aspect of this method, a modified plant cell that is selected is a cell of a Solanaceae plant. In another aspect, a modified plant cell that is selected is a cell of a tobacco plant. In another aspect, a modified plant cell that is selected is a cell of a *Nicotiana* plant. In another aspect, a modified plant cell that is selected is a cell of a *Nicotiana tabacum* plant. In a further aspect, the method further comprises regenerating a plant from the selected at least one modified plant cell.

In a further aspect, a method for transforming a plant comprises transforming at least one plant cell via *Agrobacterium* mediated transformation. In another aspect, a method for transforming a plant comprises transforming at least one plant cell via biolistic mediated transformation. In a further aspect, a method for transforming a plant comprises transforming at least one plant cell with at least one recombinant polynucleotide. In a further aspect, a method for transforming a plant comprises transforming at least one plant cell concurrently with at least two recombinant polynucleotides. In a further aspect, a method for transforming a plant comprises transforming at least one plant cell with at least three additional recombinant polynucleotides. In a further aspect, a method for transforming a plant comprises transforming at least one plant cell concurrently with at least four recombinant polynucleotides. In a further aspect, a method for transforming a plant comprises transforming at least one plant cell concurrently with at least five recombinant polynucleotides.

In another aspect, a method for transforming a plant comprises transforming at least one plant cell comprising a recombinant polynucleotide where a recombinant polynucleotide comprises a tissue-preferred promoter and a coding region from a pigment regulatory factor. In a further aspect of this method, a tissue-preferred promoter and a coding region are native to a plant genome. In a further aspect of this method, a tissue-preferred promoter and a coding region are native to a *Nicotiana* genome. In a further aspect of this method, a tissue-preferred promoter and a coding region are native to a *Nicotiana tabacum* genome. In another aspect of this method, a recombinant polynucleotide comprises a terminator. In a further aspect of this method, a tissue-preferred promoter, coding region, and terminator are native to a plant genome. In a further aspect of this method, a tissue-preferred promoter, coding region, and terminator are native to a *Nicotiana* genome. In another aspect of this method, a recombinant polynucleotide further comprises a second promoter and a second coding region. In a further aspect of this method, a recombinant polynucleotide further comprises a second terminator. In a further aspect of this method, a second coding region encodes a small RNA. In a further aspect, a small RNA is selected from the group consisting of a small RNA precursor, microRNA (miRNA), transfer RNA (tRNA), small interfering RNA (siRNA), trans-acting siRNA (tasiRNA), and ribosomal RNA (rRNA). In a further aspect, a second coding region encodes a protein.

In another aspect, a method provided for, and disclosed, in the present specification comprises transforming at least one modified plant cell. In a further aspect, a method for transforming a plant comprises selecting a modified plant cell that is a transgenic plant cell. In a further aspect, a method for transforming a plant comprises selecting a transformed callus cell derived from a plant cell.

In another aspect, a method provided for, and disclosed, in the present specification comprises selecting at least one modified plant cell expressing a recombinant polynucleotide. In a further aspect, a method for transforming a plant comprises selecting at least one modified plant cell expressing a pigment as a visual marker. In a further aspect, a method for transforming a plant comprises selecting a plant cell expresses a carotenoid as a visual marker. In a further aspect, a method for transforming a plant comprises selecting a plant cell expresses a phenylpropanoid as a visual marker. In a further aspect, a method for transforming a plant comprises selecting a plant cell expresses an anthocyanin as a visual marker.

In another aspect, the present specification provides for, and includes, a method of transforming a plant comprising transforming at least one plant cell with a recombinant polynucleotide. In a further aspect of this method, a recombinant polynucleotide comprises a tissue-preferred promoter comprising a sequence selected form the group consisting of SEQ ID NO:1 to 7, a complement thereof, or a functional fragment thereof. In a further aspect of this method, a tissue-preferred promoter comprises a sequence that is at least 70% identical to or complimentary to a sequence selected from the group consisting of SEQ ID NO:1 to 7. In a further aspect of this method, a tissue-preferred promoter comprises a sequence that is at least 75% identical to or complimentary to a sequence selected from the group consisting of SEQ ID NO:1 to 7. In a further aspect of this method, a tissue-preferred promoter comprises a sequence that is at least 80% identical to or complimentary to a sequence selected from the group consisting of SEQ ID NO:1 to 7. In a further aspect of this method, a tissue-preferred promoter comprises a sequence that is at least 85% identical to or complimentary to a sequence selected from the group consisting of SEQ ID NO:1 to 7. In a further aspect of this method, a tissue-preferred promoter comprises a sequence that is at least 90% identical to or complimentary to a sequence selected from the group consisting of SEQ ID NO:1 to 7. In a further aspect of this method, a tissue-preferred promoter comprises a sequence that is at least 95% identical to or complimentary to a sequence selected from the group consisting of SEQ ID NO:1 to 7. In a further aspect of this method, a tissue-preferred promoter comprises a sequence that is at least 96% identical to or complimentary to a sequence selected from the group consisting of SEQ ID NO:1 to 7. In a further aspect of this method, a tissue-preferred promoter comprises a sequence that is at least 97% identical to or complimentary to a sequence selected from the group consisting of SEQ ID NO:1 to 7. In a further aspect of this method, a tissue-preferred promoter comprises a sequence that is at least 98% identical to or complimentary to a sequence selected from the group consisting of SEQ ID NO:1 to 7. In a further aspect of this method, a tissue-preferred promoter comprises a sequence that is at least 99% identical to or complimentary to a sequence selected from the group consisting of SEQ ID NO:1 to 7. In a further aspect of this method, a tissue-preferred promoter comprises a sequence that is between 70 and 99% identical to or complimentary to a sequence selected from the group consisting of SEQ ID NO:1 to 7. In a further aspect of this method, a tissue-preferred promoter comprises a sequence that is between 75 and 95% identical to or complimentary to a sequence selected from the group consisting of SEQ ID NO:1 to 7. In a further aspect of this method, a tissue-preferred promoter comprises a sequence that is between 80 and 90% identical to or complimentary to a sequence selected from the group consisting of SEQ ID NO:1 to 7. In a further aspect of this method, a tissue-preferred promoter comprises a sequence that is between 80 and 85% identical to or complimentary to a sequence selected from the group consisting of SEQ ID NO:1 to 7. In a further aspect of this method, a tissue-preferred promoter comprises a sequence that is between 85 and 90% identical to or complimentary to a sequence selected from the group consisting of SEQ ID NO:1 to 7. In a further aspect of this method, a tissue-preferred promoter comprises a sequence that is between 9 and 99% identical to or complimentary to a sequence selected from the group consisting of SEQ ID NO:1 to 7. In a further aspect of this method, a tissue-preferred promoter comprises a sequence that is between 96 and 99% identical to or complimentary to a sequence selected from the group consisting of SEQ ID NO:1 to 7. In a further aspect of this method, a tissue-preferred promoter comprises a sequence that is between 97 and 99% identical to or complimentary to a sequence selected from the group consisting of SEQ ID NO:1 to 7. In a further aspect of this method, a tissue-preferred promoter comprises a sequence that is between 98 and 99% identical to or complimentary to a sequence selected from the group consisting of SEQ ID NO:1 to 7.

In another aspect, the present specification provides for, and includes, a method of transforming a plant comprising transforming at least one plant cell with a recombinant polynucleotide. In a further aspect of this method, a recombinant polynucleotide comprises a coding region having a sequence selected from the group consisting of SEQ ID NO:8 to 10, a complement thereof, or a functional fragment thereof. In a further aspect of this method, a coding region comprises a sequence that is at least 70% identical to or complimentary to a sequence selected from the group consisting of SEQ ID NO:8 to 10. In a further aspect of this method, a coding region comprises a sequence that is at least 75% identical to or complimentary to a sequence selected from the group consisting of SEQ ID NO:8 to 10. In a further aspect of this method, a coding region comprises a sequence that is at least 80% identical to or complimentary to a sequence selected from the group consisting of SEQ ID NO:8 to 10. In a further aspect of this method, a coding region comprises a sequence that is at least 85% identical to or complimentary to a sequence selected from the group consisting of SEQ ID NO:8 to 10. In a further aspect of this method, a coding region comprises a sequence that is at least 90% identical to or complimentary to a sequence selected from the group consisting of SEQ ID NO:8 to 10. In a further aspect of this method, a coding region comprises a sequence that is at least 95% identical to or complimentary to a sequence selected from the group consisting of SEQ ID NO:8 to 10. In a further aspect of this method, a coding region comprises a sequence that is at least 96% identical to or complimentary to a sequence selected from the group consisting of SEQ ID NO:8 to 10. In a further aspect of this method, a coding region comprises a sequence that is at least 97% identical to or complimentary to a sequence selected from the group consisting of SEQ ID NO:8 to 10. In a further aspect of this method, a coding region comprises a sequence that is at least 98% identical to or complimentary to a sequence selected from the group consisting of SEQ ID NO:8 to 10. In a further aspect of this method, a coding region comprises a sequence that is at least 99% identical to or complimentary to a sequence selected from the group consisting of SEQ ID NO:8 to 10. In a further aspect of this method, a coding region comprises a sequence that is between 70 and 99% identical to or complimentary to a sequence selected from the group consisting of SEQ ID NO:8 to 10. In a further aspect of this method, a coding region comprises a sequence that is between 75 and 95% identical to or complimentary to a sequence selected from the group consisting of SEQ ID NO:8 to 10. In a further aspect of this method, a coding region comprises a sequence that is between 80 and 90% identical to or complimentary to a sequence selected from the group consisting of SEQ ID NO:8 to 10. In a further aspect of this method, a coding region comprises a sequence that is between 80 and 85% identical to or complimentary to a sequence selected from the group consisting of SEQ ID NO:8 to 10. In a further aspect of this method, a coding region comprises a sequence that is between 85 and 90% identical to or complimentary to a sequence selected from the group consisting of SEQ ID NO:8 to 10. In a further aspect of this method, a coding region comprises a sequence that is between 95 and 99% identical to or complimentary to a sequence selected from the group consisting of SEQ ID NO:8 to 10. In a further aspect of this method, a coding region comprises a sequence that is between 96 and 99% identical to or complimentary to a sequence selected from the group consisting of SEQ ID NO:8 to 10. In a further aspect of this method, a coding region comprises a sequence that is between 97 and 99% identical to or complimentary to a sequence selected from the group consisting of SEQ ID NO:8 to 10. In a further aspect of this method, a coding region comprises a sequence that is between 98 and 99% identical to or complimentary to a sequence selected from the group consisting of SEQ ID NO:8 to 10.

In another aspect, the present specification provides for, and includes, a method of transforming a plant comprising transforming at least one plant cell with a recombinant polynucleotide. In a further aspect of this method, a recombinant polynucleotide further comprises a sequence encoding a transcription terminator. In a further aspect of this method, the present specification provides for a terminator comprising the sequence of SEQ ID NO:11, a complement thereof, or a functional fragment thereof. In a further aspect of this method, a terminator comprises a sequence that is at least 70% identical to or complimentary to SEQ ID NO:11. In a further aspect of this method, a terminator comprises a sequence that is at least 75% identical to or complimentary to SEQ ID NO:11. In a further aspect of this method, a terminator comprises a sequence that is at least 80% identical to or complimentary to SEQ ID NO:11. In a further aspect of this method, a terminator comprises a sequence that is at least 85% identical to or complimentary to SEQ ID NO:11. In a further aspect of this method, a terminator comprises a sequence that is at least 90% identical to or complimentary to SEQ ID NO:11. In a further aspect of this method, a terminator comprises a sequence that is at least 95% identical to or complimentary to SEQ ID NO:11. In a further aspect of this method, a terminator comprises a sequence that is at least 96% identical to or complimentary to SEQ ID NO:11. In a further aspect of this method, a terminator comprises a sequence that is at least 97% identical to or complimentary to SEQ ID NO:11. In a further aspect of this method, a terminator comprises a sequence that is at least 98% identical to or complimentary to SEQ ID NO:11. In a further aspect of this method, a terminator comprises a sequence that is at least 99% identical to or complimentary to SEQ ID NO:11. In a further aspect of this method, a terminator comprises a sequence that is between 70 and 99% identical to or complimentary to SEQ ID NO:11. In a further aspect of this method, a terminator comprises a sequence that is between 75 and 95% identical to or complimentary to SEQ ID NO:11. In a further aspect of this method, a terminator comprises a sequence that is between 80 and 90% identical to or complimentary to SEQ ID NO:11. In a further aspect of this method, a terminator comprises a sequence that is between 80 and 85% identical to or complimentary to SEQ ID NO:11. In a further aspect of this method, a terminator comprises a sequence that is between 85 and 90% identical to or complimentary to SEQ ID NO:11. In a further aspect of this method, a terminator comprises a sequence that is between 95 and 99% identical to or complimentary to SEQ ID NO:11. In a further aspect of this method, a terminator comprises a sequence that is between 96 and 99% identical to or complimentary to SEQ ID NO:11. In a further aspect of this method, a terminator comprises a sequence that is between 97 and 99% identical to or complimentary to SEQ ID NO:11. In a further aspect of this method, a terminator comprises a sequence that is between 98 and 99% identical to or complimentary to SEQ ID NO:11.

In another aspect, the present specification provides for, and includes, a method of transforming a plant comprising transforming at least one plant cell with a recombinant polynucleotide. In a further aspect of this method, a recombinant polynucleotide comprises a sequence selected from the group consisting of SEQ ID NO:12 to 32. In a further aspect of this method, the present specification provides a recombinant polynucleotide comprising a sequence that is at least 70% identical to or complimentary to the sequence selected from the group consisting of SEQ ID NO:12 to 32. In a further aspect of this method, a recombinant polynucleotide comprises a sequence that is at least 75% identical to or complimentary to the sequence selected from the group consisting of SEQ ID NO:12 to 32. In a further aspect of this method, a recombinant polynucleotide comprises a sequence that is at least 80% identical to or complimentary to the sequence selected from the group consisting of SEQ ID NO:12 to 32. In a further aspect of this method, a recombinant polynucleotide comprises a sequence that is at least 85% identical to or complimentary to the sequence selected from the group consisting of SEQ ID NO:12 to 32. In a further aspect of this method, a recombinant polynucleotide comprises a sequence that is at least 90% identical to or complimentary to the sequence selected from the group consisting of SEQ ID NO:12 to 32. In a further aspect of this method, a recombinant polynucleotide comprises a sequence that is at least 95% identical to or complimentary to the sequence selected from the group consisting of SEQ ID NO:12 to 32. In a further aspect of this method, a recombinant polynucleotide comprises a sequence that is at least 96% identical to or complimentary to the sequence selected from the group consisting of SEQ ID NO:12 to 32. In a further aspect of this method, a recombinant polynucleotide comprises a sequence that is at least 97% identical to or complimentary to the sequence selected from the group consisting of SEQ ID NO:12 to 32. In a further aspect of this method, a recombinant polynucleotide comprises a sequence that is at least 98% identical to or complimentary to the sequence selected from the group consisting of SEQ ID NO:12 to 32. In a further aspect of this method, a recombinant polynucleotide comprises a sequence that is at least 99% identical to or complimentary to the sequence selected from the group consisting of SEQ ID NO:12 to 32. In a further aspect of this method, a recombinant polynucleotide comprises a sequence that is between 70 and 99% identical to or complimentary to the sequence selected from the group consisting of SEQ ID NO:12 to 32. In a further aspect of this method, a recombinant polynucleotide comprises a sequence that is between 75 and 95% identical to or complimentary to the sequence selected from the group consisting of SEQ ID NO:12 to 32. In a further aspect of this method, a recombinant polynucleotide comprises a sequence that is between 80 and 90% identical to or complimentary to the sequence selected from the group consisting of SEQ ID NO:12 to 32. In a further aspect of this method, a recombinant polynucleotide comprises a sequence that is between 80 and 85% identical to or complimentary to the sequence selected from the group consisting of SEQ ID NO:12 to 32. In a further aspect of this method, a recombinant polynucleotide comprises a sequence that is between 85 and 90% identical to or complimentary to the sequence selected from the group consisting of SEQ ID NO:12 to 32. In a further aspect of this method, a recombinant polynucleotide comprises a sequence that is between 95 and 99% identical to or complimentary to the sequence selected from the group consisting of SEQ ID NO:12 to 32. In a further aspect of this method, a recombinant polynucleotide comprises a sequence that is between 96 and 99% identical to or complimentary to the sequence selected from the group consisting of SEQ ID NO:12 to 32. In a further aspect of this method, a recombinant polynucleotide comprises a sequence that is between 97 and 99% identical to or complimentary to the sequence selected from the group consisting of SEQ ID NO:12 to 32. In a further aspect of this method, a recombinant polynucleotide comprises a sequence that is between 98 and 99% identical to or complimentary to the sequence selected from the group consisting of SEQ ID NO:12 to 32.

The use of the term "polynucleotide" is not intended to limit the present disclosure to polynucleotides comprising DNA. Those of ordinary skill in the art will recognize that polynucleotides and nucleic acid molecules can comprise ribonucleotides and combinations of ribonucleotides (RNAs) and deoxyribonucleotides (DNAs). Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like.

As used herein, the term "polypeptide" refers to a chain of at least two covalently linked amino acids.

Nucleic acid molecules, polypeptides, or proteins provided herein can be isolated or substantially purified. An "isolated" or "purified" nucleic acid molecule, polypeptide, protein, or biologically active portion thereof, is substantially or essentially free from components that normally accompany or interact with the polynucleotide or protein as found in its naturally occurring environment. For example, an isolated or purified polynucleotide or protein is substantially free of other cellular material, or culture medium when produced by recombinant techniques, or substantially free of chemical precursors or other chemicals when chemically synthesized. In another aspect, an isolated polypeptide provided herein is substantially free of cellular material in preparations having less than 30%, less than 20%, less than 10%, less than 5%, or less than 1% (by dry weight) of chemical precursors or non-protein-of-interest chemicals. Fragments of the disclosed polynucleotides and polypeptides encoded thereby are also encompassed by the present invention. Fragments of a polynucleotide may encode polypeptide fragments that retain the biological activity of the native polypeptide. Alternatively, fragments of a polynucleotide that are useful as hybridization probes or PCR primers using methods known in the art generally do not encode fragment polypeptides retaining biological activity. Fragments of a polynucleotide provided herein can range from at least 20 nucleotides, 50 nucleotides, 70 nucleotides, 100 nucleotides, 150 nucleotides, 200 nucleotides, 250 nucleotides, 300 nucleotides, and up to the full-length polynucleotide encoding the polypeptides of the invention, depending on the desired outcome.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting in plant cells one or more recombinant nucleic acids and polypeptides described here. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

As understood in the art, the term "callus" (plural: calli) may generally refer to a group of disorganized plant cells that are predominately undifferentiated. See, Plant Biochemistry 517 to 528 (Dey and Harborne eds., Academic Press) 1997. Callus can be derived from explants of many different tissue types such as leaf, hypocotyl, stem and root. Maintenance of calli on culture medium and subsequent transition in shoot or root tissue requires supplemental hormones including, but not limited to, auxin, cytokinin, and gibberellins. See, Skoog and Tsui, *Amer. J. of Bot.* 35(10):782-787 (1948). Whole plants can be regenerated from callus tissue.

As commonly understood in the art, the term "promoter" may generally refer to a DNA sequence that contains an RNA polymerase binding site, transcription start site, and/or TATA box and assists or promotes the transcription and expression of an associated transcribable polynucleotide sequence and/or gene (or transgene). A promoter may be synthetically produced, varied or derived from a known or naturally occurring promoter sequence or other promoter sequence (e.g., as provided herein). A promoter may also include a chimeric promoter comprising a combination of two or more heterologous sequences. A promoter of the present invention may thus include variants of promoter sequences that are similar in composition, but not identical to or complimentary to, other promoter sequence(s) known or provided herein. As used herein, a "heterologous promoter" in the context of a DNA construct refers to either: (i) a promoter that is derived from a source distinct from the operably linked structural gene or coding region or (ii) a promoter derived from the same source as the operably linked structural gene or coding region, where the promoter's sequence is modified from its original form. As used herein, the term "operably linked" refers to a functional linkage between a promoter or other regulatory element and an associated transcribable polynucleotide sequence or coding sequence of a gene (or transgene), such that the promoter, etc., operates to initiate, assist, affect, cause, and/or promote the transcription and expression of the associated coding or transcribable polynucleotide sequence, at least in particular tissue(s), developmental stage(s), and/or under certain condition(s). A "plant expressible promoter" refers to a promoter that may be used to express in a plant, plant cell and/or plant tissue an associated coding sequence, transgene or transcribable polynucleotide sequence that is operably linked to the promoter.

A promoter may be classified according to a variety of criteria relating to the pattern of expression of a coding sequence or gene (including a transgene) operably linked to the promoter, such as constitutive, developmental, tissue-specific, inducible, etc. Promoters that initiate transcription in all or most tissues of the plant are referred to as "constitutive" promoters. Promoters that initiate transcription during certain periods or stages of development are referred to as "developmental" promoters. Promoters whose expression is enhanced in certain tissues of the plant relative to other plant tissues are referred to as "tissue-enhanced" or "tissue-preferred" promoters. Thus, a "tissue-preferred" promoter causes relatively higher or preferential expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. A promoter that expresses in a certain cell type of the plant is referred to as a "cell type specific" promoter. An "inducible" promoter is a promoter that initiates transcription in response to an environmental stimulus such as cold, drought or light, or other stimuli, such as wounding or chemical application. A promoter may also be classified in terms of its origin, such as being heterologous, homologous, chimeric, synthetic, etc. A "heterologous" promoter is a promoter sequence having a different origin relative to its associated transcribable sequence, coding sequence, or gene (or transgene), and/or not naturally occurring in the plant species to be transformed. The term "heterologous" may refer more broadly to a combination of two or more DNA molecules or sequences when such a combination is not normally found in nature. For example, two or more DNA molecules or sequences would be heterologous with respect to each other if they are normally found in different genomes or at different loci in the same genome, or if they are not identically combined in nature.

As used herein, a "callus" promoter includes any promoter that initiates, causes, drives, etc., transcription or expression of its associated gene, transgene or transcribable DNA sequence in callus tissue derived from any part of a plant. Such a "callus" promoter may be further defined as initiating, causing, driving, etc., transcription or expression of its associated gene/transgene or transcribable DNA sequence in one or more tissue(s) of a plant, such as one or more floral tissue(s). Such a "callus" promoter may be further defined as a "callus preferred" promoter that initiates, causes, drives, etc., transcription or expression of its associated gene, transgene or transcribable DNA sequence at least preferentially or mostly, if not exclusively, in callus tissue derived from any part of a plant (as opposed to floral tissue). However, a "callus" and a "callus preferred" promoter may each also permit, allow, cause, drive, etc., transcription or expression of its associated gene, transgene or transcribable DNA sequence during reproductive phase(s) or stage(s) of development in one or more cells or tissues of the plant, such as in one or more vegetative or reproductive tissue(s). In fact, a "callus" promoter may even initiate, cause, drive, etc., transcription or expression of its associated gene, transgene or transcribable DNA sequence in one or more reproductive or vegetative tissues at a greater level or extent than in callus tissue(s).

Examples of callus-preferred promoters include, but are not limited to the promoter of the following *Nicotiana tabacum* genes: Pathogeneis-related 5 (PR5) (SEQ ID NO:1), Proline Rich Protein (PRP) (SEQ ID NO:2), Alcohol dehydrogenase (AD) (SEQ ID NO:3), Extensin 3-like (EX3-like) (SEQ ID NO:4), Extensin 1-like (EX1-like) (SEQ ID NO:5), Pathogeneis-related 1a (PR1a) (SEQ ID NO:6), and S-adenosyl-L-homocysteine hydrolase (SAHH) (SEQ ID NO:7) (See Table 2).

As understood in the art, the term "coding region" or "open reading frame" may generally refer to a polynucleotide sequence that encodes a protein. A coding region begins with the DNA triplet "ATG" which encodes the amino acid methionine and typically ends with the DNA triplet "TAG", "TGA", or "TAA" that encodes a stop codon. Alternatively, "coding region" or "open reading frame" may refer to a polypeptide sequence that comprises a methionine and typically a stop codon.

As understood in the art, the term "transcription terminator" or "terminator" refers to a regulatory polynucleotide sequence that marks the end of a gene or open reading frame in genomic DNA and signifies where transcription will stop when a transcript is being produced from an open reading frame.

As understood in the art, a "recombinant" polynucleotide is made by human means or intervention through molecular biology engineering techniques, which can include the amplification or replication of such molecules upon introduction into a host cell, and the subsequent extraction and/or purification of the polynucleotide from the representative host cell. Polynucleotide embodiments include but are not limited to ribonucleic acids (RNA) and deoxyribonucleic acids (DNA). Protein embodiments can be expressed from DNA constructs in which the open reading frame encoding the protein is operably linked to elements such as a promoter and any other regulatory elements function al for expression in a particular system.

As understood in the art, a "phenylpropanoid" is a member of a family or organic compounds derived from phenylalanine and tyrosine. As understood in the art, an "anthocyanin" is a class of flavonoids that are downstream branch of the phenylpropanoid biosynthesis pathway. Increasing or decreasing activity of phenylpropanoid regulatory genes can affect the amount of precursor available for the anthocyanin branch of the pathway As understood in the art, a "carotenoid" is an organic pigment. Exemplary carotenoids produced in plants are carotenes such as beta-carotene and alpha-carotene.

As used herein, a "visual marker" refers to a selectable trait that can be discerned in a cell or callus without damaging, destroying, introducing outside chemical agents, or otherwise manipulating a cell or callus other than visualization with a light microscope. In a preferred embodiment, a visual marker is a pigment. As used herein, "pigment" refers to a material that changes the color of reflected or transmitted light in the cell or callus of which it is present. A pigment of the instant Specification may be soluble in hydrophobic and hydrophilic solutions. In a preferred aspect, an anthocyanin behaves as a pigment and visual marker in a cell or callus of the current Specification.

As used herein, a "biosynthetic enzyme" refers to a protein that functions in the synthesis of pigments, phenylpropanoids, anthocyanins or other proteins affecting the activity or stability of pigments, phenylpropanoids, anthocyanins. These proteins catalyze reactions that result in the transformation of one molecular structure into another structure as part of a biosynthesis pathway. Exemplary biosynthetic enzymes include but are limited to Anthocyanidin synthase2 (NtANS2) and Dihyfroflavonol-4-reductase (NtDFR2). The activity of a biosynthetic enzyme effects the total concentration of different molecule species that compose a biosynthetic pathway. In a further aspect, a biosynthetic enzyme can be a pigment biosynthetic enzyme. In a further aspect, a biosynthetic enzyme can be a phenylpropanoid biosynthetic enzyme. In a preferred aspect, a biosynthetic enzyme can be an anthocyanin biosynthetic enzyme.

As used herein, a "regulatory transcription factor" is a protein that binds a promoter element of a target gene to modulate the transcription of one or more genes involved in antioxidant biosynthesis, transport, catabolism, or other processes affecting the level of one or more antioxidants. Exemplary regulatory transcription factors include AtPAP1, NtPAP1, AtAN1, NtAN1, AtAN2, and NtAN2. A regulatory transcription factor can bind DNA as part of a protein complex or individually. A regulatory transcription factor can have a single target or multiple targets and can bind different targets with varying affinities. The activity of a regulatory transcription factor can be to activate, repress, or attenuate transcription from a target loci. In a further aspect, a regulatory transcription factor can be a pigment regulatory transcription factor. In a further aspect, a regulatory transcription factor can be a phenylpropanoid regulatory transcription factor. In a preferred aspect, a regulatory transcription factor can be an anthocyanin regulatory transcription factor.

As used herein, a "transport protein" can be a transmembrane protein that actively or passively moves molecules across a biological membrane. A transport protein can aid in the movement of ions, small molecules or macromolecules. A transport protein can be referred to as a transmembrane transporter, a transmembrane pump, an anion transport protein, a cation transport protein, or an escort protein. Transport proteins can also facilitate the movement of molecules or proteins in vesicles composed of biological membrane. A transport protein can be integrated into a biological membrane. A transport protein can be anchored to a biological membrane via different modifications such as but not limited to myristolation, prenylation or palmitoylation. In a further aspect, a transport protein can be a pigment transport protein. In a further aspect, a transport protein can be a phenylpropanoid transport protein. In a preferred aspect, a transport protein can be an anthocyanin transport protein.

In one aspect, a modified tobacco plant comprises one or more mutations in a gene encoding a polypeptide having at least 50%, 55%, 60%, 65%, 70%, 75%, 80%, 85%, 90%, 95%, 97%, 98%, 99%, or 100% identity to a sequence selected from the group consisting of SEQ ID No. 41 to 44. In another aspect, a modified tobacco plant comprises one or more mutations in a gene comprise a coding sequence having at least 50%, 55%, 60%, 65%, 70%, 75%, 80%, 85%, 90%, 95%, 97%, 98%, 99%, or 100% identity to a sequence selected from the group consisting of SEQ ID No. 8 to 11.

In one aspect, a modified plant, seed, plant component, plant cell, or plant genome provided herein comprises one or more transgenes. As used herein, a "transgene" refers to a polynucleotide that has been transferred into a genome by any method known in the art. In one aspect, a transgene is an exogenous polynucleotide. In one aspect, a transgene is an endogenous polynucleotide that is integrated into a new genomic locus where it is not normally found.

As used herein, "modified", in the context of plants, seeds, plant components, plant cells, and plant genomes, refers to a state containing changes or variations from their natural or native state. For instance, a "native transcript" of a gene refers to an RNA transcript that is generated from an unmodified gene. Typically, a native transcript is a sense transcript. Modified plants or seeds contain molecular changes in their genetic materials, including either genetic or epigenetic modifications. Typically, modified plants or seeds, or a parental or progenitor line thereof, have been subjected to mutagenesis, genome editing (e.g., without being limiting, via methods using site-specific nucleases), genetic transformation (e.g., without being limiting, via methods of *Agrobacterium* transformation or microprojectile bombardment), or a combination thereof. In one aspect, a modified plant provided herein comprises no non-plant genetic material or sequences. In yet another aspect, a modified plant provided herein comprises no interspecies genetic material or sequences. In one aspect, this disclosure provides methods and compositions related to modified plants, seeds, plant components, plant cells, and products made from modified plants, seeds, plant parts, and plant cells. In one aspect, a modified seed provided herein gives rise to a modified plant provided herein. In one aspect, a modified plant, seed, plant component, plant cell, or plant genome provided herein comprises a recombinant DNA construct or vector provided herein. In another aspect, a product provided herein comprises a modified plant, plant component, plant cell, or plant chromosome or genome provided herein. The present disclosure provides modified plants with desirable or enhanced properties, e.g., without being limiting, disease, insect, or pest tolerance (for example, virus tolerance, bacteria tolerance, fungus tolerance, nematode tolerance, arthropod tolerance, gastropod tolerance); herbicide tolerance; environmental stress resistance; quality improvements such as yield, nutritional enhancements, environmental or stress tolerances; any desirable changes in plant physiology, growth, development, morphology or plant product(s) including starch production, modified oils production, high oil production, modified fatty acid content, high protein production, fruit ripening, enhanced animal and human nutrition, biopolymer production, pharmaceutical peptides and secretable peptides production; improved processing traits; improved digestibility; low raffinose; industrial enzyme production; improved flavor; nitrogen fixation; hybrid seed production; and fiber production.

In one aspect, a recombinant DNA construct of the present disclosure comprises a promoter capable of driving gene transcription in a plant, operably linked to a polynucleotide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID Nos. 8 to 10. In a further aspect, a recombinant DNA construct of the present disclosure comprises a promoter capable of driving gene transcription in a plant, operably linked to a polynucleotide encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID Nos. 33 to 35. In one aspect, a recombinant DNA construct or expression cassette in a transgene provided herein comprises a promoter selected from the group consisting of a constitutive promoter, an inducible promoter, and a tissue-preferred promoter (for example, without being limiting, a callus-preferred promoter, a leaf-specific promoter, a shoot-specific promoter, a root-specific promoter, or a meristem-specific promoter).

Additional exemplary tissue-preferred promoters include those disclosed in Yamamoto et al. (1997) Plant J. 12(2): 255-265; Kawamata et al. (1997) Plant Cell Physiol. 38(7): 792-803; Hansen et al. (1997) Mol. Gen. Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol. Biol. 23(6):1129-1138; Matsuoka et al. (1993) Proc Natl. Acad. Sci. USA 90(20):9586-9590; and Guevara-Garcia et al. (1993) Plant J. 4(3):495-505.

In one aspect, a transgene provided herein comprises a heterologous or non-tobacco promoter or coding sequence. In another aspect, a transgene provided herein comprises a endogenous or tobacco-origin promoter or coding sequence. As used herein, "heterologous" refers to a sequence that originates from a foreign species, or, if from the same species, is substantially modified from its native form in composition and/or genomic locus by deliberate human intervention. The term also is applicable to nucleic acid constructs, also referred to herein as "polynucleotide constructs" or "nucleotide constructs." In this manner, a "heterologous" nucleic acid construct is intended to mean a construct that originates from a foreign species, or, if from the same species, is substantially modified from its native form in composition and/or genomic locus by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest.

Also provided herein are the transformation of tobacco plants with recombinant constructs or expression cassettes described herein using any suitable transformation methods known in the art. Methods for introducing polynucleotide sequences into tobacco plants are known in the art and include, but are not limited to, stable transformation methods, transient transformation methods, and virus-mediated methods. "Stable transformation" refers to transformation where the nucleotide construct of interest introduced into a plant integrates into a genome of the plant and is capable of being inherited by the progeny thereof. "Transient transformation" is intended to mean that a sequence is introduced into the plant and is only temporally expressed or is only transiently present in the plant.

In one aspect, methods and compositions provided herein comprise the introduction of one or more polynucleotides into one or more plant cells. In one aspect, a plant genome provided herein is modified to include an introduced polynucleotide or recombinant DNA construct. As used herein, "plant genome" refers to a nuclear genome, a mitochondrial genome, or a plastid (e.g., chloroplast) genome of a plant cell. In another aspect, a polynucleotide provided herein is integrated into an artificial chromosome. In one aspect, an artificial chromosome comprising a polynucleotide provided herein is integrated into a plant cell. In another aspect, a polynucleotide provide herein is native to a plant genome meaning that the entirety of its sequence is derived from a plant genome and not a bacterial or animal genome. In a preferred aspect, a polynucleotide provide herein is native to a tobacco genome.

In one aspect, transgenes provided herein comprise a recombinant DNA construct. In one aspect, recombinant DNA constructs or expression cassettes provided herein can comprise a selectable marker gene for the selection of transgenic cells. Selectable marker genes include, but are not limited to, genes encoding antibiotic resistance, such as those encoding neomycin phosphotransferase II (NPTII) and hygromycin phosphotransferase (HPT), as well as genes conferring resistance to herbicidal compounds, such as glufosinate ammonium, bromoxynil, imidazolinones, triazolopyrimidines, sulfonylurea (e.g., chlorsulfuron and sulfometuron methyl), and 2,4-dichlorophenoxyacetate (2,4-D). Non-plant-origin visual selectable markers include phenotypic markers such as β-galactosidase and fluorescent proteins such as green fluorescent protein (GFP). In a preferred aspect, transgenes provided herein comprise a plant-origin visual selectable marker In one aspect, methods and compositions provided herein comprise a vector. As used herein, the terms "vector" or "plasmid" are used interchangeably and refer to a circular, double-stranded DNA molecule that is physically separate from chromosomal DNA. In one aspect, a plasmid or vector used herein is capable of replication in vivo. A "transformation vector," as used herein, is a plasmid that is capable of transforming a plant cell. In an aspect, a plasmid provided herein is a bacterial plasmid. In another aspect, a plasmid provided herein is an *Agrobacterium* Ti plasmid or derived from an *Agrobacterium* Ti plasmid.

In one aspect, a plasmid or vector provided herein is a recombinant vector. As used herein, the term "recombinant vector" refers to a vector formed by laboratory methods of genetic recombination, such as molecular cloning. In another aspect, a plasmid provided herein is a synthetic plasmid. As used herein, a "synthetic plasmid" is an artificially created plasmid that is capable of the same functions (e.g., replication) as a natural plasmid (e.g., Ti plasmid). Without being limited, one skilled in the art can create a synthetic plasmid de novo via synthesizing a plasmid by individual nucleotides, or by splicing together nucleic acid molecules from different pre-existing plasmids.

Vectors are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6xHis tag, glutathione S-transferase (GST)).

Suitable methods of introducing polynucleotides (e.g., transgenes, recombinant vectors, recombinant DNA constructs, expression constructs) into plant cells of the present disclosure include microinjection (Crossway et al. (1986) *Biotechniques* 4:320-334), electroporation (Shillito et al. (1987) *Meth. Enzymol.* 153:313-336; Riggs et al. (1986) *Proc. Natl. Acad. Sci. USA* 83:5602-5606), *Agrobacterium*-mediated transformation (U.S. Pat. Nos. 5,104,310, 5,149,645, 5,177,010, 5,231,019, 5,463,174, 5,464,763, 5,469,976, 4,762,785, 5,004,863, 5,159,135, 5,563,055, and 5,981,840), direct gene transfer (Paszkowski et al. (1984) *EMBO J.* 3:2717-2722), and ballistic particle acceleration (see, for example, U.S. Pat. Nos. 4,945,050, 5,141,131, 5,886,244, 5,879,918, and 5,932,782; Tomes et al. (1995) in *Plant Cell, Tissue, and Organ Culture Fundamental Methods*, ed. Gamborg and Phillips (Springer-Verlag, Berlin); McCabe et al. (1988) *Biotechnology* 6:923-926). Also see Weissinger et al. (1988) *Ann. Rev. Genet.* 22:421-477; Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation). In one aspect, a bacterial cell provided herein comprises a recombinant DNA construct or recombinant vector provided herein.

In another aspect, recombinant constructs or expression cassettes provided herein may be introduced into plants by contacting plants with a virus or viral nucleic acids. Generally, such methods involve incorporating an expression cassette of the present disclosure within a viral DNA or RNA molecule. It is recognized that promoters for use in the expression cassettes provided herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221.

Any plant tissue that can be subsequently propagated using clonal methods, whether by organogenesis or embryogenesis, may be transformed with a recombinant construct or an expression cassette provided herein. By "organogenesis" in intended the process by which shoots and roots are developed sequentially from meristematic centers. By "embryogenesis" is intended the process by which shoots and roots develop together in a concerted fashion (not sequentially), whether from somatic cells or gametes. Exemplary tissues that are suitable for various transformation protocols described herein include, but are not limited to, callus tissue, existing meristematic tissue (e.g., apical meristems, axillary buds, and root meristems) and induced meristem tissue (e.g., cotyledon meristem and hypocotyl meristem), hypocotyls, cotyledons, leaf disks, pollen, embryos, and the like.

It is understood that any modified tobacco plant of the present disclosure can further comprise additional agronomically desirable traits, for example, by transformation with a genetic construct or transgene using a technique known in the art. Without limitation, an example of a desired trait is herbicide resistance, pest resistance, disease resistance, high yield, high grade index value, curability, curing quality, mechanical harvestability, holding ability, leaf quality, height, plant maturation (e.g., early maturing, early to medium maturing, medium maturing, medium to late maturing, or late maturing), stalk size (e.g., a small, medium, or a large stalk), or leaf number per plant (e.g., a small (e.g., 5-10 leaves), medium (e.g., 11-15 leaves), or large (e.g., 16-21) number of leaves), or any combination. In one aspect, tobacco plants capable of producing cured leaves with reduced TSNA or seeds provided herein comprise one or more transgenes expressing one or more insecticidal proteins, such as, for example, a crystal protein of *Bacillus thuringiensis* or a vegetative insecticidal protein from *Bacillus cereus*, such as VIP3 (see, for example, Estruch et al. (1997) *Nat. Biotechnol.* 15:137). In another aspect, tobacco plants provided herein further comprise an introgressed trait conferring resistance to brown stem rot (U.S. Pat. No. 5,689,035) or resistance to cyst nematodes (U.S. Pat. No. 5,491,081).

The level and/or activity of polypeptides provided herein may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides and recombinogenic oligonucleobases. Such nucleotide constructs and methods of use are known in the art. See, U.S. Pat. Nos. 5,565,350; 5,731,181; 5,756,325; 5,760,012; 5,795,972 and 5,871,984; each of which is incorporated herein by reference as if set forth in its entirety. See also, International Patent Application Publication Nos. WO 98/149350, WO 99/107865 and WO 99/125921; and Beetham et al. (1999) Proc. Natl. Acad. Sci. USA 96:8774-8778; each of which is incorporated herein by reference as if set forth in its entirety.

The present disclosure also provides compositions and methods for inhibiting the expression or function of one or more polypeptides that suppress, directly or indirectly, the production or accumulation of one or more antioxidants in a plant, particularly plants of the *Nicotiana tabacum* genus, including tobacco plants of various commercial varieties.

In one aspect, inhibition of the expression of one or more polypeptides provided herein may be obtained by RNA interference (RNAi) by expression of a transgene capable of producing an inhibitory sequence provided herein. In one aspect, RNAi comprises expressing a non-coding RNA. As used herein, a "non-coding RNA" is selected from the group consisting of a microRNA (miRNA), a small interfering RNA (siRNA), a trans-acting siRNA (ta-siRNA), a transfer RNA (tRNA), a ribosomal RNA (rRNA), an intron, a hairpin RNA (hpRNA), and an intron-containing hairpin RNA (ihpRNA). In one aspect, a single non-coding RNA provided herein inhibits the expression of at least 1, at least 2, at least 3, at least 4, at least 5, at least 6, at least 7, at least 8, at least 9, at least 10, or more than 10 polypeptides. In one aspect, a non-coding RNA provided herein is stably transformed into a plant genome. In another aspect, a non-coding RNA provided herein is transiently transformed into a plant genome.

As used herein, the terms "suppress," "inhibit," "inhibition," "inhibiting", and "downregulation" are defined as any method known in the art or described herein that decreases the expression or function of a gene product (e.g., an mRNA, a protein, a non-coding RNA). "Inhibition" can be in the context of a comparison between two cells, for example, a modified cell versus a control cell. Inhibition of expression or function of a gene product can also be in the context of a comparison between plant cells, organelles, organs, tissues, or plant components within the same plant or between different plants, and includes comparisons between developmental or temporal stages within the same plant or plant component or between plants or plant components. "Inhibition" includes any relative decrement of function or production of a gene product of interest, up to and including complete elimination of function or production of that gene product. The term "inhibition" encompasses any method or composition that down-regulates translation and/or transcription of the target gene product or functional activity of the target gene product. "Inhibition" need not comprise complete elimination of expression of a gene product. In an aspect, a gene product in a modified cell provided herein comprises expression that is at least 1%, at least 2%, at least 3%, at least 4%, at least 5%, at least 10%, at least 20%, at least 25%, at least 30%, at least 40%, at least 50%, at least 60%, at least 70%, at least 80%, at least 90%, at least 95%, or 100% lower than the expression of the gene product in a control cell. In another aspect, a gene product in a modified cell provided herein comprises expression that is between 1% and 100%, between 1% and 95%, between 1% and 90%, between 1% and 80%, between 1% and 70%, between 1% and 60%, between 1% and 50%, between 1% and 40%, between 1% and 30%, between 1% and 25%, between 1% and 20%, between 1% and 15%, between 1% and 10%, between 1% and 5%, between 5% and 25%, between 5% and 50%, between 5% and 75%, between 5% and 100%, between 10% and 25%, between 10% and 50%, between 10% and 75%, between 10% and 100%, between 25% and 50%, between 25% and 75%, between 25% and 100%, or between 50% and 100% lower than the expression of the gene product in a control cell.

As used herein, a "target site" refers to a location of a polynucleotide sequence that is bound to and cleaved by a site-specific nuclease introducing a double stranded break into the nucleic acid backbone. In another aspect a target site comprises at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides. In another aspect, a target site provided herein is at least 10, at least 20, at least 30, at least 40, at least 50, at least 75, at least 100, at least 125, at least 150, at least 200, at least 250, at least 300, at least 400, or at least 500 nucleotides. In one aspect a site-specific nuclease binds to a target site. In another aspect a site-specific nuclease binds to a target site via a guiding non-coding RNA (i.e., such as, without being limiting, a CRISPR RNA or single-guide RNA (both described in detail below)). In one aspect, a non-coding RNA provided herein is complementary to a target site. It will be appreciated that perfect complementarity is not required for a non-coding RNA to bind to a target site; at least 1, at least 2, at least 3, at least 4, or at least 5, at least 6, at least 7 or at least 8 mismatches between a target site and a non-coding RNA can be tolerated. As used herein, a "target region" or a "targeted region" refers to a polynucleotide sequence that is desired to be modified. In one aspect, a "target region," "targeted region", or a "target gene" is flanked by two or more, three or more, four or more, five or more, six or more, seven or more, eight or more, nine or more, or ten or more target sites. A "target gene" refers to a polynucleotide sequence encoding a gene that is desired to be modified or from which transcript expression is desired to be modulated. In one aspect, a polynucleotide sequence comprising a target gene further comprises one or more target sites. In another aspect, a transgene is said to be targeting a target site or a target gene. In another aspect, a target region comprises one or more, two or more, three or more, four or more, five or more, six or more, seven or more, eight or more, nine or more, or ten or more target genes. Without being limiting, in one aspect a target region can be subject to deletion or inversion. As used herein, "flanked" when used to describe a target region, refers to two or more target sites physically surrounding the target region, with one target site on each side of the target region.

A target site can be positioned in a polynucleotide sequence encoding a leader, an enhancer, a transcriptional start site, a promoter, a 5'-UTR, an exon, an intron, a 3'-UTR, a polyadenylation site, or a termination sequence. It will be appreciated that a target site can be also be positioned upstream or downstream of a sequence encoding a leader, an enhancer, a transcriptional start site, a promoter, a 5'-UTR, an exon, an intron, a 3'-UTR, a polyadenylation site, or a termination sequence. In one aspect, a target site is positioned within 10, within 20, within 30, within 40, within 50, within 75, within 100, within 125, within 150, within 200, within 250, within 300, within 400, within 500, within 600, within 700, within 800, within 900, within 1000, within 1250, within 1500, within 2000, within 2500, within 5000, within 10,000, or within 25,000 nucleotides of a polynucleotide encoding a leader, an enhancer, a transcriptional start site, a promoter, a 5'-UTR, an exon, an intron, a 3'-UTR, a polyadenylation site, a gene, or a termination sequence.

As used herein, "upstream" refers to a nucleic acid sequence that is positioned before the 5' end of a linked nucleic acid sequence. As used herein, "downstream" refers to a nucleic acid sequence is positioned after the 3' end of a linked nucleic acid sequence. As used herein, "5'" refers to the start of a coding DNA sequence or the beginning of an RNA molecule. As used herein, "3'" refers to the end of a coding DNA sequence or the end of an RNA molecule. It will be appreciated that an "inversion" refers to reversing the orientation of a given polynucleotide sequence. For example, if the sample sequence 5'-ATGATC-3' is inverted it will read 5'-CTAGTA-3' in reverse orientation. Additionally, the sample sequence 5'-ATGATC-3' is considered to be in "opposite orientation" to the sample sequence 5'-CTAGTA-3'.

As used herein, "genome editing" or editing refers to targeted mutagenesis, insertion, deletion, inversion, substitution, or translocation of a nucleotide sequence of interest in a genome using a targeted editing technique. A nucleotide sequence of interest can be of any length, e.g., at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides. As used herein, a "targeted editing technique" refers to any method, protocol, or technique that allows the precise and/or targeted editing of a specific location in a genome (e.g., the editing is not random). Without being limiting, use of a site-specific nuclease is one example of a targeted editing technique. Another non-limiting example of a targeted editing technique is the use of one or more tether guide Oligos (tgOligos). As used herein, a "targeted edit" refers to a targeted mutagenesis, insertion, deletion, inversion, or substitution caused by a targeted editing technique. A nucleotide sequence of interest can be an endogenous genomic sequence or a transgenic sequence.

In one aspect, a "targeted editing technique" refers to any method, protocol, or technique that allows the precise and/or targeted editing of a specific location in a genome (e.g., the editing is not random). Without being limiting, use of a site-specific nuclease is one example of a targeted editing technique.

In one aspect, a targeted editing technique is used to edit an endogenous locus or an endogenous gene. In another aspect, a targeted editing technique is used to edit a transgene. As used herein, an "endogenous gene" or a "native copy" of a gene refers to a gene that originates from within a given organism, cell, tissue, genome, or chromosome. An "endogenous gene" or a "native copy" of a gene is a gene that was not previously modified by human action. As used herein, a "plant native" polynucleotide can be found in, and originates from a plant genome and excludes polynucleotides of bacterial, fungal, or animal origins. As used herein, a "tobacco native" or "native to a *Nicotiana* genome" include polynucleotides that can be found in, and originate from a tobacco genome and excludes polynucleotides not found in an unmodified tobacco genome.

In one aspect, a modified tobacco plant described here further comprises one or more mutations are introduced via a system selected from the group consisting of chemical mutagenesis, irradiation mutagenesis, transposon mutagenesis, *Agrobacterium*-mediated transformation, a meganuclease, a zinc-finger nuclease (ZFN), a transcription activator-like effector nuclease (TALEN), a clustered regularly-interspaced short palindromic repeats CRISPR/Cas9 system, a CRISPR/Cpf1 system, a CRISPR/Csm 1 system, and a combination thereof.

The screening and selection of mutagenized tobacco plants can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

In one aspect, a modified plant or plant genome provided herein is mutated or edited by a nuclease selected from the group consisting of a meganuclease, a zinc-finger nuclease (ZFN), a transcription activator-like effector nuclease (TALEN), a CRISPR/Cas9 nuclease, a CRISPR/Cpf1 nuclease, a CRISPR/CasX nuclease, a CRISPR/CasY nuclease, or a CRISPR/Csm 1 nuclease. As used herein, "editing" or "genome editing" refers to targeted mutagenesis of at least 1, at least 2, at least 3, at least 4, at least 5, at least 6, at least 7, at least 8, at least 9, or at least 10 nucleotides of an endogenous plant genome nucleic acid sequence, or removal or replacement of an endogenous plant genome nucleic acid sequence. In one aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with an endogenous nucleic acid sequence. In one aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide selected from the group consisting of SEQ ID NOs:8 to 11, and fragments thereof. In another aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide encoding a polypeptide selected from the group consisting of SEQ ID NOs:33 to 35.

Meganucleases, ZFNs, TALENs, CRISPR/Cas9, CRISPR/Cpf1, CRISPR/CasX, CRISPR/CasY, and CRISPR/Csm 1 induce a double-strand DNA break at a target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of donor nucleic acid sequences by HR. In one aspect, a method provided herein comprises editing a plant genome with a nuclease provided herein to mutate at least 1, at least 2, at least 3, at least 4, at least 5, at least 6, at least 7, at least 8, at least 9, at least 10, or more than 10 nucleotides in the plant genome via HR with a donor polynucleotide. In one aspect, a mutation provided herein is caused by genome editing using a nuclease. In another aspect, a mutation provided herein is caused by non-homologous end-joining or homologous recombination.

Having now generally described the invention, the same will be more readily understood through reference to the following examples that are provided by way of illustration, and are not intended to be limiting of the present invention, unless specified.

Each periodical, patent, and other document or reference cited herein is herein incorporated by reference in its entirety.

EXAMPLES

Example 1. Identification of Pigment Regulatory Factors as Visual Markers

In order to identify gene products capable of behaving as visual markers, genes functioning in the phenylpropanoid pathway are analyzed. Anthocyanins are derived from the phenylpropanoid pathway and are water soluble pigments that can appear red, purple, or blue. To test suitability of the transcriptional regulators AtPAP1 and NtAN2 as visual markers, an AtPAP1 expression construct is generated and tested.

An expression vector, p45-2-7, is used as a backbone to generate multiple transformation vectors. p45-2-7 contains a CsVMV promoter, a NOS terminator, and a cassette comprising a kanamycin selection marker (NPT II) operably linked to a Ubiquitin promoter and a NOS terminator. Nucleic acid vectors comprising transgenes of interest are introduced into tobacco leaf discs via *Agrobacterium* transformation. See, for example, Mayo et al., 2006, *Nat Protoc.* 1:1105-11 and Horsch et al., 1985, *Science* 227:1229-1231.

Example 2. Protoplast Transformation

Narrow Leaf Madole (NLM) tobacco plants are grown in Magenta™ GA-7 boxes and leaf are cut into strips and digested in cell degrading enzyme solution overnight to generate protoplasts for transformation. Freshly isolated protoplasts are resuspended to a concentration of $2 \times 10^5$ cells/ml and subjected to PEG mediated DNA transfection using a modified *Arabidopsis* protoplast transfection protocol (See Sheen 2007, Nature Protocols). The pUBI:AtPAP1: tHSP construct is synthesized by Genscript and delivered in the backbone of a pUC57 plasmid. The AtPAP1 expression cassette is amplified by PCR using primers annealing specifically to the ubiquitin promoter and the heat shock protein terminator. Gel-purified PCR product is diluted to 1 ug/ul and used for protoplast transfection. Transfected protoplasts are immobilized in 1% agarose beads and subjected to tissue culture for regeneration.

Example 3. Regeneration and Selection of Transformed Callus Comprising pUBI:AtPAP1

Figure 1B:
FIG. 1B is a zoom in of a calli comprising pUBI:AtPAP1.

Transformed protoplasts are transferred to Petri plates (½ MS medium) for regeneration. The plates contain 20 mls of TOM K regeneration medium. The Petri plate is sealed with parafilm prior to incubation in dim light (60-80 mE/ms) with 18 hours on, 6 hours off photoperiods at 24 degrees Celsius for three days. Protoplasts are sub-cultured bi-weekly to fresh TOM K medium in dim light with 18 hours on, 6 hours off photoperiods at 24 degrees Celsius until calli becomes discernable. During screening, calli comprising a pUBI: AtPAP1:tHSP cassette appear purple while calli derived from untransformed protoplasts appear white or yellow (See FIG. 1). Amplicon sequencing of purple calli confirm the presence of pUBI:AtPAP1:tHSP cassette. Candidate calli are further cultured and non-pigmented parts are removed off till purple shoots emerge. Purple pigmented shoots are transferred into MS box and cultured for rooting and well developed plants are potted for further growth.

Example 4. Identification of Callus Induced Genes

Tobacco plants at eight different developmental stages including leaf derived callus, seedlings, leaf, stem root, petiole, flower and shoot buds, are dissected into different tissue types are used for transcription profiling. Quantification of transcripts for each different tissue type and developmental time point is aggregated into a database. EdgeR in CLC genomic workbench is used to perform a differential gene expression analysis. Gene expression data is filtered for Callus induced expression for comparison to all other tissue types. False Discovery Rate (DFR) adjustment is performed on all p-values and a cut-off of an FDR corrected p value of <0.05 is used. Results are then filtered for high callus expression. PR5, Proline Rich Protein (PRP), Alcohol dehydrogenase (AD), Extensin3-like (EX3-like), Extensin1-like (EX1-like), PR1a, and S-adenosyl-L-homocysteine hydrolase (SAHH) are identified as genes showing callus-preferred expression patterns. The list of differentially expressed candidate genes is displayed as Reads Per Kilobase of transcript per Million mapped reads (RPKM) (See Table 3) and fold difference as compared to other tissues (See Table 4).

TABLE 3

Reads Per Kilobase of transcript per Million mapped reads (RPKM) for callus-preferred candidate genes.

| | Calli | Seedling | Leaf | Stem | Root | Petiole | Flower | Shoot buds |
|---|---|---|---|---|---|---|---|---|
| PR5 | 508.9 | 82.2 | 0.5 | 1.0 | 159.9 | 1.9 | 0.9 | 1623.7 |
| Proline rich protein | 2029.5 | 42.6 | 8.4 | 634.9 | 425.0 | 73.8 | 7.0 | 569.9 |
| Alcohol dehydrogenase | 762.2 | 109.5 | 1.7 | 150.4 | 44.1 | 50.4 | 14.8 | 38.1 |
| Extensin 3-like | 1193.2 | 72.9 | 7.4 | 696.6 | 608.2 | 121.5 | 49.3 | 97.4 |
| Extensin 1-like | 1910.1 | 122.5 | 31.7 | 702.6 | 912.5 | 98.9 | 140.6 | 276.1 |
| PR1a | 1009.5 | 41.9 | 265.7 | 2.6 | 57.3 | 23.8 | 7.8 | 423.4 |
| S-adenosyl-L-homocysteine hydrolase | 1115.0 | 326.2 | 136.5 | 423.0 | 411.0 | 273.9 | 633.3 | 555.3 |

TABLE 4

Fold difference as compared to other tissue types for callus-preferred candidate genes

| | Calli/ Seeding | Calli/ Leaf | Calli/ Stem | Calli/ Root | Calli/ Petiol | Calli/ Flower | Calli/ Shoot Buds |
|---|---|---|---|---|---|---|---|
| PR5 | 6.2 | 1032.9 | 494.3 | 3.2 | 271.1 | 576.0 | 0.3 |
| Proline rich protein | 47.7 | 242.9 | 3.2 | 4.8 | 27.5 | 289.7 | 3.6 |
| Alcohol dehydrogenase | 7.0 | 447.4 | 5.1 | 17.3 | 15.1 | 51.5 | 20.0 |
| Extensin 3-like | 16.4 | 161.7 | 1.7 | 2.0 | 9.8 | 24.2 | 12.2 |
| Extensin 1-like | 15.6 | 60.2 | 2.7 | 2.1 | 19.3 | 13.6 | 6.9 |
| PR1a | 24.1 | 3.8 | 386.0 | 17.6 | 42.3 | 129.8 | 2.4 |
| S-adenosyl-L-homocysteine hydrolase | 3.4 | 8.2 | 2.6 | 2.7 | 4.1 | 1.8 | 2.0 |

Example 5. Creation of Visual Marker Constructs Comprising pNtPR5

A construct is created combining the tissue preferred promoter pNtPR5, the coding region of NtPAP1, and the terminator NtHSP-T (See Table 2). Three additional constructs are created with this promoter and terminator combination substituting either AtPAP1, AtAN1, or NtAn2 as the coding region. The plant transformation vector p45-2-7 is used as a backbone and the promoter, coding region, and terminator are combined using standard molecular cloning procedures. Protoplasts are transformed and regenerated into callus as described in Examples 3 and 4. Transformed callus comprising pNtPR5:NtPAP1:HSP-T, pNtPR5:AtPAP1:HSP-T, pNtPR5:AtAN1:HSP-T, and pNtPR5:NtAN2:HSP-T are visually selected based on color and regenerated into tobacco plants. The presence of the construct is confirmed using amplicon sequencing.

Example 6. Creation of Visual Marker Constructs Comprising pNtPRP

A construct is created combining the tissue preferred promoter pNtPRP, the coding region of NtPAP1, and the terminator NtHSP-T (See Table 2). Three additional constructs are created with this promoter and terminator combination substituting either AtPAP1, AtAN1, or NtAn2 as the coding region. The plant transformation vector p45-2-7 is used as a backbone and the promoter, coding region, and terminator are combined during construction using standard molecular cloning procedures. Protoplasts are transformed and regenerated into callus as described in Examples 3 and 4. Transformed callus comprising pNtPRP:NtPAP1:HSP-T, pNtPRP:AtPAP1:HSP-T, pNtPRP:AtAN1:HSP-T, and pNtPRP:NtAN2:HSP-T are visually selected based on color and regenerated into tobacco plants. The presence of the construct is confirmed using amplicon sequencing.

Example 7. Creation of Visual Marker Constructs Comprising pNtAD

A construct is created combining the tissue preferred promoter pNtAD, the coding region of NtPAP1, and the terminator NtHSP-T (See Table 2). Three additional constructs are created with this promoter and terminator combination substituting either AtPAP1, AtAN1, or NtAn2 as the coding region. The plant transformation vector p45-2-7 is used as a backbone and the promoter, coding region, and terminator are combined during construction using standard molecular cloning procedures. Protoplasts are transformed and regenerated into callus as described in Examples 3 and 4. Transformed callus comprising pNtAD:NtPAP1:HSP-T, pNtAD:AtPAP1:HSP-T, pNtAD:AtAN1:HSP-T, and pNtAD:NtAN2:HSP-T are visually selected based on color and regenerated into tobacco plants. The presence of the construct is confirmed using amplicon sequencing.

Example 8. Creation of Visual Marker Constructs Comprising pNtEX3-Like

A construct is created combining the tissue preferred promoter pNtEX3-like, the coding region of NtPAP1, and the terminator NtHSP-T (See Table 2). Three additional constructs are created with this promoter and terminator combination substituting either AtPAP1, AtAN1, or NtAn2 as the coding region. The plant transformation vector p45-2-7 is used as a backbone and the promoter, coding region, and terminator are combined during construction using standard molecular cloning procedures. Protoplasts are transformed and regenerated into callus as described in Examples 3 and 4. Transformed callus comprising pNtEX3-like:NtPAP1:HSP-T, pNtEX3-like:AtPAP1:HSP-T, pNtEX3-like:AtAN1:HSP-T, and pNtEX3-like:NtAN2:HSP-T are visually selected based on color and regenerated into tobacco plants. The presence of the construct is confirmed using amplicon sequencing.

Example 9. Creation of Visual Marker Constructs Comprising pNtEX1-Like

A construct is created combining the tissue preferred promoter pNtEX1-like, the coding region of NtPAP1, and the terminator NtHSP-T (See Table 2). Three additional constructs are created with this promoter and terminator combination substituting either AtPAP1, AtAN1, or NtAn2 as the coding region. The plant transformation vector p45-2-7 is used as a backbone and the promoter, coding region, and terminator are combined during construction using standard molecular cloning procedures. Protoplasts are transformed and regenerated into callus as described in Examples 3 and 4. Transformed callus comprising pNtEX1-like:NtPAP1:HSP-T, pNtEX1-like:AtPAP1:HSP-T, pNtEX1-like:AtAN1:HSP-T, and pNtEX1-like:NtAN2:HSP-T are visually selected based on color and regenerated into tobacco plants. The presence of the construct is confirmed using amplicon sequencing.

Example 10. Creation of Visual Marker Constructs Comprising pNtPR1a

A construct is created combining the tissue preferred promoter pNtPR1a, the coding region of NtPAP1, and the terminator NtHSP-T (See Table 2). Three additional constructs are created with this promoter and terminator combination substituting either AtPAP1, AtAN1, or NtAn2 as the coding region. The plant transformation vector p45-2-7 is used as a backbone and the promoter, coding region, and terminator are combined during construction using standard molecular cloning procedures. Protoplasts are transformed and regenerated into callus as described in Examples 3 and 4. Transformed callus comprising pNtPR1a:NtPAP1:HSP-T, pNtPR1a:AtPAP1:HSP-T, pNtPR1a:AtAN1:HSP-T, and pNtPR1a:NtAN2:HSP-T are visually selected based on color and regenerated into tobacco plants. The presence of the construct is confirmed using amplicon sequencing.

Example 11. Creation of Visual Marker Constructs Comprising pNtSAHH

A construct is created combining the tissue preferred promoter pNtSAHH, the coding region of NtPAP1, and the terminator NtHSP-T (See Table 2). Three additional constructs are created with this promoter and terminator combination substituting either AtPAP1, AtAN1, or NtAn2 as the coding region. The plant transformation vector p45-2-7 is used as a backbone and the promoter, coding region, and terminator are combined during construction using standard molecular cloning procedures. Protoplasts are transformed and regenerated into callus as described in Examples 3 and 4. Transformed callus comprising pNtSAHH:NtPAP1:HSP-T, pNtSAHH:AtPAP1:HSP-T, pNtSAHH:AtAN1:HSP-T, and pNtSAHH:NtAN2:HSP-T are visually selected based on color and regenerated into tobacco plants. The presence of the construct is confirmed using amplicon sequencing.

The invention claimed is:

1. A tobacco callus, comprising a recombinant polynucleotide comprising:
   a. a heterologous tissue-preferred promoter comprising a sequence at least 95% identical to SEQ ID NO:1; and
   b. a coding region from a gene encoding a sequence at least 90% identical to SEQ ID NO:10,
   wherein the polynucleotide sequence of said promoter and coding region are in operable linkage and wherein said transformed tobacco callus is visibly pigmented.

2. The transgenic plant, or part thereof, of claim 1, wherein said tissue-preferred promoter comprises a sequence at least 97% identical to SEQ ID NO:1.

3. The transgenic plant, or part thereof, of claim 1, wherein said tissue-preferred promoter comprises SEQ ID NO:1.

4. The transgenic plant, or part thereof, of claim 1, wherein said coding region comprises a sequence at least 95% identical to SEQ ID NO:10.

5. The transgenic plant, or part thereof, of claim 1, wherein said coding region comprises the sequence of SEQ ID NO:10.

6. The transgenic plant, or part thereof, of claim 1, wherein said recombinant polynucleotide comprises at least 80% homology to the sequence of SEQ ID NO:26.

7. The transgenic plant, or part thereof, of claim 1, wherein said recombinant polynucleotide comprises the sequence of SEQ ID NO:26.

8. A method of transforming a tobacco plant said method comprising:
   a. transforming at least one tobacco plant cell with a nucleic acid molecule comprising a gene of interest and a recombinant polynucleotide comprising a heterologous tissue-preferred promoter comprising a sequence at least 95% identical to SEQ ID NO:1 and a coding region from a gene encoding a sequence at least 90% identical to SEQ ID NO:10, wherein the polynucleotide sequence of said promoter and coding region are in operable linkage;

b. selecting at least one transgenic plant cell expressing said nucleic acid molecule and said recombinant polynucleotide;

c. regenerating a transgenic tobacco callus from said transgenic tobacco cell; and d. selecting at least one visibly pigmented transgenic tobacco callus comprising said nucleic acid molecule; and e. producing at least one progeny tobacco plant comprising said nucleic acid molecule but not said recombinant polynucleotide from said modified plant from said selected visibly pigmented transgenic tobacco callus.

9. The method of claim 8, wherein said tissue-preferred promoter comprises a sequence at least 97% identical to a sequence of SEQ ID NO:1.

10. The method of claim 8, wherein said tissue-preferred promoter comprises the sequence of SEQ ID NO:1.

11. The method of claim 8, wherein said coding region from a gene encoding a sequence at least 95% identical to SEQ ID NO:10.

12. The method of claim 8, wherein said coding region from a gene encoding a sequence of SEQ ID NO:10.

13. The method of claim 8, wherein said recombinant polynucleotide comprises at least 90% homology to the sequence of SEQ ID NO:26.

14. The method of claim 8, wherein said recombinant polynucleotide comprises the sequence of SEQ ID NO:26.

15. A method of transforming a tobacco plant, said method comprising:

a. transforming at least one plant cell with a nucleic acid molecule comprising a gene of interest and a recombinant polynucleotide comprising a heterologous tissue-preferred promoter comprising a sequence at least 95% identical to SEQ ID NO:1 and a coding region from a gene encoding a sequence at least 90% identical to SEQ ID NO:10, wherein the polynucleotide sequence of said promoter and coding region are in operable linkage; and b. selecting at least one transgenic tobacco plant cell expressing said nucleic acid molecule and said recombinant polynucleotide, wherein said at least one transgenic tobacco plant cell comprises visible pigmentation.

16. The method of claim 15, wherein said tissue-preferred promoter comprises a sequence at least 97% identical to SEQ ID NO: 1.

17. The method of claim 15, wherein said tissue-preferred promoter comprises the sequence of SEQ ID NO: 1.

18. The method of claim 15, wherein said coding region from a gene encoding a sequence at least 95% identical to SEQ ID NO:10.

19. The method of claim 15, wherein said coding region from a gene encoding a sequence of SEQ ID NO:9 or SEQ ID NO:10.

20. The method of claim 15, wherein said recombinant polynucleotide comprises at least 90% homology to the sequence of SEQ ID NO:26.

21. The method of claim 15, wherein said recombinant polynucleotide comprises the sequence of SEQ ID NO:26.

* * * * *

SEQUENCE LISTING

```
<160> NUMBER OF SEQ ID NOS: 36

<210> SEQ ID NO 1
<211> LENGTH: 1533
<212> TYPE: DNA
<213> ORGANISM: Nicotiana tabacum

<400> SEQUENCE: 1
tttagtggac attttagtaa gaagattggt tgttggatgt atatattgac atttgagtta      60 aggggttta tatagtggta tggcggcttt ttgcactgtg gacattaata tttttggcact    120 tgatatatta ttattattat tatattaata taggaataat catgaaagat gctttggtaa    180
aggtagagct aggcggctaa atgtgaaggc ctgacaagtg ataatttatt atgcacacac    240
atatatagaa gctaaataat ttatttggtg ataatgatca cgagcaaact ttgtcacgct    300
aatatgtcca cttgaaataa tacgccaccg ataatatcca ctataaaaca tggactgaac    360
tagaaattcg ggttgagccc aatagctttt gttcaaataa tatatttatg ttaagtgttt    420
```

```
tattaagtat gtacaaatat taaatttaga atacagttat aattataagc acttggaaac       480
gttgttttaa gattcaaaac caatataatt aaaatacttg ctccgctccg taaaacaaga       540
tatacagcct tcaagcaata cattttgttc agtcgggtca tattccacta ttttttcacta      600 cttttacttc acgttttttta caagctattt atccagtaca tcctttgaac tgaaatcata     660
attatttacc tgcaattatt actataggta tccctagcta cttaatttca tttaaaatta      720
gctataacta gcactagttt atggaatttg gagatgattg tgcgcacaag ctagctttgt      780
ggaatttgga gacgagcttt gcagccggtt tcaatctttc gactacattt gctattggag      840
tcactgagta aaatacttat tttcagtcgg ctgtgtttac actaaattta tgaatgcatg      900
ccattagtct tcacacacac atatataata tatagcttaa taaccctggt taaatgatac      960
aatatattat cagtttaatg aataaatatt tgcctaatta ttacccactc tgcattacca    1020
agtcttcata aatgaaagat ttataatcaa gaaattagat caagaattct aacatatatc    1080
aagtggatta actaatagaa aacgtatatg catctacagt taaaaaaagg ttaagcaaat    1140
ggggtgggtt ggatcttcaa cgttgtgcaa ttcggaattc cccaatttat tgaccattta    1200
cagatcaagt tcacatatta gttagtctga ttttgactta acgtttgtta caattctctt    1260
tttcattttt aaggaaaaaa aagttctgca tccgataatt ggagatcaat atgtaataca    1320
agttagcttc tatgttcata ataattgtca ggctcttacg aatagccgcc aggcatctttt   1380 caagattatt cctttattaa tataatatat caagtgccaa tatatatatg attattgtct    1440
atagtgcaaa aagccgccac acccctatat aaacccccctt aactcaaatg tcaatatatc   1500
aacaccaatt ttcttactaa aaagtccact aaa                                  1533

<210> SEQ ID NO 2
<211> LENGTH: 1185
<212> TYPE: DNA
<213> ORGANISM: Nicotiana tabacum

<400> SEQUENCE: 2
acctcttcct tctctctatc tccattttttt atttatgttt tactaaatta ctttttatttc    60 ataacaacat gtcttgttca tgttttacta agttgctttt atttcataac agcatcataa     120
taaaatacag gaattttcaa gcgaagcaga gtcacttcca aaagtagaaa cacttagaac     180
ttctgctaag ggtaattaac aacttttggt cctttaggag gcacaatata ctagacgaag    240
aattgaactt gatcttactt acggcaaagg ctaataatag catcacgtta gtgaactaca    300
acgccaacta aaaagaaaaa agaaaataat taagaccagt aaatatgcat gttcactctc    360
aaatattgag gggaaaaaaa ccgagaatct aattatctac aaatgttcat tcattagggt    420
agtaggaaaa ttttaatttt atcttaattt gaaccaacta caatatttta ttttaaaaca    480
aataaaattg gaatagcacc ggttttttta ttttatattt tttgggtatc cgaaagtgta    540
tgggcgctag gaactacctc cgtctttact tcttttgttg ctagtaatag gaactccttt    600
aatgttttga cagtgaaaat actagtatat taattaacta atttgtctct ataccatgat    660
ttataatatt acggttgaag tgatagctca tggaagagga agcactgatg gtgtgaaaat    720
atttacacaa tcagatcatt tattatatta ttatggataa atttctcgat aagtattaat    780
tgataagtat tcggataaaa gtaggttata atctaatttt ttttatacta ttagtattag    840
tatatataat tcgttacatt tacatataca tcttctatgt tttattcata gatgtagaca    900
ctggcgagga acatggcaaa ttgcaacacc ttatgtggct aataatgcat tcaagagaat    960
ttgagtaaat atctaatttg cttgtgctgc cagctaaaac cttggggaca catggtttct   1020
```

```
agaacttaat tcttttaata ttctctttta ctctaattca tactttgca tcctatataa    1080 acccaccttc tataacctt gcaatatcaa acaaagcaac aatctactta taactactaa    1140
agttgatagt tatatcaatc attaagaaat tttagactct tagaa                   1185
```

<210> SEQ ID NO 3
<211> LENGTH: 1048
<212> TYPE: DNA
<213> ORGANISM: Nicotiana tabacum

<400> SEQUENCE: 3

```
actaaaagtg aatccttccc cacaaaaac ttagtttga atgcacgaga ttctacaaat     60 aaaagaaag aagaaataa aggtataat tagagcgcac gtgaaataaa aatactatca    120
atttgaatga aaacttgaaa ataaaataaa aatagaagt atcatgtttt gaaggattca    180 atttagtat tatttaatt tatatatatg attatttgt caggtgggtc attcctgttt      240
taattgaatt attatttatt agacgaaaa aaaatcttg aataagaaa atctggtgac     300 tatttatgaa atttacccctt caattgtatg tgtaaaacac ttatatccaa gtttataaga   360 ttttagcaa ataaaatac ttcaaatttt ttaagctatt cgcttgaaaa taaaattaag     420
acatgttaac atagattact ttctctatta ccaaattctt gtgttacttt cttaaagttg    480
agtcgagtag tattgataaa taaaatagtc aatatgtttt ccactgttct gaacaaaaat    540 agttttttt tttttttt tttatgtatt ttcataattt tgaattattt aaattgagt        600 tttggaagat gaattcacgt ttgaccaaaa aggagagatg aatcgtgtct atccaaaaat    660 aaaacaaaa tgggcgtgta aaaataaca ttttttggt gggtcaaaac atcgttaggt      720
ttaataaatc aaatcgattt ttctcttgaa atattaccac caccttttc ttattactcg     780 acaaaaactc aaacagtaac acaaaacaaa cagccaaaaa ccggtttcga aacccagcg    840 accaaaacat ggaatggtt ttactttggc ctgttgtatt caacttttcg atttcacgat    900 tctatattt caggtataaa tacccccagct aatgcagtgc cacatcacac ctcaagatat   960
ttaactcagt attcagaaac aacaaaagtt cttctctaca taaaatttc ctattttagt   1020 gatcagtgaa ggaaatcaag aaaaataa                                     1048
```

<210> SEQ ID NO 4
<211> LENGTH: 2000
<212> TYPE: DNA
<213> ORGANISM: Nicotiana tabacum

<400> SEQUENCE: 4

```
cattggagtt ttattaaccc gcctcgatag aggcggggct atacaatctg ataaggtgat     60
cgaggatgaa agggagcccc tcgactttgc tcacgaagaa tcggagcaga ataacaattt    120
gccaaaagga aggatggatt tggcctaggg ttatttggta ttgacggcaa aaattaacga    180
tgacggggtc gagggggccc aacgtgaaag ggtaagtgta aacacttaga aacccttcca    240
catgagtggt gatatctttt tcggggggtcg ggatcaccac ctctttgcct tcccagttgc   300
ggtctttctt tacctgctta aggtatccct cagttattga gcatatatac ctcgacattg    360
gctcgcatcg atcaggaatc gacgaggctt tatcggtctt aaaatcggag tttagcacgc    420 accccccaaga atgcattcct caagacgggg atccaccagc gttttccgt cggtcggttg    480 agaagatgaa gcaacttctt tttgtggtac catttcgat gttttgcca ttcttgtgta      540 agtttgaaga agaggaagat aataggactt gacatttgag acatgattaa cagcaaagcc    600
```

```
tgaagatttg taaaagggac gaacttaaga gatgtaaaag ctttagatat tagaaggaag    660
tgaaagtaaa gtttgaatca atgaggaagt gatctattta ttggactcac ggcgacagtt    720
caaaggcact agtggccgac aaccaactaa cactcattaa tgacttggaa aactgtactg    780
acgggacgtt ttggtcactc ccgtcgctta cgtcatgagg atgtcgtcat tacaggtcga    840
gatagaaaat tgaaggctca attcgtttct tgtcatttca ctccaaaaaa cgaggagact    900
atctgtatac ggttaaaatc gggcccaccc gattttacta tttgaccgag actaggaggt    960
tgcatcgaag aatggcctcg taacagaaca gactaaatca cgaggataag gtactgagtt   1020
cataatcgag gtaccggtcg agatcgaggc tagtagtgat cgaaaccaaa tgagacagac   1080
atcgagcaag atcgaagata gcacaataac agaaaggcga gatatccacg actggtcgag   1140
gatcatggca taaatctcga aacgaatcaa attagaaaca gttaattagc taatcatgaa   1200
tttacttctg taattagaat tataccataa gtgaaattcc tctactattt ataggggtt    1260 ctaatcattt ggaagacaca tggttcacag atatcaaaga aatgtaattc tctttctcgt   1320
ttatactatt gttcatcagc ttgttatatt ttaattgttc ttacatcaac cagttcgagg   1380
gtatccaaac ttgagggctg agttccattc taacacaagt ttgctttact ttatagttta   1440
tttctattat taatcttcat atttatcaat tggtattaag tgaaattacg tgtacttaga   1500
acaatattat aaatttaatt gttatccaat tttaaggata aataagaaca ttcattaaag   1560
ttaaaagaga catataaaaa aagctattgc tcagatttct gcaactgaaa tcgtgcaaag   1620
ttgaggcatc cacacttgtt tttcaaagct tcggtactgt atacaaagat agaaagtaaa   1680
ggagactttt ctctttaaat tattgcatca gaaatagtat agctgccata atagtttatt   1740
aattccagct atgcttagct tgcagcctct atcgaacaaa aaagtatac caactcaagt    1800 caatttgagc cgacaacatg acaaaaccaa atcaaaatgc atactctagc ttttttactt   1860
tggtaggttt taagtaatct agtgagactt ttaccttcat tcatgaaaat cttggaaagg   1920
gtaattgtat aattgaaagc tatataaagg ggtcggagtg aagcttaaga ggacaacaac   1980
ttttctcatt tgtttcaaag                                              2000

<210> SEQ ID NO 5
<211> LENGTH: 2000
<212> TYPE: DNA
<213> ORGANISM: Nicotiana tabacum

<400> SEQUENCE: 5
cagtaggcat caattactat atattttaca agtaattaaa tgataaacaa atgcaatatt     60
tgtttagttt ccatatttct ttttcaaggc actcctttaa ttactcatcc attcaaatgg    120
atcttctcat ttttcagacg gttttttagga ctccctctat ctcaaattat ctatcgagat    180
ttttaaaaaa aaaattgtct caaattattt tcattttgga aatttaagat aaaattaatt    240 atatttttt catttacccct taatggtaat tattcttgaa tatggagata gcacatcgag     300
taaatattca ataagagag attatatctt ataacataaa taagagtaaa atagtccaaa     360
attcctcata attaatattt tttaagggta tgtaaaagaa aaacacgaca ataaatttga    420
gacggagaga ataccttctt tttgaccttt tgtaaataaa tattaaaata tcctcaacat    480
ttcctaggtt aatttctctc tctccctaat aatttcaaaa agttatcatt gtgatactca    540
aatatattgg tcttagcaca atttgagcat tgcatgttgt atgcctggat cctcctgggt    600 gccattttc ctttgctttt ggatacccttt ttgcaacttt agtccattgc tggaacatga    660 tttttttgtac ctcttgtctg ttcccatgat gataaactat gataactaac attttcagaa    720
```

```
atattggatt gaattagata tattttcaat attgagctac aaaactcgtt gaatattttg        780
ccctatttgg ttggtaataa aagtgggtca catgcacagt ttttctcttg tcttctctag        840
attaagctct ttggaaatga cctactgaaa atgctacaca taaaactccc ccactcctcc        900
ccaagttgag gggtgggagg tttgatttgg acccttaccc tattgttaat atcgaaatag        960
ataatacaaa ggacgggaac ataaaaccaa aacctccgat aaaacaccaa agttgatgat       1020
ctaagttaag ttattgattc ttatacgttg attggaagtg cacaatggtc tttgcatact       1080
atcaaagtat gaattggttc ttgaattata tctcttaata tgatgtattg tgtttaatta       1140
attctctact attctctatt tttataggct aaaagatcct gacatgcttc ttgaacacat       1200
gtgaaggtta gttaactata gtcagaagta cacaagaatt aacttgtaca cctatccgtg       1260
atcgaaaaac ttaacttgtt ctaagctgaa ctgagtcctc ctatccatgt ccgattcttc       1320
actagaagca ttaatcatac aaggagaatt caacttaatt tactgtattg gttatcattt       1380
acatagttta gttataaaac tttggagcga cacaatgatt gacactacta atcatgattg       1440
aatattaact tcactcgatt tatcaatttc tcatacaagt gaattaattt cactctttgt       1500
gatttcagta gtaaatgtca gtttcatag ttttttcttt ttgaaattag tcatacatgt       1560
gaatagaaca ttaatttaag ttaaaagcta gctgctctga tttctgtaac tgaaatcgtg       1620
caaagttgag gcatccacat ttgttttca aagttccagt actgtctaaa aagatagaaa       1680
gtaaaaggag acttttctct ttgaattatt gcatcagaaa tagtatagct gccataatag       1740
tttattcctt tgcttagctt gcagcctcta tcgaacaaaa aaagtgtacc aactcaggtc       1800
aatttgagcc gacaacatga caaaaccaaa tcaaaatgca tatatactct agcttttta       1860 ctttactttg gtaggtttta agtgagactt ttaccttcat ttatgaaaat cttgaaaagg       1920
gtaattgtct aaatgaaagc tatataaagg ggtcgtagtg aagcttaaga agacaacaac       1980
ttttctcatt tgtttcaaag                                                  2000

<210> SEQ ID NO 6
<211> LENGTH: 2000
<212> TYPE: DNA
<213> ORGANISM: Nicotiana tabacum

<400> SEQUENCE: 6
ctatataagg ccatccgtga attgaataaa ctatccaatt attttcttcc acaaaaattt         60
caattctact tttagttatt cttttttaata ttgagcttgc aattctattt tgattcttca       120
ctcatgacat gctacgtaga gaaccttcaa tacatcataa gagatggacc aagcaatgca       180
taactcaaat aagtccatac aaatttgctg aaagataaag ttattctact ttctttgaac       240
ccaaatctga taaatcttga caatcagatt tgctactatg atttctcact gtatcatttg       300
ttttattcta taaagttaat gaggaatgta ttaattattt aagataccctt acttttctg       360 attttttgatc ttatagtcaa gtcgtgaggc acaatttgcg accctgatgg cgcaaacctt       420
tacctaggga tcgtagcaca taaacgtttt taaggactaa gatatacgag gatgtcaatt       480
atcataatgt agggtctaag ttttcatttt tttttttgca tctaatagag tataattttt       540
tttaatcatc acgataactt gatttacaat aatatgtact ctgtttactt ttacttgaca       600
cgttttgatt tttcacgccc tttaagaaaa aatgattgaa atgcataatt taccatgata       660
ctcatattaa ttgatgcata ttttattgga tttgagaaaa tgatttgaaa tgagtaataa       720
atattgtggg tataacagga aaaaaaattg tcttctctta acatgcataa agtgaagagt       780
```

| | | |
|---|---|---|
| aaaaagaaaa tctattttg tatacatgtc aaacaaaagt gaacggagga gatgacaaat | 840 | |
| tgctaaatgg caatagttac aaaattcttc aattactctt tttcataaca aaacactggt | 900 | |
| ctctcttgta agtattggtc tatacttcac cacctaaagc attggccgaa gtcttttaa | 960 | |
| ggagtttggt tgtcatttat ccatttaaat taaagggaaa ataagtgaac gccattacag | 1020 | |
| cgagatgctt tagggtgcta tttcttggaa aaataaagta gttaaatctt aaaacaccct | 1080 | |
| cgaggatttc aaactctagc ttcactaaaa cttgagcttt cttttccact aatgtcgaaa | 1140 | |
| aacgaaataa acataagcta tttacaaaaa taaaaaaata ctccatttga atctaaagtc | 1200 | |
| aagtcgtgat tgggataaga aaatagaaat ttatttatac tccagatcaa gccgtgattg | 1260 | |
| gaatgagata atagaaaagt atgatagtac atgagtaaca tcaagttgga aattaaggga | 1320 | |
| aggaaattag agaagaact gaagaatatc caaatattct ttacgtccaa atttgatagt | 1380 | |
| tatttaacgt catcgagatg acggccatgt tcaagttttc cacaaatatt gagaaaagaa | 1440 | |
| agaaagacac aaactgtgtt tggtattatt atagttttt cttttagaga attgattgta | 1500 | |
| catataagaa attaatataa gatttagaaa taagattatt agaaaatca aacatcaaag | 1560 | |
| tatttatttt aaattctttt tccaatggac attcccattc tgaaaaaaag agatataaaa | 1620 | |
| tggaagtaaa attaatcaga tcgttaaatg tagaaaatat taataacact taaccataac | 1680 | |
| cagtctactt tatttaacaa aaagcacatc tgatagatca aaaaagtgtt taacttcatg | 1740 | |
| cattgacaat ttaaaattat tttgcaacat cgggtaaaac tatttacaa caattggtaa | 1800 | |
| ctgcatatat aagtttaata tggtaaccta gaaaatagga taaattatct ataacaggat | 1860 | |
| atattacatt gatattacca tgtcaaaaaa tttagtaagt acatgaataa tcaccgtgaa | 1920 | |
| atcttcaaga tttctcctat aaataccctt ggtagtaaat ctagttttc cattcaagat | 1980 | |
| acaacatttc tcctatagtc | 2000 | |

<210> SEQ ID NO 7
<211> LENGTH: 2000
<212> TYPE: DNA
<213> ORGANISM: Nicotiana tabacum

<400> SEQUENCE: 7

| | | |
|---|---|---|
| attaattgta aataaatata cttatcattt tcggagaata tccaatatta tatatataat | 60 | |
| ttttatactt atgagtttcg ggctagatat ttattctaag ctaagtacta caaatactgt | 120 | |
| gatataaggc tctaaacttt cctaccctaa aagagtctac gttttactac gctaaaaagg | 180 | |
| tctcactttt actacgctaa aaataatct aaactaaaca tcgcaaaaac aaacaagtaa | 240 | |
| acatgacaat ttaacaaata aatttttttg actaatttac aagtatattt atacaacact | 300 | |
| aaaattaaat ccggataaaa attaacatgc tagttttggc aaaaataaac acaaaactat | 360 | |
| atacaaacca tacaaatcaa ataatattca atattataca agtttcaact aaaattaaat | 420 | |
| cgaaataccct ggattcggaa actaaataaa tcggattttt gacttcaaaa aagagattcc | 480 | |
| agcgtaccac gaccctcaac tataatgtgg gaccaccaat cttcacccttt tatgtgtcgg | 540 | |
| ggggacccaa aaatttttt tttttttaaa aaactgggca gatcgctgag gaggggacca | 600 | |
| aatttttttg aaagttttcg gctgaatgaa gaagaagaag aaaggtttag ggttttgttt | 660 | |
| tagggtatgg cgccaacagt attggcgcta tgctgacacc gcctgaaaag tagggtatg | 720 | |
| gcgccaacac tgttggcgct atgctgacat gtcagtaaac tctctgatat ggcgccaact | 780 | |
| atgttggcgt tatatatatt tgtgttactt ttcctttttt acacttatta atgtagtttg | 840 | |
| agtcaaaaaa aacaataata aagttccgga ctcgagatgt aaggggttgt caattttcac | 900 | |

| | |
|---|---|
| tttgtcagtc gctaagagta attatgaata ttcttttatc aatattggac ctcaaacttt | 960 |
| atccattgta agaaaaaaaa gttgtaaaat atttgtgtca cttaattaaa cggtcgtagt | 1020 |
| agttagtagt agtgacatag tcctttcgtt tgatagtata tcaaattgga acaatttaca | 1080 |
| tttgcaccaa agcataaagg gaaagcatga aaaagagaaa gtgcaaaaga gaaaaataca | 1140 |
| acaacaacaa gaatatttca gtataattct ataagtaggg tctggagaga gtagaatacc | 1200 |
| cctaacctag aagggcagga agaatattaa agtaaaaaag ataaaagatt acaaataaaa | 1260 |
| taaaagaaaa aacaaacaaa catacaaaat taatttgtgc ataatgctta tagtaattgc | 1320 |
| caatttgcca tgaatatctt ccaccgggct atcttggtca tgttaatcac tctatcctgt | 1380 |
| tttcaaacaa ttttttactct aaaaatttgc atgttatatt aattggtggg tgagccagaa | 1440 |
| attttaaaca aaaaatcaaa atacggtaca ctaaaagatt ttttataaaa aagaattcac | 1500 |
| caagttatat atatacacaa tctttctttt ttttaaatct tacgatgacc aattttttcg | 1560 |
| acaaagaata ttcacttaaa cccttgttca tacatagctg gcaattgga ttaataatga | 1620 |
| aaataatact ttaaattttg gaaagaaaat attatttatt ctccaaaaga aaccaagaaa | 1680 |
| ttagattcat caaaaaataa tgaccaccat tagcccacct cccaaatctc tattcctttt | 1740 |
| agacttttaa ccaaattttc agatctacca aaccccaatt tatccaataa acttttcaga | 1800 |
| tctaaaaata aaaatattca gatctggaac aaatcttgac cgtccatttt catcattcat | 1860 |
| atctatttaa taccactcac ctccgccctt tactccttgc aacactcttc ttctcctcta | 1920 |
| aaaacccctta tagaagaaga ggaaaaagcc tttcaaatct catctcaaac cacctaattt | 1980 |
| ctctcatact cgctcgaccc | 2000 |

<210> SEQ ID NO 8
<211> LENGTH: 747
<212> TYPE: DNA
<213> ORGANISM: Arabidopsis thaliana

<400> SEQUENCE: 8

| | |
|---|---|
| atggagggtt cgtccaaagg gctgcgaaaa ggtgcttgga ctactgaaga agatagtctc | 60 |
| ttgagacagt gcattaataa gtatggagaa ggcaaatggc accaagttcc tgtaagagct | 120 |
| gggctaaacc ggtgcaggaa aagttgtaga ttaagatggt tgaactattt gaagccaagt | 180 |
| atcaagagag gaaacttag ctctgatgaa gtcgatcttc ttcttcgcct tcataggctt | 240 |
| ctagggaata ggtggtcttt aattgctgga agattacctg gtcggaccgc aaatgacgtc | 300 |
| aagaattact ggaacactca tctgagtaag aaacatgaac cgtgttgtaa gataaagatg | 360 |
| aaaaagagag acattacgcc cattcctaca acaccggcac taaaaaacaa tgtttataag | 420 |
| cctcgacctc gatccttcac agttaacaac gactgcaacc atctcaatgc cccaccaaaa | 480 |
| gttgacgtta atcctccatg ccttggactt aacatcaata tgtttgtga caatagtatc | 540 |
| atatacaaca aagataagaa gaaagaccaa ctagtgaata atttgattga tggagataat | 600 |
| atgtggttag agaaattcct agaggaaagc caagaggtag atattttggt tcctgaagcg | 660 |
| acgacaacag aaaaggggga caccttggct tttgacgttg atcaactttg gagtcttttc | 720 |
| gatggagaga ctgtgaaatt tgattag | 747 |

<210> SEQ ID NO 9
<211> LENGTH: 2016
<212> TYPE: DNA
<213> ORGANISM: Nicotiana tabacum

<400> SEQUENCE: 9

```
atgacggaga taccgcctaa cagccagatg aaaaccatgt tgcagaaggc agtgcaatcg      60
gttcaatgga catatactct tttctggcaa ttatgtcccc aacaaggggc gttagtgtgg     120
agagatggat attacaatgg ggctataaag actagaaaga cagtgcagcc aatggaagtt     180
agcgctgagg aagcttctct tcacagaagc caacagctta gagaacttta cgaatcactt     240
tccgccggcg agtcaaatca gccagcgaga aggccgtcgg cagctttgtc accggaggac     300
ttgacggagt ccgagtggtt ttatctcatg tgtgtttctt tctcttttcc tcctggcatc     360
ggattacctg gcaaggctta ttcgaagaaa catcacatat ggatcatggg cgcaaacgag     420
gttgatagca aagtcttctg tagagctatt cttgccaaga gcgcccgcat acagacggtc     480
gttggtattc ctctcttgga tggtgtactg gaactgggaa ctacagaaag ggttcaagaa     540
gagattggat tcataaacca tgtaaagagc tttttcactg agcaacaaca acctcagcta     600
ccaaagccag ccttatctga gcactccact tccaatccca ccacctttc cgagccacat     660
ttttactccg gcaatacttc gccatctgct aatgttgata ttgcgcatca agatggcgga     720
gctgccggcg aagaagatga ggaggaggaa gaagaagaag atgatgatga agccgagttg     780
gactcggata gtatagcgat tcaaagcgcg gctaatccta ttgccgttga ggctagtgaa     840
ctcatgcagc ttgatgtgtc cgaggctata cagctcggct cgcccgatga tgactctgat     900
aatatggact ctgattttca tttggttggc gctggaaaca cggctcatga ctaccagcgc     960
caagctgact ctttcaaagc cgagaccgcc attagctggc cgcacttcca agaccttcaa    1020
caattaccag gtggctctag ttatgatgaa ttatcacaag aagacacaca ctattctcaa    1080
acagtgtcaa ccattctcga caccgaagc tccaaatttt cctctacaac aatgggctgt    1140
atttctcatg actcggccca atctgccttc acattgtgcc ctagcaccac cgtctgcagc    1200
ccgaatcccg cccactgccg ccacgacgac tcacttgtcg acggtggcgg cgcctcccag    1260
tggctgctca aaagcatact cttcactgtc ccatttcttc acactaaata ccaatctgaa    1320
gcttctccaa agtcacgtga cgtcgccact gttgattcct ccagtactgc ttctcgcttt    1380
cgcaaaggct gtagtataac gtcgcaagaa gagccaagtg aaaccatgt acttgcagaa    1440
cgacgtcgta gagagaagct aaatgagcgt tttatcatat taaggtctct tgtacctttt    1500
gtaacgaaaa tggacaaagc ctccattttg ggtgacacca tagagtatgt caagcagtta    1560
cgtaagaaag ttcaggatct tgaagctcgt gctcgcgaca cggagcactc cagagatgca    1620
gataaaaaag gtggcacagc tacagtgaag gtgttgcaag gaaggggtaa gaggagaatg    1680
aatacggtag atggaagtgt tggtggaggg caggcaacga taacggcgtc cccaccgtca    1740
acgacggaaa atgaggaggt tgtgcaagta caagtatcaa ttatcgaaag cgatgcattg    1800
gtggagctcc ggtgtccgta caaagagggg ttgctgttaa atgtaatgca gatgctaagg    1860
gaactcaaag tggaagttgt agccattcaa tcagctctta ataatggcgt cttcttggct    1920
gagttaagag ctaaggtaaa agagaatata tgtggaagga aagcaagcat tttggaagta    1980
aaaaggtcaa tacatcagat aatccctaga gattaa                              2016
```

<210> SEQ ID NO 10
<211> LENGTH: 663
<212> TYPE: DNA
<213> ORGANISM: Nicotiana tabacum

<400> SEQUENCE: 10

```
atgaatattt gtactaataa gtcgtcgtca ggagtgaaga aaggtgcatg gactgaagaa      60
```

```
gaagatgttc tattgaaaaa atgcatcgag aaatatggag aaggaaagtg gcatcaagtt      120
cctcttagag ctggtttgaa tagatgcaga aagagctgca gattaaggtg gctaaattat      180
ctaaggccac atataaagag aggagacttc tcttttgatg aagtagatct cattttgagg      240
cttcataagc tgttaggcaa cagatggtca cttattgctg gtagacttcc tggaaggacg      300
gcaaacgatg tcaaaaacta ctggaacagc catcttcgca agaagttaat tgctcctcat      360
gatcaaaagg agagcaagca aaaagcaaag aagatcacca tattcagacc tcggcctcga      420
accttctcaa agacaaatac ttgtgttaaa agtaacacaa atactgtaga taaggatatt      480
gaaggcagca gcgaaataat tagattcaac gataatttga agccaacaac tgaagaattg      540
acggatgatg gaattcaatg gtgggccgat ttactagcta acaattacaa caataatggg      600
attgaggaag ctgataattc atcaccaact ttgttgcatg aggaaatgcc acttctcagt      660
tga                                                                    663

<210> SEQ ID NO 11
<211> LENGTH: 500
<212> TYPE: DNA
<213> ORGANISM: Nicotiana tabacum

<400> SEQUENCE: 11
aataacagag ggcgcgcgag cggtggctac tgatcgccta tgagttctgt gattctactt       60
gtaatttcag aagtgttttc agtgtcttgt tttctggaag tccgtctggt ttttagtaac      120
ttttagctca aaaatgtgtc tgtacgatgg tatttgtatg tttgtgggtc ttttacatat      180
acgcttgtaa tcgatcaatg tagaatgctg tgtgcctttt ccgtcaacag cttatttagt      240
gtttactctg tatacgtata tctaatatat agtactgatt ctttcatctg gtgatttgtt      300
ttcctaaaga gattattatc atagctttaa ttgaatgata caaagaggtg ttgcctggct      360
tcaccagagc agaaatttc attgatatag ggtacaaatg tcattcacat aatgttaaga      420
gataagtttt tcaatgtcct caagagccca ccaagagttt cttccgggaa ttgcttaaat      480
tatcttaaat ttaaattgta                                                  500

<210> SEQ ID NO 12
<211> LENGTH: 2806
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
cccgggttta gtggacattt tagtaagaag attggttgtt ggatgtatat attgacattt       60
gagttaaggg ggtttatata gtggtatggc ggcttttgc actgtggaca ttaatatttt      120
ggcacttgat atattattat tattattata ttaatatagg aataatcatg aaagatgctt      180
tggtaaaggt agagctaggc ggctaaatgt gaaggcctga caagtgataa tttattatgc      240
acacacatat atagaagcta ataatttat ttggtgataa tgatcacgag caaactttgt      300
cacgctaata tgtccacttg aaataatacg ccaccgataa tatccactat aaaacatgga      360
ctgaactaga aattcgggtt gagcccaata gcttttgttc aaataatata tttatgttaa      420
gtgttttatt aagtatgtac aaatattaaa tttagaatac agttataatt ataagcactt      480
ggaaacgttg ttttaagatt caaaaccaat ataattaaaa tacttgctcc gctccgtaaa      540
acaagatata cagccttcaa gcaatacatt ttgttcagtc gggtcatatt ccactatttt      600
```

```
tcactactttt tacttcacgt tttttacaag ctatttatcc agtacatcct ttgaactgaa      660
atcataatta tttacctgca attattacta taggtatccc tagctactta atttcattta      720
aaattagcta taactagcac tagtttatgg aatttggaga tgattgtgcg cacaagctag      780
ctttgtggaa tttggagacg agctttgcag ccggtttcaa tctttcgact acatttgcta      840
ttggagtcac tgagtaaaat acttatttc agtcggctgt gtttacacta aatttatgaa      900
tgcatgccat tagtcttcac acacacatat ataatatata gcttaataac cctggttaaa      960
tgatacaata tattatcagt ttaatgaata atatttgcc taattattac ccactctgca     1020
ttaccaagtc ttcataaatg aaagatttat aatcaagaaa ttagatcaag aattctaaca     1080
tatatcaagt ggattaacta atagaaaacg tatatgcatc tacagttaaa aaaaggttaa     1140
gcaaatgggg tggttggat cttcaacgtt gtgcaattcg gaattcccca atttattgac      1200
catttacaga tcaagttcac atattagtta gtctgatttt gacttaacgt ttgttacaat     1260
tctctttttc attttaagg aaaaaaaagt tctgcatccg ataattggag atcaatatgt      1320
aatacaagtt agcttctatg ttcataataa ttgtcaggct cttacgaata gccgccaggc     1380
atctttcaag attattcctt tattaatata atatatcaag tgccaatata tatatgatta     1440
ttgtctatag tgcaaaaagc cgccacaccc ctatataaac ccccttaact caaatgtcaa     1500
tatatcaaca ccaattttct tactaaaaag tccactaaac tcgagatgga gggttcgtcc     1560
aaagggctgc gaaaaggtgc ttggactact gaagaagata gtctcttgag acagtgcatt     1620
aataagtatg gagaaggcaa atggcaccaa gttcctgtaa gagctgggct aaaccggtgc     1680
aggaaaagtt gtagattaag atggttgaac tatttgaagc caagtatcaa gagaggaaaa     1740
cttagctctg atgaagtcga tcttcttctt cgccttcata ggcttctagg aataggtgg     1800 tctttaattg ctggaagatt acctggtcgg accgcaaatg acgtcaagaa ttactggaac     1860
actcatctga gtaagaaaca tgaaccgtgt tgtaagataa agatgaaaaa gagagacatt     1920
acgcccattc ctacaacacc ggcactaaaa aacaatgttt ataagcctcg acctcgatcc     1980
ttcacagtta acaacgactg caaccatctc aatgccccac caaaagttga cgttaatcct     2040
ccatgccttg gacttaacat caataatgtt tgtgacaata gtatcatata caacaaagat     2100
aagaagaaag accaactagt gaataatttg attgatggag ataatatgtg gttagagaaa     2160
ttcctagagg aaagccaaga ggtagatatt ttggttcctg aagcgacgac aacagaaaag     2220
ggggacacct tggcttttga cgttgatcaa cttttggagtc ttttcgatgg agagactgtg     2280
aaatttgatt agtctagaaa taacagaggg cgcgcgagcg gtggctactg atcgcctatg     2340
agttctgtga ttctacttgt aatttcagaa gtgttttcag tgtcttgttt tctggaagtc     2400
cgtctggttt ttagtaactt ttagctcaaa atgtgtctg tacgatggta tttgtatgtt      2460
tgtgggtctt ttacatatac gcttgtaatc gatcaatgta gaatgctgtg tgccttttcc     2520
gtcaacagct tatttagtgt ttactctgta tacgtatatc taatatatag tactgattct     2580
ttcatctggt gatttgtttt cctaaagaga ttattatcat agctttaatt gaatgataca     2640
aagaggtgtt gcctggcttc accagagcag aaattttcat tgatataggg tacaaatgtc     2700
attcacataa tgttaagaga taagttttc aatgtcctca agagcccacc aagagtttct      2760
tccgggaatt gcttaaatta tcttaaattt aaattgtagt ttaaac                    2806
```

<210> SEQ ID NO 13
<211> LENGTH: 2458
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 13

```
cccgggacct cttccttctc tctatctcca ttttttattt atgttttact aaattacttt      60
tatttcataa caacatgtct tgttcatgtt ttactaagtt gcttttattt cataacagca     120
tcataataaa atacaggaat tttcaagcga agcagagtca cttccaaaag tagaaacact     180
tagaacttct gctaagggta attaacaact tttggtcctt taggaggcac aatatactag     240
acgaagaatt gaacttgatc ttacttacgg caaaggctaa taatagcatc acgttagtga     300
actacaacgc caactaaaaa gaaaaagaa aataattaag accagtaaat atgcatgttc      360
actctcaaat attggggga aaaaaaccga gaatctaatt atctacaaat gttcattcat      420
tagggtagta ggaaaatttt aattttatct taatttgaac caactacaat attttatttt     480
aaaacaaata aaattggaat agcaccggtt tttttatttt atatttttg ggtatccgaa      540
agtgtatggg cgctaggaac tacctccgtc tttacttctt ttgttgctag taataggaac     600
tcctttaatg ttttgacagt gaaaatacta gtatattaat taactaattt gtctctatac     660
catgatttat aatattacgg ttgaagtgat agctcatgga agaggaagca ctgatggtgt     720
gaaaatattt acacaatcag atcatttatt atattattat ggataaattt ctcgataagt     780
attaattgat aagtattcgg ataaaagtag gttataatct aatttttttt atactattag     840
tattagtata tataattcgt tacatttaca tatacatctt ctatgtttta ttcatagatg     900
tagacactgg cgaggaacat ggcaaattgc aacacccttat gtggctaata atgcattcaa    960
gagaatttga gtaaatatct aatttgcttg tgctgccagc taaaaccttg gggacacatg    1020
gtttctagaa cttaattct ttaatatttc tctttactct aattcatact tttgcatcct    1080
atataaaccc accttctata acctttgcaa tatcaaacaa agcaacaatc tacttataac    1140
tactaaagtt gatagttata tcaatcatta agaaatttta gactcttaga actcgagatg    1200
gagggttcgt ccaaagggct gcgaaaaggt gcttggacta ctgaagaaga tagtctcttg    1260
agacagtgca ttaataagta tggagaaggc aaatggcacc aagttcctgt aagagctggg    1320
ctaaaccggt gcaggaaaag ttgtagatta agatggttga actatttgaa gccaagtatc    1380
aagagaggaa aacttagctc tgatgaagtc gatcttcttc ttcgccttca taggcttcta    1440
gggaataggt ggtctttaat tgctggaaga ttacctggtc ggaccgcaaa tgacgtcaag    1500
aattactgga acactcatct gagtaagaaa catgaaccgt gttgtaagat aaagatgaaa    1560
aagagagaca ttacgcccat tcctacaaca ccggcactaa aaaacaatgt ttataagcct    1620
cgacctcgat ccttcacagt taacaacgac tgcaaccatc tcaatgcccc accaaaagtt    1680
gacgttaatc ctccatgcct tggacttaac atcaataatg tttgtgacaa tagtatcata    1740
tacaacaaag ataagaagaa agaccaacta gtgaataatt tgattgatgg agataatatg    1800
tggttagaga aattcctaga ggaaagccaa gaggtagata ttttggttcc tgaagcgacg    1860
acaacagaaa aggggggacac cttggctttt gacgttgatc aactttggag tcttttcgat    1920
ggagagactg tgaaatttga ttagtctaga ataacagag ggcgcgcgag cggtggctac    1980
tgatcgccta tgagttctgt gattctactt gtaatttcag aagtgttttc agtgtcttgt    2040
tttctggaag tccgtctggt ttttagtaac ttttagctca aaaatgtgtc tgtacgatgg    2100
tatttgtatg tttgtgggtc ttttacatat acgcttgtaa tcgatcaatg tagaatgctg    2160
```

| | |
|---|---|
| tgtgccttttt ccgtcaacag cttatttagt gtttactctg tatacgtata tctaatatat | 2220 |
| agtactgatt ctttcatctg gtgatttgtt ttcctaaaga gattattatc atagctttaa | 2280 |
| ttgaatgata caaagaggtg ttgcctggct tcaccagagc agaaattttc attgatatag | 2340 |
| ggtacaaatg tcattcacat aatgttaaga gataagtttt tcaatgtcct caagagccca | 2400 |
| ccaagagttt cttccgggaa ttgcttaaat tatcttaaat ttaaattgta gtttaaac | 2458 |

<210> SEQ ID NO 14
<211> LENGTH: 2321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

| | |
|---|---|
| cccgggacta aaagtgaatc cttccccaca aaaaacttag ttttgaatgc acgagattct | 60 |
| acaaataaaa agaaagaaag aaataaaagg tataattaga gcgcacgtga aataaaaata | 120 |
| ctatcaattt gaatgaaaac ttgaaaataa aataaaaaat agaagtatca tgttttgaag | 180 |
| gattcaattt tagtattatt ttaatttata tatatgatta ttttgtcagg tgggtcattc | 240 |
| ctgttttaat tgaattatta tttattagac gaaaaaaaaa atcttggaat aagaaaatct | 300 |
| ggtgactatt tatgaaattt acccttcaat tgtatgtgta aaacacttat atccaagttt | 360 |
| ataagatttt tagcaaaata aaatacttca aatttttttaa gctattcgct tgaaaataaa | 420 |
| attaagacat gttaacatag attactttct ctattaccaa attcttgtgt tactttctta | 480 |
| aagttgagtc gagtagtatt gataaataaa atagtcaata tgttttccac tgttctgaac | 540 |
| aaaaatagtt tttttttttt tttttttta tgtattttca taattttgaa ttatttaaat | 600 |
| ttgagttttg gaagatgaat tcacgtttga ccaaaaagga gagatgaatc gtgtctatcc | 660 |
| aaaaataaaa acaaaatggg cgtgtaaaaa ataacatttt tttggtgggt caaaacatcg | 720 |
| ttaggtttaa taaatcaaat cgatttttct cttgaaatat taccaccacc ttttttcttat | 780 |
| tactcgacaa aaactcaaac agtaacacaa aacaaacagc caaaaaccgg tttcgaaaac | 840 |
| ccagcgacca aaacatggaa atggttttac tttggcctgt tgtattcaac ttttcgattt | 900 |
| cacgattcta tattttcagg tataaatacc ccagctaatg cagtgccaca tcacacctca | 960 |
| agatatttaa ctcagtattc agaaacaaca aaagttcttc tctacataaa attttcctat | 1020 |
| tttagtgatc agtgaaggaa atcaagaaaa ataactcgag atggagggtt cgtccaaagg | 1080 |
| gctgcgaaaa ggtgcttgga ctactgaaga agatagtctc ttgagacagt gcattaataa | 1140 |
| gtatggagaa ggcaaatggc accaagttcc tgtaagagct gggctaaacc ggtgcaggaa | 1200 |
| aagttgtaga ttaagatggt tgaactattt gaagccaagt atcaagagag gaaaacttag | 1260 |
| ctctgatgaa gtcgatcttc ttcttcgcct tcataggctt ctagggaata ggtggtcttt | 1320 |
| aattgctgga agattacctg tcggaccgc aaatgacgtc aagaattact ggaacactca | 1380 |
| tctgagtaag aaacatgaac cgtgttgtaa gataaagatg aaaagagag acattacgcc | 1440 |
| cattcctaca acaccggcac taaaaaacaa tgtttataag cctcgacctc gatccttcac | 1500 |
| agttaacaac gactgcaacc atctcaatgc cccaccaaaa gttgacgtta atcctccatg | 1560 |
| ccttggactt aacatcaata atgtttgtga caatagtatc atatacaaca aagataagaa | 1620 |
| gaaagaccaa ctagtgaata atttgattga tggagataat atgtggttag agaaattcct | 1680 |
| agaggaaagc caagaggtag atattttggt tcctgaagcg acgacaacag aaaaggggga | 1740 |

```
caccttggct tttgacgttg atcaactttg gagtcttttc gatggagaga ctgtgaaatt    1800
tgattagtct agaaataaca gagggcgcgc gagcggtggc tactgatcgc ctatgagttc    1860
tgtgattcta cttgtaattt cagaagtgtt ttcagtgtct tgttttctgg aagtccgtct    1920 ggttttagt aacttttagc tcaaaaatgt gtctgtacga tggtatttgt atgtttgtgg     1980
gtcttttaca tatacgcttg taatcgatca atgtagaatg ctgtgtgcct tttccgtcaa    2040
cagcttattt agtgtttact ctgtatacgt atatctaata tatagtactg attcttttcat  2100 ctggtgattt gttttcctaa agagattatt atcatagctt taattgaatg atacaaagag   2160
gtgttgcctg gcttcaccag agcagaaatt tcattgata tagggtacaa atgtcattca    2220
cataatgtta agagataagt ttttcaatgt cctcaagagc ccaccaagag tttcttccgg   2280
gaattgctta aattatctta aatttaaatt gtagtttaaa c                       2321
```

<210> SEQ ID NO 15
<211> LENGTH: 3273
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
cccgggcatt ggagttttat taacccgcct cgatagaggc ggggctatac aatctgataa     60
ggtgatcgag gatgaaaggg agcccctcga ctttgctcac gaagaatcgg agcagaataa    120
caatttgcca aaaggaagga tggatttggc ctagggttat ttggtattga cggcaaaaat    180
taacgatgac ggggtcgagg gggcccaacg tgaaagggta agtgtaaaca cttagaaacc    240
cttccacatg agtggtgata tcttttcgg gggtcgggat caccacctct ttgccttccc     300
agttgcggtc tttctttacc tgcttaaggt atccctcagt tattgagcat atatacctcg    360
acattggctc gcatcgatca ggaatcgacg aggcttatc ggtcttaaaa tcggagttta    420
gcacgcaccc ccaagaatgc attcctcaag acggggatcc accagcgttt ttccgtcggt    480
cggttgagaa gatgaagcaa cttctttttg tggtaccatt ttcgatgttt ttgccattct    540
tgtgtaagtt tgaagaagag gaagataata ggacttgaca tttgagacat gattaacagc    600
aaagcctgaa gatttgtaaa agggacgaac ttaagagatg taaaagcttt agatattaga    660
aggaagtgaa agtaaagttt gaatcaatga ggaagtgatc tatttattgg actcacggcg    720
acagttcaaa ggcactagtg gccgacaacc aactaacact cattaatgac ttggaaaact    780
gtactgacgg gacgttttgg tcactcccgt cgcttacgtc atgaggatgt cgtcattaca    840
ggtcgagata gaaaattgaa ggctcaattc gtttcttgtc atttcactcc aaaaaacgag    900
gagactatct gtatacggtt aaaatcgggc ccacccgatt ttactatttg accgagacta    960
ggaggttgca tcgaagaatg gcctcgtaac agaacagact aaatcacgag gataaggtac    1020
tgagttcata atcgaggtac cggtcgagat cgaggctagt agtgatcgaa accaaatgag    1080
acagacatcg agcaagatcg aagatagcac aataacagaa aggcgagata tccacgactg    1140
gtcgaggatc atggcataaa tctcgaaacg aatcaaatta gaaacagtta attagctaat    1200
catgaattta cttctgtaat tagaattata ccataagtga aattcctcta ctatttatag    1260
ggggttctaa tcatttggaa gacacatggt tcacagatat caaagaaatg taattctctt    1320
tctcgtttat actattgttc atcagcttgt tatattttaa ttgttcttac atcaaccagt    1380
tcgagggtat ccaaacttga gggctgagtt ccattctaac acaagtttgc tttacttttat  1440
```

```
agtttatttc tattattaat cttcatattt atcaattggt attaagtgaa attacgtgta    1500
cttagaacaa tattataaat ttaattgtta tccaatttta aggataaata agaacattca    1560
ttaaagttaa aagagacata taaaaaaagc tattgctcag atttctgcaa ctgaaatcgt    1620
gcaaagttga ggcatccaca cttgtttttc aaagcttcgg tactgtatac aaagatagaa    1680
agtaaaggag actttctctc ttaaattatt gcatcagaaa tagtatagct gccataatag    1740
tttattaatt ccagctatgc ttagcttgca gcctctatcg aacaaaaaaa gtataccaac    1800
tcaagtcaat ttgagccgac aacatgacaa aaccaaatca aaatgcatac tctagctttt    1860
ttactttggt aggttttaag taatctagtg agacttttac cttcattcat gaaaatcttg    1920
gaaagggtaa ttgtataatt gaaagctata taaaggggtc ggagtgaagc ttaagaggac    1980
aacaactttt ctcatttgtt tcaaagctcg agatggaggg ttcgtccaaa gggctgcgaa    2040
aaggtgcttg gactactgaa gaagatagtc tcttgagaca gtgcattaat aagtatggag    2100
aaggcaaatg gcaccaagtt cctgtaagag ctgggctaaa ccggtgcagg aaagttgta    2160 gattaagatg gttgaactat ttgaagccaa gtatcaagag aggaaaactt agctctgatg    2220
aagtcgatct tcttcttcgc cttcataggc ttctagggaa taggtggtct ttaattgctg    2280
gaagattacc tggtcggacc gcaaatgacg tcaagaatta ctggaacact catctgagta    2340
agaaacatga accgtgttgt aagataaaga tgaaaaagag agacattacg cccattccta    2400
caacaccggc actaaaaaac aatgtttata agcctcgacc tcgatccttc acagttaaca    2460
acgactgcaa ccatctcaat gccccaccaa agttgacgt taatcctcca tgccttggac    2520
ttaacatcaa taatgtttgt gacaatagta tcatatacaa caaagataag aagaaagacc    2580
aactagtgaa taatttgatt gatggagata atatgtggtt agagaaattc ctagaggaaa    2640
gccaagaggt agatattttg gttcctgaag cgacgacaac agaaaagggg acaccttgg    2700 cttttgacgt tgatcaactt tggagtctt tcgatggaga gactgtgaaa tttgattagt    2760
ctagaaataa cagagggcgc gcgagcggtg gctactgatc gcctatgagt tctgtgattc    2820
tacttgtaat ttcagaagtg ttttcagtgt cttgttttct ggaagtccgt ctggttttta    2880 gtaacttttta gctcaaaaat gtgtctgtac gatggtattt gtatgtttgt gggtctttta    2940
catatacgct tgtaatcgat caatgtagaa tgctgtgtgc cttttccgtc aacagcttat    3000
ttagtgttta ctctgtatac gtatatctaa tatatagtac tgattctttc atctggtgat    3060
ttgttttcct aaagagatta ttatcatagc tttaattgaa tgatacaaag aggtgttgcc    3120
tggcttcacc agagcagaaa ttttcattga tatagggtac aaatgtcatt cacataatgt    3180
taagagataa gttttttcaat gtcctcaaga gcccaccaag agtttcttcc gggaattgct    3240
taaattatct taaatttaaa ttgtagttta aac                                3273
```

<210> SEQ ID NO 16
<211> LENGTH: 3273
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
cccgggcagt aggcatcaat tactatatat tttacaagta attaaatgat aaacaaatgc      60
aatatttgtt tagtttccat atttctttt caaggcactc ctttaattac tcatccattc     120
aaatggatct tctcattttt cagacggttt ttaggactcc ctctatctca aattatctat     180
```

```
cgagattttt aaaaaaaaaa ttgtctcaaa ttattttcat tttggaaatt taagataaaa    240
ttaattatat ttttttcatt tacccttaat ggtaattatt cttgaatatg agatagcac    300 atcgagtaaa tattcaataa agagagatta tatcttataa cataaataag agtaaaatag    360
tccaaaattc ctcataatta atattttta agggtatgta aaagaaaaac acgacaaata    420
atttgagacg gagagaatac cttcttttg accttttgta aataaatatt aaaatatcct    480
caacatttcc taggttaatt tctctctctc cctaataatt tcaaaaagtt atcattgtga    540
tactcaaata tattggtctt agcacaattt gagcattgca tgttgtatgc ctggatcctc    600
ctgggtgcca ttttcctttt gcttttggat acctttttgc aactttagtc cattgctgga    660
acatgatttt ttgtacctct tgtctgttcc catgatgata actatgata actaacattt    720 tcagaaatat tggattgaat tagatatatt ttcaatattg agctacaaaa ctcgttgaat    780
attttgccct atttggttgg taataaaagt gggtcacatg cacagttttt ctcttgtctt    840
ctctagatta agctctttgg aaatgaccta ctgaaaatgc tacacataaa actcccccac    900
tcctccccaa gttgagggt gggaggtttg atttggaccc ttaccctatt gttaatatcg    960
aaatagataa tacaaaggac gggaacataa aaccaaaacc tccgataaaa caccaaagtt   1020
gatgatctaa gttaagttat tgattcttat acgttgattg gaagtgcaca atggtctttg   1080
catactatca aagtatgaat tggttcttga attatatctc ttaatatgat gtattgtgtt   1140
taattaattc tctactattc tctattttta taggctaaaa gatcctgaca tgcttcttga   1200
acacatgtga aggttagtta actatagtca gaagtacaca agaattaact tgtacaccta   1260
tccgtgatcg aaaaacttaa cttgttctaa gctgaactga gtcctcctat ccatgtccga   1320
ttcttcacta gaagcattaa tcatacaagg agaattcaac ttaatttact gtattggtta   1380
tcatttacat agtttagtta taaaactttg gagcgacaca atgattgaca ctactaatca   1440
tgattgaata ttaacttcac tcgatttatc aatttctcat acaagtgaat taatttcact   1500
ctttgtgatt tcagtagtaa atgtcaagtt tcatagtttt ttcttttga aattagtcat   1560 acatgtgaat agaacattaa tttaagttaa aagctagctg ctctgatttc tgtaactgaa   1620
atcgtgcaaa gttgaggcat ccacatttgt ttttcaaagt tccagtactg tctaaaaaga   1680
tagaaagtaa aaggagactt ttctctttga attattgcat cagaaatagt atagctgcca   1740
taatagttta ttccttttgct tagcttgcag cctctatcga acaaaaaaag tgtaccaact   1800
caggtcaatt tgagccgaca acatgacaaa accaaatcaa aatgcatata tactctagct   1860 ttttttacttt actttggtag gttttaagtg agacttttac cttcatttat gaaaatcttg   1920
aaaagggtaa ttgtctaaat gaaagctata taaaggggtc gtagtgaagc ttaagaagac   1980
aacaactttt ctcatttgtt tcaaagctcg agatggaggg ttcgtccaaa gggctgcgaa   2040
aaggtgcttg gactactgaa gaagatagtc tcttgagaca gtgcattaat aagtatggag   2100
aaggcaaatg gcaccaagtt cctgtaagag ctgggctaaa ccggtgcagg aaagttgta   2160 gattaagatg gttgaactat ttgaagccaa gtatcaagag aggaaaactt agctctgatg   2220
aagtcgatct tcttcttcgc cttcataggc ttctagggaa taggtggtct ttaattgctg   2280
gaagattacc tggtcggacc gcaaatgacg tcaagaatta ctggaacact catctgagta   2340
agaaacatga accgtgttgt aagataaaga tgaaaagag agacattacg cccattccta   2400
caacaccggc actaaaaaac aatgtttata agcctcgacc tcgatccttc acagttaaca   2460
acgactgcaa ccatctcaat gccccaccaa agttgacgt taatcctcca tgccttggac   2520
ttaacatcaa taatgtttgt gacaatagta tcatatacaa caaagataag aagaaagacc   2580
```

```
aactagtgaa taatttgatt gatggagata atatgtggtt agagaaattc ctagaggaaa    2640
gccaagaggt agatattttg gttcctgaag cgacgacaac agaaaagggg gacaccttgg    2700
cttttgacgt tgatcaactt tggagtcttt tcgatggaga gactgtgaaa tttgattagt    2760
ctagaaataa cagagggcgc gcgagcggtg gctactgatc gcctatgagt tctgtgattc    2820
tacttgtaat ttcagaagtg ttttcagtgt cttgttttct ggaagtccgt ctggttttta    2880
gtaactttta gctcaaaaat gtgtctgtac gatggtattt gtatgtttgt gggtctttta    2940
catatacgct tgtaatcgat caatgtagaa tgctgtgtgc ttttccgtc aacagcttat     3000 ttagtgttta ctctgtatac gtatatctaa tatatagtac tgattctttc atctggtgat    3060
ttgttttcct aaagagatta ttatcatagc tttaattgaa tgatacaaag aggtgttgcc    3120
tggcttcacc agagcagaaa ttttcattga tagggtac aaatgtcatt cacataatgt      3180
taagagataa gttttcaat gtcctcaaga gcccaccaag agtttcttcc gggaattgct      3240
taaattatct taaatttaaa ttgtagttta aac                                  3273
```

<210> SEQ ID NO 17
<211> LENGTH: 3273
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
cccgggctat ataaggccat ccgtgaattg aataaactat ccaattattt tcttccacaa      60
aaatttcaat tctacttta gttattcttt ttaatattga gcttgcaatt ctattttgat     120
tcttcactca tgacatgcta cgtagagaac cttcaataca tcataagaga tggaccaagc    180
aatgcataac tcaaataagt ccatacaaat ttgctgaaag ataaagttat tctactttct    240
ttgaacccaa atctgataaa tcttgacaat cagatttgct actatgattt ctcactgtat    300
catttgtttt attctataaa gttaatgagg aatgtattaa ttatttaaga taccttactt    360
tttctgattt ttgatcttat agtcaagtcg tgaggcacaa tttgcgaccc tgatggcgca    420 aaccttacc tagggatcgt agcacataaa cgttttaag gactaagata tacgaggatg      480
tcaattatca taatgtaggg tctaagtttt cattttttt tttgcatcta atagagtata     540 attttttta atcatcacga taacttgatt tacaataata tgtactctgt ttactttac     600 ttgacacgtt ttgattttc acgccctta agaaaaatg attgaaatgc ataatttacc      660
atgatactca tattaattga tgcatatttt attggatttg agaaaatgat ttgaaatgag    720
taataaaata tgtgggtata acaggaaaaa aaattgtctt ctcttaacat gcataaagtg    780
aagagtaaaa agaaaatcta ttttgtata catgtcaaac aaaagtgaac ggaggagatg     840
acaaattgct aaatggcaat agttacaaaa ttcttcaatt actctttttc ataacaaaac    900
actggtctct cttgtaagta ttggtctata cttcaccacc taaagcattg gccgaagtct    960
ttttaaggag tttggttgtc atttatccat ttaaattaaa gggaaaataa gtgaacgcca   1020
ttacagcgat atgctttagg gtgctatttc ttggaaaaat aaagtagtta atcttaaaa    1080 caccctcgag gatttcaaac tctagcttca ctaaaacttg agctttcttt tccactaatg   1140
tcgaaaaacg aaataaacat aagctattta caaaaataaa aaatactcc atttgaatct    1200 aaagtcaagt cgtgattggg ataagaaaat agaaatttat ttatactcca gatcaagccg   1260
tgattggaat gagataatag aaaagtatga tagtacatga gtaacatcaa gttggaaatt   1320
```

```
aagggaagga aattagagaa agaactgaag aatatccaaa tattctttac gtccaaattt    1380
gatagttatt taacgtcatc gagatgacgg ccatgttcaa gttttccaca aatattgaga    1440
aaagaaagaa agacacaaac tgtgtttggt attattatag ttttttcttt tagagaattg    1500
attgtacata taagaaatta atataagatt tagaaataag attattagaa aaatcaaaca    1560
tcaaagtatt tattttaaat tcttttccca atggacattc ccattctgaa aaaagagat     1620 ataaaatgga agtaaaatta atcagatcgt taaatgtaga aaatattaat aacacttaac    1680
cataaccagt ctactttatt taacaaaaag cacatctgat agatcaaaaa agtgtttaac    1740
ttcatgcatt gacaatttaa aattattttg caacatcggg taaaactatt ttacaacaat    1800
tggtaactgc atatataagt ttaatatggt aacctagaaa ataggataaa ttatctataa    1860
caggatatat tacattgata ttaccatgtc aaaaaattta gtaagtacat gaataatcac    1920
cgtgaaatct tcaagatttc tcctataaat acccttggta gtaaatctag ttttttccatt   1980 caagatacaa catttctcct atagtcctcg agatggaggg ttcgtccaaa gggctgcgaa    2040
aaggtgcttg gactactgaa gaagatagtc tcttgagaca gtgcattaat aagtatggag    2100
aaggcaaatg gcaccaagtt cctgtaagag ctgggctaaa ccggtgcagg aaaagttgta    2160
gattaagatg gttgaactat ttgaagccaa gtatcaagag aggaaaactt agctctgatg    2220
aagtcgatct tcttcttcgc cttcataggc ttctagggaa taggtggtct ttaattgctg    2280
gaagattacc tggtcggacc gcaaatgacg tcaagaatta ctggaacact catctgagta    2340
agaaacatga accgtgttgt aagataaaga tgaaaaagag agacattacg cccattccta    2400
caacaccggc actaaaaaac aatgtttata agcctcgacc tcgatccttc acagttaaca    2460
acgactgcaa ccatctcaat gccccaccaa aagttgacgt taatcctcca tgccttggac    2520
ttaacatcaa taatgtttgt gacaatagta tcatatacaa caaagataag aagaaagacc    2580
aactagtgaa taatttgatt gatggagata atatgtggtt agagaaattc ctagaggaaa    2640
gccaagaggt agatattttg gttcctgaag cgacgacaac agaaaagggg gacaccttgg    2700
cttttgacgt tgatcaactt tggagtcttt tcgatggaga gactgtgaaa tttgattagt    2760
ctagaaataa cagagggcgc gcgagcggtg gctactgatc gcctatgagt tctgtgattc    2820
tacttgtaat ttcagaagtg ttttcagtgt cttgttttct ggaagtccgt ctggttttta    2880 gtaacttttta gctcaaaaat gtgtctgtac gatggtattt gtatgtttgt gggtctttta    2940
catatacgct tgtaatcgat caatgtagaa tgctgtgtgc cttttccgtc aacagcttat    3000
ttagtgttta ctctgtatac gtatatctaa tatatagtac tgattctttc atctggtgat    3060
ttgttttcct aaagagatta ttatcatagc tttaattgaa tgatacaaag aggtgttgcc    3120
tggcttcacc agagcagaaa ttttcattga tatagggtac aaatgtcatt cacataatgt    3180
taagagataa gttttttcaat gtcctcaaga gcccaccaag agtttcttcc gggaattgct    3240
taaattatct taaattaaa ttgtagttta aac                                  3273
```

<210> SEQ ID NO 18
<211> LENGTH: 3273
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
cccgggatta attgtaaata aatatactta tcattttcgg agaatatcca atattatata    60
```

```
tataattttt atacttatga gtttcgggct agatatttat tctaagctaa gtactacaaa    120
tactgtgata taaggctcta aactttccta ccctaaaaga gtctacgttt tactacgcta    180
aaaaggtcta cattttacta cgctaaaaaa taatctaaac taaacatcgc aaaaacaaac    240
aagtaaacat gacaatttaa caaataaatt ttttgactaa atttacaagt atatttatac    300
aacactaaaa ttaaatccgg ataaaaatta acatgctagt tttggcaaaa ataaacacaa    360
aactatatac aaaccataca aatcaaataa tattcaatat tatacaagtt tcaactaaaa    420
ttaaatcgaa atacctggat tcggaaacta aataaatcgg atttttgact tcaaaaaaga    480
gattccagcg taccacgacc ctcaactata atgtgggacc accaatcttc acctttttatg   540 tgtcgggggg acccaaaaat ttttttttt tttaaaaaac tgggcagatc gctgaggagg    600
ggaccaaatt tttttgaaag ttttcggctg aatgaagaag aagaagaaag gtttagggtt    660
ttgttttagg gtatggcgcc aacagtattg gcgctatgct gacaccgcct gaaaagtagg    720
ggtatggcgc caacactgtt ggcgctatgc tgacatgtca gtaaactctc tgatatggcg    780
ccaactatgt tggcgttata tatatttgtg ttactttttcc ttttttacac ttattaatgt   840
agtttgagtc aaaaaaaaca ataataaagt tccggactcg agatgtaagg ggttgtcaat    900
tttcactttg tcagtcgcta agagtaatta tgaatattct tttatcaata ttggacctca    960
aactttatcc attgtaagaa aaaaagttg taaaatattt gtgtcactta attaaacggt    1020
cgtagtagtt agtagtagtg acatagtcct ttcgtttgat agtatatcaa attggaacaa   1080
tttacatttg caccaaagca taagggaaa gcatgaaaaa gagaaagtgc aaaagagaaa    1140
aatacaacaa caacaagaat atttcagtat aattctataa gtagggtctg gagagagtag   1200 aatacccta acctagaagg gcaggaagaa tattaaagta aaaaagataa aagattacaa    1260
ataaaataaa agaaaaaaca aacaaacata caaaattaat ttgtgcataa tgcttatagt    1320
aattgccaat ttgccatgaa tatcttccac cgggctatct tggtcatgtt aatcactcta   1380
tcctgttttc aaacaatttt tactctaaaa atttgcatgt tatattaatt ggtgggtgag   1440
ccagaaattt taaacaaaaa atcaaaatac ggtacactaa aagattttt ataaaaaaga    1500 attcaccaag ttatatatat acacaatctt tctttttttt aaatcttacg atgaccaatt   1560
ttttcgacaa agaatattca cttaaaccct tgttcataca tagcttggca attggattaa    1620
taatgaaaat aatactttaa attttggaaa gaaatatta tttattctcc aaaagaaacc    1680
aagaaattag attcatcaaa aaataatgac caccattagc ccacctccca aatctctatt    1740
ccttttagac ttttaaccaa attttcagat ctaccaaacc ccaatttatc caataaactt    1800
ttcagatcta aaaataaaaa tattcagatc tggaacaaat cttgaccgtc cattttcatc   1860
attcatatct atttaatacc actcacctcc gcccttact ccttgcaaca ctcttcttct    1920
cctctaaaaa cccttataga agaagaggaa aaagcctttc aaatctcatc tcaaaccacc   1980
taatttctct catactcgct cgaccccctcg agatggaggg ttcgtccaaa gggctgcgaa   2040
aaggtgcttg gactactgaa gaagatagtc tcttgagaca gtgcattaat aagtatggag   2100
aaggcaaatg gcaccaagtt cctgtaagag ctgggctaaa ccggtgcagg aaaagttgta   2160
gattaagatg gttgaactat ttgaagccaa gtatcaagag aggaaaactt agctctgatg   2220
aagtcgatct tcttcttcgc cttcataggc ttctagggaa taggtggtct ttaattgctg   2280
gaagattacc tggtcggacc gcaaatgacg tcaagaatta ctggaacact catctgagta   2340
agaaacatga accgtgttgt aagataaaga tgaaaaagag agacattacg cccattccta   2400
```

```
caacaccggc actaaaaaac aatgtttata agcctcgacc tcgatccttc acagttaaca    2460
acgactgcaa ccatctcaat gccccaccaa aagttgacgt taatcctcca tgccttggac    2520
ttaacatcaa taatgtttgt gacaatagta tcatatacaa caaagataag aagaaagacc    2580
aactagtgaa taatttgatt gatggagata atatgtggtt agagaaattc ctagaggaaa    2640
gccaagaggt agatattttg gttcctgaag cgacgacaac agaaaagggg gacaccttgg    2700
cttttgacgt tgatcaactt tggagtcttt tcgatggaga gactgtgaaa tttgattagt    2760
ctagaaataa cagagggcgc gcgagcggtg gctactgatc gcctatgagt tctgtgattc    2820
tacttgtaat ttcagaagtg ttttcagtgt cttgttttct ggaagtccgt ctggttttta    2880 gtaacttta gctcaaaaat gtgtctgtac gatggtattt gtatgtttgt gggtctttta    2940
catatacgct tgtaatcgat caatgtagaa tgctgtgtgc cttttccgtc aacagcttat    3000
ttagtgttta ctctgtatac gtatatctaa tatatagtac tgattctttc atctggtgat    3060
ttgttttcct aaagagatta ttatcatagc tttaattgaa tgatacaaag aggtgttgcc    3120
tggcttcacc agagcagaaa ttttcattga tatagggtac aaatgtcatt cacataatgt    3180
taagagataa gttttttcaat gtcctcaaga gcccaccaag agtttcttcc gggaattgct    3240
taaattatct taaatttaaa ttgtagttta aac                                 3273
```

<210> SEQ ID NO 19
<211> LENGTH: 4075
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
cccggggttta gtggacattt tagtaagaag attggttgtt ggatgtatat attgacattt      60
gagttaaggg ggtttatata gtggtatggc ggcttttgc actgtggaca ttaatatttt     120
ggcacttgat atattattat tattattata ttaatatagg aataatcatg aaagatgctt     180
tggtaaaggt agagctaggc ggctaaatgt gaaggcctga caagtgataa tttattatgc     240
acacacatat atagaagcta ataaattat ttggtgataa tgatcacgag caaactttgt      300
cacgctaata tgtccacttg aaataatacg ccaccgataa tatccactat aaaacatgga     360
ctgaactaga aattcgggtt gagcccaata gcttttgttc aaataatata tttatgttaa     420
gtgttttatt aagtatgtac aaatattaaa tttagaatac agttataatt ataagcactt     480
ggaaacgttg ttttaagatt caaaccaat ataattaaaa tacttgctcc gctccgtaaa     540
acaagatata cagccttcaa gcaatacatt ttgttcagtc gggtcatatt ccactatttt    600
tcactacttt tacttcacgt tttttacaag ctatttatcc agtacatcct ttgaactgaa    660
atcataatta tttacctgca attattacta taggtatccc tagctactta atttcattta    720
aaattagcta taactagcac tagtttatgg aatttggaga tgattgtgcg cacaagctag    780
ctttgtggaa tttggagacg agctttgcag ccggtttcaa tctttcgact acatttgcta    840
ttggagtcac tgagtaaaat acttattttc agtcggctgt gtttacacta aatttatgaa    900
tgcatgccat tagtcttcac acacacatat ataatatata gcttaataac cctggttaaa    960
tgatacaata tattatcagt ttaatgaata atatttgcc taattattac ccactctgca   1020
ttaccaagtc ttcataaatg aaagatttat aatcaagaaa ttagatcaag aattctaaca   1080
tatatcaagt ggattaacta atagaaaacg tatatgcatc tacagttaaa aaaggttaa    1140
```

```
gcaaatgggg tgggttggat cttcaacgtt gtgcaattcg gaattcccca atttattgac    1200
catttacaga tcaagttcac atattagtta gtctgatttt gacttaacgt ttgttacaat    1260 tctcttttc  attttaagg  aaaaaaagt  tctgcatccg ataattggag atcaatatgt    1320
aatacaagtt agcttctatg ttcataataa ttgtcaggct cttacgaata gccgccaggc    1380
atctttcaag attattcctt tattaatata atatatcaag tgccaatata tatatgatta    1440
ttgtctatag tgcaaaaagc cgccacaccc ctatataaac cccttaact  caaatgtcaa    1500 tatatcaaca ccaattttct tactaaaaag tccactaaac tcgagatgac ggagataccg    1560
cctaacagcc agatgaaaac catgttgcag aaggcagtgc aatcggttca atggacatat    1620
actcttttct ggcaattatg tccccaacaa ggggcgttag tgtggagaga tggatattac    1680 aatgggcta  taaagactag aaagacagtg cagccaatgg aagttagcgc tgaggaagct    1740
tctcttcaca gaagccaaca gcttagagaa ctttacgaat cactttccgc cggcgagtca    1800
aatcagccag cgagaaggcc gtcggcagct ttgtcaccgg aggacttgac ggagtccgag    1860
tggttttatc tcatgtgtgt ttctttctct tttcctcctg gcatcggatt acctggcaag    1920
gcttattcga agaaacatca catatggatc atgggcgcaa acgaggttga tagcaaagtc    1980
ttctgtagag ctattcttgc caagagcgcc cgcatacaga cggtcgttgg tattcctctc    2040
ttggatggtg tactggaact gggaactaca gaaagggttc aagaagagat tggattcata    2100
aaccatgtaa agagcttttt cactgagcaa caacaacctc agctaccaaa gccagcctta    2160
tctgagcact ccacttccaa tcccaccacc ttttccgagc cacatttta  ctccggcaat    2220 acttcgccat ctgctaatgt tgatattgcg catcaagatg gcggagctgc cggcgaagaa    2280
gatgaggagg aggaagaaga agaagatgat gatgaagccg agttggactc ggatagtata    2340
gcgattcaaa gcgcggctaa tcctattgcc gttgaggcta gtgaactcat gcagcttgat    2400
gtgtccgagg ctatacagct cggctcgccc gatgatgact ctgataatat ggactctgat    2460
tttcatttgg ttggcgctgg aaacacggct catgactacc agcgccaagc tgactctttc    2520
aaagccgaga ccgccattag ctggccgcac ttccaagacc ttcaacaatt accaggtggc    2580
tctagttatg atgaattatc acaagaagac acacactatt ctcaaacagt gtcaaccatt    2640
ctcgaacacc gaagctccaa attttcctct acaacaatgg gctgtatttc tcatgactcg    2700
gcccaatctg ccttcacatt gtgccctagc accaccgtct gcagcccgaa tcccgcccac    2760
tgccgccacg acgactcact tgtcgacggt ggcggcgcct cccagtggct gctcaaaagc    2820
atactcttca ctgtcccatt tcttcacact aaataccaat ctgaagcttc tccaaagtca    2880
cgtgacgtcg ccactgttga ttcctccagt actgcttctc gctttcgcaa aggctgtagt    2940
ataacgtcgc aagaagagcc aagtggaaac catgtacttg cagaacgacg tcgtagagag    3000
aagctaaatg agcgttttat catattaagg tctcttgtac cttttgtaac gaaaatggac    3060
aaagcctcca ttttgggtga caccatagag tatgtcaagc agttacgtaa gaaagttcag    3120
gatcttgaag ctcgtgctcg cgacacggag cactccagag atgcagataa aaaaggtggc    3180
acagctacag tgaaggtgtt gcaaggaagg ggtaagagga gaatgaatac ggtagatgga    3240
agtgttggtg gagggcaggc aacgataacg gcgtccccac cgtcaacgac ggaaaatgag    3300
gaggttgtgc aagtacaagt atcaattatc gaaagcgatg cattggtgga gctccggtgt    3360
ccgtacaaag aggggttgct gttaaatgta atgcagatgc taagggaact caaagtggaa    3420
gttgtagcca ttcaatcagc tcttaataat ggcgtcttct tggctgagtt aagagctaag    3480
gtaaaagaga atatatgtgg aaggaaagca agcatttgg  aagtaaaaag gtcaatacat    3540
```

```
cagataatcc ctagagatta atctagaaat aacagagggc gcgcgagcgg tggctactga    3600
tcgcctatga gttctgtgat tctacttgta atttcagaag tgttttcagt gtcttgtttt    3660
ctggaagtcc gtctggtttt tagtaacttt tagctcaaaa atgtgtctgt acgatggtat    3720
ttgtatgttt gtgggtcttt tacatatacg cttgtaatcg atcaatgtag aatgctgtgt    3780
gccttttccg tcaacagctt atttagtgtt tactctgtat acgtatatct aatatatagt    3840
actgattctt tcatctggtg atttgttttc ctaaagagat tattatcata gctttaattg    3900
aatgatacaa agaggtgttg cctggcttca ccagagcaga aattttcatt gatatagggt    3960
acaaatgtca ttcacataat gttaagagat aagttttttca atgtcctcaa gagcccacca    4020
agagtttctt ccgggaattg cttaaattat cttaaattta aattgtagtt taaac         4075
```

<210> SEQ ID NO 20
<211> LENGTH: 3727
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
cccgggacct cttccttctc tctatctcca ttttttattt atgttttact aaattacttt     60
tatttcataa caacatgtct tgttcatgtt ttactaagtt gcttttattt cataacagca    120
tcataataaa atacaggaat tttcaagcga agcagagtca cttccaaaag tagaaacact    180
tagaacttct gctaagggta attaacaact tttggtcctt taggaggcac aatatactag    240
acgaagaatt gaacttgatc ttacttacgg caaaggctaa taatagcatc acgttagtga    300
actacaacgc caactaaaaa gaaaaaagaa aataattaag accagtaaat atgcatgttc    360
actctcaaat attgagggga aaaaaaccga gaatctaatt atctacaaat gttcattcat    420
tagggtagta ggaaaatttt aattttatct taatttgaac caactacaat attttatttt    480
aaaacaaata aaattggaat agcaccggtt tttttatttt atatttttg ggtatccgaa     540 agtgtatggg cgctaggaac tacctccgtc tttacttctt ttgttgctag taataggaac    600
tcctttaatg ttttgacagt gaaaatacta gtatattaat taactaattt gtctctatac    660
catgatttat aatattacgg ttgaagtgat agctcatgga agaggaagca ctgatggtgt    720
gaaaatattt acacaatcag atcatttatt atattattat ggataaattt ctcgataagt    780
attaattgat aagtattcgg ataaaagtag gttataatct aatttttttt atactattag    840
tattagtata tataattcgt tacatttaca tatacatctt ctatgtttta ttcatagatg    900
tagacactgg cgaggaacat ggcaaattgc aacaccttat gtggctaata atgcattcaa    960
gagaatttga gtaaatatct aatttgcttg tgctgccagc taaaaccttg gggacacatg   1020
gtttctagaa cttaatttct ttaatatttc tctttactct aattcatact tttgcatcct   1080
atataaaccc accttctata acctttgcaa tatcaaacaa agcaacaatc tacttataac   1140
tactaaagtt gatagttata tcaatcatta agaaatttta gactcttaga actcgagatg   1200
acggagatac cgcctaacag ccagatgaaa accatgttgc agaaggcagt gcaatcggtt   1260
caatggacat atactctttt ctggcaatta tgtccccaac aagggcgtt agtgtgggaga   1320 gatggatatt acaatgggc tataaagact agaaagacag tgcagccaat ggaagttagc    1380
gctgaggaag cttctcttca cagaagccaa cagcttagaa aacttacga atcactttcc    1440 gccggcgagt caaatcagcc agcgagaagg ccgtcggcag cttgtcacc ggaggacttg     1500
```

```
acggagtccg agtggtttta tctcatgtgt gtttctttct cttttcctcc tggcatcgga    1560
ttacctggca aggcttattc gaagaaacat cacatatgga tcatgggcgc aaacgaggtt    1620
gatagcaaag tcttctgtag agctattctt gccaagagcg cccgcataca gacggtcgtt    1680
ggtattcctc tcttggatgg tgtactggaa ctgggaacta cagaaagggt tcaagaagag    1740
attggattca taaaccatgt aaagagcttt tcactgagc aacaacaacc tcagctacca    1800
aagccagcct tatctgagca ctccacttcc aatcccacca cctttccga gccacatttt    1860 tactccggca atacttcgcc atctgctaat gttgatattg cgcatcaaga tggcggagct    1920
gccggcgaag aagatgagga ggaggaagaa gaagaagatg atgatgaagc cgagttggac    1980
tcggatagta tagcgattca aagcgcggct aatcctattg ccgttgaggc tagtgaactc    2040
atgcagcttg atgtgtccga ggctatacag ctcggctcgc ccgatgatga ctctgataat    2100
atggactctg attttcattt ggttggcgct ggaaacacgg ctcatgacta ccagcgccaa    2160
gctgactctt tcaaagccga gaccgccatt agctggccgc acttccaaga ccttcaacaa    2220
ttaccaggtg gctctagtta tgatgaatta tcacaagaag acacacacta ttctcaaaca    2280
gtgtcaacca ttctcgaaca ccgaagctcc aaattttcct ctacaacaat gggctgtatt    2340
tctcatgact cggcccaatc tgccttcaca ttgtgcccta gcaccaccgt ctgcagcccg    2400
aatcccgccc actgccgcca cgacgactca cttgtcgacg gtggcggcgc ctcccagtgg    2460
ctgctcaaaa gcatactctt cactgtccca tttcttcaca ctaaatacca atctgaagct    2520
tctccaaagt cacgtgacgt cgccactgtt gattcctcca gtactgcttc tcgctttcgc    2580
aaaggctgta gtataacgtc gcaagaagag ccaagtggaa accatgtact tgcagaacga    2640
cgtcgtagag agaagctaaa tgagcgtttt atcatattaa ggtctcttgt accttttgta    2700
acgaaaatgg acaaagcctc catttttgggt gacaccatag agtatgtcaa gcagttacgt    2760
aagaaagttc aggatcttga agctcgtgct cgcgacacgg agcactccag agatgcagat    2820
aaaaaaggtg gcacagctac agtgaaggtg ttgcaaggaa ggggtaagag gagaatgaat    2880
acggtagatg gaagtgttgg tggagggcag gcaacgataa cggcgtcccc accgtcaacg    2940
acggaaaatg aggaggttgt gcaagtacaa gtatcaatta tcgaaagcga tgcattggtg    3000
gagctccggt gtccgtacaa agaggggttg ctgttaaatg taatgcagat gctaagggaa    3060
ctcaaagtgg aagttgtagc cattcaatca gctcttaata atggcgtctt cttggctgag    3120
ttaagagcta aggtaaaaga gaatatatgt ggaaggaaag caagcatttt ggaagtaaaa    3180
aggtcaatac atcagataat ccctagagat taatctagaa ataacagagg gcgcgcgagc    3240
ggtggctact gatcgcctat gagttctgtg attctacttg taatttcaga agtgttttca    3300
gtgtcttgtt ttctggaagt ccgtctggtt tttagtaact tttagctcaa aaatgtgtct    3360
gtacgatggt atttgtatgt ttgtgggtct tttacatata cgcttgtaat cgatcaatgt    3420
agaatgctgt gtgcctttc cgtcaacagc ttatttagtg tttactctgt atacgtatat    3480
ctaatatata gtactgattc tttcatctgg tgatttgttt tcctaaagag attattatca    3540
tagctttaat tgaatgatac aaagaggtgt tgcctggctt caccagagca gaaattttca    3600
ttgatatagg gtacaaatgt cattcacata atgttaagag ataagttttt caatgtcctc    3660
aagagcccac caagagtttc ttccgggaat tgcttaaatt atcttaaatt taaattgtag    3720
tttaaac                                                             3727
```

<210> SEQ ID NO 21

-continued

<211> LENGTH: 3590
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

| | | | | | |
|---|---|---|---|---|---|
| cccgggacta | aaagtgaatc | cttccccaca | aaaacttag | ttttgaatgc | acgagattct | 60 |
| acaaataaaa | agaaagaaag | aaataaaagg | tataattaga | gcgcacgtga | aataaaaata | 120 |
| ctatcaattt | gaatgaaaac | ttgaaaataa | aataaaaaat | agaagtatca | tgttttgaag | 180 |
| gattcaattt | tagtattatt | ttaatttata | tatatgatta | ttttgtcagg | tgggtcattc | 240 |
| ctgttttaat | tgaattatta | tttattagac | gaaaaaaaaa | atcttggaat | aagaaaatct | 300 |
| ggtgactatt | tatgaaattt | acccttcaat | tgtatgtgta | aaacacttat | atccaagttt | 360 |
| ataagatttt | tagcaaaata | aaatacttca | aatttttaa | gctattcgct | tgaaaataaa | 420 |
| attaagacat | gttaacatag | attactttct | ctattaccaa | attcttgtgt | tactttctta | 480 |
| aagttgagtc | gagtagtatt | gataaataaa | atagtcaata | tgttttccac | tgttctgaac | 540 |
| aaaaatagtt | tttttttttt | ttttttttta | tgtattttca | taattttgaa | ttatttaaat | 600 |
| ttgagttttg | gaagatgaat | tcacgtttga | ccaaaaagga | gagatgaatc | gtgtctatcc | 660 |
| aaaaataaaa | acaaaatggg | cgtgtaaaaa | ataacatttt | tttggtgggt | caaaacatcg | 720 |
| ttaggtttaa | taaatcaaat | cgattttct | cttgaaatat | taccaccacc | tttttcttat | 780 |
| tactcgacaa | aaactcaaac | agtaacacaa | aacaaacagc | caaaaaccgg | tttcgaaaac | 840 |
| ccagcgacca | aaacatggaa | atggttttac | tttggcctgt | tgtattcaac | ttttcgattt | 900 |
| cacgattcta | tattttcagg | tataaatacc | ccagctaatg | cagtgccaca | tcacacctca | 960 |
| agatatttaa | ctcagtattc | agaaacaaca | aaagttcttc | tctacataaa | attttcctat | 1020 |
| tttagtgatc | agtgaaggaa | atcaagaaaa | ataactcgag | atgacggaga | taccgcctaa | 1080 |
| cagccagatg | aaaaccatgt | tgcagaaggc | agtgcaatcg | gttcaatgga | catatactct | 1140 |
| tttctggcaa | ttatgtcccc | aacaaggggc | gttagtgtgg | agagatggat | attacaatgg | 1200 |
| ggctataaag | actagaaaga | cagtgcagcc | aatggaagtt | agcgctgagg | aagcttctct | 1260 |
| tcacagaagc | caacagctta | gagaacttta | cgaatcactt | tccgccggcg | agtcaaatca | 1320 |
| gccagcgaga | aggccgtcgg | cagctttgtc | accggaggac | ttgacggagt | ccgagtggtt | 1380 |
| ttatctcatg | tgtgtttctt | tctcttttcc | tcctggcatc | ggattacctg | gcaaggctta | 1440 |
| ttcgaagaaa | catcacatat | ggatcatggg | cgcaaacgag | gttgatagca | agtcttctg | 1500 |
| tagagctatt | cttgccaaga | gcgcccgcat | acagacggtc | gttggtattc | ctctcttgga | 1560 |
| tggtgtactg | gaactgggaa | ctacagaaag | ggttcaagaa | gagattggat | tcataaacca | 1620 |
| tgtaaagagc | tttttcactg | agcaacaaca | acctcagcta | ccaaagccag | ccttatctga | 1680 |
| gcactccact | tccaatccca | ccacctttc | cgagccacat | ttttactccg | gcaatacttc | 1740 |
| gccatctgct | aatgttgata | ttgcgcatca | agatggcgga | gctgccggcg | aagaagatga | 1800 |
| ggaggaggaa | gaagaagaag | atgatgatga | agccgagttg | gactcggata | gtatagcgat | 1860 |
| tcaaagcgcg | gctaatccta | ttgccgttga | ggctagtgaa | ctcatgcagc | ttgatgtgtc | 1920 |
| cgaggctata | cagctcggct | cgcccgatga | tgactctgat | aatatggact | ctgattttca | 1980 |
| tttggttggc | gctggaaaca | cggctcatga | ctaccagcgc | caagctgact | ctttcaaagc | 2040 |
| cgagaccgcc | attagctggc | cgcacttcca | agaccttcaa | caattaccag | gtggctctag | 2100 |

| | |
|---|---:|
| ttatgatgaa ttatcacaag aagacacaca ctattctcaa acagtgtcaa ccattctcga | 2160 |
| acaccgaagc tccaaatttt cctctacaac aatgggctgt atttctcatg actcggccca | 2220 |
| atctgccttc acattgtgcc ctagcaccac cgtctgcagc ccgaatcccg cccactgccg | 2280 |
| ccacgacgac tcacttgtcg acggtggcgg cgcctcccag tggctgctca aaagcatact | 2340 |
| cttcactgtc ccatttcttc acactaaata ccaatctgaa gcttctccaa agtcacgtga | 2400 |
| cgtcgccact gttgattcct ccagtactgc ttctcgcttt cgcaaaggct gtagtataac | 2460 |
| gtcgcaagaa gagccaagtg gaaaccatgt acttgcagaa cgacgtcgta gagagaagct | 2520 |
| aaatgagcgt tttatcatat taaggtctct tgtacctttt gtaacgaaaa tggacaaagc | 2580 |
| ctccattttg ggtgacacca tagagtatgt caagcagtta cgtaagaaag ttcaggatct | 2640 |
| tgaagctcgt gctcgcgaca cggagcactc cagagatgca gataaaaaag gtggcacagc | 2700 |
| tacagtgaag gtgttgcaag gaagggggtaa gaggagaatg aatacggtag atggaagtgt | 2760 |
| tggtggaggg caggcaacga taacggcgtc cccaccgtca acgacggaaa atgaggaggt | 2820 |
| tgtgcaagta caagtatcaa ttatcgaaag cgatgcattg gtggagctcc ggtgtccgta | 2880 |
| caaagagggg ttgctgttaa atgtaatgca gatgctaagg gaactcaaag tggaagttgt | 2940 |
| agccattcaa tcagctctta ataatggcgt cttcttggct gagttaagag ctaaggtaaa | 3000 |
| agagaatata tgtggaagga aagcaagcat tttggaagta aaaaggtcaa tacatcagat | 3060 |
| aatccctaga gattaatcta gaaataacag agggcgcgcg agcggtggct actgatcgcc | 3120 |
| tatgagttct gtgattctac ttgtaatttc agaagtgttt tcagtgtctt gttttctgga | 3180 |
| agtccgtctg gtttttagta acttttagct caaaaatgtg tctgtacgat ggtatttgta | 3240 |
| tgtttgtggg tcttttacat atacgcttgt aatcgatcaa tgtagaatgc tgtgtgcctt | 3300 |
| ttccgtcaac agcttattta gtgttactc tgtatacgta tatctaatat atagtactga | 3360 |
| ttctttcatc tggtgatttg ttttcctaaa gagattatta tcatagcttt aattgaatga | 3420 |
| tacaaagagg tgttgcctgg cttcaccaga gcagaaattt tcattgatat agggtacaaa | 3480 |
| tgtcattcac ataatgttaa gagataagtt tttcaatgtc ctcaagagcc caccaagagt | 3540 |
| ttcttccggg aattgcttaa attatcttaa atttaaattg tagtttaaac | 3590 |

<210> SEQ ID NO 22
<211> LENGTH: 4542
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 22

| | |
|---|---:|
| cccgggcatt ggagttttat taacccgcct cgatagaggc ggggctatac aatctgataa | 60 |
| ggtgatcgag gatgaaaggg agcccctcga ctttgctcac gaagaatcgg agcagaataa | 120 |
| caatttgcca aaaggaagga tggatttggc ctagggttat ttggtattga cggcaaaaat | 180 |
| taacgatgac ggggtcgagg gggcccaacg tgaaagggta agtgtaaaca cttagaaacc | 240 |
| cttccacatg agtggtgata tcttttttcgg gggtcgggat caccacctct ttgccttccc | 300 |
| agttgcggtc tttctttacc tgcttaaggt atccctcagt tattgagcat atatacctcg | 360 |
| acattggctc gcatcgatca ggaatcgacg aggctttatc ggtcttaaaa tcggagttta | 420 |
| gcacgcaccc ccaagaatgc attcctcaag acggggatcc accagcgttt ttccgtcggt | 480 |
| cggttgagaa gatgaagcaa cttcttttg tggtaccatt ttcgatgttt ttgccattct | 540 |

```
tgtgtaagtt tgaagaagag gaagataata ggacttgaca tttgagacat gattaacagc    600
aaagcctgaa gatttgtaaa agggacgaac ttaagagatg taaaagcttt agatattaga    660
aggaagtgaa agtaaagttt gaatcaatga ggaagtgatc tatttattgg actcacggcg    720
acagttcaaa ggcactagtg gccgacaacc aactaacact cattaatgac ttggaaaact    780
gtactgacgg gacgttttgg tcactcccgt cgcttacgtc atgaggatgt cgtcattaca    840
ggtcgagata gaaaattgaa ggctcaattc gtttcttgtc atttcactcc aaaaaacgag    900
gagactatct gtatacggtt aaaatcgggc ccacccgatt ttactatttg accgagacta    960
ggaggttgca tcgaagaatg gcctcgtaac agaacagact aaatcacgag gataaggtac   1020
tgagttcata atcgaggtac cggtcgagat cgaggctagt agtgatcgaa accaaatgag   1080
acagacatcg agcaagatcg aagatagcac aataacagaa aggcgagata tccacgactg   1140
gtcgaggatc atggcataaa tctcgaaacg aatcaaatta gaaacagtta attagctaat   1200
catgaattta cttctgtaat tagaattata ccataagtga aattcctcta ctatttatag   1260
ggggttctaa tcatttggaa gacacatggt tcacagatat caaagaaatg taattctctt   1320
tctcgtttat actattgttc atcagcttgt tatattttaa ttgttcttac atcaaccagt   1380
tcgagggtat ccaaacttga gggctgagtt ccattctaac acaagtttgc tttacttttat  1440
agtttatttc tattattaat cttcatattt atcaattggt attaagtgaa attacgtgta   1500
cttagaacaa tattataaat ttaattgtta tccaatttta aggataaata gaacattca    1560
ttaaagttaa aagagacata taaaaaagc tattgctcag atttctgcaa ctgaaatcgt    1620
gcaaagttga ggcatccaca cttgtttttc aaagcttcgg tactgtatac aaagatagaa   1680
agtaaaggag acttttctct ttaaattatt gcatcagaaa tagtatagct gccataatag   1740
tttattaatt ccagctatgc ttagcttgca gcctctatcg aacaaaaaaa gtataccaac   1800
tcaagtcaat ttgagccgac aacatgacaa accaaatca aaatgcatac tctagctttt    1860
ttactttggt aggttttaag taatctagtg agacttttac cttcattcat gaaaatcttg   1920
gaaagggtaa ttgtataatt gaaagctata taaaggggtc ggagtgaagc ttaagaggac   1980
aacaactttt ctcatttgtt tcaaagctcg agatgacgga gataccgcct aacagccaga   2040
tgaaaaccat gttgcagaag gcagtgcaat cggttcaatg gacatatact cttttctggc   2100
aattatgtcc ccaacaaggg gcgttagtgt ggagagatgg atattacaat ggggctataa   2160
agactagaaa gacagtgcag ccaatggaag ttagcgctga ggaagcttct cttcacagaa   2220
gccaacagct tagagaactt tacgaatcac tttccgccgg cgagtcaaat cagccagcga   2280
gaaggccgtc ggcagctttg tcaccggagg acttgacgga gtccgagtgg ttttatctca   2340
tgtgtgtttc tttctctttt cctcctggca tcggattacc tggcaaggct tattcgaaga   2400
aacatcacat atggatcatg ggcgcaaacg aggttgatag caaagtcttc tgtagagcta   2460
ttcttgccaa gagcgcccgc atacagacgt cgttggtat tcctctcttg gatggtgtac    2520
tggaactggg aactacagaa agggttcaag aagagattgg attcataaac catgtaaaga   2580
gcttttcac tgagcaacaa caacctcagc taccaaagcc agccttatct gagcactcca   2640
cttccaatcc caccaccttt tccgagccac attttactc cggcaatact cgccatctg    2700
ctaatgttga tattgcgcat caagatggcg gagctgccgg cgaagaagat gaggaggagg   2760
aagaagaaga agatgatgat gaagccgagt tggactcgga tagtatagcg attcaaagcg   2820
cggctaatcc tattgccgtt gaggctagtg aactcatgca gcttgatgtg tccgaggcta   2880
tacagctcgg ctcgcccgat gatgactctg ataatatgga ctctgatttt catttggttg   2940
```

```
gcgctggaaa cacggctcat gactaccagc gccaagctga ctctttcaaa gccgagaccg    3000
ccattagctg gccgcacttc caagaccttc aacaattacc aggtggctct agttatgatg    3060
aattatcaca agaagacaca cactattctc aaacagtgtc aaccattctc gaacaccgaa    3120
gctccaaatt ttcctctaca acaatgggct gtatttctca tgactcggcc caatctgcct    3180
tcacattgtg ccctagcacc accgtctgca gcccgaatcc cgcccactgc cgccacgacg    3240
actcacttgt cgacggtggc ggcgcctccc agtggctgct caaaagcata ctcttcactg    3300
tcccatttct tcacactaaa taccaatctg aagcttctcc aaagtcacgt gacgtcgcca    3360
ctgttgattc ctccagtact gcttctcgct ttcgcaaagg ctgtagtata acgtcgcaag    3420
aagagccaag tggaaaccat gtacttgcag aacgacgtcg tagagagaag ctaaatgagc    3480
gttttatcat attaaggtct cttgtacctt ttgtaacgaa aatggacaaa gcctccattt    3540
tgggtgacac catagagtat gtcaagcagt tacgtaagaa agttcaggat cttgaagctc    3600
gtgctcgcga cacggagcac tccagagatg cagataaaaa aggtggcaca gctacagtga    3660
aggtgttgca aggaagggt aagaggagaa tgaatacggt agatggaagt gttggtggag    3720
ggcaggcaac gataacggcg tccccaccgt caacgacgga aaatgaggag gttgtgcaag    3780
tacaagtatc aattatcgaa agcgatgcat tggtggagct ccggtgtccg tacaaagagg    3840
ggttgctgtt aaatgtaatg cagatgctaa gggaactcaa agtggaagtt gtagccattc    3900
aatcagctct taataatggc gtcttcttgg ctgagttaag agctaaggta aaagagaata    3960
tatgtggaag gaaagcaagc attttggaag taaaaaggtc aatacatcag ataatcccta    4020
gagattaatc tagaaataac agagggcgcg cgagcggtgg ctactgatcg cctatgagtt    4080
ctgtgattct acttgtaatt tcagaagtgt tttcagtgtc ttgttttctg gaagtccgtc    4140
tggtttttag taacttttag ctcaaaaatg tgtctgtacg atggtatttg tatgtttgtg    4200
ggtcttttac atatacgctt gtaatcgatc aatgtagaat gctgtgtgcc ttttccgtca    4260
acagcttatt tagtgtttac tctgtatacg tatatctaat atatagtact gattctttca    4320
tctggtgatt tgttttccta aagagattat tatcatagct ttaattgaat gatacaaaga    4380
ggtgttgcct ggcttcacca gagcagaaat tttcattgat atagggtaca aatgtcattc    4440
acataatgtt aagagataag tttttcaatg tcctcaagag cccaccaaga gtttcttccg    4500
ggaattgctt aaattatctt aaatttaaat tgtagtttaa ac                       4542
```

<210> SEQ ID NO 23
<211> LENGTH: 4542
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
cccgggcagt aggcatcaat tactatatat tttacaagta attaaatgat aaacaaatgc      60
aatatttgtt tagtttccat atttcttttt caaggcactc ctttaattac tcatccattc     120
aaatggatct tctcattttt cagacggttt ttaggactcc ctctatctca aattatctat     180
cgagattttt aaaaaaaaaa ttgtctcaaa ttatttcat tttggaaatt taagataaaa      240
ttaattatat ttttttcatt taccttaat ggtaattatt cttgaatatg gagatagcac      300
atcgagtaaa tattcaataa agagagatta tatcttataa cataaataag agtaaaatag     360
tccaaaattc ctcataatta atattttta agggtatgta aagaaaaac acgacaaata       420
```

```
atttgagacg gagagaatac cttcttttttg accttttgta aataaatatt aaaatatcct    480
caacatttcc taggttaatt tctctctctc cctaataatt tcaaaaagtt atcattgtga    540
tactcaaata tattggtctt agcacaattt gagcattgca tgttgtatgc ctggatcctc    600
ctgggtgcca tttttccttt gcttttggat acctttttgc aactttagtc cattgctgga    660
acatgatttt ttgtacctct tgtctgttcc catgatgata aactatgata actaacattt    720
tcagaaatat tggattgaat tagatatatt ttcaatattg agctacaaaa ctcgttgaat    780
attttgccct atttggttgg taataaaagt gggtcacatg cacagttttt ctcttgtctt    840
ctctagatta agctctttgg aaatgaccta ctgaaaatgc tacacataaa actccccac     900 tcctccccaa gttgaggggt gggaggtttg atttggaccc ttaccctatt gttaatatcg    960
aaatagataa tacaaaggac gggaacataa aaccaaaacc tccgataaaa caccaaagtt    1020
gatgatctaa gttaagttat tgattcttat acgttgattg gaagtgcaca atggtctttg    1080
catactatca aagtatgaat tggttcttga attatatctc ttaatatgat gtattgtgtt    1140
taattaattc tctactattc tctatttta taggctaaaa gatcctgaca tgcttcttga    1200
acacatgtga aggttagtta actatagtca gaagtacaca agaattaact tgtacaccta    1260
tccgtgatcg aaaaacttaa cttgttctaa gctgaactga gtcctcctat ccatgtccga    1320
ttcttcacta gaagcattaa tcatacaagg agaattcaac ttaatttact gtattggtta    1380
tcatttacat agtttagtta taaaactttg gagcgacaca atgattgaca ctactaatca    1440
tgattgaata ttaacttcac tcgatttatc aatttctcat acaagtgaat taatttcact    1500
ctttgtgatt tcagtagtaa atgtcaagtt tcatagttt ttctttttga aattagtcat     1560
acatgtgaat agaacattaa tttaagttaa aagctagctg ctctgatttc tgtaactgaa    1620
atcgtgcaaa gttgaggcat ccacatttgt ttttcaaagt tccagtactg tctaaaaga     1680 tagaaagtaa aaggagactt ttctctttga attattgcat cagaaatagt atagctgcca    1740
taatagttta ttcctttgct tagcttgcag cctctatcga acaaaaaaag tgtaccaact    1800
caggtcaatt tgagccgaca acatgacaaa accaaatcaa aatgcatata tactctagct    1860
tttttacttt actttggtag gttttaagtg agacttttac cttcatttat gaaaatcttg    1920
aaaagggtaa ttgtctaaat gaaagctata taaaggggtc gtagtgaagc ttaagaagac    1980
aacaactttt ctcatttgtt tcaaagctcg agatgacgga gataccgcct aacagccaga    2040
tgaaaaccat gttgcagaag gcagtgcaat cggttcaatg gacatatact cttttctggc    2100
aattatgtcc ccaacaaggg gcgttagtgt ggagagatgg atattacaat ggggctataa    2160
agactagaaa gacagtgcag ccaatggaag ttagcgctga ggaagcttct cttcacagaa    2220
gccaacagct tagagaactt tacgaatcac tttccgccgg cgagtcaaat cagccagcga    2280
gaaggccgtc ggcagctttg tcaccggagg acttgacgga gtccgagtgg ttttatctca    2340
tgtgtgtttc tttctctttt cctcctggca tcgattacc tggcaggct tattcgaaga     2400 aacatcacat atggatcatg ggcgcaaacg aggttgatag caaagtcttc tgtagagcta    2460
ttcttgccaa gagcgcccgc atacagacgg tcgttggtat tcctctcttg gatggtgtac    2520
tggaactggg aactacagaa agggttcaag aagagattgg attcataaac catgtaaaga    2580 gcttttcac tgagcaacaa caacctcagc taccaaagcc agccttatct gagcactcca     2640
cttccaatcc caccaccttt tccgagccac attttactc cggcaatact tcgccatctg     2700
ctaatgttga tattgcgcat caagatggcg gagctgccgg cgaagaagat gaggaggagg    2760
```

-continued

```
aagaagaaga agatgatgat gaagccgagt tggactcgga tagtatagcg attcaaagcg    2820
cggctaatcc tattgccgtt gaggctagtg aactcatgca gcttgatgtg tccgaggcta    2880
tacagctcgg ctcgcccgat gatgactctg ataatatgga ctctgatttt catttggttg    2940
gcgctggaaa cacggctcat gactaccagc gccaagctga ctctttcaaa gccgagaccg    3000
ccattagctg gccgcacttc aagaccttc aacaattacc aggtggctct agttatgatg    3060
aattatcaca agaagacaca cactattctc aaacagtgtc aaccattctc gaacaccgaa    3120
gctccaaatt ttcctctaca caatgggct gtatttctca tgactcggcc caatctgcct    3180
tcacattgtg ccctagcacc accgtctgca gcccgaatcc cgcccactgc cgccacgacg    3240
actcacttgt cgacggtggc ggcgcctccc agtggctgct caaaagcata ctcttcactg    3300
tcccatttct tcacactaaa taccaatctg aagcttctcc aaagtcacgt gacgtcgcca    3360
ctgttgattc ctccagtact gcttctcgct ttcgcaaagg ctgtagtata acgtcgcaag    3420
aagagccaag tggaaaccat gtacttgcag aacgacgtcg tagagagaag ctaaatgagc    3480
gttttatcat attaaggtct cttgtacctt ttgtaacgaa aatggacaaa gcctccattt    3540
tgggtgacac catagagtat gtcaagcagt tacgtaagaa agttcaggat cttgaagctc    3600
gtgctcgcga cacggagcac tccagagatg cagataaaaa aggtggcaca gctacagtga    3660
aggtgttgca aggaaggggt aagaggagaa tgaatacggt agatggaagt gttggtggag    3720
ggcaggcaac gataacggcg tccccaccgt caacgacgaa aaatgaggag gttgtgcaag    3780
tacaagtatc aattatcgaa agcgatgcat tggtggagct ccggtgtccg tacaaagagg    3840
ggttgctgtt aaatgtaatg cagatgctaa gggaactcaa agtggaagtt gtagccattc    3900
aatcagctct taataatggc gtcttcttgg ctgagttaag agctaaggta aaagagaata    3960
tatgtggaag gaaagcaagc attttggaag taaaaaggtc aatacatcag ataatcccta    4020
gagattaatc tagaaataac agagggcgcg cgagcggtgg ctactgatcg cctatgagtt    4080
ctgtgattct acttgtaatt tcagaagtgt tttcagtgtc ttgtttctg gaagtccgtc    4140 tggtttttag taacttttag ctcaaaaatg tgtctgtacg atggtatttg tatgtttgtg    4200
ggtcttttac atatacgctt gtaatcgatc aatgtagaat gctgtgtgcc ttttccgtca    4260
acagcttatt tagtgtttac tctgtatacg tatatctaat atatagtact gattctttca    4320
tctggtgatt tgttttccta aagagattat tatcatagct ttaattgaat gatacaaaga    4380
ggtgttgcct ggcttcacca gagcagaaat tttcattgat atagggtaca aatgtcattc    4440
acataatgtt aagagataag tttttcaatg tcctcaagag cccaccaaga gtttcttccg    4500
ggaattgctt aaattatctt aaatttaaat tgtagtttaa ac                      4542
```

<210> SEQ ID NO 24
<211> LENGTH: 4542
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
cccgggctat ataaggccat ccgtgaattg aataaactat ccaattattt tcttccacaa      60
aaatttcaat tctactttta gttattcttt ttaatattga gcttgcaatt ctatttgat     120 tcttcactca tgcatgcta cgtagagaac cttcaataca tcataagaga tggaccaagc    180
aatgcataac tcaaataagt ccatacaaat ttgctgaaag ataaagttat tctactttct    240
```

```
ttgaacccaa atctgataaa tcttgacaat cagatttgct actatgattt ctcactgtat    300
catttgtttt attctataaa gttaatgagg aatgtattaa ttatttaaga taccttactt    360
tttctgattt ttgatcttat agtcaagtcg tgaggcacaa tttgcgaccc tgatggcgca    420
aaccttacc  tagggatcgt agcacataaa cgttttaag  gactaagata tacgaggatg    480
tcaattatca taatgtaggg tctaagtttt cattttttt  tttgcatcta atagagtata    540
atttttttta atcatcacga taacttgatt tacaataata tgtactctgt ttacttttac    600
ttgacacgtt ttgatttttc acgcccttta agaaaaaatg attgaaatgc ataatttacc    660
atgatactca tattaattga tgcatatttt attggatttg agaaaatgat ttgaaatgag    720
taataaatat tgtgggtata acaggaaaaa aaattgtctt ctcttaacat gcataaagtg    780
aagagtaaaa agaaaatcta tttttgtata catgtcaaac aaaagtgaac ggaggagatg    840
acaaattgct aaatggcaat agttacaaaa ttcttcaatt actctttttc ataacaaaac    900
actggtctct cttgtaagta ttggtctata cttcaccacc taaagcattg gccgaagtct    960
ttttaaggag tttggttgtc atttatccat ttaaattaaa gggaaaataa gtgaacgcca   1020
ttacagcgag atgctttagg gtgctatttc ttggaaaaat aaagtagtta aatcttaaaa   1080
caccctcgag gatttcaaac tctagcttca ctaaaacttg agctttcttt tccactaatg   1140
tcgaaaaacg aaataaacat aagctattta caaaaataaa aaaatactcc atttgaatct   1200
aaagtcaagt cgtgattggg ataagaaaat agaaattat  ttatactcca gatcaagccg   1260
tgattggaat gagataatag aaaagtatga tagtacatga gtaacatcaa gttggaaatt   1320
aagggaagga aattagagaa agaactgaag aatatccaaa tattctttac gtccaaattt   1380
gatagttatt taacgtcatc gagatgacgg ccatgttcaa gttttccaca aatattgaga   1440
aaagaaagaa agacacaaac tgtgtttggt attattatag ttttttcttt tagagaattg   1500
attgtacata taagaaatta atataagatt tagaaataag attattagaa aaatcaaaca   1560
tcaaagtatt tattttaaat tcttttttcca atggacattc ccattctgaa aaaaagagat   1620
ataaaatgga agtaaaatta atcagatcgt taaatgtaga aaatattaat aacacttaac   1680
cataaccagt ctactttatt taacaaaaag cacatctgat agatcaaaaa agtgtttaac   1740
ttcatgcatt gacaatttaa aattattttg caacatcggg taaaactatt ttacaacaat   1800
tggtaactgc atatataagt ttaatatggt aacctagaaa ataggataaa ttatctataa   1860
caggatatat tacattgata ttaccatgtc aaaaaattta gtaagtacat gaataatcac   1920
cgtgaaatct tcaagatttc tcctataaat acccttggta gtaaatctag tttttccatt   1980
caagatacaa catttctcct atagtcctcg agatgacgga gataccgcct aacagccaga   2040
tgaaaaccat gttgcagaag gcagtgcaat cggttcaatg gacatatact cttttctggc   2100
aattatgtcc ccaacaaggg gcgttagtgt ggagagatgg atattacaat ggggctataa   2160
agactagaaa gacagtgcag ccaatggaag ttagcgctga ggaagcttct cttcacagaa   2220
gccaacagct tagagaactt tacgaatcac tttccgccgg cgagtcaaat cagccagcga   2280
gaaggccgtc ggcagctttg tcaccggagg acttgacgga gtccgagtgg ttttatctca   2340
tgtgtgtttc tttctctttt cctcctggca tcggattacc tggcaaggct tattcgaaga   2400
aacatcacat atggatcatg ggcgcaaacg aggttgatag caaagtcttc tgtagagcta   2460
ttcttgccaa gagcgcccgc atacagacgg tcgttggtat tcctctcttg gatggtgtac   2520
tggaactggg aactacagaa agggttcaag aagagattgg attcataaac catgtaaaga   2580
gcttttttcac tgagcaacaa caacctcagc taccaaagcc agccttatct gagcactcca   2640
```

```
cttccaatcc caccacctt tccgagccac attttactc cggcaatact tcgccatctg   2700
ctaatgttga tattgcgcat caagatggcg gagctgccgg cgaagaagat gaggaggag   2760 aagaagaaga agatgatgat gaagccgagt tggactcgga tagtatagcg attcaaagcg   2820
cggctaatcc tattgccgtt gaggctagtg aactcatgca gcttgatgtg tccgaggcta   2880
tacagctcgg ctcgcccgat gatgactctg ataatatgga ctctgatttt catttggttg   2940
gcgctggaaa cacggctcat gactaccagc gccaagctga ctctttcaaa gccgagaccg   3000
ccattagctg gccgcacttc caagaccttc aacaattacc aggtggctct agttatgatg   3060
aattatcaca agaagacaca cactattctc aaacagtgtc aaccattctc gaacaccgaa   3120
gctccaaatt ttcctctaca acaatgggct gtatttctca tgactcggcc caatctgcct   3180
tcacattgtg ccctagcacc accgtctgca gcccgaatcc cgcccactgc cgccacgacg   3240
actcacttgt cgacggtggc ggcgcctccc agtggctgct caaaagcata ctcttcactg   3300
tcccatttct tcacactaaa taccaatctg aagcttctcc aaagtcacgt gacgtcgcca   3360
ctgttgattc ctccagtact gcttctcgct ttcgcaaagg ctgtagtata acgtcgcaag   3420
aagagccaag tggaaaccat gtacttgcag aacgacgtcg tagagagaag ctaaatgagc   3480
gttttatcat attaaggtct cttgtacctt ttgtaacgaa aatggacaaa gcctccattt   3540
tgggtgacac catagagtat gtcaagcagt acgtaagaa agttcaggat cttgaagctc   3600
gtgctcgcga cacggagcac tccagagatg cagataaaa aaggtggcaca gctacagtga   3660 aggtgttgca aggaagggt aagaggagaa tgaatacggt agatggaagt gttggtggag   3720
ggcaggcaac gataacggcg tccccaccgt caacgacgga aaatgaggag gttgtgcaag   3780
tacaagtatc aattatcgaa agcgatgcat tggtggagct ccggtgtccg tacaaagagg   3840
ggttgctgtt aaatgtaatg cagatgctaa gggaactcaa agtggaagtt gtagccattc   3900
aatcagctct taataatggc gtcttcttgg ctgagttaag agctaaggta aaagagaata   3960
tatgtggaag gaaagcaagc attttggaag taaaaaggtc aatacatcag ataatcccta   4020
gagattaatc tagaaataac agagggcgcg cgagcggtgg ctactgatcg cctatgagtt   4080
ctgtgattct acttgtaatt tcagaagtgt tttcagtgtc ttgttttctg gaagtccgtc   4140
tggtttttag taacttttag ctcaaaaatg tgtctgtacg atggtatttg tatgtttgtg   4200
ggtcttttac atatacgctt gtaatcgatc aatgtagaat gctgtgtgcc ttttccgtca   4260
acagcttatt tagtgtttac tctgtatacg tatatctaat atatagtact gattctttca   4320
tctggtgatt tgtttccta aagagattat tatcatagct ttaattgaat gatacaaaga   4380
ggtgttgcct ggcttcacca gagcagaaat tttcattgat atagggtaca aatgtcattc   4440
acataatgtt aagagataag tttttcaatg tcctcaagag cccaccaaga gtttcttccg   4500
ggaattgctt aaattatctt aaatttaaat tgtagtttaa ac                     4542
```

<210> SEQ ID NO 25
<211> LENGTH: 4542
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
cccgggatta attgtaaata aatatactta tcattttcgg agaatatcca atattatata    60 tataatttt atacttatga gtttcgggct agatatttat tctaagctaa gtactacaaa   120
```

```
tactgtgata taaggctcta aactttccta ccctaaaaga gtctacgttt tactacgcta    180
aaaaggtcta cattttacta cgctaaaaaa taatctaaac taaacatcgc aaaaacaaac    240
aagtaaacat gacaatttaa caaataaatt tttttgacta atttacaagt atatttatac    300
aacactaaaa ttaaatccgg ataaaaatta acatgctagt tttggcaaaa ataaacacaa    360
aactatatac aaaccataca aatcaaataa tattcaatat tatacaagtt tcaactaaaa    420
ttaaatcgaa atacctggat tcggaaacta aataaatcgg attttgact tcaaaaaaga    480 gattccagcg taccacgacc ctcaactata atgtgggacc accaatcttc accttttatg    540
tgtcgggggg acccaaaaat tttttttttt tttaaaaaac tgggcagatc gctgaggagg    600
ggaccaaatt tttttgaaag ttttcggctg aatgaagaag aagaagaaag gtttagggtt    660 ttgtttagg gtatggcgcc aacagtattg gcgctatgct gacaccgcct gaaaagtagg    720
ggtatggcgc caacactgtt ggcgctatgc tgacatgtca gtaaactctc tgatatggcg    780
ccaactatgt tggcgttata tatttgtg ttacttttcc ttttttacac ttattaatgt    840
agtttgagtc aaaaaaaaca ataataaagt tccggactcg agatgtaagg ggttgtcaat    900
tttcactttg tcagtcgcta agagtaatta tgaatattct tttatcaata ttggacctca    960
aactttatcc attgtaagaa aaaaagttg taaatatt gtgtcactta attaaacggt    1020
cgtagtagtt agtagtagtg acatagtcct ttcgtttgat agtatatcaa attggaacaa    1080
tttacatttg caccaaagca taagggaaa gcatgaaaaa gagaaagtgc aaaagagaaa    1140
aatacaacaa caacaagaat atttcagtat aattctataa gtagggtctg gagagagtag    1200
aataccccta acctagaagg gcaggaagaa tattaaagta aaaaagataa aagattacaa    1260
ataaaataaa agaaaaaca aacaaacata caaaattaat ttgtgcataa tgcttatagt    1320
aattgccaat ttgccatgaa tatcttccac cgggctatct tggtcatgtt aatcactcta    1380 tcctgtttc aaacaatttt tactctaaaa atttgcatgt tatattaatt ggtgggtgag    1440
ccagaaattt taaacaaaaa atcaaaatac ggtacactaa aagattttt ataaaaaga    1500 attcaccaag ttatatatat acacaatctt tcttttttt aaatcttacg atgaccaatt    1560
ttttcgacaa agaatattca cttaaaccct tgttcataca tagcttggca attggattaa    1620
taatgaaaat aatactttaa attttggaaa gaaatatta tttattctcc aaaagaaacc    1680
aagaaattag attcatcaaa aaataatgac caccattagc ccacctccca aatctctatt    1740 cctttagac ttttaaccaa attttcagat ctaccaaacc ccaatttatc caataaactt    1800
ttcagatcta aaaataaaaa tattcagatc tggaacaaat cttgaccgtc cattttcatc    1860
attcatatct atttaatacc actcacctcc gcccttact ccttgcaaca ctcttcttct    1920
cctctaaaaa cccttataga agaaggaa aaagcctttc aaatctcatc tcaaaccacc    1980
taatttctct catactcgct cgacccctcg agatgacgga gataccgcct aacagccaga    2040
tgaaaaccat gttgcagaag gcagtgcaat cggttcaatg gacatatact cttttctggc    2100
aattatgtcc ccaacaaggg gcgttagtgt ggagagatgg atattacaat ggggctataa    2160
agactagaaa gacagtgcag ccaatggaag ttagcgctga ggaagcttct cttcacagaa    2220
gccaacagct tagagaactt tacgaatcac tttccgccgg cgagtcaaat cagccagcga    2280
gaaggccgtc ggcagctttg tcaccggagg acttgacgga gtccgagtgg ttttatctca    2340
tgtgtgtttc tttctctttt cctcctggca tcggattacc tggcaggct tattcgaaga    2400 aacatcacat atggatcatg ggcgcaaacg aggttgatag caaagtcttc tgtagagcta    2460
```

| | |
|---|---|
| ttcttgccaa gagcgcccgc atacagacgg tcgttggtat tcctctcttg gatggtgtac | 2520 |
| tggaactggg aactacagaa agggttcaag aagagattgg attcataaac catgtaaaga | 2580 |
| gcttttcac tgagcaacaa caacctcagc taccaaagcc agccttatct gagcactcca | 2640 |
| cttccaatcc caccaccttt tccgagccac attttactc cggcaatact tcgccatctg | 2700 |
| ctaatgttga tattgcgcat caagatggcg gagctgccgg cgaagaagat gaggaggagg | 2760 |
| aagaagaaga agatgatgat gaagccgagt tggactcgga tagtatagcg attcaaagcg | 2820 |
| cggctaatcc tattgccgtt gaggctagtg aactcatgca gcttgatgtg tccgaggcta | 2880 |
| tacagctcgg ctcgcccgat gatgactctg ataatatgga ctctgatttt catttggttg | 2940 |
| gcgctggaaa cacggctcat gactaccagc gccaagctga ctctttcaaa gccgagaccg | 3000 |
| ccattagctg gccgcacttc caagaccttc aacaattacc aggtggctct agttatgatg | 3060 |
| aattatcaca agaagacaca cactattctc aaacagtgtc aaccattctc gaacaccgaa | 3120 |
| gctccaaatt ttcctctaca caatgggct gtatttctca tgactcggcc caatctgcct | 3180 |
| tcacattgtg ccctagcacc accgtctgca gcccgaatcc cgcccactgc cgccacgacg | 3240 |
| actcacttgt cgacggtggc ggcgcctccc agtggctgct caaaagcata ctcttcactg | 3300 |
| tcccatttct tcacactaaa taccaatctg aagcttctcc aaagtcacgt gacgtcgcca | 3360 |
| ctgttgattc ctccagtact gcttctcgct ttcgcaaagg ctgtagtata acgtcgcaag | 3420 |
| aagagccaag tggaaaccat gtacttgcag aacgacgtcg tagagagaag ctaaatgagc | 3480 |
| gttttatcat attaaggtct cttgtacctt ttgtaacgaa aatggacaaa gcctccattt | 3540 |
| tgggtgacac catagagtat gtcaagcagt tacgtaagaa agttcaggat cttgaagctc | 3600 |
| gtgctcgcga cacggagcac tccagagatg cagataaaaa aggtggcaca gctacagtga | 3660 |
| aggtgttgca aggaaggggt aagaggagaa tgaatacggt agatggaagt gttggtggag | 3720 |
| ggcaggcaac gataacggcg tccccaccgt caacgacgga aaatgaggag gttgtgcaag | 3780 |
| tacaagtatc aattatcgaa agcgatgcat tggtggagct ccggtgtccg tacaaagagg | 3840 |
| ggttgctgtt aaatgtaatg cagatgctaa gggaactcaa agtggaagtt gtagccattc | 3900 |
| aatcagctct taataatggc gtcttcttgg ctgagttaag agctaaggta aaagagaata | 3960 |
| tatgtggaag gaaagcaagc attttggaag taaaaaggtc aatacatcag ataatcccta | 4020 |
| gagattaatc tagaaataac agagggcgcg cgagcggtgg ctactgatcg cctatgagtt | 4080 |
| ctgtgattct acttgtaatt tcagaagtgt tttcagtgtc ttgttttctg gaagtccgtc | 4140 |
| tggtttttag taacttttag ctcaaaaatg tgtctgtacg atggtatttg tatgtttgtg | 4200 |
| ggtcttttac atatacgctt gtaatcgatc aatgtagaat gctgtgtgcc ttttccgtca | 4260 |
| acagcttatt tagtgtttac tctgtatacg tatatctaat atatagtact gattctttca | 4320 |
| tctggtgatt tgttttccta aagagattat tatcatagct ttaattgaat gatacaaaga | 4380 |
| ggtgttgcct ggcttcacca gagcagaaat tttcattgat atagggtaca aatgtcattc | 4440 |
| acataatgtt aagagataag ttttcaatg tcctcaagag cccaccaaga gtttcttccg | 4500 |
| ggaattgctt aaattatctt aaatttaaat tgtagtttaa ac | 4542 |

<210> SEQ ID NO 26
<211> LENGTH: 2722
<212> TYPE: DNA
<213> ORGANISM: Artificial Sequence
<220> FEATURE:
<223> OTHER INFORMATION: Description of Artificial Sequence: Synthetic
    polynucleotide

```
<400> SEQUENCE: 26
cccgggttta gtggacattt tagtaagaag attggttgtt ggatgtatat attgacattt      60
gagttaaggg ggtttatata gtggtatggc ggcttttgc actgtggaca ttaatatttt     120
ggcacttgat atattattat tattattata ttaatatagg aataatcatg aaagatgctt     180
tggtaaaggt agagctaggc ggctaaatgt gaaggcctga caagtgataa tttattatgc     240
acacacatat atagaagcta aataatttat ttggtgataa tgatcacgag caaactttgt     300
cacgctaata tgtccacttg aaataatacg ccaccgataa tatccactat aaaacatgga     360
ctgaactaga aattcgggtt gagcccaata gcttttgttc aaataatata tttatgttaa     420
gtgttttatt aagtatgtac aaatattaaa tttagaatac agttataatt ataagcactt     480
ggaaacgttg ttttaagatt caaaaccaat ataattaaaa tacttgctcc gctccgtaaa     540
acaagatata cagccttcaa gcaatacatt ttgttcagtc gggtcatatt ccactatttt     600
tcactacttt tacttcacgt ttttacaag ctatttatcc agtacatcct ttgaactgaa      660
atcataatta tttacctgca attattacta taggtatccc tagctactta atttcattta     720
aaattagcta taactagcac tagttttatg aatttggaga tgattgtgcg cacaagctag     780
ctttgtggaa tttggagacg agctttgcag ccggtttcaa tctttcgact acatttgcta     840
ttggagtcac tgagtaaaat acttattttc agtcggctgt gtttacacta aatttatgaa     900
tgcatgccat tagtcttcac acacacatat ataatatata gcttaataac ctggttaaa     960 tgatacaata tattatcagt ttaatgaata aatatttgcc taattattac ccactctgca    1020
ttaccaagtc ttcataaatg aaagatttat aatcaagaaa ttagatcaag aattctaaca    1080
tatatcaagt ggattaacta atagaaaacg tatatgcatc tacagttaaa aaaaggttaa    1140
gcaaatgggg tgggttggat cttcaacgtt gtgcaattcg gaattcccca atttattgac    1200
catttacaga tcaagttcac atattagtta gtctgatttt gacttaacgt ttgttacaat    1260 tctcttttt attttaagg aaaaaaaagt tctgcatccg ataattggag atcaatatgt      1320
aatacaagtt agcttctatg ttcataataa ttgtcaggct cttacgaata gccgccaggc    1380
atctttcaag attattcctt tattaatata atatatcaag tgccaatata tatatgatta    1440
ttgtctatag tgcaaaaagc cgccacaccc ctatataaac ccccttaact caaatgtcaa    1500
tatatcaaca ccaattttct tactaaaaag tccactaaac tcgagatgaa tatttgtact    1560
aataagtcgt cgtcaggagt gaagaaaggt gcatggactg aagaagaaga tgttctattg    1620
aaaaaatgca tcgagaaata tggagaagga aagtggcatc aagttcctct tagagctggt    1680
ttgaatagat gcagaaagag ctgcagatta aggtggctaa attatctaag gccacatata    1740
aagagaggga acttctcttt tgatgaagta gatctcattt tgaggcttca taagctgtta    1800
ggcaacagat ggtcacttat tgctggtaga cttcctggaa ggacggcaaa cgatgtcaaa    1860
aactactgga acagccatct tcgcaagaag ttaattgctc ctcatgatca aaaggagagc    1920
aagcaaaaag caaagaagat caccatattc agacctcggc ctcgaacctt ctcaaagaca    1980
aatacttgtg ttaaaagtaa cacaaatact gtagataagg atattgaagg cagcagcgaa    2040 ataattgat tcaacgataa tttgaagcca acaactgaag aattgacgga tgatggaatt     2100
caatggtggg ccgatttact agctaacaat tacaacaata tgggattga ggaagctgat     2160 aattcatcac caactttgtt gcatgaggaa atgccacttc tcagttgatc tagaaataac    2220
agagggcgcg cgagcggtgg ctactgatcg cctatgagtt ctgtgattct acttgtaatt    2280
tcagaagtgt tttcagtgtc ttgttttctg gaagtccgtc tggtttttag taacttttag    2340
```

```
ctcaaaaatg tgtctgtacg atggtatttg tatgtttgtg ggtcttttac atatacgctt    2400
gtaatcgatc aatgtagaat gctgtgtgcc ttttccgtca acagcttatt tagtgtttac    2460
tctgtatacg tatatctaat atatagtact gattctttca tctggtgatt tgttttccta    2520
aagagattat tatcatagct ttaattgaat gatacaaaga ggtgttgcct ggcttcacca    2580
gagcagaaat tttcattgat atagggtaca aatgtcattc acataatgtt aagagataag    2640
tttttcaatg tcctcaagag cccaccaaga gtttcttccg ggaattgctt aaattatctt    2700
aaatttaaat tgtagtttaa ac                                              2722

<210> SEQ ID NO 27
<211> LENGTH: 2374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
cccgggacct cttccttctc tctatctcca ttttttattt atgttttact aaattacttt      60
tatttcataa caacatgtct tgttcatgtt ttactaagtt gcttttattt cataacagca     120
tcataataaa atacaggaat tttcaagcga agcagagtca cttccaaaag tagaaacact     180
tagaacttct gctaagggta attaacaact tttggtcctt taggaggcac aatatactag     240
acgaagaatt gaacttgatc ttacttacgg caaaggctaa taatagcatc acgttagtga     300
actacaacgc caactaaaaa gaaaaaagaa aataattaag accagtaaat atgcatgttc     360
actctcaaat attgagggga aaaaaaccga gaatctaatt atctacaaat gttcattcat     420
tagggtagta ggaaaatttt aatttttatct taatttgaac caactacaat atttttatttt     480 aaaacaaata aaattggaat agcaccggtt ttttttatttt atatttttttg ggtatccgaa     540 agtgtatggg cgctaggaac tacctccgtc tttacttctt ttgttgctag taataggaac     600
tcctttaatg ttttgacagt gaaaatacta gtatattaat taactaattt gtctctatac     660
catgatttat aatattacgg ttgaagtgat agctcatgga agaggaagca ctgatggtgt     720
gaaaatattt acacaatcag atcatttatt atattattat ggataaattt ctcgataagt     780
attaattgat aagtattcgg ataaaagtag gttataatct aatttttttt atactattag     840
tattagtata tataattcgt tacatttaca tatacatctt ctatgtttta ttcatagatg     900
tagacactgg cgaggaacat ggcaaattgc aacaccttat gtggctaata atgcattcaa     960
gagaatttga gtaaatatct aatttgcttg tgctgccagc taaaaccttg gggacacatg    1020
gtttctagaa cttaatttct ttaatatttc tctttactct aattcatact tttgcatcct    1080
atataaaccc accttctata acctttgcaa tatcaaacaa agcaacaatc tacttataac    1140
tactaaagtt gatagttata tcaatcatta agaaattta gactcttaga actcgagatg    1200
aatatttgta ctaataagtc gtcgtcagga gtgaagaaag gtgcatggac tgaagaagaa    1260
gatgttctat tgaaaaaatg catcgagaaa tatggagaag gaaagtggca tcaagttcct    1320
cttagagctg gttgaatag atgcagaaag agctgcagat taaggtggct aaaattatcta    1380 aggccacata taagagagg agacttctct tttgatgaag tagatctcat tttgaggctt    1440
cataagctgt taggcaacag atggtcactt attgctggta gacttcctgg aaggacggca    1500
aacgatgtca aaaactactg gaacagccat cttcgcaaga agttaattgc tcctcatgat    1560
caaaaggaga gcaagcaaaa agcaaagaag atcaccatat tcagacctcg gcctcgaacc    1620
```

```
ttctcaaaga caaatacttg tgttaaaagt aacacaaata ctgtagataa ggatattgaa    1680
ggcagcagcg aaataattag attcaacgat aatttgaagc caacaactga agaattgacg    1740
gatgatggaa ttcaatggtg ggccgattta ctagctaaca attacaacaa taatgggatt    1800
gaggaagctg ataattcatc accaactttg ttgcatgagg aaatgccact tctcagttga    1860
tctagaaata acagagggcg cgcgagcggt ggctactgat cgcctatgag ttctgtgatt    1920
ctacttgtaa tttcagaagt gttttcagtg tcttgttttc tggaagtccg tctgtttttt    1980
agtaactttt agctcaaaaa tgtgtctgta cgatggtatt tgtatgtttg tgggtctttt    2040
acatatacgc ttgtaatcga tcaatgtaga atgctgtgtg cctttccgt caacagctta     2100 tttagtgttt actctgtata cgtatatcta atatatagta ctgattcttt catctggtga    2160 tttgtttttcc taaagagatt attatcatag ctttaattga atgatacaaa gaggtgttgc   2220
ctggcttcac cagagcagaa attttcattg atatagggta caaatgtcat tcacataatg    2280
ttaagagata agttttttcaa tgtcctcaag agcccaccaa gagtttcttc cgggaattgc   2340
ttaaattatc ttaaatttaa attgtagttt aaac                                2374
```

<210> SEQ ID NO 28
<211> LENGTH: 2237
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
cccgggacta aaagtgaatc cttccccaca aaaaacttag ttttgaatgc acgagattct     60
acaaataaaa agaaagaaag aaataaaagg tataattaga gcgcacgtga aataaaaata   120
ctatcaattt gaatgaaaac ttgaaaataa aataaaaaat agaagtatca tgttttgaag   180
gattcaattt tagtattatt ttaatttata tatatgatta ttttgtcagg tgggtcattc   240 ctgtttttaat tgaattatta tttattagac gaaaaaaaaa atcttggaat aagaaaatct   300
ggtgactatt tatgaaattt acccttcaat tgtatgtgta aaacacttat atccaagttt   360
ataagatttt tagcaaaata aaatacttca aatttttttaa gctattcgct tgaaaataaa   420
attaagacat gttaacatag attactttct ctattaccaa attcttgtgt tactttctta   480
aagttgagtc gagtagtatt gataaataaa atagtcaata tgttttccac tgttctgaac   540
aaaaatagtt tttttttttt ttttttttta tgtattttca taattttgaa ttatttaaat   600
ttgagttttg gaagatgaat tcacgtttga ccaaaaagga gagatgaatc gtgtctatcc   660
aaaaataaaa acaaatgggc cgtgtaaaaa ataacatttt tttggtgggt caaaacatcg   720
ttaggtttaa taaatcaaat cgatttttct cttgaaatat taccaccacc tttttcttat   780
tactcgacaa aaactcaaac agtaacacaa aacaaacagc caaaaaccgg tttcgaaaac   840
ccagcgacca aaacatggaa atggttttac tttggcctgt tgtattcaac ttttcgattt   900
cacgattcta tattttcagg tataaatacc ccagctaatg cagtgccaca tcacacctca   960
agatatttaa ctcagtattc agaaacaaca aaagttcttc tctacataaa attttcctat   1020
tttagtgatc agtgaaggaa atcaagaaaa ataactcgag atgaatattt gtactaataa   1080
gtcgtcgtca ggagtgaaga aaggtgcatg gactgaagaa gaagatgttc tattgaaaaa   1140
atgcatcgag aaatatggag aaggaaagtg gcatcaagtt cctcttagag ctggtttgaa   1200
tagatgcaga aagagctgca gattaaggtg gctaaattat ctaaggccac atataaagag   1260
```

```
aggagacttc tcttttgatg aagtagatct cattttgagg cttcataagc tgttaggcaa    1320
cagatggtca cttattgctg gtagacttcc tggaaggacg gcaaacgatg tcaaaaacta    1380
ctggaacagc catcttcgca agaagttaat tgctcctcat gatcaaaagg agagcaagca    1440
aaaagcaaag aagatcacca tattcagacc tcggcctcga accttctcaa agacaaatac    1500
ttgtgttaaa agtaacacaa atactgtaga taaggatatt gaaggcagca gcgaaataat    1560
tagattcaac gataatttga agccaacaac tgaagaattg acggatgatg aattcaatg    1620 gtgggccgat ttactagcta acaattacaa caataatggg attgaggaag ctgataattc    1680
atcaccaact ttgttgcatg aggaaatgcc acttctcagt tgatctagaa ataacagagg    1740
gcgcgcgagc ggtggctact gatcgcctat gagttctgtg attctacttg taatttcaga    1800
agtgttttca gtgtcttgtt ttctggaagt ccgtctggtt tttagtaact tttagctcaa    1860
aaatgtgtct gtacgatggt atttgtatgt ttgtgggtct tttacatata cgcttgtaat    1920
cgatcaatgt agaatgctgt gtgccttttc cgtcaacagc ttatttagtg tttactctgt    1980
atacgtatat ctaatatata gtactgattc tttcatctgg tgatttgttt tcctaaagag    2040
attattatca tagctttaat tgaatgatac aaagaggtgt tgcctggctt caccagagca    2100
gaaattttca ttgatatagg gtacaaatgt cattcacata atgttaagag ataagttttt    2160
caatgtcctc aagagcccac caagagtttc ttccgggaat tgcttaaatt atcttaaatt    2220
taaattgtag tttaaac                                                   2237

<210> SEQ ID NO 29
<211> LENGTH: 3189
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
cccgggcatt ggagttttat taacccgcct cgatagaggc ggggctatac aatctgataa      60
ggtgatcgag gatgaaaggg agccctcga ctttgctcac gaagaatcgg agcagaataa     120
caatttgcca aaaggaagga tggatttggc ctagggttat ttggtattga cggcaaaaat     180
taacgatgac ggggtcgagg gggcccaacg tgaaagggta agtgtaaaca cttagaaacc     240
cttccacatg agtggtgata tcttttttcgg gggtcgggat caccacctct ttgccttccc     300
agttgcggtc tttctttacc tgcttaaggt atccctcagt tattgagcat atatacctcg     360
acattggctc gcatcgatca ggaatcgacg aggctttatc ggtcttaaaa tcggagttta     420
gcacgcaccc ccaagaatgc attcctcaag acggggatcc accagcgttt ttccgtcggt     480
cggttgagaa gatgaagcaa cttctttttg tggtaccatt ttcgatgttt ttgccattct     540
tgtgtaagtt tgaagaagag gaagataata ggacttgaca tttgagacat gattaacagc     600
aaagcctgaa gatttgtaaa agggacgaac ttaagagatg taaaagcttt agatattaga     660
aggaagtgaa agtaaagttt gaatcaatga ggaagtgatc tatttattgg actcacggcg     720
acagttcaaa ggcactagtg gccgacaacc aactaacact cattaatgac ttggaaaact     780
gtactgacgg gacgttttgg tcactcccgt cgcttacgtc atgaggatgt cgtcattaca     840
ggtcgagata gaaattgaa ggctcaattc gtttcttgtc atttcactcc aaaaaacgag     900
gagactatct gtatacggtt aaaatcgggc ccacccgatt ttactatttg accgagacta     960
ggaggttgca tcgaagaatg gcctcgtaac agaacagact aaatcacgag gataaggtac    1020
```

```
tgagttcata atcgaggtac cggtcgagat cgaggctagt agtgatcgaa accaaatgag    1080
acagacatcg agcaagatcg aagatagcac aataacagaa aggcgagata tccacgactg    1140
gtcgaggatc atggcataaa tctcgaaacg aatcaaatta gaaacagtta attagctaat    1200
catgaattta cttctgtaat tagaattata ccataagtga aattcctcta ctatttatag    1260
ggggttctaa tcatttggaa gacacatggt tcacagatat caagaaaatg taattctctt    1320
tctcgtttat actattgttc atcagcttgt tatattttaa ttgttcttac atcaaccagt    1380
tcgagggtat ccaaacttga gggctgagtt ccattctaac acaagtttgc tttactttat    1440
agtttatttc tattattaat cttcatattt atcaattggt attaagtgaa attacgtgta    1500
cttagaacaa tattataaat ttaattgtta tccaattttta aggataaata agaacattca    1560
ttaaagttaa aagagacata taaaaaaagc tattgctcag atttctgcaa ctgaaatcgt    1620
gcaaagttga ggcatccaca cttgtttttc aaagcttcgg tactgtatac aaagatagaa    1680
agtaaaggag acttttctct ttaaattatt gcatcagaaa tagtatagct gccataatag    1740
tttattaatt ccagctatgc ttagcttgca gcctctatcg aacaaaaaaa gtataccaac    1800
tcaagtcaat ttgagccgac aacatgacaa aaccaaatca aatgcatac tctagctttt    1860 ttactttggt aggttttaag taatctagtg agacttttac cttcattcat gaaaatcttg    1920
gaaagggtaa ttgtataatt gaagctata taaaggggtc ggagtgaagc ttaagaggac    1980
aacaactttt ctcatttgtt tcaaagctcg agatgaatat ttgtactaat aagtcgtcgt    2040
caggagtgaa gaaaggtgca tggactgaag aagaagatgt tctattgaaa aaatgcatcg    2100
agaaatatgg agaaggaaag tggcatcaag ttcctcttag agctggtttg aatagatgca    2160
gaaagagctg cagattaagg tggctaaatt atctaaggcc acatataaag agaggagact    2220
tctcttttga tgaagtagat ctcatttttga ggcttcataa gctgttaggc aacagatggt    2280
cacttattgc tggtagactt cctggaagga cggcaaacga tgtcaaaaac tactggaaca    2340
gccatcttcg caagaagtta attgctcctc atgatcaaaa ggagagcaag caaaaagcaa    2400
agaagatcac catattcaga cctcggcctc gaaccttctc aaagacaaat acttgtgtta    2460
aaagtaacac aaatactgta gataaggata ttgaaggcag cagcgaaata attagattca    2520
acgataattt gaagccaaca actgaagaat tgacggatga tggaattcaa tggtgggccg    2580
atttactagc taacaattac aacaataatg ggattgagga agctgataat tcatcaccaa    2640
ctttgttgca tgaggaaatg ccacttctca gttgatctag aaataacaga gggcgcgcga    2700
gcggtggcta ctgatcgcct atgagttctg tgattctact tgtaatttca gaagtgtttt    2760
cagtgtcttg ttttctggaa gtccgtctgg tttttagtaa cttttagctc aaaaatgtgt    2820
ctgtacgatg gtatttgtat gtttgtgggt cttttacata tacgcttgta atcgatcaat    2880
gtagaatgct gtgtgccttt tccgtcaaca gcttatttag tgtttactct gtatacgtat    2940
atctaatata tagtactgat tctttcatct ggtgatttgt tttcctaaag agattattat    3000
catagcttta attgaatgat acaaagaggt gttgcctggc ttcaccagag cagaaatttt    3060
cattgatata gggtacaaat gtcattcaca taatgttaag agataagttt ttcaatgtcc    3120
tcaagagccc accaagagtt tcttccggga attgcttaaa ttatcttaaa tttaaattgt    3180
agtttaaac                                                           3189
```

<210> SEQ ID NO 30
<211> LENGTH: 3189
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 30

| | | | | | |
|---|---|---|---|---|---|
| cccgggcagt | aggcatcaat | tactatatat | tttacaagta | attaaatgat | aaacaaatgc | 60 |
| aatatttgtt | tagtttccat | atttcttttt | caaggcactc | ctttaattac | tcatccattc | 120 |
| aaatggatct | tctcattttt | cagacggttt | ttaggactcc | ctctatctca | aattatctat | 180 |
| cgagatttt | aaaaaaaaaa | ttgtctcaaa | ttattttcat | tttggaaatt | taagataaaa | 240 |
| ttaattatat | ttttttcatt | tacccttaat | ggtaattatt | cttgaatatg | gagatagcac | 300 |
| atcgagtaaa | tattcaataa | agagagatta | tatcttataa | cataaataag | agtaaaatag | 360 |
| tccaaaattc | ctcataatta | atatttttta | agggtatgta | aaagaaaaac | acgacaaata | 420 |
| atttgagacg | gagagaatac | cttctttttg | acctttgta | aataaatatt | aaaatatcct | 480 |
| caacatttcc | taggttaatt | tctctctctc | cctaataatt | tcaaaaagtt | atcattgtga | 540 |
| tactcaaata | tattggtctt | agcacaattt | gagcattgca | tgttgtatgc | ctggatcctc | 600 |
| ctgggtgcca | ttttcctttt | gcttttggat | accttttgc | aactttagtc | cattgctgga | 660 |
| acatgatttt | ttgtacctct | tgtctgttcc | catgatgata | aactatgata | actaacattt | 720 |
| tcagaaatat | tggattgaat | tagatatatt | ttcaatattg | agctacaaaa | ctcgttgaat | 780 |
| attttgccct | atttggttgg | taataaaagt | gggtcacatg | cacagttttt | ctcttgtctt | 840 |
| ctctagatta | agctctttgg | aaatgaccta | ctgaaaatgc | tacacataaa | actcccccac | 900 |
| tcctccccaa | gttgagggt | gggaggtttg | atttggaccc | ttaccctatt | gttaatatcg | 960 |
| aaatagataa | tacaaaggac | gggaacataa | aaccaaaacc | tccgataaaa | caccaaagtt | 1020 |
| gatgatctaa | gttaagttat | tgattcttat | acgttgattg | gaagtgcaca | atggtctttg | 1080 |
| catactatca | aagtatgaat | tggttcttga | attatatctc | ttaatatgat | gtattgtgtt | 1140 |
| taattaattc | tctactattc | tctattttta | taggctaaaa | gatcctgaca | tgcttcttga | 1200 |
| acacatgtga | aggttagtta | actatagtca | gaagtacaca | agaattaact | tgtacaccta | 1260 |
| tccgtgatcg | aaaaacttaa | cttgttctaa | gctgaactga | gtcctcctat | ccatgtccga | 1320 |
| ttcttcacta | gaagcattaa | tcatacaagg | agaattcaac | ttaatttact | gtattggtta | 1380 |
| tcatttacat | agtttagtta | taaaactttg | gagcgacaca | atgattgaca | ctactaatca | 1440 |
| tgattgaata | ttaacttcac | tcgatttatc | aatttctcat | acaagtgaat | taatttcact | 1500 |
| ctttgtgatt | tcagtagtaa | atgtcaagtt | tcatagttt | ttcttttga | aattagtcat | 1560 |
| acatgtgaat | agaacattaa | tttaagttaa | aagctagctg | ctctgatttc | tgtaactgaa | 1620 |
| atcgtgcaaa | gttgaggcat | ccacatttgt | ttttcaaagt | tccagtactg | tctaaaaaga | 1680 |
| tagaaagtaa | aaggagactt | ttctctttga | attattgcat | cagaaatagt | atagctgcca | 1740 |
| taatagttta | ttcctttgct | tagcttgcag | cctctatcga | acaaaaaaag | tgtaccaact | 1800 |
| caggtcaatt | tgagccgaca | acatgacaaa | accaaatcaa | aatgcatata | tactctagct | 1860 |
| tttttacttt | actttggtag | gttttaagtg | agacttttac | cttcatttat | gaaaatcttg | 1920 |
| aaaagggtaa | ttgtctaaat | gaaagctata | taagggggtc | gtagtgaagc | ttaagaagac | 1980 |
| aacaactttt | ctcatttgtt | tcaaagctcg | agatgaatat | ttgtactaat | aagtcgtcgt | 2040 |
| caggagtgaa | gaaaggtgca | tggactgaag | aagaagatgt | tctattgaaa | aaatgcatcg | 2100 |
| agaaatatgg | agaaggaaag | tggcatcaag | ttcctcttag | agctggtttg | aatagatgca | 2160 |

```
gaaagagctg cagattaagg tggctaaatt atctaaggcc acatataaag agaggagact    2220
tctcttttga tgaagtagat ctcattttga ggcttcataa gctgttaggc aacagatggt    2280
cacttattgc tggtagactt cctggaagga cggcaaacga tgtcaaaaac tactggaaca    2340
gccatcttcg caagaagtta attgctcctc atgatcaaaa ggagagcaag caaaaagcaa    2400
agaagatcac catattcaga cctcggcctc gaaccttctc aaagacaaat acttgtgtta    2460
aaagtaacac aaatactgta gataaggata ttgaaggcag cagcgaaata attagattca    2520
acgataattt gaagccaaca actgaagaat tgacggatga tggaattcaa tggtgggccg    2580
atttactagc taacaattac aacaataatg ggattgagga agctgataat tcatcaccaa    2640
ctttgttgca tgaggaaatg ccacttctca gttgatctag aaataacaga gggcgcgcga    2700
gcggtggcta ctgatcgcct atgagttctg tgattctact tgtaatttca gaagtgtttt    2760
cagtgtcttg ttttctggaa gtccgtctgg tttttagtaa cttttagctc aaaaatgtgt    2820
ctgtacgatg gtatttgtat gtttgtgggt cttttacata tacgcttgta atcgatcaat    2880
gtagaatgct gtgtgccttt tccgtcaaca gcttatttag tgtttactct gtatacgtat    2940
atctaatata tagtactgat tctttcatct ggtgatttgt tttcctaaag agattattat    3000
catagcttta attgaatgat acaaagaggt gttgcctggc ttcaccagag cagaaatttt    3060
cattgatata gggtacaaat gtcattcaca taatgttaag agataagttt ttcaatgtcc    3120
tcaagagccc accaagagtt tcttccggga attgcttaaa ttatcttaaa tttaaattgt    3180
agtttaaac                                                            3189

<210> SEQ ID NO 31
<211> LENGTH: 3189
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
cccgggctat ataaggccat ccgtgaattg aataaactat ccaattattt tcttccacaa      60
aaatttcaat tctacttttta gttattcttt ttaatattga gcttgcaatt ctattttgat    120
tcttcactca tgacatgcta cgtagagaac cttcaataca tcataagaga tggaccaagc    180
aatgcataac tcaaataagt ccatacaaat ttgctgaaag ataaagttat tctactttct    240
ttgaacccaa atctgataaa tcttgacaat cagatttgct actatgattt ctcactgtat    300
catttgtttt attctataaa gttaatgagg aatgtattaa ttatttaaga taccttactt    360
tttctgattt ttgatcttat agtcaagtcg tgaggcacaa tttgcgaccc tgatggcgca    420 aaccttacc tagggatcgt agcacataaa cgttttttaag gactaagata tacgaggatg    480
tcaattatca taatgtaggg tctaagtttt cattttttt tttgcatcta atagagtata    540 attttttta atcatcacga taacttgatt tacaataata tgtactctgt ttacttttac    600
ttgacacgtt ttgatttttc acgccctttaa agaaaaaatg attgaaatgc ataatttacc    660
atgatactca tattaattga tgcatatttt attggatttg agaaaatgat ttgaaatgag    720
taataaatat tgtgggtata acaggaaaaaa aaattgtctt ctcttaacat gcataaagtg    780
aagagtaaaa agaaaatcta ttttttgtata catgtcaaac aaaagtgaac ggaggagatg    840
acaaattgct aaatgcaat agttacaaaa ttcttcaatt actctttttc ataacaaaac    900
actggtctct cttgtaagta ttggtctata cttcaccacc taaagcattg gccgaagtct    960
```

```
ttttaaggag tttggttgtc atttatccat ttaaattaaa gggaaaataa gtgaacgcca    1020
ttacagcgag atgctttagg gtgctatttc ttggaaaaat aaagtagtta aatcttaaaa    1080
caccctcgag gatttcaaac tctagcttca ctaaaacttg agctttcttt tccactaatg    1140
tcgaaaaacg aaataaacat aagctattta caaaaataaa aaaatactcc atttgaatct    1200
aaagtcaagt cgtgattggg ataagaaaat agaaatttat ttatactcca gatcaagccg    1260
tgattggaat gagataatag aaaagtatga tagtacatga gtaacatcaa gttggaaatt    1320
aagggaagga aattagagaa agaactgaag aatatccaaa tattctttac gtccaaattt    1380
gatagttatt taacgtcatc gagatgacgg ccatgttcaa gttttccaca aatattgaga    1440
aaagaaagaa agacacaaac tgtgtttggt attattatag ttttttcttt tagagaattg    1500
attgtacata taagaaatta atataagatt tagaaataag attattagaa aaatcaaaca    1560
tcaaagtatt tattttaaat tcttttttcca atggacattc ccattctgaa aaaagagat    1620 ataaaatgga agtaaaatta atcagatcgt taaatgtaga aaatattaat aacacttaac    1680
cataaccagt ctactttatt taacaaaaag cacatctgat agatcaaaaa agtgtttaac    1740
ttcatgcatt gacaatttaa aattattttg caacatcggg taaaactatt ttacaacaat    1800
tggtaactgc atatataagt ttaatatggt aacctagaaa ataggataaa ttatctataa    1860
caggatatat tacattgata ttaccatgtc aaaaaattta gtaagtacat gaataatcac    1920
cgtgaaatct tcaagatttc tcctataaat acccttggta gtaaatctag tttttccatt    1980
caagatacaa catttctcct atagtcctcg agatgaatat ttgtactaat aagtcgtcgt    2040
caggagtgaa gaaggtgca tggactgaag aagaagatgt tctattgaaa aaatgcatcg    2100
agaaatatgg agaaggaaag tggcatcaag ttcctcttag agctggtttg aatagatgca    2160
gaaagagctg cagattaagg tggctaaatt atctaaggcc acatataaag agaggagact    2220
tctcttttga tgaagtagat ctcattttga ggcttcataa gctgttaggc aacagatggt    2280
cacttattgc tggtagactt cctggaagga cggcaaacga tgtcaaaaac tactggaaca    2340
gccatcttcg caagaagtta attgctcctc atgatcaaaa ggagagcaag caaaaagcaa    2400
agaagatcac catattcaga cctcggcctc gaaccttctc aaagacaaat acttgtgtta    2460
aaagtaacac aaatactgta gataaggata ttgaaggcag cagcgaaata attagattca    2520
acgataattt gaagccaaca actgaagaat tgacggatga tggaattcaa tggtgggccg    2580
atttactagc taacaattac aacaataatg ggattgagga agctgataat tcatcaccaa    2640
ctttgttgca tgaggaaatg ccacttctca gttgatctag aaataacaga gggcgcgcga    2700
gcggtggcta ctgatcgcct atgagttctg tgattctact tgtaatttca gaagtgtttt    2760
cagtgtcttg ttttctggaa gtccgtctgg ttttttagtaa cttttagctc aaaaatgtgt    2820
ctgtacgatg gtatttgtat gtttgtgggt cttttacata tacgcttgta atcgatcaat    2880
gtagaatgct gtgtgccttt tccgtcaaca gcttatttag tgtttactct gtatacgtat    2940
atctaatata tagtactgat tctttcatct ggtgatttgt tttcctaaag agattattat    3000
catagcttta attgaatgat acaaagaggt gttgcctggc ttcaccagag cagaaatttt    3060
cattgatata gggtacaaat gtcattcaca taatgttaag agataagttt ttcaatgtcc    3120
tcaagagccc accaagagtt tcttccggga attgcttaaa ttatcttaaa tttaaattgt    3180
agtttaaac                                                           3189

<210> SEQ ID NO 32
<211> LENGTH: 3189
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
cccgggatta attgtaaata aatatactta tcattttcgg agaatatcca atattatata      60
tataattttt atacttatga gtttcgggct agatatttat tctaagctaa gtactacaaa     120
tactgtgata taaggctcta aactttccta ccctaaaaga gtctacgttt tactacgcta     180
aaaaggtcta cattttacta cgctaaaaaa taatctaaac taaacatcgc aaaaacaaac     240
aagtaaacat gacaatttaa caaataaatt tttttgacta atttacaagt atatttatac     300
aacactaaaa ttaaatccgg ataaaaatta acatgctagt tttggcaaaa ataaacacaa     360
aactatatac aaaccataca aatcaaataa tattcaatat tatacaagtt tcaactaaaa     420
ttaaatcgaa atacctggat tcggaaacta aataaatcgg attttgact tcaaaaaaga     480 gattccagcg taccacgacc ctcaactata atgtgggacc accaatcttc accttttatg     540
tgtcgggggg acccaaaaat tttttttttt tttaaaaaac tgggcagatc gctgaggagg     600
ggaccaaatt tttttgaaag ttttcggctg aatgaagaag aagaagaaag gtttagggtt     660
ttgttttagg gtatggcgcc aacagtattg gcgctatgct gacaccgcct gaaaagtagg     720
ggtatggcgc caacactgtt ggcgctatgc tgacatgtca gtaaactctc tgatatggcg     780
ccaactatgt tggcgttata tatatttgtg ttactttttcc ttttttacac ttattaatgt     840
agtttgagtc aaaaaaaaca ataataaagt tccggactcg agatgtaagg ggttgtcaat     900
tttcactttg tcagtcgcta agagtaatta tgaatattct tttatcaata ttggacctca     960
aactttatcc attgtaagaa aaaaaagttg taaaatatt gtgtcactta attaaacggt    1020
cgtagtagtt agtagtagtg acatagtcct ttcgtttgat agtatatcaa attggaacaa    1080
tttacatttg caccaaagca taagggaaa gcatgaaaaa gagaaagtgc aaaagagaaa    1140
aatacaacaa caacaagaat atttcagtat aattctataa gtagggtctg gagagagtag    1200
aataccccta acctagaagg gcaggaagaa tattaaagta aaaaagataa aagattacaa    1260
ataaaataaa agaaaaaaca aacaaacata caaaattaat ttgtgcataa tgcttatagt    1320
aattgccaat ttgccatgaa tatcttccac cgggctatct tggtcatgtt aatcactcta    1380
tcctgttttc aaacaatttt tactctaaaa atttgcatgt tatattaatt ggtgggtgag    1440
ccagaaattt taaacaaaaa atcaaaatac ggtacactaa aagattttt ataaaaaga     1500 attcaccaag ttatatatat acacaatctt tcttttttt aaatcttacg atgaccaatt    1560
ttttcgacaa agaatattca cttaaaccct tgttcataca tagcttggca attggattaa    1620
taatgaaaat aatactttaa attttggaaa gaaatatta tttattctcc aaaagaaacc    1680
aagaaattag attcatcaaa aaataatgac caccattagc ccacctccca aatctctatt    1740 cctttagac ttttaaccaa attttcagat ctaccaaacc ccaattatc caataaactt    1800 ttcagatcta aaaataaaa tattcagatc tggaacaaat cttgaccgtc cattttcatc    1860
attcatatct atttaatacc actcacctcc gcccttact ccttgcaaca ctcttcttct    1920
cctctaaaaa cccttataga agaagaggaa aaagcctttc aaatctcatc tcaaaccacc    1980
taatttctct catactcgct cgacccctcg agatgaatat ttgtactaat aagtcgtcgt    2040
caggagtgaa gaaggtgca tggactgaag aagaagatgt tctattgaaa aaatgcatcg    2100
agaaatatgg agaaggaaag tggcatcaag ttcctcttag agctggtttg aatagatgca    2160
```

```
gaaagagctg cagattaagg tggctaaatt atctaaggcc acatataaag agaggagact    2220
tctcttttga tgaagtagat ctcattttga ggcttcataa gctgttaggc aacagatggt    2280
cacttattgc tggtagactt cctggaagga cggcaaacga tgtcaaaaac tactggaaca    2340
gccatcttcg caagaagtta attgctcctc atgatcaaaa ggagagcaag caaaaagcaa    2400
agaagatcac catattcaga cctcggcctc gaaccttctc aaagacaaat acttgtgtta    2460
aaagtaacac aaatactgta gataaggata ttgaaggcag cagcgaaata attagattca    2520
acgataattt gaagccaaca actgaagaat tgacggatga tggaattcaa tggtgggccg    2580
atttactagc taacaattac aacaataatg ggattgagga agctgataat tcatcaccaa    2640
ctttgttgca tgaggaaatg ccacttctca gttgatctag aaataacaga gggcgcgcga    2700
gcggtggcta ctgatcgcct atgagttctg tgattctact tgtaatttca gaagtgtttt    2760
cagtgtcttg ttttctggaa gtccgtctgg tttttagtaa cttttagctc aaaaatgtgt    2820
ctgtacgatg gtatttgtat gtttgtgggt cttttacata tacgcttgta atcgatcaat    2880
gtagaatgct gtgtgccttt tccgtcaaca gcttatttag tgtttactct gtatacgtat    2940
atctaatata tagtactgat tctttcatct ggtgatttgt tttcctaaag agattattat    3000
catagcttta attgaatgat acaaagaggt gttgcctggc ttcaccagag cagaaatttt    3060
cattgatata gggtacaaat gtcattcaca taatgttaag agataagttt ttcaatgtcc    3120
tcaagagccc accaagagtt tcttccggga attgcttaaa ttatcttaaa tttaaattgt    3180
agtttaaac                                                           3189

<210> SEQ ID NO 33
<211> LENGTH: 248
<212> TYPE: PRT
<213> ORGANISM: Arabidopsis thaliana

<400> SEQUENCE: 33

Met Glu Gly Ser Ser Lys Gly Leu Arg Lys Gly Ala Trp Thr Thr Glu
1               5                   10                  15

Glu Asp Ser Leu Leu Arg Gln Cys Ile Asn Lys Tyr Gly Glu Gly Lys
            20                  25                  30

Trp His Gln Val Pro Val Arg Ala Gly Leu Asn Arg Cys Arg Lys Ser
        35                  40                  45

Cys Arg Leu Arg Trp Leu Asn Tyr Leu Lys Pro Ser Ile Lys Arg Gly
    50                  55                  60

Lys Leu Ser Ser Asp Glu Val Asp Leu Leu Arg Leu His Arg Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr His Leu Ser Lys Lys His
            100                 105                 110

Glu Pro Cys Cys Lys Ile Lys Met Lys Lys Arg Asp Ile Thr Pro Ile
        115                 120                 125

Pro Thr Thr Pro Ala Leu Lys Asn Asn Val Tyr Lys Pro Arg Pro Arg
    130                 135                 140

Ser Phe Thr Val Asn Asn Asp Cys Asn His Leu Asn Ala Pro Pro Lys
145                 150                 155                 160

Val Asp Val Asn Pro Pro Cys Leu Gly Leu Asn Ile Asn Asn Val Cys
                165                 170                 175

Asp Asn Ser Ile Ile Tyr Asn Lys Asp Lys Lys Lys Asp Gln Leu Val
```

```
                180                 185                 190
Asn Asn Leu Ile Asp Gly Asp Asn Met Trp Leu Glu Lys Phe Leu Glu
        195                 200                 205

Glu Ser Gln Glu Val Asp Ile Leu Val Pro Glu Ala Thr Thr Thr Glu
        210                 215                 220

Lys Gly Asp Thr Leu Ala Phe Asp Val Asp Gln Leu Trp Ser Leu Phe
225                 230                 235                 240

Asp Gly Glu Thr Val Lys Phe Asp
                245

<210> SEQ ID NO 34
<211> LENGTH: 671
<212> TYPE: PRT
<213> ORGANISM: Nicotiana tabacum

<400> SEQUENCE: 34

Met Thr Glu Ile Pro Pro Asn Ser Gln Met Lys Thr Met Leu Gln Lys
1               5                   10                  15

Ala Val Gln Ser Val Gln Trp Thr Tyr Thr Leu Phe Trp Gln Leu Cys
                20                  25                  30

Pro Gln Gln Gly Ala Leu Val Trp Arg Asp Gly Tyr Tyr Asn Gly Ala
            35                  40                  45

Ile Lys Thr Arg Lys Thr Val Gln Pro Met Glu Val Ser Ala Glu Glu
50                  55                  60

Ala Ser Leu His Arg Ser Gln Gln Leu Arg Glu Leu Tyr Glu Ser Leu
65                  70                  75                  80

Ser Ala Gly Glu Ser Asn Gln Pro Ala Arg Arg Pro Ser Ala Ala Leu
                85                  90                  95

Ser Pro Glu Asp Leu Thr Glu Ser Glu Trp Phe Tyr Leu Met Cys Val
            100                 105                 110

Ser Phe Ser Phe Pro Pro Gly Ile Gly Leu Pro Gly Lys Ala Tyr Ser
        115                 120                 125

Lys Lys His His Ile Trp Ile Met Gly Ala Asn Glu Val Asp Ser Lys
130                 135                 140

Val Phe Cys Arg Ala Ile Leu Ala Lys Ser Ala Arg Ile Gln Thr Val
145                 150                 155                 160

Val Gly Ile Pro Leu Leu Asp Gly Val Leu Glu Leu Gly Thr Thr Glu
                165                 170                 175

Arg Val Gln Glu Glu Ile Gly Phe Ile Asn His Val Lys Ser Phe Phe
            180                 185                 190

Thr Glu Gln Gln Gln Pro Gln Leu Pro Lys Pro Ala Leu Ser Glu His
        195                 200                 205

Ser Thr Ser Asn Pro Thr Thr Phe Ser Glu Pro His Phe Tyr Ser Gly
        210                 215                 220

Asn Thr Ser Pro Ser Ala Asn Val Asp Ile Ala His Gln Asp Gly Gly
225                 230                 235                 240

Ala Ala Gly Glu Glu Asp Glu Glu Glu Glu Glu Asp Asp Asp
                245                 250                 255

Glu Ala Glu Leu Asp Ser Asp Ser Ile Ala Ile Gln Ser Ala Ala Asn
            260                 265                 270

Pro Ile Ala Val Glu Ala Ser Glu Leu Met Gln Leu Asp Val Ser Glu
        275                 280                 285

Ala Ile Gln Leu Gly Ser Pro Asp Asp Asp Ser Asp Asn Met Asp Ser
290                 295                 300
```

```
Asp Phe His Leu Val Gly Ala Gly Asn Thr Ala His Asp Tyr Gln Arg
305                 310                 315                 320

Gln Ala Asp Ser Phe Lys Ala Glu Thr Ala Ile Ser Trp Pro His Phe
            325                 330                 335

Gln Asp Leu Gln Gln Leu Pro Gly Gly Ser Ser Tyr Asp Glu Leu Ser
        340                 345                 350

Gln Glu Asp Thr His Tyr Ser Gln Thr Val Ser Thr Ile Leu Glu His
    355                 360                 365

Arg Ser Ser Lys Phe Ser Ser Thr Thr Met Gly Cys Ile Ser His Asp
370                 375                 380

Ser Ala Gln Ser Ala Phe Thr Leu Cys Pro Ser Thr Thr Val Cys Ser
385                 390                 395                 400

Pro Asn Pro Ala His Cys Arg His Asp Asp Ser Leu Val Asp Gly Gly
            405                 410                 415

Gly Ala Ser Gln Trp Leu Leu Lys Ser Ile Leu Phe Thr Val Pro Phe
        420                 425                 430

Leu His Thr Lys Tyr Gln Ser Glu Ala Ser Pro Lys Ser Arg Asp Val
    435                 440                 445

Ala Thr Val Asp Ser Ser Thr Ala Ser Arg Phe Arg Lys Gly Cys
450                 455                 460

Ser Ile Thr Ser Gln Glu Glu Pro Ser Gly Asn His Val Leu Ala Glu
465                 470                 475                 480

Arg Arg Arg Arg Glu Lys Leu Asn Glu Arg Phe Ile Ile Leu Arg Ser
            485                 490                 495

Leu Val Pro Phe Val Thr Lys Met Asp Lys Ala Ser Ile Leu Gly Asp
        500                 505                 510

Thr Ile Glu Tyr Val Lys Gln Leu Arg Lys Lys Val Gln Asp Leu Glu
    515                 520                 525

Ala Arg Ala Arg Asp Thr Glu His Ser Arg Asp Ala Asp Lys Lys Gly
530                 535                 540

Gly Thr Ala Thr Val Lys Val Leu Gln Gly Arg Gly Lys Arg Arg Met
545                 550                 555                 560

Asn Thr Val Asp Gly Ser Val Gly Gly Gln Ala Thr Ile Thr Ala
            565                 570                 575

Ser Pro Pro Ser Thr Thr Glu Asn Glu Glu Val Val Gln Val Gln Val
        580                 585                 590

Ser Ile Ile Glu Ser Asp Ala Leu Val Glu Leu Arg Cys Pro Tyr Lys
    595                 600                 605

Glu Gly Leu Leu Leu Asn Val Met Gln Met Leu Arg Glu Leu Lys Val
610                 615                 620

Glu Val Val Ala Ile Gln Ser Ala Leu Asn Asn Gly Val Phe Leu Ala
625                 630                 635                 640

Glu Leu Arg Ala Lys Val Lys Glu Asn Ile Cys Gly Arg Lys Ala Ser
            645                 650                 655

Ile Leu Glu Val Lys Arg Ser Ile His Gln Ile Ile Pro Arg Asp
        660                 665                 670

<210> SEQ ID NO 35
<211> LENGTH: 220
<212> TYPE: PRT
<213> ORGANISM: Nicotiana tabacum

<400> SEQUENCE: 35

Met Asn Ile Cys Thr Asn Lys Ser Ser Ser Gly Val Lys Lys Gly Ala
1               5                   10                  15
```

```
Trp Thr Glu Glu Glu Asp Val Leu Leu Lys Lys Cys Ile Glu Lys Tyr
            20                  25                  30

Gly Glu Gly Lys Trp His Gln Val Pro Leu Arg Ala Gly Leu Asn Arg
        35                  40                  45

Cys Arg Lys Ser Cys Arg Leu Arg Trp Leu Asn Tyr Leu Arg Pro His
50                  55                  60

Ile Lys Arg Gly Asp Phe Ser Phe Asp Glu Val Asp Leu Ile Leu Arg
65                  70                  75                  80

Leu His Lys Leu Leu Gly Asn Arg Trp Ser Leu Ile Ala Gly Arg Leu
                85                  90                  95

Pro Gly Arg Thr Ala Asn Asp Val Lys Asn Tyr Trp Asn Ser His Leu
            100                 105                 110

Arg Lys Lys Leu Ile Ala Pro His Asp Gln Lys Glu Ser Lys Gln Lys
        115                 120                 125

Ala Lys Lys Ile Thr Ile Phe Arg Pro Arg Pro Arg Thr Phe Ser Lys
130                 135                 140

Thr Asn Thr Cys Val Lys Ser Asn Thr Asn Thr Val Asp Lys Asp Ile
145                 150                 155                 160

Glu Gly Ser Ser Glu Ile Ile Arg Phe Asn Asp Asn Leu Lys Pro Thr
                165                 170                 175

Thr Glu Glu Leu Thr Asp Asp Gly Ile Gln Trp Trp Ala Asp Leu Leu
            180                 185                 190

Ala Asn Asn Tyr Asn Asn Asn Gly Ile Glu Glu Ala Asp Asn Ser Ser
        195                 200                 205

Pro Thr Leu Leu His Glu Glu Met Pro Leu Leu Ser
    210                 215                 220
```

<210> SEQ ID NO 36
<211> LENGTH: 2627
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
cccgggttag tattcaaacc gaataaatca agttaccaa accgaataaa tcgaaaccga      60
aaggagaaac cgcaccatac cgaatttaat taggtacgat attgatattg tattttaaaa    120
aatcgaatac caaaaatacc gaattaaaat atctaaatat cgtacagtac cgaccgataa    180
atactctata agcatcatca tgtcaccatt cctgcttgga aatagatgta ataatgtaat    240
tcaaggtgaa gatcattgaa aatgagatat ttggactctt agataattgt gcaactgata    300
tttttattta cttttttttct ttcatccaat aattgcgtta cattaaaaat gagatatttg    360
gattaatatt cttctccttg accacaaagc aaggaaagcc taaggaccga tagtaaagtt    420
gtattcgtgt ggttgcgtgt tagtttttgag cggcaaaata aattatgtta aggtaaatta    480
tttttggaac aataataaaa ttatttctgt ataatatata aatcatatat ttgaaccgta    540
gaattatcag ttaatacttg tatatgagga ggctaactac gttagagcgc taacgagaat    600
acttcatata ccgtattttt tacgataata ataatgtaat gtgaaattgc tatccaaaag    660
gcacctaatt ttgtccaccg ttcaaggaa aggacaagga agtagtagcg tgtaggtttg    720
gtgctgtaca aaataagcaa gacacgtgtt gccttattat aggataatcc ataaggcaat    780
ttcgtcttaa gtcggccatt gcacctttaa aaggagcctc tttgttccca aaatcttcat    840
```

-continued

```
cctttgattt ctctattctc aatatctcct caatttttct ctagtcttca aacacttctc    900
aaggtacatt aacttcttct ttcttttgt tcctcttatt ttatgctact tttatttaat    960
ttcgatctat atttttagga tctaaatact cattttgat ttgtttaatc gctctgtata   1020
tatgcaccaa gttgaaattt ttgtaagttt attttgttcg gtctatattt taagatctga   1080 aataccctt actgagaaaa aaaaaactca accttgattt tgttgtacct ggttgaattt   1140
gttattgttg tgtatacagt taaaaaactc aagtcttgat tttattgttt cccttttgta   1200
gtttgtatat acatagagct gaattggtgt tctaattttg gttgatttt atgtatacag   1260 tataaaatcg atcttagttt tgttcattga tttgtatttg cacaaagttg gaattttgcg   1320
tttgttattt tgatgattga aaccttttct gtatatacag ctcgagatgg agggttcgtc   1380
caaagggctg cgaaaggtg cttggactac tgaagaagat agtctcttga gacagtgcat   1440
taataagtat ggagaaggca aatggcacca agttcctgta agagctgggc taaaccggtg   1500
caggaaaagt tgtagattaa gatggttgaa ctatttgaag ccaagtatca agagaggaaa   1560
acttagctct gatgaagtcg atcttcttct tcgccttcat aggcttctag ggaataggtg   1620
gtctttaatt gctggaagat tacctggtcg gaccgcaaat gacgtcaaga attactggaa   1680
cactcatctg agtaagaaac atgaaccgtg ttgtaagata aagatgaaaa agagagacat   1740
tacgcccatt cctacaacac cggcactaaa aaacaatgtt tataagcctc gacctcgatc   1800
cttcacagtt aacaacgact gcaaccatct caatgcccca ccaaaagttg acgttaatcc   1860
tccatgcctt ggacttaaca tcaataatgt ttgtgacaat agtatcatat acaacaaaga   1920
taagaagaaa gaccaactag tgaataattt gattgatgga gataatatgt ggttagagaa   1980
attcctagag gaaagccaag aggtagatat tttggttcct gaagcgacga caacagaaaa   2040
gggggacacc ttggcttttg acgttgatca actttggagt cttttcgatg gagagactgt   2100
gaaatttgat tagtctagaa ataacagagg gcgcgcgagc ggtggctact gatcgcctat   2160
gagttctgtg attctacttg taatttcaga agtgttttca gtgtcttgtt ttctggaagt   2220
ccgtctggtt tttagtaact tttagctcaa aaatgtgtct gtacgatggt atttgtatgt   2280
ttgtgggtct tttacatata cgcttgtaat cgatcaatgt agaatgctgt gtgccttttc   2340
cgtcaacagc ttatttagtg tttactctgt atacgtatat ctaatatata gtactgattc   2400
tttcatctgg tgatttgttt tcctaaagag attattatca tagctttaat tgaatgatac   2460
aaagaggtgt tgcctggctt caccagagca gaaattttca ttgatatagg gtacaaatgt   2520
cattcacata atgttaagag ataagttttt caatgtcctc aagagcccac caagagtttc   2580
ttccgggaat tgcttaaatt atcttaaatt taaattgtag tttaaac              2627
```